United States Patent
Beck et al.

(10) Patent No.: US 10,364,443 B2
(45) Date of Patent: Jul. 30, 2019

(54) PRODUCTION OF MEVALONATE, ISOPRENE, AND ISOPRENOIDS USING GENES ENCODING POLYPEPTIDES HAVING THIOLASE, HMG-COA SYNTHASE AND HMG-COA REDUCTASE ENZYMATIC ACTIVITIES

(71) Applicants: Danisco US Inc., Palo Alto, CA (US); The Goodyear Tire & Rubber Company, Akron, OH (US)

(72) Inventors: Zachary Q. Beck, Palo Alto, CA (US); Michael C. Miller, San Francisco, CA (US); Caroline M. Peres, Palo Alto, CA (US); Yuliya A. Primak, Menlo Park, CA (US); Jeff P. Pucci, Pacifica, CA (US); Derek H. Wells, Palo Alto, CA (US)

(73) Assignees: Danisco US Inc., Palo Alto, CA (US); The Goodyear Tire & Rubber Company, Akron, OH (US)

( * ) Notice: Subject to any disclaimer, the term of this patent is extended or adjusted under 35 U.S.C. 154(b) by 0 days.

(21) Appl. No.: 15/694,193

(22) Filed: Sep. 1, 2017

(65) Prior Publication Data

US 2018/0002727 A1  Jan. 4, 2018

Related U.S. Application Data

(60) Division of application No. 14/514,962, filed on Oct. 15, 2014, now Pat. No. 9,752,162, which is a continuation of application No. 13/459,033, filed on Apr. 27, 2012, now Pat. No. 8,889,383.

(60) Provisional application No. 61/481,098, filed on Apr. 29, 2011.

(51) Int. Cl.
| | |
|---|---|
| C12N 9/04 | (2006.01) |
| C12N 9/10 | (2006.01) |
| C12P 5/00 | (2006.01) |
| C12P 7/02 | (2006.01) |
| C12N 15/81 | (2006.01) |
| C12P 7/04 | (2006.01) |
| C12P 7/42 | (2006.01) |
| C12N 15/70 | (2006.01) |

(52) U.S. Cl.
CPC ............ *C12P 5/007* (2013.01); *C12N 9/0006* (2013.01); *C12N 9/1025* (2013.01); *C12N 9/1029* (2013.01); *C12N 15/70* (2013.01); *C12N 15/81* (2013.01); *C12P 5/002* (2013.01); *C12P 7/02* (2013.01); *C12P 7/04* (2013.01); *C12P 7/42* (2013.01); *C12Y 101/01034* (2013.01); *C12Y 203/01016* (2013.01); *C12Y 203/0301* (2013.01); *Y02E 50/343* (2013.01)

(58) Field of Classification Search
CPC combination set(s) only.
See application file for complete search history.

(56) References Cited

U.S. PATENT DOCUMENTS

| | | |
|---|---|---|
| 7,371,558 B2 | 5/2008 | Cervin et al. |
| 7,541,173 B2 | 6/2009 | Bramucci et al. |
| 7,659,097 B2 | 2/2010 | Renninger et al. |
| 7,915,026 B2 | 3/2011 | Keasling et al. |
| 8,288,148 B2 | 10/2012 | Cervin et al. |
| 8,361,762 B2 | 1/2013 | Beck et al. |
| 8,455,236 B2 | 6/2013 | Beck et al. |
| 8,889,383 B2 | 11/2014 | Beck et al. |
| 9,752,162 B2 | 9/2017 | Beck et al. |
| 2008/0038805 A1 | 2/2008 | Melis |
| 2009/0282545 A1 | 11/2009 | Eichelberger et al. |
| 2010/0003716 A1 | 1/2010 | Cervin et al. |
| 2010/0048964 A1 | 2/2010 | Calabria et al. |
| 2010/0081182 A1 | 4/2010 | Paul et al. |
| 2010/0086978 A1 | 4/2010 | Beck et al. |
| 2010/0196977 A1 | 8/2010 | Chotani et al. |
| 2010/0297749 A1 | 11/2010 | Aravanis et al. |
| 2011/0045563 A1 | 2/2011 | Melis |
| 2011/0136192 A1 | 6/2011 | Paul et al. |
| 2011/0159557 A1 | 6/2011 | Beck et al. |
| 2011/0178261 A1 | 7/2011 | Feher et al. |
| 2011/0244536 A1 | 10/2011 | Nagarajan et al. |

FOREIGN PATENT DOCUMENTS

| | | |
|---|---|---|
| EP | 1 510 583 A1 | 3/2005 |
| WO | WO-98/02550 A2 | 1/1998 |
| WO | WO-98/02550 A3 | 1/1998 |
| WO | WO-00/78935 A1 | 12/2000 |
| WO | WO-2007/140339 A2 | 12/2007 |
| WO | WO-2007/140339 A3 | 12/2007 |
| WO | WO-2009/076676 A2 | 6/2009 |
| WO | WO-2009/076676 A3 | 6/2009 |

(Continued)

OTHER PUBLICATIONS

Altschul, et al. (1997). "Gapped BLAST and PSI-BLAST: A new Generation of Protein Database Search Programs," *Nucleic Acids Res.* 25(17):3389-3402.

(Continued)

*Primary Examiner* — Kagnew H Gebreyesus
(74) *Attorney, Agent, or Firm* — Mintz Levin Cohn Ferris Glovsky and Popeo P.C.

(57) ABSTRACT

The invention features compositions and methods for the increased production of mevalonate, isoprene, isoprenoid precursor molecules, and/or isoprenoids in microorganisms via the heterologous expression of the mvaE and mvaS genes from the organisms *Listeria grayi* DSM 20601, *Enterococcus faecium*, *Enterococcus gallinarum* EG2, and *Enterococcus casseliflavus*.

14 Claims, 10 Drawing Sheets

Specification includes a Sequence Listing.

(56) References Cited

FOREIGN PATENT DOCUMENTS

| | | |
|---|---|---|
| WO | WO-2009/132220 A2 | 10/2009 |
| WO | WO-2009/132220 A3 | 10/2009 |
| WO | WO-2009/132220 A9 | 10/2009 |
| WO | WO-2010/003007 A2 | 1/2010 |
| WO | WO-2010/003007 A3 | 1/2010 |
| WO | WO-2010/013077 A1 | 2/2010 |
| WO | WO-2010/031062 A1 | 3/2010 |
| WO | WO-2010/031068 A1 | 3/2010 |
| WO | WO-2010/031076 A2 | 3/2010 |
| WO | WO-2010/031076 A3 | 3/2010 |
| WO | WO-2010/031077 A1 | 3/2010 |
| WO | WO-2010/031079 A1 | 3/2010 |
| WO | WO-2010/078457 A2 | 7/2010 |
| WO | WO-2010/078457 A3 | 7/2010 |
| WO | WO-2010/078457 A3 | 10/2010 |
| WO | WO-2010/124146 A2 | 10/2010 |
| WO | WO-2010/148150 A1 | 12/2010 |
| WO | WO-2010/148256 A1 | 12/2010 |
| WO | WO-2011/034863 A1 | 3/2011 |
| WO | WO-2012/149469 A1 | 11/2012 |

OTHER PUBLICATIONS

Berka, R.M. (1989). "The Development of Gene Expression Systems for Filamentous Fungi," *Biotechnology Advances* 7(2):127-154.

Bhayana, V. et al. (1984). "Amino Acid Sequence of *Escherichia coli* Citrate Synthase," *Biochemistry* 23: 2900-2905 (Figure 5).

Bologna, F.P. et al. (2007). "*Escherichia coli* Malic Enzymes: Two Isoforms with Substantial Differences in Kinetic Properties, Metabolic Regulation, and Structure," *Journal of Bacteriology* 189:5937-5946.

Bunch, P.K. et al. (1997). "The IdhA Gene Encoding the Fermentative Lactate Dehydrogenase of *Escherichia coli*," *Microbiology* 143:187-195.

Campbell, E.I. et al. (1989). "Improved Transformation Efficiency of *Aspergillus niger* Using the Homologus niaD Gene for Nitrate Reductase," *Current Genetics* 16:53-56.

Danner, H. et al. (2011, e.pub. Apr. 12, 2011). "Four Terpene Synthases Produce Major Compounds of the Gypsy Moth Feeding-Induced Volatile Bend of *Populus trichocarpa*," *Phytochemistry* 72(9):897-908.

Datsenko, K.A. et al. (Jun. 6, 2000). "One-step Inactivation of Chromosomal Genes in *Escherichia coli* K-12 using PCR Products," *PNAS* 97(12):6640-6645.

Dawes, E.A. et al. (1966). "The Route to Ethanol Formation in *Zymomonas mobilis*," *Biochem. J.* 98:795-803.

Duckworth, H.W. et al. (1987). "Structural Basis for Regulation in Gram-Negative Bacterial Citrate Synthases," *Biochem. Soc. Symp.* 54:83-92.

Egan, S.E. et al. (Jul. 1992). "Molecular Characterization of the Entner-Doudoroff Pathway in *Escherichia coli*: Sequence Analysis and Localization of Promoters for the edd-eda Operon," *J. Bact.* 174(14):4638-4646.

Ferain, T. et al. (Feb. 1994). "*Lactobacillus plantarum* IdhL Gene: Overexpression and Deletion," *J. Bact.* 176(3):596-601.

Garms, S. et al. (2010, e-pub Jul. 20, 2010). "A Multiproduct Terpine Synthase from *Medicago truncatula* Generates Cadalane Sesquiterpenes via Two Different Mechanisms," *J Org Chem.* 75(16):5590-5600.

Harada, H. et al. (2009). "Novel Approaches and Achievements in Biosynthesis of Functional Isoprenoids in *Escherichia coli*," *Appl. Microbiol. Biotechnol.* 84:1021-1031.

Hedl, M. et al. (Apr. 2002). "*Enterococcus faecalis* Acetoacetyl-Coenzyme a Thiolase/3-Hydroxy-3-Methyglutaryl-Coenzyme a Reductase, a Dual-Function Protein of Isopentenyl Diphosphate Biosynthesis," *Journal of Bacteriology* 184(8):2116-2122.

Hsieh, F.-L. et al. (Mar. 2011). "Structure and Mechanism of an *Arabidopsis* Medium/Long-Chain-Length Prenyl Pyrophosphate Synthase," *Plant Physiology* 155(3):1079-1090.

Iwakura, M. et al. (1979). "Studies on Regulatory Functions of Malic Enzymes," *J. Biochem.* 85:1355-1365.

Jones, C.G. et al. (May 20, 2011). "Sandalwood Fragrance Biosynthesis Involves Sesquiterpene Synthases of Both the Terpene Synthase (TPS)-a and TPS-b Subfamilies, including Santalene Synthases," *J. Biol. Chem.* 286(20):17445-17454.

Kakuda, H. et al. (1994). "Identification and Characterization of the ackA (Acetate Kinase A)-pta (Phosphotransacetylase) Operon and Complementation Analysis of Acetate Utilization by an ackA-pta Deletion Mutant of *Escherichia coli*," *J. Biochem.* 116:916-922.

Keeling, C.I. et al. (Mar. 7, 2011). "Transcriptome Mining, Functional Characterization, and Phylogeny of a Large Terpene Synthase Gene Family in Spruce (*Picea* spp.)," *BMC Plant Biology* 11:43, 14 pages.

Kotlarz, D. et al. (1975). "Regulation of the Amount and of the Activity of Phosphofructokinases and Pyruvate Kinases in *Escherichia coli*," *Biochimica et Biophysica Acta* 381:257-268.

Kumeta, Y. et al. (Dec. 2010). "Characterization of 5-Guaiene Synthases from Cultured Cells of *Aquilaria*, Responsible for the Formation of the Sesquiterpenes in Agarwood," *Plant PhysioL* 154(4):1998-2007.

Lindberg, P. et al. (2010). "Engineering a Platform for Photosynthetic Isoprene Production in Cyanobacteria, Using *Synechocystis* as the Model Organism," *Metabolic Engineering* 12(1):70-79.

Ma, S. M. et al. (2011, e-pub. Jul. 28, 2011). "Optimization of a Heterologous Mevalonate Pathway Through the Use of Variant HMG-CoA Reductases," *Metabolic Engineering* 13(5):588-597.

Martin, V.J.J. et al. (Jul. 2003) "Engineering a Mevalonate Pathway in *Escherichia coli* for Production of Terpenoids," *Nature Biotechnology* 21(7):796-802.

Martin, D.M. et al. (Oct. 21, 2010). "Functional Annotation, Genome Organization and Phylogeny of the Grapevine (*Vitis vinifera*) Terpene Synthase Gene Family Based on Genome Assembly, FLcDNA Cloning, and Enzyme Assays," *BMC Plant Biology* 10:226, 22 pages.

Maurus, R. et al. (2003). "Insights into the Evolution of Allosteric Properties. The NADH Binding Site of Hexameric Type II Citrate Synthases," *Biochemistry* 42:5555-5565.

Miller, B. et al. (2001, e-pub. May 10, 2001). "First Isolation of an Isoprene Synthase Gene from Poplar and Successful Expression of the Gene in *Escherichia coli*," *Planta* 213:483-487.

Miziorko, H. M. (2011, e-pub. Oct. 7, 2010). "Enzymes of the Mevalonate Pathway of Isoprenoid Biosynthesis," *Archives of Biochemistry and Biophysics* 505(2):131-143.

Ner, S.S. et al. (Nov. 8, 1983). "Complete Sequence of the glt A Gene Encoding Citrate Synthase in *Escherichia coli*," *Biochemistry* 22(23):5243-5249.

Newman, J.D. et. al. (Nov. 5, 2006, e-pub. Jul. 28, 2006). "High-Level Production of Amorpha-4,11-Diene in a Two-Phase Partitioning Bioreactor of Metabolically Engineered *Escherichia coli*," *Biotechnology and Bioengineering* 95(4):684-691.

Ogasawara, H. et al. (2007). "PdhR (Pyruvate Dehydrogenase Complex Regulator) Controls the Respiratory Electron Transport System in *Escherichia coli*," *J. Bacteriol.* 189(15):5534-5541.

Oh, M.-K. et al. (Apr. 12, 2002). "Global Expression Profiling of Acetate-Grown *Escherichia coli*," *The Journal of Biological Chemistry* 277(15):13175-13183.

Peekhaus, N. et al. (Jul. 1998). "What's for Dinner?: Entner-Doudoroff Metabolism in *Escherichia coli*," *Journal of Bacteriology* 180(14):3495-3502.

Pitera, D. J. et al. (2007, e-pub. Nov. 23, 2006). "Balancing a Heterologous Mevalonate Pathway for Improved Isoprenoid Production in *Escherichia coli*," *Metabolic Engineering* 9:193-207.

Quant, P.A. et al. (1989). "Treatment of Rats with Glucagon or Mannoheptulose Increases Mitochondrial 3-Hydroxy-3-Methylglutaryl-CoA Synthase Activity and Decreases Succinyl-CoA Content in Liver," *Biochem. J.* 262:159-164.

Romanos, M. A. et al. (1992). "Foreign Gene Expression in Yeast: a Review," *Yeast* 8:423488.

(56) References Cited

OTHER PUBLICATIONS

Rud, A., et al. "Synthetic Promoter Library for Constitutive Gene Expression in *Lactobacillus Plantarum*," *Microbiology* (2006), 152, 1011-1019.

Sanchez, A.M. et al. (2005). "Novel Pathway Engineering Design of the Anaerobic Central Metabolic Pathway in *Escherichia coli* to Increase Succinate Yield and Productivity," *Metabolic Engineering* 7:229-239.

Sharkey, T.D. et al. (Feb. 2005). "Evolution of the Isoprene Biosynthetic Pathway in Kudzu," *Plant Physiology* 137: 700-712.

Shimizu, M. et al. (1969). "Phosphotransacetylase of *Escherichia coli* B, Purification and Properties," *Biochimica et Biophysica Acta* 191:550-558.

Silver, G.M. et al. (Jun. 2, 1995). "Characterization of Aspen Isoprene Synthase, an Enzyme Responsible for Leaf Isoprene Emission to the Atmosphere," *J. Biol. Chem.* 270(22):13010-13016.

Sprenger, G.A. (1995). "Genetics of Pentose-Phosphate Pathway Enzymes of *Echerichia coli* K-12," *Arch. Microbiol.* 164:324-330.

Stokell, D.J. et al. (Sep. 12, 2003). "Probing the Roles of Key Residues in the Unique Regulatory NADH Binding Site of Type II Citrate Synthase of *Escherichia coli*," *The Journal of Biological Chemistry* 278(37):35435-35443.

Stulke, J. et al. (2000). "Regulation of Carbon Catabolism in *Bacillus* Species," *Annu. Rev. MicrobioL* 54:849-880.

Tabata, K. et al. (2004). "Production of Mevalonate by a Metabolically-Engineered *Escherichia coli*," *Biotechnology Letters* 26:1487-1491.

Underwood, S.A. et al. (2002). "Flux through Citrate Synthase Limits the Growth of Ethanologenic *Escherichia coli* K011 During Xylose Fermentation," *Appl. Environ. Microbiol.* 68:1071-1081.

Wiegand, G. et al. (1986). "Citrate Synthase: Structure, Control, and Mechanism," *Ann. Rev. Biophys. Biophys. Chem.* 15:97-117.

Wilde, R.J. et al. (1986). "Transcript Analysis of the Citrate Synthase and Succinate Dehydrogenase Genes of *Escherichia coli* K12," *Journal of General Microbiology* 132:32393251.

Wilding, E. I. et al. (Aug. 2000). "Identification, Evolution, and Essentiality of the Mevalonate Pathway for Isopentenyl Diphosphate Biosynthesis in Gram-Positive Cocci," *Journal of Bacteriology* 182(15):4319-4327.

Wolfe, A.J. (Mar. 2005). "The Acetate Switch," *MicrobioL MoL Biol. Rev.* 69(1):12-50.

International Search Report dated Aug. 28, 2012, for PCT Patent Application No. PCT/US2012/035655, filed on Apr. 27, 2012, 6 pages.

GenBank Accession No. EFI85313.1, created Jun. 29, 2010, located at <http://www.ncbi.nlm.gov/protein/299818079?sat=17&satkey=6120006>, last visited Apr. 28, 2016, 2 pages.

GenBank Accession No. EFI85314.1, created Jun. 29, 2010, located at <http://www.ncbi.nlm.gov/protein/299818080?sat=17&satkey=6120006>, last visited Apr. 28, 2016, 2 pages.

Kuzuyama, T. et al. (2010). "Mevalonate Pathway in Bacteria and Archaea" Comprehensive Natural Products II, *Chemistry and Biology* pp. 493-516.

SEQUENCE LISTING

<160> NUMBER OF SEQ ID NOS: 64

<210> SEQ ID NO 1
<211> LENGTH: 2439
<212> TYPE: DNA

<213> ORGANISM: Listeria grayi

<400> SEQUENCE: 1

| | | | | | |
|---|---|---|---|---|---|
| atggttaaag | acattgtaat | aattgatgcc | ctccgtactc | ccatcggtaa | gtaccgcggt | 60 |
| cagctctcaa | agatgacggc | ggtggaattg | ggaaccgcag | ttacaaaggc | tctgttcgag | 120 |
| aagaacgacc | aggtcaaaga | ccatgtagaa | caagtcattt | ttggcaacgt | tttacaggca | 180 |
| gggaacggcc | agaatcccgc | ccgtcagatc | gcccttaatt | ctggcctgtc | cgcagagata | 240 |
| ccggcttcga | ctattaacca | ggtgtgtggt | tctggcctga | agcaataag | catggcgcgc | 300 |
| caacagatcc | tactcggaga | agcggaagta | atagtagcag | gaggtatcga | atccatgacg | 360 |
| aatgcgccga | gtattacata | ttataataaa | gaagaagaca | ccctctcaaa | gcctgttcct | 420 |
| acgatgacct | tcgatggtct | gaccgacgcg | tttagcggaa | agattatggg | tttaacagcc | 480 |
| gaaaatgttg | ccgaacagta | cggcgtatca | cgtgaggccc | aggacgcctt | tgcgtatgga | 540 |
| tcgcagatga | aagcagcaaa | ggcccaagaa | cagggcattt | tcgcagctga | aatactgcct | 600 |
| cttgaaatag | gggacgaagt | tattactcag | gacgaggggg | ttcgtcaaga | gaccaccctc | 660 |
| gaaaaattaa | gtctgcttcg | gaccattttt | aaagaagatg | gtactgttac | agcgggcaac | 720 |
| gcctcaacga | tcaatgatgg | cgcctcagcc | gtgatcattg | catcaaagga | gtttgctgag | 780 |
| acaaaccaga | ttccctacct | tgcgatcgta | catgatatta | cagagatagg | cattgatcca | 840 |
| tcaataatgg | gcattgctcc | cgtgagtgcg | atcaataaac | tgatcgatcg | taaccaaatt | 900 |
| agcatggaag | aaatcgatct | ctttgaaatt | aatgaggcat | tgcagcatc | ctcggtggta | 960 |
| gttcaaaaag | agttaagcat | tcccgatgaa | aagatcaata | ttggcggttc | cggtattgca | 1020 |
| ctaggccatc | ctcttggcgc | cacaggagcg | cgcattgtaa | ccaccctagc | gcaccagttg | 1080 |
| aaacgtacac | acgacgcta | tggtattgcc | tccctgtgca | ttggcggtgg | ccttggccta | 1140 |
| gcaatattaa | tagaagtgcc | tcaggaagat | cagccggtta | aaaaatttta | tcaattggcc | 1200 |
| cgtgaggacc | gtctggctag | acttcaggag | caagccgtga | tcagcccagc | tacaaaacat | 1260 |
| gtactggcag | aaatgacact | tcctgaagat | attgccgaca | atctgatcga | aaatcaaata | 1320 |
| tctgaaatgg | aaatccctct | tggtgtggct | ttgaatctga | gggtcaatga | taagagttat | 1380 |
| accatcccac | tagcaactga | ggaaccgagt | gtaatcgctg | cctgtaataa | tggtgcaaaa | 1440 |
| atggcaaacc | acctgggcgg | tttttcagtca | gaattaaaag | atggtttcct | gcgtgggcaa | 1500 |
| attgtactta | tgaacgtcaa | agaacccgca | actatcgagc | atacgatcac | ggcagagaaa | 1560 |
| gcggcaattt | tcgtgccgc | agcgcagtca | catccatcga | ttgtgaaacg | aggtggggt | 1620 |
| ctaaaagaga | tagtagtgcg | tacgttcgat | gatgatccga | cgttcctgtc | tattgatctg | 1680 |
| atagttgata | ctaaagacgc | aatgggcgct | aacatcatta | acaccattct | cgagggtgta | 1740 |
| gccggctttc | tgagggaaat | ccttaccgaa | gaaattctgt | tctctatttt | atctaattac | 1800 |
| gcaaccgaat | caattgtgac | cgccagctgt | cgcataccatt | acgaagcact | gagtaaaaaa | 1860 |
| ggtgatggta | acgaatcgc | tgaaaaagtg | gctgctgcat | ctaaatttgc | ccagttagat | 1920 |
| ccttatcgag | ctgcaaccca | caacaaaggt | attatgaatg | gtattgaggc | cgtcgttttg | 1980 |
| gcctcaggaa | atgacacacg | gcggtcgcg | gcagccgcac | atgcgtatgc | ttcacgcgat | 2040 |
| cagcactatc | ggggcttaag | ccagtggcag | gttgcagaag | gcgcgttaca | cggggagatc | 2100 |
| agtctaccac | ttgcactcgg | cagcgttggc | ggtgcaattg | aggtcttgcc | taaagcgaag | 2160 |
| gcggcattcg | aaatcatggg | gatcacagag | gcgaaggagc | tggcagaagt | cacagctgcg | 2220 |
| gtagggctgg | cgcaaaacct | ggcggcgtta | agagcgcttg | ttagtgaagg | aatacagcaa | 2280 |

| | |
|---|---|
| ggtcacatgt cgctccaggc tcgctctctt gcattatcgg taggtgctac aggcaaggaa | 2340 |
| gttgaaatcc tggccgaaaa attacagggc tctcgtatga atcaggcgaa cgctcagacc | 2400 |
| atactcgcag agatcagatc gcaaaaagtt gaattgtga | 2439 |

<210> SEQ ID NO 2
<211> LENGTH: 1158
<212> TYPE: DNA
<213> ORGANISM: Listeria grayi

<400> SEQUENCE: 2

| | |
|---|---|
| atgaccatga acgttggaat cgataaaatg tcattctttg ttccaccttacttgtggac | 60 |
| atgactgatc tggcagtagc acgggatgtc gatcccaata agtttctgat tggtattggc | 120 |
| caggaccaga tggcagttaa tccgaaaacg caggatattg tgacatttgc cacaaatgct | 180 |
| gccaaaaaca tactgtcagc tgaggacctt gataaaattg atatggtcat agtcggcacc | 240 |
| gagagtggaa tcgatgaatc caaagcgagt gccgtagtgc ttcacaggtt gctcggtatc | 300 |
| cagaagtttg ctcgctcctt tgaaatcaaa gaagcctgtt atgggggtac cgcggcttta | 360 |
| cagttcgctg taaaccacat taggaatcat cctgaatcaa aggttcttgt agttgcatca | 420 |
| gatatcgcga aatacggcct ggcttctgga ggtgaaccaa cgcaaggtgc aggcgctgtg | 480 |
| gctatgctcg tctcaactga ccctaagatc attgctttca cgacgatagc ctcgcgctt | 540 |
| acacaagata tctatgactt ctggcgacca gttggacatg actatcctat ggtcgacggg | 600 |
| cctcttagta cagagaccta catccagtca tttcagaccg tatggcagga atacacaaaa | 660 |
| cggtcgcagc atgcactggc agactttgct gcccttagct ttcatatccc gtatactaaa | 720 |
| atgggcaaaa aggcgctgct tgcaatcctt gaaggcgaat cagaggaggc tcagaaccgt | 780 |
| atactagcaa aatatgaaaa gagtatagcc tactccagaa aggcgggtaa cctgtatacc | 840 |
| ggtagcctgt atctaggact tatttcactt ctggaaaatg cagaagacct taaagctggt | 900 |
| gatttaatag gcctctttc ttacggttcc ggtgctgttg cggagttttt ctcaggaagg | 960 |
| ctggttgagg actatcagga acagctactt aaaacaaaac atgccgaaca gctggcccat | 1020 |
| agaaagcaac tgacaatcga ggagtacgaa acgatgttct ccgatcgctt ggacgtggac | 1080 |
| aaagacgccg aatacgaaga cacattagct tatagcattt cgtcagtccg aaacaccgta | 1140 |
| cgtgagtaca ggagttga | 1158 |

<210> SEQ ID NO 3
<211> LENGTH: 2442
<212> TYPE: DNA
<213> ORGANISM: Enterococcus faecium

<400> SEQUENCE: 3

| | |
|---|---|
| atgaaagaag tggttatgat tgatgcggct cgcacaccca ttgggaaata cagaggtagt | 60 |
| cttagtcctt ttacagcggt ggagctgggg acactggtca cgaaagggct gctggataaa | 120 |
| acaaagctta agaaagacaa gatagaccaa gtgatattcg gcaatgtgct tcaggcagga | 180 |
| aacggacaaa acgttgcaag acaaatagcc ctgaacagtg gcttaccagt tgacgtgccg | 240 |
| gcgatgacta ttaacgaagt ttgcgggtcc ggaatgaaag cggtgatttt agcccgccag | 300 |
| ttaatacagt taggggaggc agagttggtc attgcagggg gtacggagtc aatgtcacaa | 360 |
| gcacccatgc tgaaacctta ccagtcagag accaacgaat acggagagcc gatatcatca | 420 |
| atggttaatg acgggctgac ggatgcgttt tccaatgctc acatgggtct tactgccgaa | 480 |

```
aaggtggcga cccagttttc agtgtcgcgc gaggaacaag accggtacgc attgtccagc      540
caattgaaag cagcgcacgc ggttgaagcc ggggtgttct cagaagagat tattccggtt      600
aagattagcg acgaggatgt cttgagtgaa gacgaggcag taagaggcaa cagcactttg      660
gaaaaactgg gcaccttgcg gacggtgttt tctgaagagg gcacggttac cgctggcaat      720
gcttcaccgc tgaatgacgg cgctagtgtc gtgattcttg catcaaaaga atacgcggaa      780
aacaataatc tgccttacct ggcgacgata aaggaggttg cggaagttgg tatcgatcct      840
tctatcatgg gtattgcccc aataaaggcc attcaaaagt taacagatcg gtcgggcatg      900
aacctgtcca cgattgatct gttcgaaatt aatgaagcat tcgcggcatc tagcattgtt      960
gtttctcaag agctgcaatt ggacgaagaa aaagtgaata tctatggcgg ggcgatagct     1020
ttaggccatc caatcggcgc aagcggagcc cggatactga caaccttagc atacggcctc     1080
ctgcgtgagc aaaagcgtta tggtattgcg tcattatgta tcggcggtgg tcttggtctg     1140
gccgtgctgt tagaagctaa tatggagcag acccacaaag acgttcagaa gaaaaagttt     1200
taccagctta ccccctccga gcggagatcg cagcttatcg agaagaacgt tctgactcaa     1260
gaaacggcac ttattttcca ggagcagacg ttgtccgaag aactgtccga tcacatgatt     1320
gagaatcagg tctccgaagt ggaaattcca atgggaattg cacaaaattt tcagattaat     1380
ggcaagaaaa aatggattcc tatggcgact gaagaacctt cagtaatagc ggcagcatcg     1440
aacggcgcca aaatctgcgg gaacatttgc gcggaaacgc ctcagcggct tatgcgcggg     1500
cagattgtcc tgtctggcaa atcagaatat caagccgtga taaatgccgt gaatcatcgc     1560
aaagaagaac tgattctttg cgcaaacgag tcgtacccga gtattgttaa acgcggggga     1620
ggtgttcagg atatttctac gcgggagttt atgggttctt ttcacgcgta tttatcaatc     1680
gactttctgg tggacgtcaa ggacgcaatg ggggcaaaca tgatcaactc tattctcgaa     1740
agcgttgcaa ataaactgcg tgaatggttc ccggaagagg aaatactgtt ctccatcctg     1800
tcaaacttcg ctacggagtc cctggcatct gcatgttgcg agattccttt tgaaagactt     1860
ggtcgtaaca agaaattggt gaacagatc gccaagaaaa ttcaacaggc aggggaatat     1920
gctaagcttg acccttaccg cgcggcaacc cataacaagg ggattatgaa cggtatcgaa     1980
gccgtcgttg ccgcaacggg aaacgacaca cgggctgttt ccgcttctat tcacgcatac     2040
gccgcccgta tggcttgta ccaaggttta acggattggc agatcaaggg cgataaactg     2100
gttggtaaat taacagtccc actggctgtg gcgactgtcg gtggcgcgtc gaacatatta     2160
ccaaaagcca aagcttccct cgccatgctg gatattgatt ccgcaaaaga actggcccaa     2220
gtgatcgccg cggtaggttt agcacagaat ctggcggcgt acgtgcatt agtgacagaa     2280 ggcattcaga aggacacat gggcttgcaa gcacgttctt tagcgatttc gataggtgcc     2340
atcggtgagg agatagagca agtcgcgaaa aaactgcgtg aagctgaaaa aatgaatcag     2400
caaacggcaa tacagatttt agaaaaaatt cgcgagaaat ga                        2442
```

<210> SEQ ID NO 4
<211> LENGTH: 1155
<212> TYPE: DNA
<213> ORGANISM: Enterococcus faecium

<400> SEQUENCE: 4

```
atgaaaatcg gtattgaccg tctgtccttc ttcatcccga atttgtattt ggacatgact       60
gagctggcag aatcacgcgg ggatgatcca gctaaatatc atattggaat cggacaagat      120
cagatggcag tgaatcgcgc aaacgaggac atcataacac tgggtgcaaa cgctgcgagt      180
```

```
aagatcgtga cagagaaaga ccgcgagttg attgatatgg taatcgttgg cacggaatca    240
ggaattgacc actccaaagc aagcgccgtg attattcacc atctccttaa aattcagtcg    300
ttcgcccgtt ctttcgaggt aaaagaagct tgctatggcg gaactgctgc cctgcacatg    360
gcgaaggagt atgtcaaaaa tcatccggag cgtaaggtct tggtaattgc gtcagacatc    420
gcgcgttatg gtttggccag cggaggagaa gttactcaag gcgtggggc cgtagccatg    480 atgattacac aaaaccccg gattctttcg attgaagacg atagtgtttt tctcacagag    540
gatatctatg atttctggcg gcctgattac tccgagttcc ctgtagtgga cgggccccctt    600 tcaaactcaa cgtatataga gagttttcag aaagtttgga accggcacaa ggaattgtcc    660
ggaagagggc tggaagatta tcaagctatt gcttttcaca taccctatac gaagatgggt    720
aagaaagcgc tccagagtgt tttagaccaa accgatgaag ataaccagga gcgcttaatg    780
gctagatatg aggagtctat tcgctatagc cggagaattg gtaacctgta cacaggcagc    840
ttgtaccttg gtcttacaag cttgttggaa aactctaaaa gtttacaacc gggagatcgg    900
atcggcctct tttcctatgg cagtggtgcg gtgtccgagt tctttaccgg gtatttagaa    960
gaaaattacc aagagtacct gttcgctcaa agccatcaag aaatgctgga tagccggact   1020
cggattacgg tcgatgaata cgagaccatc ttttcagaga ctctgccaga acatggtgaa   1080
tgcgccgaat atacgagcga cgtccccttt tctataacca agattgagaa cgacattcgt   1140
tattataaaa tctga                                                    1155

<210> SEQ ID NO 5
<211> LENGTH: 2448
<212> TYPE: DNA
<213> ORGANISM: Enterococcus gallinarum

<400> SEQUENCE: 5
atggaagaag tggtaattat agatgcacgt cggactccga ttggtaaata tcacgggtcg     60
ttgaagaagt tttcagcggt ggcgctgggg acggccgtgg ctaaagacat gttcgaacgc    120
aaccagaaaa tcaaagagga gatcgcgcag gtcataattg gtaatgtctt gcaggcagga    180
aatggccaga accccgcgcg gcaagttgct cttcaatcag ggttgtccgt tgacattccc    240
gcttctacaa ttaacgaggt tgtgggtct ggtttgaaag ctatcttgat gggcatggaa    300
caaatccaac tcggcaaagc gcaagtagtg ctggcaggcg gcattgaatc aatgacaaat    360
gcgccaagcc tgtcccacta taacaaggcg gaggatacgt atagtgtccc agtgtcgagc    420
atgacactgg atggtctgac agacgcattt tctagtaaac ctatgggatt aacagcggaa    480
aacgtcgcac agcgctacgg tatctcccgt gaggcgcaag atcaattcgc atatcaatct    540
cagatgaaag cagcaaaagc gcaggcagaa acaaattcg ctaaggaaat tgtgccactg    600
gcgggtgaaa ctaaaaccat cacagctgac gaagggatca gatcccaaac aacgatggag    660
aaactggcaa gtctcaaacc tgttttaaa accgatggca ctgtaaccgc agggaatgct    720
agcaccatta tgacggggc cgcccttgtg ctgcttgcta gcaaaactta ctgcgaaact    780
aatgacatac cgtaccttgc gacaatcaaa gaaattgttg aagttggaat cgatccggag    840
attatgggca tctctccgat aaaagcgata caaacattgt tacaaaatca aaaagttagc    900
ctcgaagata ttggagtttt tgaaataaat gaagcctttg ccgcaagtag catagtggtt    960
gaatctgagt tgggattaga tccggctaaa gttaaccgtt atgggggtgg tatatcctta   1020
ggtcatgcaa ttgggggcaac cggcgctcgc ctggccactt cactggtgta tcaaatgcag   1080
```

```
gagatacaag cacgttatgg tattgcgagc ctgtgcgttg gtggtggact tggactggca    1140
atgcttttag aacgtccaac tattgagaag gctaaaccga cagacaaaaa gttctatgaa    1200
ttgtcaccag ctgaacggtt gcaagagctg gaaaatcaac agaaaatcag ttctgaaact    1260
aaacagcagt tatctcagat gatgcttgcc gaggacactg caaaccattt gatagaaaat    1320
caaatatcag agattgaact cccaatgggc gtcgggatga acctgaaggt tgatgggaaa    1380
gcctatgttg tgccaatggc gacggaagag ccgtccgtca tcgcggccat gtctaatggt    1440
gccaaaatgg ccggcgaaat tcacactcag tcgaaagaac ggctgctcag aggtcagatt    1500
gttttcagcg cgaagaatcc gaatgaaatc gaacagagaa tagctgagaa ccaagctttg    1560
attttcgaac gtgccgaaca gtcctatcct tccattgtga aaagagaggg aggtctccgc    1620
cgcattgcac ttcgtcattt tcctgccgat tctcagcagg agtctgcgga ccagtccaca    1680
tttttatcag tggacctttt tgtagatgtg aaagacgcga tgggggcaaa tatcataaat    1740
gcaatacttg agggcgtcgc agccctgttt cgcgaatggt tccccaatga ggaaattctt    1800
ttttctattc tctcgaactt ggctacggag agcttagtca cggctgtttg tgaagtccca    1860
tttagtgcac ttagcaagag aggtggtgca acggtggccc agaaaattgt gcaggcgtcg    1920
ctcttcgcaa agacagaccc ataccgcgca gtgacccaca caaagggat tatgaacggt    1980
gtagaggctg ttatgcttgc cacaggcaac gacacgcgcg cagtctcagc cgcttgtcat    2040
ggatacgcag cgcgcaccgg tagctatcag ggtctgacta actggacgat tgagtcggat    2100
cgcctggtag gcgagataac actgccgctg gccatcgcta cagttggagg cgctaccaaa    2160
gtgttgccca agctcaagc ggcactggag attagtgatg ttcactcttc tcaagagctt    2220
gcagccttag cggcgtcagt aggtttagta caaaatctcg cggccctgcg cgcactggtt    2280
tccgaaggta tacaaaaagg gcacatgtcc atgcaagccc ggtctctcgc aatcgcggtc    2340
ggtgctgaaa agccgagat cgagcaggtc gccgaaaagt tgcggcagaa cccgccaatg    2400
aatcagcagc aggcgctccg ttttcttggc gagatccgcg aacaatga                2448
```

<210> SEQ ID NO 6
<211> LENGTH: 1155
<212> TYPE: DNA
<213> ORGANISM: Enterococcus gallinarum

<400> SEQUENCE: 6

```
atgaacgtcg gcattgacaa aattaatttt ttcgttccac cgtattatct ggatatggtc     60
gacctggccc acgcacgcga agtggacccg aacaaattta caattggaat tggacaggat   120
cagatggctg tgagcaaaaa gacgcacgat atcgtaacat tcgcggctag tgccgcgaag   180
gaaattttag aacctgagga cttgcaagct atagacatgg ttatagttgg taccgaatcg   240
ggcattgacg agagcaaagc atccgcggtc gttttacatc gtttgttggg cgtacaacct   300
ttcgctcgca gttttgaaat taagaagcc tgttacgggg caaccgcagg cattcagttt   360
gccaagactc atatacaagc gaacccggag agcaaggtcc tggtaattgc aagcgatata   420
gctcggtatg gtcttcggtc aggtggagag cccacacaag gcgcaggggc agttgctatg   480
cttctcacgg caaatcccag aatcctgacc ttcgaaaacg acaatctgat gttaacgcag   540
gatatttatg acttctggag accacttggt cacgcttacc ctatggtaga tggccacctt   600
tccaatcaag tctatattga cagttttaag aaggtctggc aagcacattg cgaacgcaat   660
caagcttcta tatccgacta tgccgcgatt agttttcata ttccgtatac aaaaatgggt   720
aagaaagccc tgctcgctgt ttttgcagat gaagtggaaa ctgaacagga acgcgttatg   780
```

| | |
|---|---|
| gcacggtatg aagagtctat cgtatattca cgccggatcg gcaacttgta tacgggatca | 840 |
| ttgtacctgg ggctgatatc cttattggaa aacagttctc acctgtcggc gggcgaccgg | 900 |
| ataggattgt ttagttatgg gagtggcgct gtcagcgaat ttttctccgg tcgtttagtg | 960 |
| gcaggctatg aaaatcaatt gaacaaagag gcgcataccc agctcctgga tcagcgtcag | 1020 |
| aagctttcca tcgaagagta tgaggcgatt tttacagatt ccttagaaat tgatcaggat | 1080 |
| gcagcgttct cggatgacct gccatattcc atccgcgaga taaaaaacac gattcggtac | 1140 |
| tataaggaga gctga | 1155 |

<210> SEQ ID NO 7
<211> LENGTH: 2475
<212> TYPE: DNA
<213> ORGANISM: Enterococcus casseliflavus

<400> SEQUENCE: 7

| | |
|---|---|
| atggaagaag ttgtcatcat tgacgcactg cgtactccaa taggaaagta ccacggttcg | 60 |
| ctgaaagatt acacagctgt tgaactgggg acagtagcag caaaggcgtt gctggcacga | 120 |
| aatcagcaag caaaagaaca catagcgcaa gttattattg caacgtcct gcaagccgga | 180 |
| agtgggcaga atccaggccg acaagtcagt ttacagtcag gattgtcttc tgatatcccc | 240 |
| gctagcacga tcaatgaagt gtgtggctcg ggtatgaaag cgattctgat gggtatggag | 300 |
| caaattcagc tgaacaaagc ctctgtggtc ttaacaggcg gaattgaaag catgaccaac | 360 |
| gcgccgctgt ttagttatta caacaaggct gaggatcaat attcggcgcc ggttagcaca | 420 |
| atgatgcacg atggtctaac agatgctttc agttccaaac caatgggctt aaccgcagag | 480 |
| accgtcgctg agagatatgg aattacgcgt aaggaacaag atgaatttgc ttatcactct | 540 |
| caaatgaagg cggccaaagc ccaggcggcg aaaaagtttg atcaggaaat tgtaccccctg | 600 |
| acggaaaaat ccggaacggt tctccaggac gaaggcatca gagccgcgac aacagtcgag | 660 |
| aagctagctg agcttaaaac ggtgttcaaa aaagacggaa cagttacagc gggtaacgcc | 720 |
| tctacgataa atgatggcgc tgctatggta ttaatagcat caaaatctta ttgcgaagaa | 780 |
| caccagattc cttatctggc cgttataaag gagatcgttg aggtgggttt tgcccccgaa | 840 |
| ataatgggta tttcccccat taaggctata gacaccctgc tgaaaaatca agcactgacc | 900 |
| atagaggata taggaatatt tgagattaat gaagcctttg ctgcgagttc gattgtggta | 960 |
| gaacgcgagt tgggcctgga ccccaaaaaa gttaatcgct atggcggtgg tatatcactc | 1020 |
| ggccacgcaa ttggggcgac gggagctcgc attgcgacga ccgttgctta tcagctgaaa | 1080 |
| gatacccagg agcgctacgg tatagcttcc ttatgcgttg gtgggggtct tggattggcg | 1140 |
| atgcttctgg aaaacccatc ggccactgcc tcacaaacta attttgatga ggaatctgct | 1200 |
| tccgaaaaaa ctgagaagaa gaagttttat gcgctagctc ctaacgaacg cttagcgttt | 1260 |
| ttggaagccc aaggcgctat taccgctgct gaaaccctgg tcttccagga gatgacctta | 1320 |
| aacaaagaga cagccaatca cttaatcgaa aaccaaatca gcgaagttga aattcccttta | 1380 |
| ggcgtgggcc tgaacttaca ggtgaatggg aaagcgtata atgttcctct ggccacggag | 1440 |
| gaaccgtccg ttatcgctgc gatgtcgaat ggcgccaaaa tggctggtcc tattacaaca | 1500 |
| acaagtcagg agaggctgtt acggggtcag attgtcttca tggacgtaca ggacccagaa | 1560 |
| gcaatattag cgaaagttga atccgagcaa gctaccattt tcgcggtggc aaatgaaaca | 1620 |
| tacccgtcta tcgtgaaaag aggaggaggt ctgcgtagag tcattggcag gaatttcagt | 1680 |

```
ccggccgaaa gtgacttagc cacggcgtat gtatcaattg acctgatggt agatgttaag    1740
gatgcaatgg gtgctaatat catcaatagt atcctagaag gtgttgcgga attgtttaga    1800
aaatggttcc cagaagaaga atcctgttc tcaattctct ccaatctcgc gacagaaagt     1860
ctggtaacgg cgacgtgctc agttccgttt gataaattgt ccaaaactgg gaatggtcga    1920
caagtagctg gtaaaatagt gcacgcggcg gactttgcta agatagatcc atacagagct    1980
gccacacaca ataaaggtat tatgaatggc gttgaagcgt taatcttagc caccggtaat    2040
gacacccgtg cggtgtcggc tgcatgccac ggttacgcgg cacgcaatgg gcgaatgcaa    2100
gggcttacct cttggacgat tatcgaagat cggctgatag gctctatcac attacctttg    2160
gctattgcga cagtgggggg tgccacaaaa atcttgccaa agcacaggc cgccctggcg      2220 ctaactggcg ttgagacggc gtcggaactg gccagcctgg cggcgagtgt gggattagtt     2280
caaaatttgg ccgctttacg agcactagtg agcgagggca ttcagcaagg gcacatgagt    2340
atgcaagcta gatccctggc cattagcgta ggtgcgaaag gtactgaaat agagcaacta    2400
gctgcgaagc tgagggcagc gacgcaaatg aatcaggagc aggctcgtaa atttctgacc    2460
gaaataagaa attaa                                                      2475

<210> SEQ ID NO 8
<211> LENGTH: 1161
<212> TYPE: DNA
<213> ORGANISM: Enterococcus casseliflavus

<400> SEQUENCE: 8
atgaacgttg gaattgataa aatcaattt ttcgttccgc cctatttcat tgatatggtg       60
gatctcgctc atgcaagaga agttgacccc aacaagttca ctataggaat aggccaagat     120
cagatggcag taaacaagaa aacgcaagat atcgtaacgt tcgcgatgca cgccgcgaag     180
gatattctga ctaaggaaga tttacaggcc atagatatgg taatagtggg gactgagtct     240
gggatcgacg agagcaaggc aagtgctgtc gtattgcatc ggcttttagg tattcagcct    300
tttgcgcgct cctttgaaat taaggaggca tgctatgggg ccactgccgg ccttcagttt    360
gcaaaagctc atgtgcaggc taatccccag agcaaggtcc tggtggtagc ttccgatata    420
gcacgctacg gactggcatc cggaggagaa ccgactcaag gtgtaggtgc tgtggcaatg    480
ttgatttccg ctgatccagc tatcttgcag ttagaaaatg ataatctcat gttgacccaa    540
gatatatacg attttttggcg cccggtcggg catcaatatc ctatggtaga cggccatctg    600
tctaatgccg tctatataga cagctttaaa caagtctggc aagcacattg cgagaaaaac    660
caacggactg ctaaagatta tgctgcattg tcgttccata ttccgtacac gaaaatgggt    720
aagaaagctc tgttagcggt ttttgcggag gaagatgaga cagaacaaaa gcggttaatg    780
gcacgttatg aagaatcaat tgtatacagt cgtcggactg gaaatctgta tactggctca    840
ctctatctgg gcctgatttc cttactggag aatagtagca gtttacaggc gaacgatcgc    900
ataggtctgt ttagctatgg ttcagggggc gttgcggaat ttttcagtgg cctcttggta    960
ccgggttacg agaaacaatt agcgcaagct gcccatcaag ctcttctgga cgaccggcaa   1020
aaactgacta tcgcagagta cgaagccatg tttaatgaaa ccattgatat tgatcaggac   1080
cagtcatttg aggatgactt actgtactcc atcagagaga tcaaaaacac tattcgctac   1140
tataacgagg agaatgaata a                                              1161

<210> SEQ ID NO 9
<211> LENGTH: 815
```

<212> TYPE: PRT
<213> ORGANISM: Enterococcus gallinarum EG2

<400> SEQUENCE: 9

```
Met Glu Glu Val Val Ile Ile Asp Ala Arg Arg Thr Pro Ile Gly Lys
1               5                   10                  15

Tyr His Gly Ser Leu Lys Lys Phe Ser Ala Val Ala Leu Gly Thr Ala
            20                  25                  30

Val Ala Lys Asp Met Phe Glu Arg Asn Gln Lys Ile Lys Glu Glu Ile
        35                  40                  45

Ala Gln Val Ile Ile Gly Asn Val Leu Gln Ala Gly Asn Gly Gln Asn
    50                  55                  60

Pro Ala Arg Gln Val Ala Leu Gln Ser Gly Leu Ser Val Asp Ile Pro
65                  70                  75                  80

Ala Ser Thr Ile Asn Glu Val Cys Gly Ser Gly Leu Lys Ala Ile Leu
                85                  90                  95

Met Gly Met Glu Gln Ile Gln Leu Gly Lys Ala Gln Val Val Leu Ala
            100                 105                 110

Gly Gly Ile Glu Ser Met Thr Asn Ala Pro Ser Leu Ser His Tyr Asn
        115                 120                 125

Lys Ala Glu Asp Thr Tyr Ser Val Pro Val Ser Ser Met Thr Leu Asp
    130                 135                 140

Gly Leu Thr Asp Ala Phe Ser Ser Lys Pro Met Gly Leu Thr Ala Glu
145                 150                 155                 160

Asn Val Ala Gln Arg Tyr Gly Ile Ser Arg Glu Ala Gln Asp Gln Phe
                165                 170                 175

Ala Tyr Gln Ser Gln Met Lys Ala Ala Lys Ala Gln Ala Glu Asn Lys
            180                 185                 190

Phe Ala Lys Glu Ile Val Pro Leu Ala Gly Glu Thr Lys Thr Ile Thr
        195                 200                 205

Ala Asp Glu Gly Ile Arg Ser Gln Thr Thr Met Glu Lys Leu Ala Ser
    210                 215                 220

Leu Lys Pro Val Phe Lys Thr Asp Gly Thr Val Thr Ala Gly Asn Ala
225                 230                 235                 240

Ser Thr Ile Asn Asp Gly Ala Ala Leu Val Leu Leu Ala Ser Lys Thr
                245                 250                 255

Tyr Cys Glu Thr Asn Asp Ile Pro Tyr Leu Ala Thr Ile Lys Glu Ile
            260                 265                 270

Val Glu Val Gly Ile Asp Pro Glu Ile Met Gly Ile Ser Pro Ile Lys
        275                 280                 285

Ala Ile Gln Thr Leu Leu Gln Asn Gln Lys Val Ser Leu Glu Asp Ile
    290                 295                 300

Gly Val Phe Glu Ile Asn Glu Ala Phe Ala Ala Ser Ser Ile Val Val
305                 310                 315                 320

Glu Ser Glu Leu Gly Leu Asp Pro Ala Lys Val Asn Arg Tyr Gly Gly
                325                 330                 335

Gly Ile Ser Leu Gly His Ala Ile Gly Ala Thr Gly Ala Arg Leu Ala
            340                 345                 350

Thr Ser Leu Val Tyr Gln Met Gln Glu Ile Gln Ala Arg Tyr Gly Ile
        355                 360                 365

Ala Ser Leu Cys Val Gly Gly Gly Leu Gly Leu Ala Met Leu Leu Glu
    370                 375                 380

Arg Pro Thr Ile Glu Lys Ala Lys Pro Thr Asp Lys Lys Phe Tyr Glu
385                 390                 395                 400
```

-continued

```
Leu Ser Pro Ala Glu Arg Leu Gln Glu Leu Glu Asn Gln Gln Lys Ile
                405                 410                 415

Ser Ser Glu Thr Lys Gln Gln Leu Ser Gln Met Met Leu Ala Glu Asp
            420                 425                 430

Thr Ala Asn His Leu Ile Glu Asn Gln Ile Ser Glu Ile Glu Leu Pro
        435                 440                 445

Met Gly Val Gly Met Asn Leu Lys Val Asp Gly Lys Ala Tyr Val Val
    450                 455                 460

Pro Met Ala Thr Glu Glu Pro Ser Val Ile Ala Ala Met Ser Asn Gly
465                 470                 475                 480

Ala Lys Met Ala Gly Glu Ile His Thr Gln Ser Lys Glu Arg Leu Leu
                485                 490                 495

Arg Gly Gln Ile Val Phe Ser Ala Lys Asn Pro Asn Glu Ile Glu Gln
            500                 505                 510

Arg Ile Ala Glu Asn Gln Ala Leu Ile Phe Glu Arg Ala Glu Gln Ser
        515                 520                 525

Tyr Pro Ser Ile Val Lys Arg Glu Gly Gly Leu Arg Arg Ile Ala Leu
    530                 535                 540

Arg His Phe Pro Ala Asp Ser Gln Gln Glu Ser Ala Asp Gln Ser Thr
545                 550                 555                 560

Phe Leu Ser Val Asp Leu Phe Val Asp Val Lys Asp Ala Met Gly Ala
                565                 570                 575

Asn Ile Ile Asn Ala Ile Leu Glu Gly Val Ala Ala Leu Phe Arg Glu
            580                 585                 590

Trp Phe Pro Asn Glu Glu Ile Leu Phe Ser Ile Leu Ser Asn Leu Ala
        595                 600                 605

Thr Glu Ser Leu Val Thr Ala Val Cys Glu Val Pro Phe Ser Ala Leu
    610                 615                 620

Ser Lys Arg Gly Gly Ala Thr Val Ala Gln Lys Ile Val Gln Ala Ser
625                 630                 635                 640

Leu Phe Ala Lys Thr Asp Pro Tyr Arg Ala Val Thr His Asn Lys Gly
                645                 650                 655

Ile Met Asn Gly Val Glu Ala Val Met Leu Ala Thr Gly Asn Asp Thr
            660                 665                 670

Arg Ala Val Ser Ala Ala Cys His Gly Tyr Ala Ala Arg Thr Gly Ser
        675                 680                 685

Tyr Gln Gly Leu Thr Asn Trp Thr Ile Glu Ser Asp Arg Leu Val Gly
    690                 695                 700

Glu Ile Thr Leu Pro Leu Ala Ile Ala Thr Val Gly Gly Ala Thr Lys
705                 710                 715                 720

Val Leu Pro Lys Ala Gln Ala Ala Leu Glu Ile Ser Asp Val His Ser
                725                 730                 735

Ser Gln Glu Leu Ala Ala Leu Ala Ala Ser Val Gly Leu Val Gln Asn
            740                 745                 750

Leu Ala Ala Leu Arg Ala Leu Val Ser Glu Gly Ile Gln Lys Gly His
        755                 760                 765

Met Ser Met Gln Ala Arg Ser Leu Ala Ile Ala Val Gly Ala Glu Lys
    770                 775                 780

Ala Glu Ile Glu Gln Val Ala Glu Lys Leu Arg Gln Asn Pro Pro Met
785                 790                 795                 800

Asn Gln Gln Gln Ala Leu Arg Phe Leu Gly Glu Ile Arg Glu Gln
                805                 810                 815
```

<210> SEQ ID NO 10
<211> LENGTH: 384
<212> TYPE: PRT
<213> ORGANISM: Enterococcus gallinarum EG2

<400> SEQUENCE: 10

```
Met Asn Val Gly Ile Asp Lys Ile Asn Phe Phe Val Pro Pro Tyr Tyr
1               5                   10                  15

Leu Asp Met Val Asp Leu Ala His Ala Arg Glu Val Asp Pro Asn Lys
            20                  25                  30

Phe Thr Ile Gly Ile Gly Gln Asp Gln Met Ala Val Ser Lys Lys Thr
        35                  40                  45

His Asp Ile Val Thr Phe Ala Ala Ser Ala Ala Lys Glu Ile Leu Glu
    50                  55                  60

Pro Glu Asp Leu Gln Ala Ile Asp Met Val Ile Val Gly Thr Glu Ser
65                  70                  75                  80

Gly Ile Asp Glu Ser Lys Ala Ser Ala Val Val Leu His Arg Leu Leu
                85                  90                  95

Gly Val Gln Pro Phe Ala Arg Ser Phe Glu Ile Lys Glu Ala Cys Tyr
            100                 105                 110

Gly Ala Thr Ala Gly Ile Gln Phe Ala Lys Thr His Ile Gln Ala Asn
        115                 120                 125

Pro Glu Ser Lys Val Leu Val Ile Ala Ser Asp Ile Ala Arg Tyr Gly
    130                 135                 140

Leu Arg Ser Gly Gly Glu Pro Thr Gln Gly Ala Gly Ala Val Ala Met
145                 150                 155                 160

Leu Leu Thr Ala Asn Pro Arg Ile Leu Thr Phe Glu Asn Asp Asn Leu
                165                 170                 175

Met Leu Thr Gln Asp Ile Tyr Asp Phe Trp Arg Pro Leu Gly His Ala
            180                 185                 190

Tyr Pro Met Val Asp Gly His Leu Ser Asn Gln Val Tyr Ile Asp Ser
        195                 200                 205

Phe Lys Lys Val Trp Gln Ala His Cys Glu Arg Asn Gln Ala Ser Ile
    210                 215                 220

Ser Asp Tyr Ala Ala Ile Ser Phe His Ile Pro Tyr Thr Lys Met Gly
225                 230                 235                 240

Lys Lys Ala Leu Leu Ala Val Phe Ala Asp Glu Val Glu Thr Glu Gln
                245                 250                 255

Glu Arg Val Met Ala Arg Tyr Glu Glu Ser Ile Val Tyr Ser Arg Arg
            260                 265                 270

Ile Gly Asn Leu Tyr Thr Gly Ser Leu Tyr Leu Gly Leu Ile Ser Leu
        275                 280                 285

Leu Glu Asn Ser Ser His Leu Ser Ala Gly Asp Arg Ile Gly Leu Phe
    290                 295                 300

Ser Tyr Gly Ser Gly Ala Val Ser Glu Phe Phe Ser Gly Arg Leu Val
305                 310                 315                 320

Ala Gly Tyr Glu Asn Gln Leu Asn Lys Glu Ala His Thr Gln Leu Leu
                325                 330                 335

Asp Gln Arg Gln Lys Leu Ser Ile Glu Glu Tyr Glu Ala Ile Phe Thr
            340                 345                 350

Asp Ser Leu Glu Ile Asp Gln Asp Ala Ala Phe Ser Asp Asp Leu Pro
        355                 360                 365

Tyr Ser Ile Arg Glu Ile Lys Asn Thr Ile Arg Tyr Tyr Lys Glu Ser
    370                 375                 380
```

<210> SEQ ID NO 11
<211> LENGTH: 812
<212> TYPE: PRT
<213> ORGANISM: Listeria grayi

<400> SEQUENCE: 11

| Met | Val | Lys | Asp | Ile | Val | Ile | Asp | Ala | Leu | Arg | Thr | Pro | Ile | Gly |
|---|---|---|---|---|---|---|---|---|---|---|---|---|---|---|
| 1 | | | | 5 | | | | | 10 | | | | | 15 |

Lys Tyr Arg Gly Gln Leu Ser Lys Met Thr Ala Val Glu Leu Gly Thr
                20                  25                  30

Ala Val Thr Lys Ala Leu Phe Glu Lys Asn Asp Gln Val Lys Asp His
            35                  40                  45

Val Glu Gln Val Ile Phe Gly Asn Val Leu Gln Ala Gly Asn Gly Gln
        50                  55                  60

Asn Pro Ala Arg Gln Ile Ala Leu Asn Ser Gly Leu Ser Ala Glu Ile
65                  70                  75                  80

Pro Ala Ser Thr Ile Asn Gln Val Cys Gly Ser Gly Leu Lys Ala Ile
                85                  90                  95

Ser Met Ala Arg Gln Gln Ile Leu Leu Gly Glu Ala Glu Val Ile Val
                100                 105                 110

Ala Gly Gly Ile Glu Ser Met Thr Asn Ala Pro Ser Ile Thr Tyr Tyr
            115                 120                 125

Asn Lys Glu Glu Asp Thr Leu Ser Lys Pro Val Pro Thr Met Thr Phe
130                 135                 140

Asp Gly Leu Thr Asp Ala Phe Ser Gly Lys Ile Met Gly Leu Thr Ala
145                 150                 155                 160

Glu Asn Val Ala Glu Gln Tyr Gly Val Ser Arg Glu Ala Gln Asp Ala
                165                 170                 175

Phe Ala Tyr Gly Ser Gln Met Lys Ala Ala Lys Ala Gln Glu Gln Gly
            180                 185                 190

Ile Phe Ala Ala Glu Ile Leu Pro Leu Glu Ile Gly Asp Glu Val Ile
        195                 200                 205

Thr Gln Asp Glu Gly Val Arg Gln Glu Thr Thr Leu Glu Lys Leu Ser
    210                 215                 220

Leu Leu Arg Thr Ile Phe Lys Glu Asp Gly Thr Val Thr Ala Gly Asn
225                 230                 235                 240

Ala Ser Thr Ile Asn Asp Gly Ala Ser Ala Val Ile Ile Ala Ser Lys
                245                 250                 255

Glu Phe Ala Glu Thr Asn Gln Ile Pro Tyr Leu Ala Ile Val His Asp
            260                 265                 270

Ile Thr Glu Ile Gly Ile Asp Pro Ser Ile Met Gly Ile Ala Pro Val
        275                 280                 285

Ser Ala Ile Asn Lys Leu Ile Asp Arg Asn Gln Ile Ser Met Glu Glu
    290                 295                 300

Ile Asp Leu Phe Glu Ile Asn Glu Ala Phe Ala Ala Ser Ser Val Val
305                 310                 315                 320

Val Gln Lys Glu Leu Ser Ile Pro Asp Glu Lys Ile Asn Ile Gly Gly
                325                 330                 335

Ser Gly Ile Ala Leu Gly His Pro Leu Gly Ala Thr Gly Ala Arg Ile
            340                 345                 350

Val Thr Thr Leu Ala His Gln Leu Lys Arg Thr His Gly Arg Tyr Gly
        355                 360                 365

Ile Ala Ser Leu Cys Ile Gly Gly Gly Leu Gly Leu Ala Ile Leu Ile

```
            370                 375                 380
Glu Val Pro Gln Glu Asp Gln Pro Val Lys Lys Phe Tyr Gln Leu Ala
385                 390                 395                 400

Arg Glu Asp Arg Leu Ala Arg Leu Gln Glu Gln Ala Val Ile Ser Pro
                405                 410                 415

Ala Thr Lys His Val Leu Ala Glu Met Thr Leu Pro Glu Asp Ile Ala
                420                 425                 430

Asp Asn Leu Ile Glu Asn Gln Ile Ser Glu Met Glu Ile Pro Leu Gly
                435                 440                 445

Val Ala Leu Asn Leu Arg Val Asn Asp Lys Ser Tyr Thr Ile Pro Leu
450                 455                 460

Ala Thr Glu Glu Pro Ser Val Ile Ala Ala Cys Asn Asn Gly Ala Lys
465                 470                 475                 480

Met Ala Asn His Leu Gly Gly Phe Gln Ser Glu Leu Lys Asp Gly Phe
                485                 490                 495

Leu Arg Gly Gln Ile Val Leu Met Asn Val Lys Glu Pro Ala Thr Ile
                500                 505                 510

Glu His Thr Ile Thr Ala Glu Lys Ala Ala Ile Phe Arg Ala Ala Ala
                515                 520                 525

Gln Ser His Pro Ser Ile Val Lys Arg Gly Gly Leu Lys Glu Ile
530                 535                 540

Val Val Arg Thr Phe Asp Asp Pro Thr Phe Leu Ser Ile Asp Leu
545                 550                 555                 560

Ile Val Asp Thr Lys Asp Ala Met Gly Ala Asn Ile Ile Asn Thr Ile
                565                 570                 575

Leu Glu Gly Val Ala Gly Phe Leu Arg Glu Ile Leu Thr Glu Glu Ile
                580                 585                 590

Leu Phe Ser Ile Leu Ser Asn Tyr Ala Thr Glu Ser Ile Val Thr Ala
                595                 600                 605

Ser Cys Arg Ile Pro Tyr Glu Ala Leu Ser Lys Lys Gly Asp Gly Lys
                610                 615                 620

Arg Ile Ala Glu Lys Val Ala Ala Ser Lys Phe Ala Gln Leu Asp
625                 630                 635                 640

Pro Tyr Arg Ala Ala Thr His Asn Lys Gly Ile Met Asn Gly Ile Glu
                645                 650                 655

Ala Val Val Leu Ala Ser Gly Asn Asp Thr Arg Ala Val Ala Ala Ala
                660                 665                 670

Ala His Ala Tyr Ala Ser Arg Asp Gln His Tyr Arg Gly Leu Ser Gln
                675                 680                 685

Trp Gln Val Ala Glu Gly Ala Leu His Gly Glu Ile Ser Leu Pro Leu
690                 695                 700

Ala Leu Gly Ser Val Gly Ala Ile Glu Val Leu Pro Lys Ala Lys
705                 710                 715                 720

Ala Ala Phe Glu Ile Met Gly Ile Thr Glu Ala Lys Glu Leu Ala Glu
                725                 730                 735

Val Thr Ala Ala Val Gly Leu Ala Gln Asn Leu Ala Ala Leu Arg Ala
                740                 745                 750

Leu Val Ser Glu Gly Ile Gln Gln Gly His Met Ser Leu Gln Ala Arg
                755                 760                 765

Ser Leu Ala Leu Ser Val Gly Ala Thr Gly Lys Glu Val Glu Ile Leu
                770                 775                 780

Ala Glu Lys Leu Gln Gly Ser Arg Met Asn Gln Ala Asn Ala Gln Thr
785                 790                 795                 800
```

```
Ile Leu Ala Glu Ile Arg Ser Gln Lys Val Glu Leu
            805                 810

<210> SEQ ID NO 12
<211> LENGTH: 385
<212> TYPE: PRT
<213> ORGANISM: Listeria grayi

<400> SEQUENCE: 12

Met Thr Met Asn Val Gly Ile Asp Lys Met Ser Phe Phe Val Pro Pro
1               5                  10                  15

Tyr Phe Val Asp Met Thr Asp Leu Ala Val Ala Arg Asp Val Asp Pro
            20                  25                  30

Asn Lys Phe Leu Ile Gly Ile Gly Gln Asp Gln Met Ala Val Asn Pro
        35                  40                  45

Lys Thr Gln Asp Ile Val Thr Phe Ala Thr Asn Ala Ala Lys Asn Ile
    50                  55                  60

Leu Ser Ala Glu Asp Leu Asp Lys Ile Asp Met Val Ile Val Gly Thr
65                  70                  75                  80

Glu Ser Gly Ile Asp Glu Ser Lys Ala Ser Ala Val Val Leu His Arg
                85                  90                  95

Leu Leu Gly Ile Gln Lys Phe Ala Arg Ser Phe Glu Ile Lys Glu Ala
            100                 105                 110

Cys Tyr Gly Gly Thr Ala Ala Leu Gln Phe Ala Val Asn His Ile Arg
        115                 120                 125

Asn His Pro Glu Ser Lys Val Leu Val Val Ala Ser Asp Ile Ala Lys
    130                 135                 140

Tyr Gly Leu Ala Ser Gly Gly Glu Pro Thr Gln Gly Ala Gly Ala Val
145                 150                 155                 160

Ala Met Leu Val Ser Thr Asp Pro Lys Ile Ile Ala Phe Asn Asp Asp
                165                 170                 175

Ser Leu Ala Leu Thr Gln Asp Ile Tyr Asp Phe Trp Arg Pro Val Gly
            180                 185                 190

His Asp Tyr Pro Met Val Asp Gly Pro Leu Ser Thr Glu Thr Tyr Ile
        195                 200                 205

Gln Ser Phe Gln Thr Val Trp Gln Glu Tyr Thr Lys Arg Ser Gln His
    210                 215                 220

Ala Leu Ala Asp Phe Ala Ala Leu Ser Phe His Ile Pro Tyr Thr Lys
225                 230                 235                 240

Met Gly Lys Lys Ala Leu Leu Ala Ile Leu Glu Gly Glu Ser Glu Glu
                245                 250                 255

Ala Gln Asn Arg Ile Leu Ala Lys Tyr Glu Lys Ser Ile Ala Tyr Ser
            260                 265                 270

Arg Lys Ala Gly Asn Leu Tyr Thr Gly Ser Leu Tyr Leu Gly Leu Ile
        275                 280                 285

Ser Leu Leu Glu Asn Ala Glu Asp Leu Lys Ala Gly Asp Leu Ile Gly
    290                 295                 300

Leu Phe Ser Tyr Gly Ser Gly Ala Val Ala Glu Phe Phe Ser Gly Arg
305                 310                 315                 320

Leu Val Glu Asp Tyr Gln Glu Gln Leu Leu Lys Thr Lys His Ala Glu
                325                 330                 335

Gln Leu Ala His Arg Lys Gln Leu Thr Ile Glu Glu Tyr Glu Thr Met
            340                 345                 350

Phe Ser Asp Arg Leu Asp Val Asp Lys Asp Ala Glu Tyr Glu Asp Thr
```

```
              355                 360                 365
Leu Ala Tyr Ser Ile Ser Ser Val Arg Asn Thr Val Arg Glu Tyr Arg
    370                 375                 380

Ser
385

<210> SEQ ID NO 13
<211> LENGTH: 813
<212> TYPE: PRT
<213> ORGANISM: Enterococcus faecium

<400> SEQUENCE: 13

Met Lys Glu Val Val Met Ile Asp Ala Ala Arg Thr Pro Ile Gly Lys
1               5                   10                  15

Tyr Arg Gly Ser Leu Ser Pro Phe Thr Ala Val Glu Leu Gly Thr Leu
                20                  25                  30

Val Thr Lys Gly Leu Leu Asp Lys Thr Lys Leu Lys Lys Asp Lys Ile
            35                  40                  45

Asp Gln Val Ile Phe Gly Asn Val Leu Gln Ala Gly Asn Gly Gln Asn
        50                  55                  60

Val Ala Arg Gln Ile Ala Leu Asn Ser Gly Leu Pro Val Asp Val Pro
65                  70                  75                  80

Ala Met Thr Ile Asn Glu Val Cys Gly Ser Gly Met Lys Ala Val Ile
                85                  90                  95

Leu Ala Arg Gln Leu Ile Gln Leu Gly Glu Ala Glu Leu Val Ile Ala
                100                 105                 110

Gly Gly Thr Glu Ser Met Ser Gln Ala Pro Met Leu Lys Pro Tyr Gln
            115                 120                 125

Ser Glu Thr Asn Glu Tyr Gly Glu Pro Ile Ser Ser Met Val Asn Asp
        130                 135                 140

Gly Leu Thr Asp Ala Phe Ser Asn Ala His Met Gly Leu Thr Ala Glu
145                 150                 155                 160

Lys Val Ala Thr Gln Phe Ser Val Ser Arg Glu Glu Gln Asp Arg Tyr
                165                 170                 175

Ala Leu Ser Ser Gln Leu Lys Ala Ala His Ala Val Glu Ala Gly Val
                180                 185                 190

Phe Ser Glu Glu Ile Ile Pro Val Lys Ile Ser Asp Glu Asp Val Leu
            195                 200                 205

Ser Glu Asp Glu Ala Val Arg Gly Asn Ser Thr Leu Glu Lys Leu Gly
        210                 215                 220

Thr Leu Arg Thr Val Phe Ser Glu Glu Gly Thr Val Thr Ala Gly Asn
225                 230                 235                 240

Ala Ser Pro Leu Asn Asp Gly Ala Ser Val Val Ile Leu Ala Ser Lys
                245                 250                 255

Glu Tyr Ala Glu Asn Asn Asn Leu Pro Tyr Leu Ala Thr Ile Lys Glu
                260                 265                 270

Val Ala Glu Val Gly Ile Asp Pro Ser Ile Met Gly Ile Ala Pro Ile
            275                 280                 285

Lys Ala Ile Gln Lys Leu Thr Asp Arg Ser Gly Met Asn Leu Ser Thr
        290                 295                 300

Ile Asp Leu Phe Glu Ile Asn Glu Ala Phe Ala Ala Ser Ser Ile Val
305                 310                 315                 320

Val Ser Gln Glu Leu Gln Leu Asp Glu Glu Lys Val Asn Ile Tyr Gly
                325                 330                 335
```

```
Gly Ala Ile Ala Leu Gly His Pro Ile Gly Ala Ser Gly Ala Arg Ile
            340                 345                 350

Leu Thr Thr Leu Ala Tyr Gly Leu Leu Arg Glu Gln Lys Arg Tyr Gly
            355                 360                 365

Ile Ala Ser Leu Cys Ile Gly Gly Leu Gly Leu Ala Val Leu Leu
            370                 375                 380

Glu Ala Asn Met Glu Gln Thr His Lys Asp Val Gln Lys Lys Lys Phe
385                 390                 395                 400

Tyr Gln Leu Thr Pro Ser Glu Arg Arg Ser Gln Leu Ile Glu Lys Asn
                405                 410                 415

Val Leu Thr Gln Glu Thr Ala Leu Ile Phe Gln Glu Gln Thr Leu Ser
            420                 425                 430

Glu Glu Leu Ser Asp His Met Ile Glu Asn Gln Val Ser Glu Val Glu
            435                 440                 445

Ile Pro Met Gly Ile Ala Gln Asn Phe Gln Ile Asn Gly Lys Lys Lys
            450                 455                 460

Trp Ile Pro Met Ala Thr Glu Glu Pro Ser Val Ile Ala Ala Ala Ser
465                 470                 475                 480

Asn Gly Ala Lys Ile Cys Gly Asn Ile Cys Ala Glu Thr Pro Gln Arg
                485                 490                 495

Leu Met Arg Gly Gln Ile Val Leu Ser Gly Lys Ser Glu Tyr Gln Ala
            500                 505                 510

Val Ile Asn Ala Val Asn His Arg Lys Glu Glu Leu Ile Leu Cys Ala
            515                 520                 525

Asn Glu Ser Tyr Pro Ser Ile Val Lys Arg Gly Gly Val Gln Asp
            530                 535                 540

Ile Ser Thr Arg Glu Phe Met Gly Ser Phe His Ala Tyr Leu Ser Ile
545                 550                 555                 560

Asp Phe Leu Val Asp Val Lys Asp Ala Met Gly Ala Asn Met Ile Asn
                565                 570                 575

Ser Ile Leu Glu Ser Val Ala Asn Lys Leu Arg Glu Trp Phe Pro Glu
            580                 585                 590

Glu Glu Ile Leu Phe Ser Ile Leu Ser Asn Phe Ala Thr Glu Ser Leu
            595                 600                 605

Ala Ser Ala Cys Cys Glu Ile Pro Phe Glu Arg Leu Gly Arg Asn Lys
            610                 615                 620

Glu Ile Gly Glu Gln Ile Ala Lys Lys Ile Gln Gln Ala Gly Glu Tyr
625                 630                 635                 640

Ala Lys Leu Asp Pro Tyr Arg Ala Ala Thr His Asn Lys Gly Ile Met
                645                 650                 655

Asn Gly Ile Glu Ala Val Val Ala Ala Thr Gly Asn Asp Thr Arg Ala
            660                 665                 670

Val Ser Ala Ser Ile His Ala Tyr Ala Ala Arg Asn Gly Leu Tyr Gln
            675                 680                 685

Gly Leu Thr Asp Trp Gln Ile Lys Gly Asp Lys Leu Val Gly Lys Leu
            690                 695                 700

Thr Val Pro Leu Ala Val Ala Thr Val Gly Gly Ala Ser Asn Ile Leu
705                 710                 715                 720

Pro Lys Ala Lys Ala Ser Leu Ala Met Leu Asp Ile Asp Ser Ala Lys
                725                 730                 735

Glu Leu Ala Gln Val Ile Ala Ala Val Gly Leu Ala Gln Asn Leu Ala
            740                 745                 750

Ala Leu Arg Ala Leu Val Thr Glu Gly Ile Gln Lys Gly His Met Gly
```

```
              755                 760                 765
Leu Gln Ala Arg Ser Leu Ala Ile Ser Ile Gly Ala Ile Gly Glu Glu
              770                 775                 780
Ile Glu Gln Val Ala Lys Lys Leu Arg Glu Ala Glu Lys Met Asn Gln
785                 790                 795                 800
Gln Thr Ala Ile Gln Ile Leu Glu Lys Ile Arg Glu Lys
              805                 810

<210> SEQ ID NO 14
<211> LENGTH: 384
<212> TYPE: PRT
<213> ORGANISM: Enterococcus faecium

<400> SEQUENCE: 14

Met Lys Ile Gly Ile Asp Arg Leu Ser Phe Phe Ile Pro Asn Leu Tyr
1               5                   10                  15
Leu Asp Met Thr Glu Leu Ala Glu Ser Arg Gly Asp Asp Pro Ala Lys
                20                  25                  30
Tyr His Ile Gly Ile Gly Gln Asp Gln Met Ala Val Asn Arg Ala Asn
                35                  40                  45
Glu Asp Ile Ile Thr Leu Gly Ala Asn Ala Ala Ser Lys Ile Val Thr
    50                  55                  60
Glu Lys Asp Arg Glu Leu Ile Asp Met Val Ile Val Gly Thr Glu Ser
65                  70                  75                  80
Gly Ile Asp His Ser Lys Ala Ser Ala Val Ile Ile His His Leu Leu
                85                  90                  95
Lys Ile Gln Ser Phe Ala Arg Ser Phe Glu Val Lys Glu Ala Cys Tyr
                100                 105                 110
Gly Gly Thr Ala Ala Leu His Met Ala Lys Glu Tyr Val Lys Asn His
                115                 120                 125
Pro Glu Arg Lys Val Leu Val Ile Ala Ser Asp Ile Ala Arg Tyr Gly
                130                 135                 140
Leu Ala Ser Gly Gly Glu Val Thr Gln Gly Val Gly Ala Val Ala Met
145                 150                 155                 160
Met Ile Thr Gln Asn Pro Arg Ile Leu Ser Ile Glu Asp Asp Ser Val
                165                 170                 175
Phe Leu Thr Glu Asp Ile Tyr Asp Phe Trp Arg Pro Asp Tyr Ser Glu
                180                 185                 190
Phe Pro Val Val Asp Gly Pro Leu Ser Asn Ser Thr Tyr Ile Glu Ser
                195                 200                 205
Phe Gln Lys Val Trp Asn Arg His Lys Glu Leu Ser Gly Arg Gly Leu
                210                 215                 220
Glu Asp Tyr Gln Ala Ile Ala Phe His Ile Pro Tyr Thr Lys Met Gly
225                 230                 235                 240
Lys Lys Ala Leu Gln Ser Val Leu Asp Gln Thr Asp Glu Asp Asn Gln
                245                 250                 255
Glu Arg Leu Met Ala Arg Tyr Glu Glu Ser Ile Arg Tyr Ser Arg Arg
                260                 265                 270
Ile Gly Asn Leu Tyr Thr Gly Ser Leu Tyr Leu Gly Leu Thr Ser Leu
                275                 280                 285
Leu Glu Asn Ser Lys Ser Leu Gln Pro Gly Asp Arg Ile Gly Leu Phe
                290                 295                 300
Ser Tyr Gly Ser Gly Ala Val Ser Glu Phe Phe Thr Gly Tyr Leu Glu
305                 310                 315                 320
```

```
Glu Asn Tyr Gln Glu Tyr Leu Phe Ala Gln Ser His Gln Glu Met Leu
                325                 330                 335

Asp Ser Arg Thr Arg Ile Thr Val Asp Glu Tyr Glu Thr Ile Phe Ser
            340                 345                 350

Glu Thr Leu Pro Glu His Gly Glu Cys Ala Glu Tyr Thr Ser Asp Val
        355                 360                 365

Pro Phe Ser Ile Thr Lys Ile Glu Asn Asp Ile Arg Tyr Tyr Lys Ile
370                 375                 380
```

<210> SEQ ID NO 15
<211> LENGTH: 824
<212> TYPE: PRT
<213> ORGANISM: Enterococcus casseliflavus

<400> SEQUENCE: 15

```
Met Glu Glu Val Val Ile Ile Asp Ala Leu Arg Thr Pro Ile Gly Lys
1               5                   10                  15

Tyr His Gly Ser Leu Lys Asp Tyr Thr Ala Val Glu Leu Gly Thr Val
            20                  25                  30

Ala Ala Lys Ala Leu Leu Ala Arg Asn Gln Gln Ala Lys Glu His Ile
        35                  40                  45

Ala Gln Val Ile Ile Gly Asn Val Leu Gln Ala Gly Ser Gly Gln Asn
    50                  55                  60

Pro Gly Arg Gln Val Ser Leu Gln Ser Gly Leu Ser Ser Asp Ile Pro
65                  70                  75                  80

Ala Ser Thr Ile Asn Glu Val Cys Gly Ser Gly Met Lys Ala Ile Leu
                85                  90                  95

Met Gly Met Glu Gln Ile Gln Leu Asn Lys Ala Ser Val Val Leu Thr
            100                 105                 110

Gly Gly Ile Glu Ser Met Thr Asn Ala Pro Leu Phe Ser Tyr Tyr Asn
        115                 120                 125

Lys Ala Glu Asp Gln Tyr Ser Ala Pro Val Ser Thr Met Met His Asp
    130                 135                 140

Gly Leu Thr Asp Ala Phe Ser Ser Lys Pro Met Gly Leu Thr Ala Glu
145                 150                 155                 160

Thr Val Ala Glu Arg Tyr Gly Ile Thr Arg Lys Glu Gln Asp Glu Phe
                165                 170                 175

Ala Tyr His Ser Gln Met Lys Ala Ala Lys Ala Gln Ala Ala Lys Lys
            180                 185                 190

Phe Asp Gln Glu Ile Val Pro Leu Thr Glu Lys Ser Gly Thr Val Leu
        195                 200                 205

Gln Asp Glu Gly Ile Arg Ala Ala Thr Thr Val Glu Lys Leu Ala Glu
    210                 215                 220

Leu Lys Thr Val Phe Lys Lys Asp Gly Thr Val Thr Ala Gly Asn Ala
225                 230                 235                 240

Ser Thr Ile Asn Asp Gly Ala Ala Met Val Leu Ile Ala Ser Lys Ser
                245                 250                 255

Tyr Cys Glu Glu His Gln Ile Pro Tyr Leu Ala Val Ile Lys Glu Ile
            260                 265                 270

Val Glu Val Gly Phe Ala Pro Glu Ile Met Gly Ile Ser Pro Ile Lys
        275                 280                 285

Ala Ile Asp Thr Leu Leu Lys Asn Gln Ala Leu Thr Ile Glu Asp Ile
    290                 295                 300

Gly Ile Phe Glu Ile Asn Glu Ala Phe Ala Ala Ser Ser Ile Val Val
305                 310                 315                 320
```

```
Glu Arg Glu Leu Gly Leu Asp Pro Lys Lys Val Asn Arg Tyr Gly Gly
                325                 330                 335

Gly Ile Ser Leu Gly His Ala Ile Gly Ala Thr Gly Ala Arg Ile Ala
            340                 345                 350

Thr Thr Val Ala Tyr Gln Leu Lys Asp Thr Gln Glu Arg Tyr Gly Ile
        355                 360                 365

Ala Ser Leu Cys Val Gly Gly Leu Gly Leu Ala Met Leu Leu Glu
    370                 375                 380

Asn Pro Ser Ala Thr Ser Gln Thr Asn Phe Asp Glu Glu Ser Ala
385                 390                 395                 400

Ser Glu Lys Thr Glu Lys Lys Phe Tyr Ala Leu Ala Pro Asn Glu
                405                 410                 415

Arg Leu Ala Phe Leu Glu Ala Gln Gly Ala Ile Thr Ala Ala Glu Thr
                420                 425                 430

Leu Val Phe Gln Glu Met Thr Leu Asn Lys Glu Thr Ala Asn His Leu
        435                 440                 445

Ile Glu Asn Gln Ile Ser Glu Val Glu Ile Pro Leu Gly Val Gly Leu
    450                 455                 460

Asn Leu Gln Val Asn Gly Lys Ala Tyr Asn Val Pro Leu Ala Thr Glu
465                 470                 475                 480

Glu Pro Ser Val Ile Ala Ala Met Ser Asn Gly Ala Lys Met Ala Gly
                485                 490                 495

Pro Ile Thr Thr Thr Ser Gln Glu Arg Leu Leu Arg Gly Gln Ile Val
                500                 505                 510

Phe Met Asp Val Gln Asp Pro Glu Ala Ile Leu Ala Lys Val Glu Ser
                515                 520                 525

Glu Gln Ala Thr Ile Phe Ala Val Ala Asn Glu Thr Tyr Pro Ser Ile
        530                 535                 540

Val Lys Arg Gly Gly Gly Leu Arg Arg Val Ile Gly Arg Asn Phe Ser
545                 550                 555                 560

Pro Ala Glu Ser Asp Leu Ala Thr Ala Tyr Val Ser Ile Asp Leu Met
                565                 570                 575

Val Asp Val Lys Asp Ala Met Gly Ala Asn Ile Ile Asn Ser Ile Leu
            580                 585                 590

Glu Gly Val Ala Glu Leu Phe Arg Lys Trp Phe Pro Glu Glu Glu Ile
            595                 600                 605

Leu Phe Ser Ile Leu Ser Asn Leu Ala Thr Glu Ser Leu Val Thr Ala
        610                 615                 620

Thr Cys Ser Val Pro Phe Asp Lys Leu Ser Lys Thr Gly Asn Gly Arg
625                 630                 635                 640

Gln Val Ala Gly Lys Ile Val His Ala Ala Asp Phe Ala Lys Ile Asp
                645                 650                 655

Pro Tyr Arg Ala Ala Thr His Asn Lys Gly Ile Met Asn Gly Val Glu
                660                 665                 670

Ala Leu Ile Leu Ala Thr Gly Asn Asp Thr Arg Ala Val Ser Ala Ala
            675                 680                 685

Cys His Gly Tyr Ala Ala Arg Asn Gly Arg Met Gln Gly Leu Thr Ser
        690                 695                 700

Trp Thr Ile Ile Glu Asp Arg Leu Ile Gly Ser Ile Thr Leu Pro Leu
705                 710                 715                 720

Ala Ile Ala Thr Val Gly Gly Ala Thr Lys Ile Leu Pro Lys Ala Gln
                725                 730                 735
```

```
Ala Ala Leu Ala Leu Thr Gly Val Glu Thr Ala Ser Glu Leu Ala Ser
            740                 745                 750

Leu Ala Ala Ser Val Gly Leu Val Gln Asn Leu Ala Ala Leu Arg Ala
            755                 760                 765

Leu Val Ser Glu Gly Ile Gln Gln Gly His Met Ser Met Gln Ala Arg
            770                 775                 780

Ser Leu Ala Ile Ser Val Gly Ala Lys Gly Thr Glu Ile Glu Gln Leu
785                 790                 795                 800

Ala Ala Lys Leu Arg Ala Ala Thr Gln Met Asn Gln Glu Gln Ala Arg
            805                 810                 815

Lys Phe Leu Thr Glu Ile Arg Asn
            820

<210> SEQ ID NO 16
<211> LENGTH: 386
<212> TYPE: PRT
<213> ORGANISM: Enterococcus casseliflavus

<400> SEQUENCE: 16

Met Asn Val Gly Ile Asp Lys Ile Asn Phe Phe Val Pro Pro Tyr Phe
1               5                   10                  15

Ile Asp Met Val Asp Leu Ala His Ala Arg Glu Val Asp Pro Asn Lys
            20                  25                  30

Phe Thr Ile Gly Ile Gly Gln Asp Gln Met Ala Val Asn Lys Lys Thr
        35                  40                  45

Gln Asp Ile Val Thr Phe Ala Met His Ala Ala Lys Asp Ile Leu Thr
    50                  55                  60

Lys Glu Asp Leu Gln Ala Ile Asp Met Val Ile Val Gly Thr Glu Ser
65                  70                  75                  80

Gly Ile Asp Glu Ser Lys Ala Ser Ala Val Val Leu His Arg Leu Leu
                85                  90                  95

Gly Ile Gln Pro Phe Ala Arg Ser Phe Glu Ile Lys Glu Ala Cys Tyr
            100                 105                 110

Gly Ala Thr Ala Gly Leu Gln Phe Ala Lys Ala His Val Gln Ala Asn
        115                 120                 125

Pro Gln Ser Lys Val Leu Val Val Ala Ser Asp Ile Ala Arg Tyr Gly
    130                 135                 140

Leu Ala Ser Gly Gly Glu Pro Thr Gln Gly Val Gly Ala Val Ala Met
145                 150                 155                 160

Leu Ile Ser Ala Asp Pro Ala Ile Leu Gln Leu Glu Asn Asp Asn Leu
                165                 170                 175

Met Leu Thr Gln Asp Ile Tyr Asp Phe Trp Arg Pro Val Gly His Gln
            180                 185                 190

Tyr Pro Met Val Asp Gly His Leu Ser Asn Ala Val Tyr Ile Asp Ser
        195                 200                 205

Phe Lys Gln Val Trp Gln Ala His Cys Glu Lys Asn Gln Arg Thr Ala
    210                 215                 220

Lys Asp Tyr Ala Ala Leu Ser Phe His Ile Pro Tyr Thr Lys Met Gly
225                 230                 235                 240

Lys Lys Ala Leu Leu Ala Val Phe Ala Glu Glu Asp Glu Thr Glu Gln
                245                 250                 255

Lys Arg Leu Met Ala Arg Tyr Glu Glu Ser Ile Val Tyr Ser Arg Arg
            260                 265                 270

Thr Gly Asn Leu Tyr Thr Gly Ser Leu Tyr Leu Gly Leu Ile Ser Leu
        275                 280                 285
```

```
Leu Glu Asn Ser Ser Leu Gln Ala Asn Asp Arg Ile Gly Leu Phe
    290             295                 300

Ser Tyr Gly Ser Gly Ala Val Ala Glu Phe Phe Ser Gly Leu Leu Val
305             310                 315                 320

Pro Gly Tyr Glu Lys Gln Leu Ala Gln Ala Ala His Gln Ala Leu Leu
                325                 330                 335

Asp Asp Arg Gln Lys Leu Thr Ile Ala Glu Tyr Glu Ala Met Phe Asn
                340                 345                 350

Glu Thr Ile Asp Ile Asp Gln Asp Gln Ser Phe Glu Asp Asp Leu Leu
            355                 360                 365

Tyr Ser Ile Arg Glu Ile Lys Asn Thr Ile Arg Tyr Tyr Asn Glu Glu
        370                 375                 380

Asn Glu
385

<210> SEQ ID NO 17
<211> LENGTH: 1635
<212> TYPE: DNA
<213> ORGANISM: Populus alba

<400> SEQUENCE: 17
atggaagctc gtcgttctgc gaactacgaa cctaacagct gggactatga ttacctgctg     60
tcctccgaca cggacgagtc catcgaagta tacaaagaca agcgaaaaa gctggaagcc    120
gaagttcgtc gcgagattaa taacgaaaaa gcagaatttc tgaccctgct ggaactgatt    180
gacaacgtcc agcgcctggg cctgggttac cgtttcgagt ctgatatccg tggtgcgctg    240
gatcgcttcg tttcctccgg cggcttcgat gcggtaacca agacttccct gcacggtacg    300
gcactgtctt tccgtctgct gcgtcaacac ggttttgagg tttctcagga agcgttcagc    360
ggcttcaaag accaaaacgg caacttcctg agaacctga aggaagatat caaagctatc    420
ctgagcctgt acgaggccag cttcctggct ctggaaggcg aaaacatcct ggacgaggcg    480
aaggttttcg caatctctca tctgaaagaa ctgtctgaag aaagatcgg taagagctg    540
gcagaacagg tgaaccatgc actggaactg ccactgcatc gccgtactca gcgtctggaa    600
gcagtatggt ctatcgaggc ctaccgtaaa aaggaggacg cgaatcaggt tctgctggag    660
ctggcaattc tggattacaa catgatccag tctgtatacc agcgtgatct gcgtgaaacg    720
tcccgttggt ggcgtcgtgt gggtctggcg accaaactgc actttgctcg tgaccgcctg    780
attgagagct ctactgggc cgtgggtgta gcattcgaac cgcaatactc cgactgccgt    840
aactccgtcg caaaaatgtt ttctttcgta accattatcg acgatatcta cgatgtatac    900
ggcaccctgg acgaactgga gctgttttact gatgcagttg agcgttggga cgtaaacgcc    960
atcaacgacc tgccggatta catgaaactg tgctttctgg ctctgtataa cactattaac   1020
gaaatcgcct acgacaacct gaaagataaa ggtgagaaca tcctgccgta tctgaccaaa   1080
gcctgggctg acctgtgcaa cgctttcctg caagaagcca gtggctgta caacaaatct   1140
actccgacct tgacgacta cttcggcaac gcatggaaat cctcttctgg cccgctgcaa   1200
ctggtgttcg cttacttcgc tgtcgtgcag aacattaaaa aggaagagat cgaaaacctg   1260
caaaaatacc atgacaccat ctctcgtcct tcccatatct tccgtctgtg caatgacctg   1320
gctagcgcgt ctgcggaaat tgcgcgtggt gaaaccgcaa atagcgtttc ttgttacatg   1380
cgcactaaag gtatctccga agaactggct accgaaagcg tgatgaatct gatcgatgaa   1440
acctggaaaa agatgaacaa ggaaaaactg ggtggtagcc tgttcgcgaa accgttcgtg   1500
```

```
gaaaccgcga tcaacctggc acgtcaatct cactgcactt atcataacgg cgacgcgcat      1560
acctctccgg atgagctgac ccgcaaacgc gttctgtctg taatcactga accgattctg      1620
ccgtttgaac gctaa                                                       1635
```

<210> SEQ ID NO 18
<211> LENGTH: 900
<212> TYPE: DNA
<213> ORGANISM: Escherichia coli

<400> SEQUENCE: 18

```
atggactttc gcagcaact cgaagcctgc gttaagcagg ccaaccaggc gctgagccgt        60
tttatcgccc cactgccctt tcagaacact cccgtggtcg aaaccatgca gtatggcgca      120
ttattaggtg gtaagcgcct gcgacctttc ctggtttatg ccaccggtca tatgtttggc      180
gttagcacaa acacgctgga cgcacccgct gctgccgtag agtgtatcca cgcttactca      240
ttaattcatg atgatttacc ggcgatggat gatgacgatc tgcgccgcgg tttgccgacc      300
tgccatgtga agtttggcga agcaaacgcg attctcgctg gcgacgcttt acaaacgctg      360
gcgttctcga ttctaagcga tgccgatatg ccggaagtgt cggatcgcga cagaatttcg      420
atgatttctg aactggcgag cgccagcggt attgccggaa tgtgcggtgg tcaggcacta      480
gatttagacg cggaaggcaa acacgtacct ctggacgcgc ttgagcgtat tcatcgtcat      540
aaaaccggcg cattgattcg cgccgccgtt cgccttggtg cattaagcgc cggagataaa      600
gggcgtcgtg ctctgccagt actcgacaag tacgcagaga gcatcggcct tgccttccag      660
gttcaagatg acatcctgga tgtggtagga gatactgcaa cgttgggaaa acgccagggt      720
gccgaccagc aacttggtaa aagtacctac cctgcacttc tgggtcttga gcaagcccgg      780
aagaaagccc gggatctgat cgacgatgcc cgtcagtcgc tgaaacaact ggctgaacag      840
tcactcgata cctcggcact ggaagcgcta gcggactaca tcatccagcg taataaataa      900
```

<210> SEQ ID NO 19
<211> LENGTH: 1641
<212> TYPE: DNA
<213> ORGANISM: Artificial Sequence
<220> FEATURE:
<223> OTHER INFORMATION: Synthetic Construct

<400> SEQUENCE: 19

```
atgagcctga ccgaagaaaa accgattcgt ccgattgcaa attttccgcc tagcatttgg        60
ggtgatcagt ttctgattta tgagaaacag gttgaacagg gcgttgagca gattgttaat      120
gatctgaaaa aagaagttcg ccagctgctg aaagaagcac tggatattcc gatgaaacat      180
gccaatctgc tgaaactgat tgatgaaatt cagcgtctgg gtatcccgta tcattttgaa      240
cgtgaaattg atcatgccct gcagtgcatt tatgaaacct atggtgataa ttggaatggt      300
gatcgtagca gcctgtggtt tcgtctgatg cgtaaacagg ttattatgt tacctgcgac      360 gtgtttaaca actataaaga taaaaacggt gcctttaaac agagcctggc aaatgatgtt      420
gaaggtctgc tggaactgta tgaagcaacc agcatgcgtg ttccgggtga aattattctg      480
gaagatgcac tgggttttac ccgtagccgt ctgagcatga tgaccaaaga tgcatttagc      540
accaatccgg cactgtttac gaaatccag cgtgcactga acagccgct gtggaaacgt       600 ctgcctcgta ttgaagcagc acagtatatt ccgttttatc agcagcagga tagccataac      660 aaaccctgc tgaaactggc aaaactggaa tttaatctgc tgcagagcct gcataaagaa      720
```

| | |
|---|---:|
| gaactgagcc acgtttgtaa atggtggaaa gccttcgaca tcaaaaaaaa cgcaccgtgt | 780 |
| ctgcgtgatc gtattgttga atgttatttt tggggtctgg gtagcggttt tgaaccgcag | 840 |
| tatagccgtg cacgtgtgtt ttttaccaaa gcagttgcag ttattaccct gatcgatgat | 900 |
| acctatgacg catatggcac ctatgaggaa ctgaaaatct ttaccgaagc cgttgaacgt | 960 |
| tggagcatta cctgtctgga taccctgccg gaatatatga aaccgatcta taaactgttc | 1020 |
| atggacacct ataccgagat ggaagaattt ctggcaaaag aaggtcgtac cgacctgttt | 1080 |
| aattgcggta agaatttgt gaaagaattc gtgcgtaacc tgatggttga agcaaaatgg | 1140 |
| gccaatgaag gtcatattcc gaccaccgaa gaacatgatc cggttgtgat tattaccggt | 1200 |
| ggtgcaaacc tgctgaccac cacctgttat ctgggtatga gcgatatttt caccaaagaa | 1260 |
| agcgttgaat gggcagttag cgcaccgcct ctgtttcgtt atagcggtat tctgggtcgt | 1320 |
| cgtctgaacg atctgatgac ccataaagca gaacaagaac gtaaacatag cagcagcagc | 1380 |
| ctggaaagct atatgaaaga atataacgtg aacgaagagt atgcacagac cctgatttac | 1440 |
| aaagaagttg aggacgtttg aaagatatc aaccgtgaat atctgaccac gaaaaacatt | 1500 |
| ccgcgtccgc tgctgatggc agttatttat ctgtgtcagt tcctggaagt tcagtatgca | 1560 |
| ggtaaagata actttacgcg tatgggcgac gaatataaac atctgattaa aagcctgctg | 1620 |
| gtgtatccga tgagcattta a | 1641 |

<210> SEQ ID NO 20
<211> LENGTH: 1734
<212> TYPE: DNA
<213> ORGANISM: Artificial Sequence
<220> FEATURE:
<223> OTHER INFORMATION: Synthetic Construct

<400> SEQUENCE: 20

| | |
|---|---:|
| atgagcaccc tgccgattag cagcgttagc tttagcagca gcaccagtcc gctggttgtt | 60 |
| gatgataaag ttagcaccaa accggatgtt attcgtcaca ccatgaactt taatgcaagc | 120 |
| atttggggtg atcagtttct gacctatgat gaaccggaag atctggtgat gaaaaaacag | 180 |
| ctggttgaag aactgaaaga agaagttaaa aaagagctga tcaccatcaa aggtagcaat | 240 |
| gaaccgatgc agcatgttaa actgattgaa ctgatcgatg ccgttcagcg tctgggtatt | 300 |
| gcatatcatt ttgaagaaga atcgaagaa gccctgcagc atattcatgt tacctatggt | 360 |
| gaacagtggg tggataaaga aaatctgcag agcattagcc tgtggtttcg tctgctgcgt | 420 |
| cagcagggtt ttaatgttag cagcggtgtg tttaaagatt ttatgacga gaaaggcaaa | 480 |
| ttcaaagaaa gcctgtgtaa tgatgcacag ggtattctgg cactgtatga agcagcattt | 540 |
| atgcgtgttg aagatgaaac cattctggat aatgcactgg aatttaccaa agtgcacctg | 600 |
| gatatcattg caaaagatcc gagctgtgat agcagcctgc gtacccagat tcatcaggca | 660 |
| ctgaaacagc cgctgcgtcg tcgtctggca cgcattgaag cactgcatta tgccgatt | 720 |
| tatcagcaag aaaccagcca taatgaagat ctgctgaaac tggcaaaact ggatttagc | 780 |
| gttctgcagt ccatgcacaa aaaagaactg agccatattt gtaaatggtg aaagatctg | 840 |
| gatctgcaga taaaactgcc gtatgttcgt gatcgtgttg tggaaggtta ttttggatt | 900 |
| ctgagcatct attatgaacc gcagcatgca cgtacccgta tgtttctgat gaaaacctgt | 960 |
| atgtggctgg ttgtgctgga tgatacgttt gataattatg caccgacga ggaactggaa | 1020 |
| atctttaccc aggcagttga cgttggagc attagttgtc tggatatgct gccggaatac | 1080 |
| atgaaactga tttatcaaga actggtgaac ctgcacgttg aaatggaaga aagtctgggc | 1140 |

```
aaaggtggta aaaacattag caatagtctg tgtcagggtc gttggcagaa agaactgggt    1200
agtcagatta ccctggttga aaccaaaatg gcaaaacgtg gtgttcatgc ccagccgctg    1260
gaagagtata tgagcgttag catggttacc ggcacctatg gtctgatgat tgcacgtagc    1320
tatgttggtc gtggtgatat tgttaccgaa gataccttta aatgggtgag cagctatccg    1380
cctattatca aagcaagctg tgttattgtt cgcctgatgg atgatattgt gagccacaaa    1440
gaagaacaag aacgcggtca tgttgccagc agcattgaat gttatagcaa agaaagtggt    1500
gcaagcgaag aagaagcctg cgaatatatc agccgtaaag tggaagatgc ctggaaagtt    1560
attaatcgtg aaagcctgcg tccgaccgca gttccgtttc gctgctgat gcctgcaatt     1620 aacctggcac gtatgtgtga agttctgtat agcgttaatg atggttttac ccatgccgaa    1680
ggtgatatga atcctatat gaaaagcttc ttcgtgcatc cgatggttgt ttaa            1734
```

<210> SEQ ID NO 21
<211> LENGTH: 8712
<212> TYPE: DNA
<213> ORGANISM: Artificial Sequence
<220> FEATURE:
<223> OTHER INFORMATION: Synthetic Construct

<400> SEQUENCE: 21

```
cccgtcttac tgtcgggaat tcgcgttggc cgattcatta atgcagattc tgaaatgagc      60
tgttgacaat taatcatccg gctcgtataa tgtgtggaat tgtgagcgga taacaatttc     120
acacaggaaa cagcgccgct gagaaaaagc gaagcggcac tgctctttac aatttatcag     180
acaatctgtg tgggcactcg accggaatta tcgattaact ttattattaa aaattaaaga     240
ggtatatatt aatgtatcga ttaaataagg aggaataaac catggttaaa gacattgtaa     300
taattgatgc cctccgtact cccatcggta gtaccgcgg tcagctctca aagatgacgg      360
cggtggaatt gggaaccgca gttacaaagg ctctgttcga gaagaacgac caggtcaaag     420
accatgtaga acaagtcatt tttggcaacg ttttacaggc agggaacggc cagaatcccg     480
cccgtcagat cgccctt aat tctggcctgt ccgcagagat accggcttcg actattaacc     540
aggtgtgtgg ttctggcctg aaagcaataa gcatggcgcg ccaacagatc ctactcggag     600
aagcggaagt aatagtagca ggaggtatcg aatccatgac gaatgcgccg agtattacat     660
attataataa agaagaagac accctctcaa agcctgttcc tacgatgacc ttcgatggtc     720
tgaccgacgc gtttagcgga aagattatgg gtttaacagc cgaaaatgtt gccgaacagt     780
acggcgtatc acgtgaggcc caggacgcct ttgcgtatgg atcgcagatg aaagcagcaa     840
aggcccaaga acagggcatt ttcgcagctg aaatactgcc tcttgaaata ggggacgaag     900
ttattactca ggacgagggg gttcgtcaag agaccaccct cgaaaaatta agtctgcttc     960
ggaccatttt taagaagat ggtactgtta cagcgggcaa cgcctcaacg atcaatgatg     1020
gcgcctcagc cgtgatcatt gcatcaaagg agtttgctga caaaccag attccctacc      1080 ttgcgatcgt acatgatatt acagagatag gcattgatcc atcaataatg ggcattgctc    1140
ccgtgagtgc gatcaataaa ctgatcgatc gtaaccaaat tagcatggaa gaaatcgatc    1200 tcttttgaaat taatgaggca tttgcagcat cctcggtggt agttcaaaaa gagttaagca    1260
ttcccgatga aagatcaat attggcggtt ccggtattgc actaggccat cctcttggcg      1320
ccacaggagc gcgcattgta accacccctag cgcaccagtt gaaacgtaca cacgacgct    1380 atggtattgc ctccctgtgc attggcggtg gccttggcct agcaatatta atagaagtgc    1440
```

```
ctcaggaaga tcagccggtt aaaaaatttt atcaattggc ccgtgaggac cgtctggcta    1500
gacttcagga gcaagccgtg atcagcccag ctacaaaaca tgtactggca gaaatgacac    1560
ttcctgaaga tattgccgac aatctgatcg aaaatcaaat atctgaaatg gaaatccctc    1620
ttggtgtggc tttgaatctg agggtcaatg ataagagtta taccatccca ctagcaactg    1680
aggaaccgag tgtaatcgct gcctgtaata atggtgcaaa aatggcaaac cacctgggcg    1740
gttttcagtc agaattaaaa gatgttttcc tgcgtgggca aattgtactt atgaacgtca    1800
aagaacccgc aactatcgag catacgatca cggcagagaa agcggcaatt tttcgtgccg    1860
cagcgcagtc acatccatcg attgtgaaac gaggtggggg tctaaaagag atagtagtgc    1920
gtacgttcga tgatgatccg acgttcctgt ctattgatct gatagttgat actaaagacg    1980
caatgggcgc taacatcatt aacaccattc tcgaggtgt agccggcttt ctgagggaaa    2040
tccttaccga agaaattctg ttctctattt tatctaatta cgcaaccgaa tcaattgtga    2100
ccgccagctg tcgcatacct tacgaagcac tgagtaaaaa aggtgatggt aaacgaatcg    2160
ctgaaaaagt ggctgctgca tctaaatttg cccagttaga tccttatcga gctgcaaccc    2220
acaacaaagg tattatgaat ggtattgagg ccgtcgtttt ggcctcagga aatgacacac    2280
gggcggtcgc ggcagccgca catgcgtatg cttcacgcga tcagcactat cggggcttaa    2340
gccagtggca ggttgcagaa ggcgcgttac acggggagat cagtctacca cttgcactcg    2400
gcagcgttgg cggtgcaatt gaggtcttgc ctaaagcgaa ggcggcattc gaaatcatgg    2460
ggatcacaga ggcgaaggag ctggcagaag tcacagctgc ggtagggctg cgcaaaaacc    2520
tggcggcgtt aagagcgctt gttagtgaag gaatacagca aggtcacatg tcgctccagg    2580
ctcgctctct tgcattatcg gtaggtgcta caggcaagga agttgaaatc ctggccgaaa    2640
aattacaggg ctctcgtatg aatcaggcga acgctcagac catactcgca gagatcagat    2700
cgcaaaaagt tgaattgtga tctagacgca ctaggaggat ataccaatga ccatgaacgt    2760
tggaatcgat aaaaatgtca tctttgttcc accttacttt gtggacatga ctgatctggc    2820
agtagcacgg gatgtcgatc ccaataagtt tctgattggt attggccagg accagatggc    2880
agttaatccg aaaacgcagg atattgtgac atttgccaca aatgctgcca aaaacatact    2940
gtcagctgag gaccttgata aaattgatat ggtcatagtc ggcaccgaga gtggaatcga    3000
tgaatccaaa gcgagtgccg tagtgcttca caggttgctc ggtatccaga agtttgctcg    3060 ctccttgaa atcaaagaag cctgttatgg gggtaccgcg gctttacagt tcgctgtaaa    3120
ccacattagg aatcatcctg aatcaaaggt tcttgtagtt gcatcagata tcgcgaaata    3180
cggcctggct tctggaggtg aaccaacgca aggtgcaggc gctgtggcta tgctcgtctc    3240 aactgacccct aagatcattg ctttcaacga cgatagcctc cgcgcttacac aagatatcta    3300 tgacttctgg cgaccagttg gacatgacta tcctatggtc gacgggcctc ttagtacaga    3360
gacctacatc cagtcatttc agaccgtatg gcaggaatac acaaaacggt cgcagcatgc    3420
actggcagac tttgctgccc ttagctttca tatcccgtat actaaaatgg gcaaaaaggc    3480
gctgcttgca atccttgaag gcgaatcaga ggaggctcag aaccgtatac tagcaaaata    3540
tgaaaagagt atagcctact ccagaaaggc gggtaacctg tataccggta gcctgtatct    3600
aggacttatt tcacttctgg aaaatgcaga agaccttaaa gctggtgatt aataggcct    3660 cttttcttac ggttccggtg ctgttgcgga gtttttctca ggaaggctgg ttgaggacta    3720
tcaggaacag ctacttaaaa caaaacatgc cgaacagctg gccctagaa agcaactgac    3780 aatcgaggag tacgaaacga tgttctccga tcgcttggac gtggacaaag acgccgaata    3840
```

```
cgaagacaca ttagcttata gcatttcgtc agtccgaaac accgtacgtg agtacaggag    3900
ttgactgcag ctggtaccat atgggaattc gaagcttggg cccgaacaaa aactcatctc    3960
agaagaggat ctgaatagcg ccgtcgacca tcatcatcat catcattgag tttaaacggt    4020
ctccagcttg gctgttttgg cggatgagag aagattttca gcctgataca gattaaatca    4080
gaacgcagaa gcggtctgat aaaacagaat ttgcctggcg gcagtagcgc ggtggtccca    4140
cctgacccca tgccgaactc agaagtgaaa cgccgtagcg ccgatggtag tgtggggtct    4200
ccccatgcga gagtagggaa ctgccaggca tcaaataaaa cgaaaggctc agtcgaaaga    4260
ctgggccttt cgttttatct gttgtttgtc ggtgaacgct ctcctgagta ggacaaatcc    4320
gccgggagcg gatttgaacg ttgcgaagca acggcccgga gggtggcggg caggacgccc    4380
gccataaact gccaggcatc aaattaagca gaaggccatc ctgacggatg ccttttttgc    4440
gtttctacaa actctttttg tttatttttc taaatacatt caaatatgta tccgctcatg    4500
agacaataac cctgataaat gcttcaataa tctggcgtaa tagcgaagag gcccgcaccg    4560
atcgcccttc ccaacagttg cgcagcctga atggcgaatg gcgcctgatg cggtattttc    4620
tccttacgca tctgtgcggt atttcacacc gcatatggtg cactctcagt acaatctgct    4680
ctgatgccgc atagttaagc cagccccgac acccgccaac acccgctgac gagcttagta    4740
aagccctcgc tagattttaa tgcggatgtt gcgattactt cgccaactat tgcgataaca    4800
agaaaaagcc agcctttcat gatatatctc ccaatttgtg tagggcttat tatgcacgct    4860
taaaaataat aaaagcagac ttgacctgat agtttggctg tgagcaatta tgtgcttagt    4920
gcatctaacg cttgagttaa gccgcgccgc gaagcggcgt cggcttgaac gaattgttag    4980
acattatttg ccgactacct tggtgatctc gcctttcacg tagtggacaa attcttccaa    5040
ctgatctgcg cgcgaggcca agcgatcttc ttcttgtcca agataagcct gtctagcttc    5100
aagtatgacg ggctgatact gggccggcag gcgctccatt gcccagtcgg cagcgacatc    5160
cttcggcgcg attttgccgg ttactgcgct gtaccaaatg cgggacaacg taagcactac    5220
atttcgctca tcgccagccc agtcgggcgg cgagttccat agcgttaagg tttcatttag    5280
cgcctcaaat agatcctgtt caggaaccgg atcaaagagt tcctccgccg ctggacctac    5340
caaggcaacg ctatgttctc ttgcttttgt cagcaagata gccagatcaa tgtcgatcgt    5400
ggctggctcg aagatacctg caagaatgtc attgcgctgc cattctccaa attgcagttc    5460
gcgcttagct ggataacgcc acggaatgat gtcgtcgtgc acaacaatgg tgacttctac    5520
agcgcggaga atctcgctct ctccagggga agccgaagtt tccaaaaggt cgttgatcaa    5580
agctcgccgc gttgtttcat caagccttac ggtcaccgta accagcaaat caatatcact    5640
gtgtggcttc aggccgccat ccactgcgga gccgtacaaa tgtacggcca gcaacgtcgg    5700
ttcgagatgg cgctcgatga cgccaactac ctctgatagt tgagtcgata cttcggcgat    5760
caccgcttcc ctcatgatgt ttaactttgt tttagggcga ctgccctgct gcgtaacatc    5820
gttgctgctc cataacatca acatcgacc cacggcgtaa cgcgcttgct gcttggatgc    5880
ccgaggcata gactgtaccc caaaaaaaca gtcataacaa gccatgaaaa ccgccactgc    5940
gccgttacca ccgctgcgtt cggtcaaggt tctggaccag ttgcgtgagc gcatacgcta    6000
cttgcattac agcttacgaa ccgaacaggc ttatgtccac tgggttcgtg ccttcatccg    6060
tttccacggt gtgcgtcacc cggcaacctt gggcagcagc gaagtcgagg catttctgtc    6120
ctggctggcg aacgagcgca aggtttcggt ctccacgcat cgtcaggcat tggcggcctt    6180
```

```
gctgttcttc tacggcaagg tgctgtgcac ggatctgccc tggcttcagg agatcggaag    6240
acctcggccg tcgcggcgct tgccggtggt gctgacccg gatgaagtgg ttcgcatcct     6300
cggttttctg gaaggcgagc atcgtttgtt cgcccagctt ctgtatggaa cgggcatgcg    6360
gatcagtgag ggtttgcaac tgcgggtcaa ggatctggat ttcgatcacg gcacgatcat    6420
cgtgcgggag ggcaagggct ccaaggatcg ggccttgatg ttacccgaga gcttggcacc    6480
cagcctgcgc gagcagggga attaattccc acggggttttg ctgcccgcaa acgggctgtt   6540
ctggtgttgc tagtttgtta tcagaatcgc agatccggct tcagccggtt tgccggctga   6600
aagcgctatt tcttccagaa ttgccatgat ttttttccca cgggaggcgt cactggctcc    6660
cgtgttgtcg gcagctttga ttcgataagc agcatcgcct gtttcaggct gtctatgtgt    6720
gactgttgag ctgtaacaag ttgtctcagg tgttcaattt catgttctag ttgctttgtt    6780
ttactggttt cacctgttct attaggtgtt acatgctgtt catctgttac attgtcgatc    6840
tgttcatggt gaacagcttt gaatgcacca aaaactcgta aaagctctga tgtatctatc    6900
tttttacac cgttttcatc tgtgcatatg gacagttttc cctttgatat gtaacggtga    6960
acagttgttc tacttttgtt tgttagtctt gatgcttcac tgatagatac aagagccata   7020
agaacctcag atccttccgt atttagccag tatgttctct agtgtggttc gttgttttg    7080
cgtgagccat gagaacgaac cattgagatc atacttactt tgcatgtcac tcaaaaattt    7140
tgcctcaaaa ctggtgagct gaattttgc agttaaagca tcgtgtagtg ttttcttag     7200
tccgttatgt aggtaggaat ctgatgtaat ggttgttggt attttgtcac cattcatttt    7260
tatctggttg ttctcaagtt cggttacgag atccatttgt ctatctagtt caacttggaa    7320
aatcaacgta tcagtcgggc ggcctcgctt atcaaccacc aatttcatat gctgtaagt    7380
gtttaaatct ttacttattg gtttcaaaac ccattggtta agcctttaa actcatggta    7440
gttattttca agcattaaca tgaacttaaa ttcatcaagg ctaatctcta tatttgcctt    7500
gtgagtttc ttttgtgtta gttcttttaa taaccactca taaatcctca tagagtattt     7560
gttttcaaaa gacttaacat gttccagatt atatttatg aatttttta actggaaaag     7620
ataaggcaat atctcttcac taaaaactaa ttctaatttt tcgcttgaga acttggcata   7680
gtttgtccac tggaaaatct caaagccttt aaccaaagga ttcctgattt ccacagttct   7740
cgtcatcagc tctctggttg ctttagctaa tacaccataa gcatttttccc tactgatgtt   7800
catcatctga gcgtattggt tataagtgaa cgataccgtc cgttcttttcc ttgtagggtt   7860
ttcaatcgtg gggttgagta gtgccacaca gcataaaatt agcttggttt catgctccgt    7920
taagtcatag cgactaatcg ctagttcatt tgctttgaaa acaactaatt cagacataca    7980
tctcaattgg tctaggtgat tttaatcact ataccaattg agatgggcta gtcaatgata    8040
attactagtc cttttccttt gagttgtggg tatctgtaaa ttctgctaga cctttgctgg    8100
aaaacttgta aattctgcta gaccctctgt aaattccgct agacctttgt gtgttttttt    8160
tgtttatatt caagtggtta taatttatag aataaagaaa gaataaaaaa agataaaaag    8220
aatagatccc agccctgtgt ataactcact actttagtca gttccgcagt attacaaaag    8280
gatgtcgcaa acgctgtttg ctcctctaca aaacagacct taaaacccta aaggcttaag    8340
tagcaccctc gcaagctcgg gcaaatcgct gaatattcct tttgtctccg accatcaggc    8400
acctgagtcg ctgtcttttt cgtgacattc agttcgctgc gctcacggct ctggcagtga    8460
atgggggtaa atggcactac aggcgccttt tatggattca tgcaaggaaa ctacccataa    8520
tacaagaaaa gcccgtcacg ggcttctcag ggcgttttat ggcgggtctg ctatgtggtg    8580
```

| | | |
|---|---|---|
| ctatctgact ttttgctgtt cagcagttcc tgccctctga ttttccagtc tgaccacttc | 8640 | |
| ggattatccc gtgacaggtc attcagactg gctaatgcac ccagtaaggc agcggtatca | 8700 | |
| tcaacaggct ta | 8712 | |

<210> SEQ ID NO 22
<211> LENGTH: 8712
<212> TYPE: DNA
<213> ORGANISM: Artificial Sequence
<220> FEATURE:
<223> OTHER INFORMATION: Synthetic Construct

<400> SEQUENCE: 22

| | |
|---|---|
| cccgtcttac tgtcgggaat tcgcgttggc cgattcatta atgcagattc tgaaatgagc | 60 |
| tgttgacaat taatcatccg gctcgtataa tgtgtggaat tgtgagcgga taacaatttc | 120 |
| acacaggaaa cagcgccgct gagaaaaagc gaagcggcac tgctctttac aatttatcag | 180 |
| acaatctgtg tgggcactcg accggaatta tcgattaact ttattattaa aaattaaaga | 240 |
| ggtatatatt aatgtatcga ttaaataagg aggaataaac catgaaagaa gtggttatga | 300 |
| ttgatgcggc tcgcacaccc attgggaaat acagaggtag tcttagtcct tttacagcgg | 360 |
| tggagctggg gacactggtc acgaaagggc tgctggataa acaaagctt aagaaagaca | 420 |
| agatagacca agtgatattc ggcaatgtgc ttcaggcagg aaacggacaa acgttgcaa | 480 |
| gacaaatagc cctgaacagt ggcttaccag ttgacgtgcc ggcgatgact attaacgaag | 540 |
| tttgcgggtc cggaatgaaa gcggtgattt tagcccgcca gttaatacag ttagggggagg | 600 |
| cagagttggt cattgcaggg ggtacggagt caatgtcaca agcacccatg ctgaaaacctt | 660 |
| accagtcaga gaccaacgaa tacgagagc cgatatcatc aatggttaat gacgggctga | 720 |
| cggatgcgtt ttccaatgct cacatgggtc ttactgccga aaaggtggcg acccagtttt | 780 |
| cagtgtcgcg cgaggaacaa gaccggtacg cattgtccag ccaattgaaa gcagcgcacg | 840 |
| cggttgaagc cggggtgttc tcagaagaga ttattccggt taagattagc gacgaggatg | 900 |
| tcttgagtga agacgaggca gtaagaggca acagcacttt ggaaaaactg ggcacccttgc | 960 |
| ggacggtgtt ttctgaagag ggcacggtta ccgctggcaa tgcttcaccg ctgaatgacg | 1020 |
| gcgctagtgt cgtgattctt gcatcaaaag aatacgcgga aaacaataat ctgccttacc | 1080 |
| tggcgacgat aaaggaggtt gcggaagttg gtatcgatcc ttctatcatg ggtattgccc | 1140 |
| caataaaggc cattcaaaag ttaacagatc ggtcgggcat gaacctgtcc acgattgatc | 1200 |
| tgttcgaaat taatgaagca ttcgcggcat ctagcattgt tgtttctcaa gagctgcaat | 1260 |
| tggacgaaga aaaagtgaat atctatggcg gggcgatagc tttaggccat ccaatcggcg | 1320 |
| caagcggagc ccgatactg acaaccttag catacgcct cctgcgtgag caaaagcgtt | 1380 |
| atggtattgc gtcattatgt atcggcggtg gtcttggtct ggccgtgctg ttagaagcta | 1440 |
| atatggagca gacccacaaa gacgttcaga agaaaaagtt ttaccagctt accccctccg | 1500 |
| agcggagatc gcagcttatc gagaagaacg ttctgactca agaaacggca cttattttcc | 1560 |
| aggagcagac gttgtccgaa gaactgtccg atcacatgat tgagaatcag gtctccgaag | 1620 |
| tggaaattcc aatgggaatt gcacaaaatt ttcagattaa tggcaagaaa aaatggattc | 1680 |
| ctatggcgac tgaagaacct tcagtaatag cggcagcatc gaacggcgcc aaaatctgcg | 1740 |
| ggaacatttg cgcggaaacg cctcagcggc ttatgcgcgg gcagattgtc ctgtctggca | 1800 |
| aatcagaata tcaagccgtg ataaatgccg tgaatcatcg caagaagaa ctgattcttt | 1860 |

```
gcgcaaacga gtcgtacccg agtattgtta aacgcggggg aggtgttcag gatatttcta   1920
cgcgggagtt tatgggttct tttcacgcgt atttatcaat cgactttctg gtggacgtca   1980
aggacgcaat gggggcaaac atgatcaact ctattctcga aagcgttgca aataaactgc   2040
gtgaatggtt cccggaagag gaaatactgt tctccatcct gtcaaacttc gctacggagt   2100
ccctggcatc tgcatgttgc gagattcctt ttgaaagact tggtcgtaac aaagaaattg   2160
gtgaacagat cgccaagaaa attcaacagg caggggaata tgctaagctt gacccttacc   2220
gcgcggcaac ccataacaag gggattatga acggtatcga agccgtcgtt gccgcaacgg   2280
gaaacgacac acgggctgtt tccgcttcta ttcacgcata cgccgcccgt aatggcttgt   2340
accaaggttt aacggattgg cagatcaagg gcgataaact ggttggtaaa ttaacagtcc   2400
cactggctgt ggcgactgtc ggtggcgcgt cgaacatatt accaaaagcc aaagcttccc   2460
tcgccatgct ggatattgat tccgcaaaag aactggccca agtgatcgcc gcggtaggtt   2520
tagcacagaa tctggcggcg ttacgtgcat tagtgacaga aggcattcag aaaggacaca   2580
tgggcttgca agcacgttct ttagcgattt cgataggtgc catcggtgag gagatagagc   2640
aagtcgcgaa aaaactgcgt gaagctgaaa aaatgaatca gcaaacggca atacagattt   2700
tagaaaaaat tcgcgagaaa tgatctagac gcactaggag gatataccaa tgaaaatcgg   2760
tattgaccgt ctgtccttct tcatcccgaa tttgtatttg gacatgactg agctggcaga   2820
atcacgcggg gatgatccag ctaaatatca tattggaatc ggacaagatc agatggcagt   2880
gaatcgcgca aacgaggaca tcataacact gggtgcaaac gctgcgagta agatcgtgac   2940
agagaaagac cgcgagttga ttgatatggt aatcgttggc acggaatcag gaattgacca   3000
ctccaaagca agcgccgtga ttattcacca tctccttaaa attcagtcgt tcgcccgttc   3060
tttcgaggta aaagaagctt gctatggcgg aactgctgcc ctgcacatgg cgaaggagta   3120
tgtcaaaaat catccggagc gtaaggtctt ggtaattgcg tcagacatcg cgcgttatgg   3180
tttggccagc ggaggagaag ttactcaagg cgtgggggcc gtagccatga tgattacaca   3240 aaaccccgg attctttcga ttgaagacga tagtgttttt ctcacagagg atatctatga   3300
tttctggcgg cctgattact ccgagttccc tgtagtggac gggccccttt caaactcaac   3360
gtatatagag agttttcaga agtttggaa ccggcacaag gaattgtccg gaagagggct   3420
ggaagattat caagctattg cttttcacat accctatacg aagatgggta agaaagcgct   3480
ccagagtgtt ttagaccaaa ccgatgaaga taaccaggag cgcttaatgg ctagatatga   3540
ggagtctatt cgctatagcc ggagaattgg taacctgtac acaggcagct tgtaccttgg   3600
tcttacaagc ttgttggaaa actctaaaag tttacaaccg ggagatcgga tcggcctctt   3660
ttcctatggc agtggtgcgg tgtccgagtt ctttaccggg tatttagaag aaaattacca   3720
agagtacctg ttcgctcaaa gccatcaaga aatgctggat agccggactc ggattacggt   3780
cgatgaatac gagaccatct tttcagagac tctgccagaa catggtgaat gcgccgaata   3840
tacgagcgac gtcccctttt ctataaccaa gattgagaac gacattcgtt attataaaat   3900
ctgactgcag ctggtaccat atgggaattc gaagcttggg cccgaacaaa aactcatctc   3960
agaagaggat ctgaatagcg ccgtcgacca tcatcatcat catcattgag tttaaacggt   4020
ctccagcttg gctgttttgg cggatgagag aagattttca gcctgataca gattaaatca   4080
gaacgcagaa gcggtctgat aaaacagaat ttgcctggcg gcagtagcgc ggtggtccca   4140
cctgacccca tgccgaactc agaagtgaaa cgccgtagcg ccgatggtag tgtgggtct   4200 ccccatgcga gagtagggaa ctgccaggca tcaaataaaa cgaaaggctc agtcgaaaga   4260
```

```
ctgggccttt cgttttatct gttgtttgtc ggtgaacgct ctcctgagta ggacaaatcc    4320
gccgggagcg gatttgaacg ttgcgaagca acggcccgga gggtggcggg caggacgccc    4380
gccataaact gccaggcatc aaattaagca gaaggccatc ctgacggatg cctttttgc    4440 gtttctacaa actctttttg tttattttc taaatacatt caaatatgta tccgctcatg    4500
agacaataac cctgataaat gcttcaataa tctggcgtaa tagcgaagag cccgcaccg    4560 atcgcccttc ccaacagttg cgcagcctga atggcgaatg gcgcctgatg cggtattttc    4620
tccttacgca tctgtgcggt atttcacacc gcatatggtg cactctcagt acaatctgct    4680
ctgatgccgc atagttaagc cagccccgac acccgccaac acccgctgac gagcttagta    4740
aagccctcgc tagattttaa tgcggatgtt gcgattactt cgccaactat gcgataaca    4800 agaaaaagcc agcctttcat gatatatctc ccaatttgtg tagggcttat tatgcacgct    4860
taaaaataat aaaagcagac ttgacctgat agtttggctg tgagcaatta tgtgcttagt    4920
gcatctaacg cttgagttaa gccgcgccgc gaagcggcgt cggcttgaac gaattgttag    4980
acattatttg ccgactacct tggtgatctc gcctttcacg tagtggacaa attcttccaa    5040
ctgatctgcg cgcgaggcca agcgatcttc ttcttgtcca agataagcct gtctagcttc    5100
aagtatgacg ggctgatact gggccggcag gcgctccatt gcccagtcgg cagcgacatc    5160
cttcggcgcg attttgccgg ttactgcgct gtaccaaatg cgggacaacg taagcactac    5220
atttcgctca tcgccagccc agtcgggcgg cgagttccat agcgttaagg tttcatttag    5280
cgcctcaaat agatcctgtt caggaaccgg atcaaagagt tcctccgccg ctggacctac    5340
caaggcaacg ctatgttctc ttgcttttgt cagcaagata gccagatcaa tgtcgatcgt    5400
ggctggctcg aagatacctg caagaatgtc attgcgctgc cattctccaa attgcagttc    5460
gcgcttagct ggataacgcc acggaatgat gtcgtcgtgc acaacaatgg tgacttctac    5520
agcgcggaga atctcgctct ctccagggga agccgaagtt ccaaaaggt cgttgatcaa    5580 agctcgccgc gttgtttcat caagccttac ggtcaccgta accagcaaat caatatcact    5640
gtgtggcttc aggccgccat ccactgcgga gccgtacaaa tgtacggcca gcaacgtcgg    5700
ttcgagatgg cgctcgatga cgccaactac ctctgatagt tgagtcgata cttcggcgat    5760
caccgcttcc ctcatgatgt ttaactttgt tttagggcga ctgccctgct gcgtaacatc    5820
gttgctgctc cataacatca aacatcgacc cacggcgtaa cgcgcttgct gcttggatgc    5880
ccgaggcata gactgtaccc caaaaaaaca gtcataacaa gccatgaaaa ccgccactgc    5940
gccgttacca ccgctgcgtt cggtcaaggt tctggaccag ttgcgtgagc gcatacgcta    6000
cttgcattac agcttacgaa ccgaacaggc ttatgtccac tgggttcgtg ccttcatccg    6060
tttccacggt gtgcgtcacc cggcaacctt gggcagcagc gaagtcgagg catttctgtc    6120
ctggctggcg aacgagcgca aggtttcggt ctccacgcat cgtcaggcat tggcggcctt    6180
gctgttcttc tacggcaagg tgctgtgcac ggatctgccc tggcttcagg atcggaag    6240 acctcggccg tcgcggcgct tgccggtggt gctgaccccg gatgaagtgg ttcgcatcct    6300
cggttttctg gaaggcgagc atcgtttgtt cgcccagctt ctgtatggaa cgggcatgcg    6360
gatcagtgag ggtttgcaac tgcgggtcaa ggatctggat ttcgatcacg gcacgatcat    6420
cgtgcgggag ggcaagggct ccaaggatcg ggccttgatg ttacccgaga gcttggcacc    6480
cagcctgcgc gagcagggga attaattccc acgggttttg ctgcccgcaa acgggctgtt    6540
ctggtgttgc tagtttgtta tcagaatcgc agatccggct tcagccggtt tgccggctga    6600
```

```
aagcgctatt tcttccagaa ttgccatgat ttttcccca cgggaggcgt cactggctcc    6660
cgtgttgtcg gcagctttga ttcgataagc agcatcgcct gtttcaggct gtctatgtgt    6720
gactgttgag ctgtaacaag ttgtctcagg tgttcaattt catgttctag ttgctttgtt    6780
ttactggttt cacctgttct attaggtgtt acatgctgtt catctgttac attgtcgatc    6840
tgttcatggt gaacagcttt gaatgcacca aaaactcgta aaagctctga tgtatctatc    6900
ttttttacac cgttttcatc tgtgcatatg gacagttttc cctttgatat gtaacggtga    6960
acagttgttc tacttttgtt tgttagtctt gatgcttcac tgatagatac aagagccata    7020
agaacctcag atccttccgt atttagccag tatgttctct agtgtggttc gttgtttttg    7080
cgtgagccat gagaacgaac cattgagatc atacttactt tgcatgtcac tcaaaaattt    7140
tgcctcaaaa ctggtgagct gaattttgc agtaaagca tcgtgtagtg ttttcttag      7200 tccgttatgt aggtaggaat ctgatgtaat ggttgttggt attttgtcac cattcatttt    7260
tatctggttg ttctcaagtt cggttacgag atccatttgt ctatctagtt caacttggaa    7320
aatcaacgta tcagtcgggc ggcctcgctt atcaaccacc aatttcatat tgctgtaagt    7380
gtttaaatct ttacttattg gtttcaaaac ccattggtta agcctttaa actcatggta     7440 gttattttca agcattaaca tgaacttaaa ttcatcaagg ctaatctcta tatttgcctt    7500
gtgagttttc ttttgtgtta gttctttaa taaccactca taaatcctca tagagtattt     7560
gttttcaaaa gacttaacat gttccagatt atatttatg aatttttta actggaaaag      7620 ataaggcaat atctcttcac taaaaactaa ttctaatttt tcgcttgaga acttggcata    7680
gtttgtccac tggaaaatct caaagccttt aaccaaagga ttcctgattt ccacagttct    7740
cgtcatcagc tctctggttg ctttagctaa taccataa gcattttccc tactgatgtt     7800
catcatctga gcgtattggt tataagtgaa cgataccgtc cgttctttcc ttgtagggtt    7860
ttcaatcgtg gggttgagta gtgccacaca gcataaaatt agcttggttt catgctccgt    7920
taagtcatag cgactaatcg ctagttcatt tgctttgaaa acaactaatt cagacataca    7980
tctcaattgg tctaggtgat tttaatcact ataccaattg agatgggcta gtcaatgata    8040
attactagtc cttttccttt gagttgtggg tatctgtaaa ttctgctaga cctttgctgg    8100
aaaacttgta aattctgcta gaccctctgt aaattccgct agacctttgt gtgttttttt    8160
tgtttatatt caagtggtta taatttatag aataaagaaa gaataaaaaa agataaaaag    8220
aatagatccc agccctgtgt ataactcact actttagtca gttccgcagt attacaaaag    8280
gatgtcgcaa acgctgtttg ctcctctaca aaacagacct taaaacccta aaggcttaag    8340
tagcaccctc gcaagctcgg gcaaatcgct gaatattcct tttgtctccg accatcaggc    8400
acctgagtcg ctgtcttttt cgtgacattc agttcgctgc gctcacggct ctggcagtga    8460
atgggggtaa atggcactac aggcgccttt tatggattca tgcaaggaaa ctacccataa    8520
tacaagaaaa gcccgtcacg ggcttctcag ggcgttttat ggcgggtctg ctatgtggtg    8580
ctatctgact ttttgctgtt cagcagttcc tgccctctga ttttccagtc tgaccacttc    8640
ggattatccc gtgacaggtc attcagactg gctaatgcac ccagtaaggc agcggtatca    8700
tcaacaggct ta                                                       8712
```

<210> SEQ ID NO 23  
<211> LENGTH: 8719  
<212> TYPE: DNA  
<213> ORGANISM: Artificial Sequence  
<220> FEATURE:  
<223> OTHER INFORMATION: Synthetic Construct

<400> SEQUENCE: 23

```
cccgtcttac tgtcgggaat tcgcgttggc cgattcatta atgcagattc tgaaatgagc    60
tgttgacaat taatcatccg gctcgtataa tgtgtggaat tgtgagcgga taacaatttc   120
acacaggaaa cagcgccgct gagaaaaagc gaagcggcac tgctctttaa caatttatca   180
gacaatctgt gtgggcactc gaccggaatt atcgattaac tttattatta aaaattaaag   240
aggtatatat taatgtatcg attaaataag gaggaataaa ccatggaaga agtggtaatt   300
atagatgcac gtcggactcc gattggtaaa tatcacgggt cgttgaagaa gttttcagcg   360
gtggcgctgg gacgccgt ggctaaagac atgttcgaac gcaaccagaa atcaaagag      420
gagatcgcgc aggtcataat tggtaatgtc ttgcaggcag gaaatggcca gaaccccgcg   480
cggcaagttg ctcttcaatc agggttgtcc gttgacattc ccgcttctac aattaacgag   540
gtttgtgggt ctggtttgaa agctatcttg atgggcatgg aacaaatcca actcggcaaa   600
gcgcaagtag tgctggcagg cggcattgaa tcaatgacaa atgcgccaag cctgtcccac   660
tataacaagg cggaggatac gtatagtgtc ccagtgtcga gcatgacact ggatggtctg   720
acagacgcat tttctagtaa acctatggga ttaacagcgg aaaacgtcgc acagcgctac   780
ggtatctccc gtgaggcgca agatcaattc gcatatcaat ctcagatgaa agcagcaaaa   840
gcgcaggcag aaaacaaatt cgctaaggaa attgtgccac tggcgggtga aactaaaacc   900
atcacagctg acgaagggat cagatcccaa acaacgatgg agaaactggc aagtctcaaa   960
cctgttttta aaaccgatgg cactgtaacc gcagggaatg ctagcaccat taatgacggg  1020
gccgcccttg tgctgcttgc tagcaaaact tactgcgaaa ctaatgacat accgtacctt  1080
gcgacaatca aagaaattgt tgaagttgga atcgatccgg agattatggg catctctccg  1140
ataaaagcga tacaaacatt gttacaaaat caaaaagtta gcctcgaaga tattggagtt  1200
tttgaaataa atgaagcctt tgccgcaagt agcatagtgg ttgaatctga gttgggatta  1260
gatccggcta aagttaaccg ttatggggt ggtatatcct taggtcatgc aattgggca   1320
accggcgctc gcctggccac ttcactggtg tatcaaatgc aggagataca agcacgttat  1380
ggtattgcga gcctgtgcgt tggtggtgga cttggactgg caatgctttt agaacgtcca  1440
actattgaga aggctaaacc gacagacaaa aagttctatg aattgtcacc agctgaacgg  1500
ttgcaagagc tggaaaatca acagaaaatc agttctgaaa ctaaacagca gttatctcag  1560
atgatgcttg ccgaggacac tgcaaaccat ttgatagaaa atcaaatatc agagattgaa  1620
ctcccaatgg gcgtcgggat gaacctgaag gttgatggga agcctatgt tgtgccaatg   1680
gcgacggaag agccgtccgt catcgcggcc atgtctaatg gtgccaaaat ggccggcgaa  1740
attcacactc agtcgaaaga acggctgctc agaggtcaga ttgttttcag cgcgaagaat  1800
ccgaatgaaa tcgaacagag aatagctgag aaccaagctt tgattttcga acgtgccgaa  1860
cagtcctatc cttccattgt gaaaagagag ggaggtctcc gccgcattgc acttcgtcat  1920
tttcctgccg attctcagca ggagtctgcg gaccagtcca cattttatc agtggacctt   1980
tttgtagatg tgaaagacgc gatgggggca aatatcataa atgcaatact tgagggcgtc  2040
gcagccctgt ttcgcgaatg gttccccaat gaggaaattc ttttttctat tctctcgaac  2100
ttggctacgg agagcttagt cacggctgtt tgtgaagtcc catttagtgc acttagcaag  2160
agaggtggtg caacggtggc ccagaaaatt gtgcaggcgt cgctcttcgc aaagacagac  2220
ccataccgcg cagtgaccca caacaagggg attatgaacg gtgtagaggc tgttatgctt  2280
```

```
gccacaggca acgacacgcg cgcagtctca gccgcttgtc atggatacgc agcgcgcacc    2340
ggtagctatc agggtctgac taactggacg attgagtcgg atcgcctggt aggcgagata    2400
acactgccgc tggccatcgc tacagttgga ggcgctacca aagtgttgcc caaagctcaa    2460
gcggcactgg agattagtga tgttcactct tctcaagagc ttgcagcctt agcggcgtca    2520
gtaggtttag tacaaaatct cgcggccctg cgcgcactgg tttccgaagg tatacaaaaa    2580
gggcacatgt ccatgcaagc ccggtctctc gcaatcgcgg tcggtgctga aaaagccgag    2640
atcgagcagg tcgccgaaaa gttgcggcag aacccgccaa tgaatcagca gcaggcgctc    2700
cgttttcttg gcgagatccg cgaacaatga tctagacgca ctaggaggat ataccaatga    2760
acgtcggcat tgacaaaatt aattttttcg ttccaccgta ttatctggat atggtcgacc    2820
tggcccacgc acgcgaagtg gacccgaaca aatttacaat ggaattgga caggatcaga    2880 tggctgtgag caaaaagacg cacgatatcg taacattcgc ggctagtgcc gcgaaggaaa    2940
ttttagaacc tgaggacttg caagctatag acatggttat agttggtacc gaatcgggca    3000
ttgacgagag caaagcatcc gcggtcgttt tacatcgttt gttgggcgta caacctttcg    3060
ctcgcagttt tgaaattaaa gaagcctgtt acggggcaac cgcaggcatt cagtttgcca    3120
agactcatat acaagcgaac ccggagagca aggtcctggt aattgcaagc gatatagctc    3180
ggtatggtct tcggtcaggt ggagagccca cacaaggcgc aggggcagtt gctatgcttc    3240
tcacggcaaa tcccagaatc ctgaccttcg aaaacgacaa tctgatgtta acgcaggata    3300
tttatgactt ctggagacca cttggtcacg cttaccctat ggtagatggc cacctttcca    3360
atcaagtcta tattgacagt tttaagaagg tctggcaagc acattgcgaa cgcaatcaag    3420
cttctatatc cgactatgcc gcgattagtt ttcatattcc gtatacaaaa atgggtaaga    3480
aagccctgct cgctgttttt gcagatgaag tggaaactga acaggaacgc gttatggcac    3540
ggtatgaaga gtctatcgta tattcacgcc ggatcggcaa cttgtatacg ggatcattgt    3600
acctggggct gatatcctta ttggaaaaca gttctcacct gtcggcgggc gaccggatag    3660
gattgtttag ttatgggagt ggcgctgtca gcgaattttt ctccggtcgt ttagtggcag    3720
gctatgaaaa tcaattgaac aaagaggcgc atacccagct cctggatcag cgtcagaagc    3780
tttccatcga agagtatgag gcgattttta cagattcctt agaaattgat caggatgcag    3840
cgttctcgga tgacctgcca tattccatcc gcgagataaa aaacacgatt cggtactata    3900
aggagagctg actgcagctg gtaccatatg ggaattcgaa gcttgggccc gaacaaaaac    3960
tcatctcaga agaggatctg aatagcgccg tcgaccatca tcatcatcat cattgagttt    4020
aaacggtctc cagcttggct gttttggcgg atgagagaag attttcagcc tgatacagat    4080
taaatcagaa cgcagaagcg gtctgataaa acagaatttg cctggcggca gtagcgcggt    4140
ggtcccacct gaccccatgc cgaactcaga agtgaaacgc cgtagcgccg atggtagtgt    4200
ggggtctccc catgcgagag tagggaactg ccaggcatca aataaaacga aaggctcagt    4260
cgaaagactg ggcctttcgt tttatctgtt gtttgtcggt gaacgctctc ctgagtagga    4320
caaatccgcc gggagcggat ttgaacgttg cgaagcaacg gcccggaggg tggcgggcag    4380
gacgcccgcc ataaactgcc aggcatcaaa ttaagcagaa ggccatcctg acggatggcc    4440 ttttttgcgtt tctacaaact cttttttgttt attttttctaa atacattcaa atatgtatcc    4500
gctcatgaga caataaccct gataaatgct tcaataatct ggcgtaatag cgaagaggcc    4560
cgcaccgatc gcccttccca acagttgcgc agcctgaatg gcgaatggcg cctgatgcgg    4620
tattttctcc ttacgcatct gtgcggtatt tcacaccgca tatggtgcac tctcagtaca    4680
```

```
atctgctctg atgccgcata gttaagccag ccccgacacc cgccaacacc cgctgacgag   4740
cttagtaaag ccctcgctag attttaatgc ggatgttgcg attacttcgc caactattgc   4800
gataacaaga aaaagccagc ctttcatgat atatctccca atttgtgtag ggcttattat   4860
gcacgcttaa aaataataaa agcagacttg acctgatagt ttggctgtga caattatgt    4920 gcttagtgca tctaacgctt gagttaagcc gcgccgcgaa gcggcgtcgg cttgaacgaa   4980
ttgttagaca ttatttgccg actaccttgg tgatctcgcc tttcacgtag tggacaaatt   5040
cttccaactg atctgcgcgc gaggccaagc gatcttcttc ttgtccaaga taagcctgtc   5100
tagcttcaag tatgacgggc tgatactggg ccggcaggcg ctccattgcc cagtcggcag   5160
cgacatcctt cggcgcgatt ttgccggtta ctgcgctgta ccaaatgcgg gacaacgtaa   5220
gcactacatt tcgctcatcg ccagcccagt cgggcggcga gttccatagc gttaaggttt   5280
catttagcgc ctcaaataga tcctgttcag gaaccggatc aaagagttcc tccgccgctg   5340
gacctaccaa ggcaacgcta tgttctcttg cttttgtcag caagatagcc agatcaatgt   5400
cgatcgtggc tggctcgaag atacctgcaa gaatgtcatt gcgctgccat tctccaaatt   5460
gcagttcgcg cttagctgga taacgccacg gaatgatgtc gtcgtgcaca acaatggtga   5520
cttctacagc gcggagaatc tcgctctctc cagggggaagc cgaagtttcc aaaaggtcgt   5580
tgatcaaagc tcgccgcgtt gtttcatcaa gccttacggt caccgtaacc agcaaatcaa   5640
tatcactgtg tggcttcagg ccgccatcca ctgcggagcc gtacaaatgt acggccagca   5700
acgtcggttc gagatggcgc tcgatgacgc caactacctc tgatagttga gtcgatactt   5760
cggcgatcac cgcttccctc atgatgttta actttgtttt agggcgactg ccctgctgcg   5820
taacatcgtt gctgctccat aacatcaaac atcgacccac ggcgtaacgc gcttgctgct   5880
tggatgcccg aggcatagac tgtaccccaa aaaaacagtc ataacaagcc atgaaaaccg   5940
ccactgcgcc gttaccaccg ctgcgttcgg tcaaggttct ggaccagttg cgtgagcgca   6000
tacgctactt gcattacagc ttacgaaccg aacaggctta tgtccactgg gttcgtgcct   6060
tcatccgttt ccacggtgtg cgtcacccgg caaccttggg cagcagcgaa gtcgaggcat   6120
ttctgtcctg gctggcgaac gagcgcaagg tttcggtctc cacgcatcgt caggcattgg   6180
cggccttgct gttcttctac ggcaaggtgc tgtgcacgga tctgccctgg cttcaggaga   6240
tcggaagacc tcggccgtcg cggcgcttgc cggtggtgct gaccccggat gaagtggttc   6300
gcatcctcgg ttttctggaa ggcgagcatc gtttgttcgc ccagcttctg tatggaacgg   6360
gcatgcggat cagtgagggt ttgcaactgc gggtcaagga tctggatttc gatcacggca   6420
cgatcatcgt gcgggagggc aagggctcca aggatcgggc cttgatgtta cccgagagct   6480
tggcacccag cctgcgcgag caggggaatt aattcccacg ggttttgctg cccgcaaacg   6540
ggctgttctg gtgttgctag tttgttatca gaatcgcaga tccggcttca gccggtttgc   6600
cggctgaaag cgctatttct tccagaattg ccatgatttt ttccccacgg gaggcgtcac   6660
tggctcccgt gttgtcggca gctttgattc gataagcagc atcgcctgtt tcaggctgtc   6720
tatgtgtgac tgttgagctg taacaagttg tctcaggtgt tcaatttcat gttctagttg   6780
ctttgtttta ctggtttcac ctgttctatt aggtgttaca tgctgttcat ctgttacatt   6840
gtcgatctgt tcatggtgaa cagctttgaa tgcaccaaaa actcgtaaaa gctctgatgt   6900
atctatcttt tttacaccgt tttcatctgt gcatatggac agttttccct ttgatatgta   6960
acggtgaaca gttgttctac ttttgtttgt tagtcttgat gcttcactga tagatacaag   7020
```

| | |
|---|---|
| agccataaga acctcagatc cttccgtatt tagccagtat gttctctagt gtggttcgtt | 7080 |
| gttttttgcgt gagccatgag aacgaaccat tgagatcata cttactttgc atgtcactca | 7140 |
| aaaattttgc ctcaaaactg gtgagctgaa ttttttgcagt taaagcatcg tgtagtgttt | 7200 |
| ttcttagtcc gttatgtagg taggaatctg atgtaatggt tgttggtatt ttgtcaccat | 7260 |
| tcattttat ctggttgttc tcaagttcgg ttacgagatc catttgtcta tctagttcaa | 7320 |
| cttggaaaat caacgtatca gtcgggcggc ctcgcttatc aaccaccaat ttcatattgc | 7380 |
| tgtaagtgtt taaatctta cttattggtt tcaaaaccca ttggttaagc cttttaaact | 7440 |
| catggtagta attttcaagc attaacatga acttaaattc atcaaggcta atctctatat | 7500 |
| ttgccttgtg agttttctt tgtgttagtt cttttaataa ccactcataa atcctcatag | 7560 |
| agtatttgtt ttcaaaagac ttaacatgtt ccagattata ttttatgaat tttttaact | 7620 |
| ggaaaagata aggcaatatc tcttcactaa aaactaattc taattttcg cttgagaact | 7680 |
| tggcatagtt tgtccactgg aaaatctcaa agcctttaac caaaggattc ctgatttcca | 7740 |
| cagttctcgt catcagctct ctggttgctt tagctaatac accataagca ttttccctac | 7800 |
| tgatgttcat catctgagcg tattggttat aagtgaacga taccgtccgt tctttccttg | 7860 |
| tagggttttc aatcgtgggg ttgagtagtg ccacacagca taaaattagc ttggtttcat | 7920 |
| gctccgttaa gtcatagcga ctaatcgcta gttcatttgc tttgaaaaca actaattcag | 7980 |
| acatacatct caattggtct aggtgatttt aatcactata ccaattgaga tgggctagtc | 8040 |
| aatgataatt actagtcctt ttcctttgag ttgtgggtat ctgtaaattc tgctagacct | 8100 |
| ttgctggaaa acttgtaaat tctgctagac cctctgtaaa ttccgctaga cctttgtgtg | 8160 |
| ttttttttgt ttatattcaa gtggttataa tttatagaat aaagaaagaa taaaaaaga | 8220 |
| taaaagaat agatcccagc cctgtgtata actcactact ttagtcagtt ccgcagtatt | 8280 |
| acaaaaggat gtcgcaaacg ctgtttgctc ctctacaaaa cagaccttaa aaccctaaag | 8340 |
| gcttaagtag caccctcgca agctcgggca aatcgctgaa tattccttt gtctccgacc | 8400 |
| atcaggcacc tgagtcgctg tcttttcgt gacattcagt tcgctgcgct cacggctctg | 8460 |
| gcagtgaatg ggggtaaatg gcactacagg cgccttttat ggattcatgc aaggaaacta | 8520 |
| cccataatac aagaaaagcc cgtcacgggc ttctcagggc gttttatggc gggtctgcta | 8580 |
| tgtggtgcta tctgactttt tgctgttcag cagttcctgc cctctgattt tccagtctga | 8640 |
| ccacttcgga ttatcccgtg acaggtcatt cagactggct aatgcaccca gtaaggcagc | 8700 |
| ggtatcatca acaggctta | 8719 |

<210> SEQ ID NO 24
<211> LENGTH: 73
<212> TYPE: DNA
<213> ORGANISM: Artificial Sequence
<220> FEATURE:
<223> OTHER INFORMATION: Synthetic Construct

<400> SEQUENCE: 24

| | |
|---|---|
| tatttaattt ttaatcatct aatttgacaa tcattcaaca aagttgttac aattaaccct | 60 |
| cactaaaggg cgg | 73 |

<210> SEQ ID NO 25
<211> LENGTH: 147
<212> TYPE: DNA
<213> ORGANISM: Artificial Sequence
<220> FEATURE:
<223> OTHER INFORMATION: Synthetic Construct

<400> SEQUENCE: 25
tcaacagctg tatccccgtt gagggtgagt tttgcttttg tatcagccat atattccacc    60
agctatttgt tagtgaataa aagtggttga attatttgct caggatgtgg cathgtcaag   120
ggctaatacg actcactata gggctcg                                       147

<210> SEQ ID NO 26
<211> LENGTH: 25
<212> TYPE: DNA
<213> ORGANISM: Artificial Sequence
<220> FEATURE:
<223> OTHER INFORMATION: Synthetic Construct

<400> SEQUENCE: 26
ggcagtatag gctgttcaca aaatc                                          25

<210> SEQ ID NO 27
<211> LENGTH: 23
<212> TYPE: DNA
<213> ORGANISM: Artificial Sequence
<220> FEATURE:
<223> OTHER INFORMATION: Synthetic Construct

<400> SEQUENCE: 27
cttgacccag cgtgcctttc agc                                            23

<210> SEQ ID NO 28
<211> LENGTH: 22
<212> TYPE: DNA
<213> ORGANISM: Artificial Sequence
<220> FEATURE:
<223> OTHER INFORMATION: Synthetic Construct

<400> SEQUENCE: 28
gtgcaaattc acaactcagc gg                                             22

<210> SEQ ID NO 29
<211> LENGTH: 22
<212> TYPE: DNA
<213> ORGANISM: Artificial Sequence
<220> FEATURE:
<223> OTHER INFORMATION: Synthetic Construct

<400> SEQUENCE: 29
caccaacgta tcgggcattg cc                                             22

<210> SEQ ID NO 30
<211> LENGTH: 24
<212> TYPE: DNA
<213> ORGANISM: Artificial Sequence
<220> FEATURE:
<223> OTHER INFORMATION: Synthetic Construct

<400> SEQUENCE: 30
ggcttaccgt ttacgctttc cagc                                           24

<210> SEQ ID NO 31
<211> LENGTH: 23
<212> TYPE: DNA
<213> ORGANISM: Artificial Sequence
<220> FEATURE:
<223> OTHER INFORMATION: Synthetic Construct

<400> SEQUENCE: 31
ctaatgcaat acgtgtcccg agc                                                  23

<210> SEQ ID NO 32
<211> LENGTH: 99
<212> TYPE: DNA
<213> ORGANISM: Artificial Sequence
<220> FEATURE:
<223> OTHER INFORMATION: Synthetic Construct

<400> SEQUENCE: 32
aaaattttca ttctgtgaca gagaaaaagt agccgaagat gacggtttgt cacatggagt         60
tggcaggatg tttgattaca tgggaattag ccatggtcc                                99

<210> SEQ ID NO 33
<211> LENGTH: 100
<212> TYPE: DNA
<213> ORGANISM: Artificial Sequence
<220> FEATURE:
<223> OTHER INFORMATION: Synthetic Construct

<400> SEQUENCE: 33
gaccagccgc gtaacctggc aaaatcggtt acggttgagt aataaatgga tgccctgcgt         60
aagcggggca ttttcttgg tgtaggctgg agctgcttcg                               100

<210> SEQ ID NO 34
<211> LENGTH: 20
<212> TYPE: DNA
<213> ORGANISM: Artificial Sequence
<220> FEATURE:
<223> OTHER INFORMATION: Synthetic Construct

<400> SEQUENCE: 34
gggtatgaaa gcgattctga                                                     20

<210> SEQ ID NO 35
<211> LENGTH: 20
<212> TYPE: DNA
<213> ORGANISM: Artificial Sequence
<220> FEATURE:
<223> OTHER INFORMATION: Synthetic Construct

<400> SEQUENCE: 35
agcccaaggc gctattaccg                                                     20

<210> SEQ ID NO 36
<211> LENGTH: 20
<212> TYPE: DNA
<213> ORGANISM: Artificial Sequence
<220> FEATURE:
<223> OTHER INFORMATION: Synthetic Construct

<400> SEQUENCE: 36
ggattagttc aaaatttggc                                                     20

<210> SEQ ID NO 37
<211> LENGTH: 20
<212> TYPE: DNA
<213> ORGANISM: Artificial Sequence
<220> FEATURE:
<223> OTHER INFORMATION: Synthetic Construct

<400> SEQUENCE: 37
cggttaatgg cacgttatga                                                     20

```
<210> SEQ ID NO 38
<211> LENGTH: 20
<212> TYPE: DNA
<213> ORGANISM: Artificial Sequence
<220> FEATURE:
<223> OTHER INFORMATION: Synthetic Construct

<400> SEQUENCE: 38
tcgttcgcct gtaaactgct                                              20

<210> SEQ ID NO 39
<211> LENGTH: 20
<212> TYPE: DNA
<213> ORGANISM: Artificial Sequence
<220> FEATURE:
<223> OTHER INFORMATION: Synthetic Construct

<400> SEQUENCE: 39
tgctctattt cagtaccttt                                              20

<210> SEQ ID NO 40
<211> LENGTH: 20
<212> TYPE: DNA
<213> ORGANISM: Artificial Sequence
<220> FEATURE:
<223> OTHER INFORMATION: Synthetic Construct

<400> SEQUENCE: 40
tgtaagttca ggcccacgcc                                              20

<210> SEQ ID NO 41
<211> LENGTH: 20
<212> TYPE: DNA
<213> ORGANISM: Artificial Sequence
<220> FEATURE:
<223> OTHER INFORMATION: Synthetic Construct

<400> SEQUENCE: 41
cctcagcctt gttgtaataa                                              20

<210> SEQ ID NO 42
<211> LENGTH: 45
<212> TYPE: DNA
<213> ORGANISM: Artificial Sequence
<220> FEATURE:
<223> OTHER INFORMATION: Synthetic Construct

<400> SEQUENCE: 42
aggaggaata aaccatgaaa acagtagtta ttattgatgc attac                  45

<210> SEQ ID NO 43
<211> LENGTH: 42
<212> TYPE: DNA
<213> ORGANISM: Artificial Sequence
<220> FEATURE:
<223> OTHER INFORMATION: Synthetic Construct

<400> SEQUENCE: 43
actactgttt tcatggttta ttcctcctta tttaatcgat ac                     42

<210> SEQ ID NO 44
<211> LENGTH: 42
<212> TYPE: DNA
<213> ORGANISM: Artificial Sequence
<220> FEATURE:
<223> OTHER INFORMATION: Synthetic Construct
```

<400> SEQUENCE: 44
aggaggaata aaccatggaa gaagttgtca tcattgacgc ac                42

<210> SEQ ID NO 45
<211> LENGTH: 35
<212> TYPE: DNA
<213> ORGANISM: Artificial Sequence
<220> FEATURE:
<223> OTHER INFORMATION: Synthetic Construct

<400> SEQUENCE: 45
acttcttcca tggtttattc ctccttattt aatcg                       35

<210> SEQ ID NO 46
<211> LENGTH: 38
<212> TYPE: DNA
<213> ORGANISM: Artificial Sequence
<220> FEATURE:
<223> OTHER INFORMATION: Synthetic Construct

<400> SEQUENCE: 46
cataagcttg tcgacccatg cgagagtagg gaactgcc                    38

<210> SEQ ID NO 47
<211> LENGTH: 34
<212> TYPE: DNA
<213> ORGANISM: Artificial Sequence
<220> FEATURE:
<223> OTHER INFORMATION: Synthetic Construct

<400> SEQUENCE: 47
catctgcagt ctcatgagcg gatacatatt tgaa                        34

<210> SEQ ID NO 48
<211> LENGTH: 33
<212> TYPE: DNA
<213> ORGANISM: Artificial Sequence
<220> FEATURE:
<223> OTHER INFORMATION: Synthetic Construct

<400> SEQUENCE: 48
catggatccc gattaaataa ggaggaataa acc                         33

<210> SEQ ID NO 49
<211> LENGTH: 33
<212> TYPE: DNA
<213> ORGANISM: Artificial Sequence
<220> FEATURE:
<223> OTHER INFORMATION: Synthetic Construct

<400> SEQUENCE: 49
gtcactcgag ggtaccagct gcagatctct tag                         33

<210> SEQ ID NO 50
<211> LENGTH: 32
<212> TYPE: DNA
<213> ORGANISM: Artificial Sequence
<220> FEATURE:
<223> OTHER INFORMATION: Synthetic Construct

<400> SEQUENCE: 50
gtcactcgag catatggtac cagctgcagt ca                          32

<210> SEQ ID NO 51
<211> LENGTH: 35

```
<212> TYPE: DNA
<213> ORGANISM: Artificial Sequence
<220> FEATURE:
<223> OTHER INFORMATION: Synthetic Construct

<400> SEQUENCE: 51
catctgcagt aagtcgtatt ggcaccacta ctcac                                35

<210> SEQ ID NO 52
<211> LENGTH: 48
<212> TYPE: DNA
<213> ORGANISM: Artificial Sequence
<220> FEATURE:
<223> OTHER INFORMATION: Synthetic Construct

<400> SEQUENCE: 52
catctgcagc atatgatcct agggcttgac aaaataagtc atcctctc                   48

<210> SEQ ID NO 53
<211> LENGTH: 30
<212> TYPE: DNA
<213> ORGANISM: Artificial Sequence
<220> FEATURE:
<223> OTHER INFORMATION: Synthetic Construct

<400> SEQUENCE: 53
catcctagga ggaggagaaa aaaaaccatg                                       30

<210> SEQ ID NO 54
<211> LENGTH: 33
<212> TYPE: DNA
<213> ORGANISM: Artificial Sequence
<220> FEATURE:
<223> OTHER INFORMATION: Synthetic Construct

<400> SEQUENCE: 54
catcatatgt tacaacattc tgtgaatttg tcg                                   33

<210> SEQ ID NO 55
<211> LENGTH: 42
<212> TYPE: DNA
<213> ORGANISM: Artificial Sequence
<220> FEATURE:
<223> OTHER INFORMATION: Synthetic Construct

<400> SEQUENCE: 55
caatctcgag actagtcaaa ggaggtaaaa aaacatggta tc                         42

<210> SEQ ID NO 56
<211> LENGTH: 44
<212> TYPE: DNA
<213> ORGANISM: Artificial Sequence
<220> FEATURE:
<223> OTHER INFORMATION: Synthetic Construct

<400> SEQUENCE: 56
gttactcgag gtttaaactt attcctttgg tagaccagtc tttg                       44

<210> SEQ ID NO 57
<211> LENGTH: 25
<212> TYPE: DNA
<213> ORGANISM: Artificial Sequence
<220> FEATURE:
<223> OTHER INFORMATION: Synthetic Construct

<400> SEQUENCE: 57
```
gtggcctggg aaatgggaaa agctg								25

<210> SEQ ID NO 58
<211> LENGTH: 24
<212> TYPE: DNA
<213> ORGANISM: Artificial Sequence
<220> FEATURE:
<223> OTHER INFORMATION: Synthetic Construct

<400> SEQUENCE: 58
cccccaatca taagtccacg ttta								24

<210> SEQ ID NO 59
<211> LENGTH: 26
<212> TYPE: DNA
<213> ORGANISM: Artificial Sequence
<220> FEATURE:
<223> OTHER INFORMATION: Synthetic Construct

<400> SEQUENCE: 59
cagatattgg aagtgctact tacggc								26

<210> SEQ ID NO 60
<211> LENGTH: 26
<212> TYPE: DNA
<213> ORGANISM: Artificial Sequence
<220> FEATURE:
<223> OTHER INFORMATION: Synthetic Construct

<400> SEQUENCE: 60
tgcggtaacg gatgctgtgt aaacgg								26

<210> SEQ ID NO 61
<211> LENGTH: 24
<212> TYPE: DNA
<213> ORGANISM: Artificial Sequence
<220> FEATURE:
<223> OTHER INFORMATION: Synthetic Construct

<400> SEQUENCE: 61
caaccgaggt cacgaccact gccg								24

<210> SEQ ID NO 62
<211> LENGTH: 24
<212> TYPE: DNA
<213> ORGANISM: Artificial Sequence
<220> FEATURE:
<223> OTHER INFORMATION: Synthetic Construct

<400> SEQUENCE: 62
gaacacgggt acgcagttcc accg								24

<210> SEQ ID NO 63
<211> LENGTH: 25
<212> TYPE: DNA
<213> ORGANISM: Artificial Sequence
<220> FEATURE:
<223> OTHER INFORMATION: Synthetic Construct

<400> SEQUENCE: 63
gatgttgcca gagtgatttt aactc								25

<210> SEQ ID NO 64
<211> LENGTH: 26
<212> TYPE: DNA
<213> ORGANISM: Artificial Sequence

```
<220> FEATURE:
<223> OTHER INFORMATION: Synthetic Construct

<400> SEQUENCE: 64
gaaactggtt gggaataact tgagcc                                          26
```

PRODUCTION OF MEVALONATE, ISOPRENE, AND ISOPRENOIDS USING GENES ENCODING POLYPEPTIDES HAVING THIOLASE, HMG-COA SYNTHASE AND HMG-COA REDUCTASE ENZYMATIC ACTIVITIES

CROSS-REFERENCE TO RELATED APPLICATIONS

This application is a divisional of U.S. patent application Ser. No. 14/514,962, filed Oct. 15, 2014, which is a continuation of U.S. patent application Ser. No. 13/459,033, filed Apr. 27, 2012, now U.S. Pat. No. 8,889,383, issued on Nov. 18, 2014, which claims priority to U.S. Provisional Application No. 61/481,098 filed Apr. 29, 2011, the disclosures of which are herein incorporated by reference in their entirety.

SUBMISSION OF SEQUENCE LISTING ON ASCII TEXT FILE

The Sequence Listing submitted in an ASCII text file, in accordance with 37 C.F.R. § 1.821(c) and (e), is incorporated herein by reference. The text file name is 048768-513D01US_SL_ST25.txt, the date of creation of the text file is May 20, 2019, and the size of the ASCII text file is 106,036 bytes.

FIELD OF THE INVENTION

This disclosure relates to compositions and methods for the increased production of mevalonate, isoprene, isoprenoids and isoprenoid precursor molecules in microorganisms, as well as methods for producing the same.

BACKGROUND OF THE INVENTION

R-Mevalonate is an intermediate of the mevalonate-dependent biosynthetic pathway that converts acetyl-CoA to isopentenyl diphosphate and dimethylallyl diphosphate. The conversion of acetyl-CoA to mevalonate can be catalyzed by the thiolase, HMG-CoA synthase and the HMG-CoA reductase activities of the upper mevalonate-dependent biosynthetic pathway (MVA pathway). Based on molar conversion of glucose to acetyl-CoA via glycolysis, the theoretical mass yield for the production of mevalonate using the upper MVA pathway enzymes thiolase, HMG-CoA synthase and the HMG-CoA reductase is 54.8%.

Commercially, mevalonate has been used as an additive in cosmetics, for the production of biodegradable polymers, and can have value as a chiral building block for the synthesis of other chemicals.

The products of the mevalonate-dependent pathway are isopentenyl pyrophosphate (IPP) and dimethylallyl diphosphate (DMAPP). IPP and DMAPP are precursors to isoprene as well as isoprenoids. Isoprene (2-methyl-1,3-butadiene) is the monomer of natural rubber and also a common structural motif to an immense variety of other naturally occurring compounds, collectively termed the isoprenoids. Isoprene is additionally the critical starting material for a variety of synthetic polymers, most notably synthetic rubbers.

Isoprenoids are compounds derived from the isoprenoid precursor molecules IPP and DMAPP. Over 29,000 isoprenoid compounds have been identified and new isoprenoids are being discovered each year. Isoprenoids can be isolated from natural products, such as microorganisms and species of plants that use isoprenoid precursor molecules as a basic building block to form the relatively complex structures of isoprenoids. Isoprenoids are vital to most living organisms and cells, providing a means to maintain cellular membrane fluidity and electron transport. In nature, isoprenoids function in roles as diverse as natural pesticides in plants to contributing to the scents associated with cinnamon, cloves, and ginger. Moreover, the pharmaceutical and chemical communities use isoprenoids as pharmaceuticals, nutraceuticals, flavoring agents, and agricultural pest control agents. Given their importance in biological systems and usefulness in a broad range of applications, isoprenoids have been the focus of much attention by scientists.

Conventional means for obtaining mevalonate and isoprenoids include extraction from biological materials (e.g., plants, microbes, and animals) and partial or total organic synthesis in the laboratory. Such means, however, have generally proven to be unsatisfactory. In particular for isoprenoids, given the often times complex nature of their molecular structure, organic synthesis is impractical given that several steps are usually required to obtain the desired product. Additionally, these chemical synthesis steps can involve the use of toxic solvents as can extraction of isoprenoids from biological materials. Moreover, these extraction and purification methods usually result in a relatively low yield of the desired isoprenoid, as biological materials typically contain only minute amounts of these molecules. Unfortunately, the difficulty involved in obtaining relatively large amounts of isoprenoids has limited their practical use.

Methods for the production of isoprene and isoprenoids at rates, titers, and purities have been disclosed (see, for example, International Patent Application Publication No. WO 2009/076676 A2 and U.S. Pat. No. 7,915,026). However, improvements to increase the production of isoprene and isoprenoids and to increase yields of the same are still needed.

Such improvements are provided herein by the disclosure of compositions and methods to increase production of mevalonate as an intermediate of the mevalonate-dependent biosynthetic pathway as well as to increase production of molecules derived from mevalonate, such as isoprene, isoprenoid precursors, and/or isoprenoids.

Throughout this specification, various patents, patent applications and other types of publications (e.g., journal articles) are referenced. The disclosure of all patents, patent applications, and publications cited herein are hereby incorporated by reference in their entirety for all purposes.

SUMMARY OF THE INVENTION

The invention provided herein discloses, inter alia, compositions and methods for the increased production of isoprene by recombinant cells. The invention also provides compositions ad methods for the increased production of mevalonate, isoprenoid precursor molecules, and/or isoprenoids in microorganisms by the expression (e.g., heterologous expression) of the mvaE and mvaS genes from the organisms *Listeria grayi* DSM 20601, *Enterococcus faecium*, *Enterococcus gallinarum* EG2, and *Enterococcus casseliflavus*.

Accordingly, provided herein are recombinant cells capable of increased production of isoprene, the cells comprising one or more heterologous nucleic acids comprising nucleotide sequences selected from the group consisting of: a mvaE gene and a mvaS gene from *E. gallinarum*; a mvaE gene and a mvaS gene from *E. casseliflavus*; a mvaE gene and a mvaS gene from *E. faecium*; and a mvaE gene and a mvaS gene from *L. grayi*, wherein said mvaE gene and mvaS gene encode polypeptides having thiolase, HMG-CoA synthase, and HMG-CoA reductase catalytic activities, and wherein the cells further comprise: one or more nucleic acids encoding polypeptides of the lower MVA pathway; and a heterologous nucleic acid encoding an isoprene synthase polypeptide, wherein the cells produce increased amounts of isoprene compared to isoprene-producing cells that do not comprise said mvaE gene and mvaS gene. In some aspects, the nucleic acids encoding polypeptides of the lower MVA pathway comprise enzymes selected from: (a) an enzyme that phosphorylates mevalonate to mevalonate 5-phosphate; (b) an enzyme that converts mevalonate 5-phosphate to mevalonate 5-pyrophosphate; and (c) an enzyme that converts mevalonate 5-pyrophosphate to isopentenyl pyrophosphate. In some aspects of any of the aspects disclosed herein, the enzyme that phosphorylates mevalonate to mevalonate 5-phosphate is selected from the group consisting of *M. mazei* mevalonate kinase, *M. burtonii* mevalonate kinase polypeptide, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In some aspects, the enzyme that phosphorylates mevalonate to mevalonate 5-phosphate is *M. mazei* mevalonate kinase. In some aspects of any of the aspects disclosed herein, the isoprene synthase polypeptide is a plant isoprene synthase polypeptide or variants thereof. In some aspects, the isoprene synthase polypeptide is a polypeptide from *Pueraria* or *Populus* or a hybrid, *Populus alba*×*Populus tremula*, or variants thereof. In some aspects, the isoprene synthase polypeptide is selected from the group consisting of *Pueraria montana, Pueraria lobata, Populus tremuloides, Populus alba, Populus nigra*, and *Populus trichocarpa*. In some aspects, the plant isoprene synthase polypeptide is a *Populus alba* isoprene synthase polypeptide. In some aspects of any of the aspects disclosed herein, the cells further comprise one or more nucleic acids encoding an isopentenyl-diphosphate delta-isomerase (IDI) polypeptide. In some aspects, wherein the nucleic acid encoding an IDI polypeptide is a heterologous nucleic acid encoding an IDI polypeptide. In some aspects, the IDI polypeptide is a yeast IDI polypeptide. In some aspects, the nucleic acid encoding an IDI polypeptide is a copy of an endogenous nucleic acid encoding an IDI polypeptide. In some aspects of any of the aspects disclosed herein, the one or more nucleic acids is placed under an inducible promoter or a constitutive promoter. In some aspects of any of the aspects disclosed herein, the one or more nucleic acids is cloned into a multicopy plasmid. In some aspects of any of the aspects disclosed herein, the one or more nucleic acids is integrated into a chromosome of the cells. In some aspects of any of the aspects disclosed herein, the cells are gram-positive bacterial cells or gram-negative bacterial cells, *Escherichia* cells, *Pantoea* cells, fungal cells, filamentous fungal cells, *Trichoderma* cells, *Aspergillus* cells, or yeast cells. In some aspects, the cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In some aspects, the cells are *E. coli*.

In another aspect, provided herein is a method of producing isoprene, comprising: culturing the host cells disclosed in any of the aspects provided herein under suitable culture conditions for production of isoprene; and producing the isoprene. In one aspect, the method further comprises recovering the isoprene.

In a further aspect, provided herein are recombinant cells capable of increased production of isoprenoid precursors, the cells comprising one or more heterologous nucleic acids comprising nucleotide sequences selected from the group consisting of: an mvaE gene and an mvaS gene from *E. gallinarum*; an mvaE gene and an mvaS gene from *E. casseliflavus*; an mvaE gene and an mvaS gene from *E. faecium*; and an mvaE gene and an mvaS gene from *L. grayi*, wherein the mvaE gene and mvaS gene encode polypeptides having thiolase, HMG-CoA synthase, and HMG-CoA reductase catalytic activities, and wherein the cells produce increase amounts of isoprenoid precursors compared to isoprenoid precursor-producing cells that do not comprise said mvaE gene and mvaS gene. In some aspects, the one or more nucleic acids is placed under an inducible promoter or a constitutive promoter. In some aspects of any of the aspects disclosed herein, the one or more nucleic acids is cloned into a multicopy plasmid. In some aspects of any of the aspects disclosed herein, the one or more nucleic acids is integrated into a chromosome of the cells. In some aspects of any of the aspects disclosed herein, the cells are gram-positive bacterial cells, gram-negative bacterial cells, *Escherichia* cells, *Pantoea* cells, fungal cells, filamentous fungal cells, *Trichoderma* cells, *Aspergillus* cells, or yeast cells. In some aspects, the cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In some aspects, the cells are *E. coli*. In some aspects of any of the aspects disclosed herein, the isoprenoid precursor is mevalonate (MVA).

In another aspect, provided herein are methods for producing isoprenoid precursors, comprising: culturing the host cells described in any of the aspects disclosed herein under suitable culture conditions for production of isoprenoid precursors; and producing the isoprenoid precursors. In one aspect, the method further comprises recovering the isoprenoid precursors.

In yet other aspects, provided herein are recombinant cells capable of increased production of isoprenoids, the cells comprising one or more heterologous nucleic acids comprising nucleotide sequences selected from the group consisting of: an mvaE gene and an mvaS gene from *E. gallinarum*; an mvaE gene and an mvaS gene from *E. casseliflavus*; an mvaE gene and an mvaS gene from *E. faecium*; and an mvaE gene and an mvaS gene from *L. grayi*, wherein said mvaE gene and mvaS gene encode polypeptides having thiolase, HMG-CoA synthase, and HMG-CoA reductase catalytic activities, and wherein the cell further comprise: one or more nucleic acids encoding polypeptides of the lower MVA pathway; and one or more nucleic acids encoding polyprenyl pyrophosphate synthases, wherein the cells produce increased amounts of isoprenoids compared to isoprenoid-producing cells that do not comprise said mvaE gene and mvaS gene. In some aspects, the nucleic acids encoding polypeptides of the lower MVA pathway comprise enzymes selected from: (a) an enzyme that phosphorylates mevalonate to mevalonate 5-phosphate; (b) an enzyme that converts mevalonate 5-phosphate to mevalonate 5-pyrophosphate; and (c) an enzyme that converts mevalonate 5-pyrophosphate to isopentenyl pyrophosphate. In some aspects of any of the aspects disclosed herein, the enzyme that phosphorylates mevalonate to mevalonate 5-phosphate is selected from the group consisting of *M. mazei* mevalonate kinase, *M. burtonii* mevalonate kinase polypeptide, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In some aspects, the enzyme that phosphorylates mevalonate to mevalonate 5-phosphate is *M. mazei* mevalonate kinase. In some aspects of any of the aspects disclosed herein, the one or more nucleic acids is placed under an inducible promoter or a constitutive promoter. In some aspects of any of the aspects disclosed herein, the one or more nucleic acids is cloned into a multicopy plasmid. In some aspects of any of the aspects disclosed herein, the one or more nucleic acids is integrated into a chromosome of the cells. In some aspects of any of the aspects disclosed herein, the cells are gram-positive bacterial cells, gram-negative bacterial cells, *Escherichia* cells, *Pantoea* cells, fungal cells, filamentous fungal cells, *Trichoderma* cells, *Aspergillus* cells, or yeast cells. In some aspects, the cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In some aspects, the cells are *E. coli*. In some aspects of any of the aspects disclosed herein, the isoprenoid is selected from group consisting of monoterpenes, diterpenes, triterpenes, tetraterpenes, sequiterpenes, and polyterpenes. In some aspects, the isoprenoid is a sesquiterpene. In some aspects of any of the aspects disclosed herein, the isoprenoid is selected from the group consisting of abietadiene, amorphadiene, carene, α-farnesene, β-farnesene, farnesol, geraniol, geranylgeraniol, linalool, limonene, myrcene, nerolidol, ocimene, patchoulol, β-pinene, sabinene, γ-terpinene, terpindene and valencene.

In another aspect, there is provided a method for producing isoprenoids, comprising: culturing the host cells described in any of the aspects disclosed herein under suitable culture conditions for production of isoprenoids; and producing the isoprenoids. In one aspect, the method further comprises recovering the isoprenoids.

In one aspect, the invention provides recombinant cells (such as bacterial cells) capable of increased production of mevalonate, the cells comprising one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus*, wherein the mvaE gene and mvaS gene encode polypeptides having thiolase, HMG-CoA synthase, and HMG-CoA reductase catalytic activities, and wherein the cells produce a higher mass yield of mevalonate compared to cells (such as bacterial cells) that do not comprise the mvaE gene and mvaS gene from *L. grayi, E. faecium, E. gallinarum*, or *E. casseliflavus*. In one aspect, the mvaE gene from *L. grayi* comprises a nucleic acid corresponding to SEQ ID NO:1. In another aspect, the mvaS gene from *L. grayi* comprises a nucleic acid corresponding to SEQ ID NO:2. In another aspect, the mvaE gene from *E. faecium* comprises a nucleic acid corresponding to SEQ ID NO:3. In another aspect, the mvaS gene from *E. faecium* comprises a nucleic acid corresponding to SEQ ID NO:4. In another aspect, the mvaE gene from *E. gallinarum* comprises a nucleic acid corresponding to SEQ ID NO:5. In another aspect, the mvaS gene from *E. gallinarum* comprises a nucleic acid corresponding to SEQ ID NO:6. In another aspect, the mvaE gene from *E. casseliflavus* comprises a nucleic acid corresponding to SEQ ID NO:7. In another aspect, the mvaS gene from *E. casseliflavus* comprises a nucleic acid corresponding to SEQ ID NO:8. In one aspect, the one or more heterologous nucleic acids can be placed under the control of an inducible promoter or under the control of a constitutive promoter. In one aspect, the one or more heterologous nucleic acids are codon optimized. In some aspects, the one or more heterologous nucleic acids are cloned into a multicopy plasmid. In another aspect, the one or more heterologous nucleic acids are integrated into a chromosome of the cell (such as a bacterial cell). In one aspect, the cells are bacterial cells which are either gram-positive cells or gram negative cells. In another aspect, the cells are bacterial cells which are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In another aspect, the bacterial cells are *E. coli* cells.

In another aspect, the invention provides recombinant cells (such as bacterial cells) capable of increased production of mevalonate, the cells comprising one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus*, wherein the mvaE gene and mvaS gene encode polypeptides having thiolase, HMG-CoA synthase, and HMG-CoA reductase catalytic activities, and wherein the cells produce a higher peak titer of mevalonate compared to cells (such as bacterial cells) that do not comprise the mvaE gene and mvaS gene from *L. grayi, E. faecium, E. gallinarum*, or *E. casseliflavus*. In one aspect, the mvaE gene from *L. grayi* comprises a nucleic acid corresponding to SEQ ID NO:1. In another aspect, the mvaS gene from *L. grayi* comprises a nucleic acid corresponding to SEQ ID NO:2. In another aspect, the mvaE gene from *E. faecium* comprises a nucleic acid corresponding to SEQ ID NO:3. In another aspect, the mvaS gene from *E. faecium* comprises a nucleic acid corresponding to SEQ ID NO:4. In another aspect, the mvaE gene from *E. gallinarum* comprises a nucleic acid corresponding to SEQ ID NO:5. In another aspect, the mvaS gene from *E. gallinarum* comprises a nucleic acid corresponding to SEQ ID NO:6. In another aspect, the mvaE gene from *E. casseliflavus* comprises a nucleic acid corresponding to SEQ ID NO:7. In another aspect, the mvaS gene from *E. casseliflavus* comprises a nucleic acid corresponding to SEQ ID NO:8. In one aspect, the one or more heterologous nucleic acids can be placed under the control of an inducible promoter or under the control of a constitutive promoter. In one aspect, the one or more heterologous nucleic acids are codon optimized. In some aspects, the one or more heterologous nucleic acids are cloned into a multicopy plasmid. In another aspect, the one or more heterologous nucleic acids are integrated into a chromosome of the cell (such as bacterial cell). In one aspect, the cells are bacterial cells which are either gram-positive cells or gram negative cells. In another aspect, the cells are bacterial cells are selected from the group consisting of E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas sp., and P. alcaligenes cells. In another aspect, the bacterial cells are E. coli cells.

In another aspect, the invention provides recombinant cells (such as bacterial cells) capable of increased production of mevalonate, the cells comprising one or more heterologous nucleic acids comprising nucleotide sequences selected from the group consisting of (a) an mvaE gene and an mvaS gene from L. grayi; (b) an mvaE gene and an mvaS gene from E. faecium; (c) an mvaE gene and an mvaS gene from E. gallinarum; and (d) an mvaE gene and an mvaS gene from E. casseliflavus, wherein the mvaE gene and mvaS gene encode polypeptides having thiolase, HMG-CoA synthase, and HMG-CoA reductase catalytic activities, and wherein the cells have a higher cell productivity index (CPI) compared to cells (such as bacterial cells) that do not comprise the mvaE gene and mvaS gene from L. grayi, E. faecium, E. gallinarum, or E. casseliflavus. In one aspect, the mvaE gene from L. grayi comprises a nucleic acid corresponding to SEQ ID NO:1. In another aspect, the mvaS gene from L. grayi comprises a nucleic acid corresponding to SEQ ID NO:2. In another aspect, the mvaE gene from E. faecium comprises a nucleic acid corresponding to SEQ ID NO:3. In another aspect, the mvaS gene from E. faecium comprises a nucleic acid corresponding to SEQ ID NO:4. In another aspect, the mvaE gene from E. gallinarum comprises a nucleic acid corresponding to SEQ ID NO:5. In another aspect, the mvaS gene from E. gallinarum comprises a nucleic acid corresponding to SEQ ID NO:6. In another aspect, the mvaE gene from E. casseliflavus comprises a nucleic acid corresponding to SEQ ID NO:7. In another aspect, the mvaS gene from E. casseliflavus comprises a nucleic acid corresponding to SEQ ID NO:8. In one aspect, the one or more heterologous nucleic acids can be placed under the control of an inducible promoter or under the control of a constitutive promoter. In one aspect, the one or more heterologous nucleic acids are codon optimized. In some aspects, the one or more heterologous nucleic acids are cloned into a multicopy plasmid. In another aspect, the one or more heterologous nucleic acids are integrated into a chromosome of the cell (such as bacterial cell). In one aspect, the cells are bacterial cells which are either gram-positive cells or gram negative cells. In another aspect, the cells are bacterial cells are selected from the group consisting of E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas sp., and P. alcaligenes cells. In another aspect, the bacterial cells are E. coli cells.

In another aspect, the invention provides recombinant cells (such as bacterial cells) capable of increased production of mevalonate, the cells comprising one or more heterologous nucleic acids comprising nucleotide sequences selected from the group consisting of (a) an mvaE gene and an mvaS gene from L. grayi; (b) an mvaE gene and an mvaS gene from E. faecium; (c) an mvaE gene and an mvaS gene from E. gallinarum; and (d) an mvaE gene and an mvaS gene from E. casseliflavus, wherein the mvaE gene and mvaS gene encode polypeptides having thiolase, HMG-CoA synthase, and HMG-CoA reductase catalytic activities, and wherein the cells produce a higher mass yield of mevalonate compared to cells (such as bacterial cells) that do not comprise the mvaE gene and mvaS gene from L. grayi, E. faecium, E. gallinarum, or E. casseliflavus. In one aspect, the mvaE gene from L. grayi comprises a nucleic acid corresponding to SEQ ID NO:1. In another aspect, the mvaS gene from L. grayi comprises a nucleic acid corresponding to SEQ ID NO:2. In another aspect, the mvaE gene from E. faecium comprises a nucleic acid corresponding to SEQ ID NO:3. In another aspect, the mvaS gene from E. faecium comprises a nucleic acid corresponding to SEQ ID NO:4. In another aspect, the mvaE gene from E. gallinarum comprises a nucleic acid corresponding to SEQ ID NO:5. In another aspect, the mvaS gene from E. gallinarum comprises a nucleic acid corresponding to SEQ ID NO:6. In another aspect, the mvaE gene from E. casseliflavus comprises a nucleic acid corresponding to SEQ ID NO:7. In another aspect, the mvaS gene from E. casseliflavus comprises a nucleic acid corresponding to SEQ ID NO:8. In one aspect, the one or more heterologous nucleic acids can be placed under the control of an inducible promoter or under the control of a constitutive promoter. In one aspect, the one or more heterologous nucleic acids are codon optimized. In some aspects, the one or more heterologous nucleic acids are cloned into a multicopy plasmid. In another aspect, the one or more heterologous nucleic acids are integrated into a chromosome of the cell (such as bacterial cell). In one aspect, the cells are bacterial cells which are either gram-positive cells or gram negative cells. In another aspect, the cells are bacterial cells are selected from the group consisting of E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas sp., and P. alcaligenes cells. In another aspect, the bacterial cells are E. coli cells.

In another aspect, the invention provides methods for increased production of mevalonate, the method comprising: (a) culturing cells comprising one or more heterologous nucleic acids comprising nucleotide sequences selected from the group consisting of (i) an mvaE gene and an mvaS gene from L. grayi; (ii) an mvaE gene and an mvaS gene from E. faecium; (iii) an mvaE gene and an mvaS gene from E. gallinarum; and (iv) an mvaE gene and an mvaS gene from E. casseliflavus, wherein the mvaE gene and mvaS gene encode polypeptides having thiolase, HMG-CoA synthase, and HMG-CoA reductase catalytic activities; and (b) producing mevalonate. In some aspects, the method further comprises the step of recovering the mevalonate. In some aspects, the cells are cultured at 34° C. In some aspects, one or more heterologous nucleic acids are expressed on a low to moderate copy plasmid. In some aspects, the one or more heterologous nucleic acids are under the control of a strong promoter.

In another aspect, the invention provides recombinant cells (such as bacterial cells) capable of increased production of isoprene, the cells comprising one or more heterologous nucleic acids comprising nucleotide sequences selected from the group consisting of (a) an mvaE gene and an mvaS gene from L. grayi; (b) an mvaE gene and an mvaS gene from E. faecium; (c) an mvaE gene and an mvaS gene from E. gallinarum; and (d) an mvaE gene and an mvaS gene from *E. casseliflavus*, wherein the mvaE gene and mvaS gene encode polypeptides having thiolase, HMG-CoA synthase, and HMG-CoA reductase catalytic activities, and wherein the cell further comprises (i) one or more heterologous nucleic acids encoding polypeptides of the lower MVA pathway; and (ii) a heterologous nucleic acid encoding an isoprene synthase polypeptide, wherein the cells produce greater amounts of isoprene compared to isoprene-producing cells (such as bacterial cells) that do not comprise said mvaE gene and mvaS gene. In one aspect, the mvaE gene from *L. grayi* comprises a nucleic acid corresponding to SEQ ID NO:1. In another aspect, the mvaS gene from *L. grayi* comprises a nucleic acid corresponding to SEQ ID NO:2. In another aspect, the mvaE gene from *E. faecium* comprises a nucleic acid corresponding to SEQ ID NO:3. In another aspect, the mvaS gene from *E. faecium* comprises a nucleic acid corresponding to SEQ ID NO:4. In another aspect, the mvaE gene from *E. gallinarum* comprises a nucleic acid corresponding to SEQ ID NO:5. In another aspect, the mvaS gene from *E. gallinarum* comprises a nucleic acid corresponding to SEQ ID NO:6. In another aspect, the mvaE gene from *E. casseliflavus* comprises a nucleic acid corresponding to SEQ ID NO:7. In another aspect, the mvaS gene from *E. casseliflavus* comprises a nucleic acid corresponding to SEQ ID NO:8. In one aspect, the one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus* are codon optimized. In one aspect, the polypeptides of the lower MVA pathway comprise enzymes selected from: (a) an enzyme that phosphorylates mevalonate to mevalonate 5-phosphate; (b) an enzyme that converts mevalonate 5-phosphate to mevalonate 5-pyrophosphate; and (c) an enzyme that converts mevalonate 5-pyrophosphate to isopentenyl pyrophosphate. In another aspect, the enzyme that phosphorylates mevalonate to mevalonate 5-phosphate is selected from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase. In another aspect, the isoprene synthase polypeptide is a plant isoprene synthase polypeptide. In one aspect, the isoprene synthase polypeptide is a polypeptide from *Pueraria* or *Populus* or a hybrid, *Populus alba*× *Populus tremula*. In another aspect, the isoprene synthase polypeptide is selected from the group consisting of *Pueraria montana* or *Pueraria lobata*, *Populus tremuloides*, *Populus alba*, *Populus nigra*, and *Populus trichocarpa*. In another aspect, the plant isoprene synthase polypeptide is a kudzu isoprene synthase polypeptide. In one aspect the cells (such as bacterial cells) further comprise one or more nucleic acids encoding an isopentenyl-diphosphate delta-isomerase (IDI) polypeptide. In another aspect, the nucleic acid encoding an IDI polypeptide is a heterologous nucleic acid encoding an IDI polypeptide. In another aspect, the IDI polypeptide is a yeast IDI polypeptide. In one aspect, the nucleic acid encoding an IDI polypeptide is a copy of an endogenous nucleic acid encoding an IDI polypeptide. In another aspect, the one or more heterologous nucleic acids are placed under an inducible promoter or a constitutive promoter. In some aspects, the one or more heterologous nucleic acids are cloned into a multicopy plasmid. In another aspect, the one or more heterologous nucleic acids are integrated into a chromosome of the cells. In yet another aspect, the cells are gram-positive bacterial cells or gram-negative bacterial cells. In other aspects, the cells are selected from the group consisting of *E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. In another aspect, the cells are *E. coli*.

In another aspect, the invention provides recombinant cells (such as bacterial cells) capable of increased production of isoprene, the cells comprising one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus*, wherein the mvaE gene and mvaS gene encode polypeptides having thiolase, HMG-CoA synthase, and HMG-CoA reductase catalytic activities, and wherein the cell further comprises (i) one or more heterologous nucleic acids encoding polypeptides of the lower MVA pathway; (ii) a heterologous nucleic acid encoding an isoprene synthase polypeptide; and (iii) one or more heterologous nucleic acids encoding polypeptides of the DXP pathway, wherein the cells produce greater amounts of isoprene compared to isoprene-producing cells (such as bacterial cells) that do not comprise said mvaE gene and mvaS gene. In one aspect, the mvaE gene from *L. grayi* comprises a nucleic acid corresponding to SEQ ID NO:1. In another aspect, the mvaS gene from *L. grayi* comprises a nucleic acid corresponding to SEQ ID NO:2. In another aspect, the mvaE gene from *E. faecium* comprises a nucleic acid corresponding to SEQ ID NO:3. In another aspect, the mvaS gene from *E. faecium* comprises a nucleic acid corresponding to SEQ ID NO:4. In another aspect, the mvaE gene from *E. gallinarum* comprises a nucleic acid corresponding to SEQ ID NO:5. In another aspect, the mvaS gene from *E. gallinarum* comprises a nucleic acid corresponding to SEQ ID NO:6. In another aspect, the mvaE gene from *E. casseliflavus* comprises a nucleic acid corresponding to SEQ ID NO:7. In another aspect, the mvaS gene from *E. casseliflavus* comprises a nucleic acid corresponding to SEQ ID NO:8. In one aspect, the one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus* are codon optimized. In one aspect the polypeptides of the lower MVA pathway comprise enzymes selected from the group consisting of: (a) an enzyme that phosphorylates mevalonate to mevalonate 5-phosphate; (b) an enzyme that converts mevalonate 5-phosphate to mevalonate 5-pyrophosphate; and (c) an enzyme that converts mevalonate 5-pyrophosphate to isopentenyl pyrophosphate. In another aspect, the enzyme that phosphorylates mevalonate to mevalonate 5-phosphate is selected from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase. In another aspect, the isoprene synthase polypeptide is a plant isoprene synthase polypeptide. In one aspect, the isoprene synthase polypeptide is a polypeptide from *Pueraria* or *Populus* or a hybrid, *Populus alba*×*Populus tremula*. In another aspect, the isoprene synthase polypeptide is selected from the group consisting of *Pueraria montana* or *Pueraria lobata*, *Populus tremuloides*, *Populus alba*, *Populus nigra*, and *Populus trichocarpa*. In another aspect, the plant isoprene synthase polypeptide is a kudzu isoprene synthase polypeptide. In one aspect the cells (such as bacterial cells) further comprise one or more nucleic acids encoding an isopentenyl-diphosphate delta-isomerase (IDI) polypeptide. In another aspect, the nucleic acid encoding an IDI polypeptide is a heterologous nucleic acid encoding an IDI polypeptide. In another aspect, the IDI polypeptide is a yeast IDI polypeptide. In one aspect, the nucleic acid encoding an IDI polypeptide is a copy of an endogenous nucleic acid encoding an IDI polypeptide. In one aspect the polypeptides of the DXP pathway comprise enzymes selected from the group consisting of: (a) an enzyme that converts pyruvate and D-glyceraldehyde 3-phosphate into 1-deoxy-d-xylulose 5-phosphate (DXP); (b) an enzyme that converts 1-deoxy-d-xylulose 5-phosphate (DXP) into 2-C-methyl-D-erythritol 4-phosphate (MEP); (c) an enzyme that converts 2-C-methyl-D-erythritol 4-phosphate (MEP) into 4-(cytidine 5'-diphospho)-2-methyl-D-erythritol (CDP-ME); (d) an enzyme that converts 4-(cytidine 5'-diphospho)-2-C-methyl-D-erythritol (CDP-ME) into 2-phospho-4-(cytidine 5'-diphospho)-2-C-methyl-D-erythritol (CDP-MEP); (e) an enzyme that converts 2-phospho-4-(cytidine 5'-diphospho)-2-C-methyl-D-erythritol (CDP-MEP) into 2-C-methyl-D-erythritol 2, 4-cyclodiphosphate (ME-CPP or cMEPP); (f) an enzyme that converts 2-C-methyl-D-erythritol 2, 4-cyclodiphosphate into (E)-4-hydroxy-3-methylbut-2-en-1-yl diphosphate (HMBPP or HDMAPP); and (g) an enzyme that converts (E)-4-hydroxy-3-methylbut-2-en-1-yl diphosphate into isopentenyl diphosphate (IPP) and dimethylallyl diphosphate (DMAPP). In another aspect, the one or more heterologous nucleic acids are placed under an inducible promoter or a constitutive promoter. In some aspects, the one or more heterologous nucleic acids are cloned into a multicopy plasmid. In another aspect, the one or more heterologous nucleic acids is integrated into a chromosome of the cells. In yet another aspect, the cells are gram-positive bacterial cells or gram-negative bacterial cells. In other aspects, the cells are selected from the group consisting of *E. coli*, *P. citrea*, *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, *B. thuringiensis*, *S. albus*, *S. lividans*, *S. coelicolor*, *S. griseus*, *Pseudomonas* sp., and *P. alcaligenes* cells. In another aspect, the cells are *E. coli*.

In another aspect, the invention provides methods for increased production of isoprene, the method comprising: (a) culturing cells (such as bacterial cells) comprising one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus*, wherein the mvaE gene and mvaS gene encode polypeptides having thiolase, HMG-CoA synthase, and HMG-CoA reductase catalytic activities, and wherein the cell further comprises (i) one or more heterologous nucleic acids encoding polypeptides of the lower MVA pathway; and (ii) a heterologous nucleic acid encoding an isoprene synthase polypeptide, wherein the cells produce greater amounts of isoprene compared to isoprene-producing cells (such as bacterial cells) that do not comprise said mvaE gene and mvaS gene. In some aspects, the cells further comprise one or more heterologous nucleic acids encoding polypeptides of the DXP pathway. In some aspects, the method further comprises the step of recovering the isoprene. In some aspects, the cells are cultured at 34° C. In some aspects, the one or more heterologous nucleic acids are expressed on an extra-chromosomal plasmid. In some aspects, the one or more heterologous nucleic acids are integrated into a chromosome of a cell (such as a bacterial cell chromosome).

In another aspect, the invention provides recombinant cells (such as bacterial cells) capable of increased production of isoprenoid precursors and/or isoprenoids, the cells comprising one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus*, wherein the mvaE gene and mvaS gene encode polypeptides having thiolase, HMG-CoA synthase, and HMG-CoA reductase catalytic activities, and wherein the cell further comprises (i) one or more heterologous nucleic acids encoding polypeptides of the lower MVA pathway; and (ii) a heterologous nucleic acid encoding a polyprenyl pyrophosphate synthase polypeptide, wherein the cells produce at least greater amounts of isoprenoids and/or isoprenoid precursors, compared to isoprene-producing cells (such as bacterial cells) that do not comprise said mvaE gene and mvaS gene. In one aspect, the mvaE gene from *L. grayi* comprises a nucleic acid corresponding to SEQ ID NO:1. In another aspect, the mvaS gene from *L. grayi* comprises a nucleic acid corresponding to SEQ ID NO:2. In another aspect, the mvaE gene from *E. faecium* comprises a nucleic acid corresponding to SEQ ID NO:3. In another aspect, the mvaS gene from *E. faecium* comprises a nucleic acid corresponding to SEQ ID NO:4. In another aspect, the mvaE gene from *E. gallinarum* comprises a nucleic acid corresponding to SEQ ID NO:5. In another aspect, the mvaS gene from *E. gallinarum* comprises a nucleic acid corresponding to SEQ ID NO:6. In another aspect, the mvaE gene from *E. casseliflavus* comprises a nucleic acid corresponding to SEQ ID NO:7. In another aspect, the mvaS gene from *E. casseliflavus* comprises a nucleic acid corresponding to SEQ ID NO:8. In one aspect, the one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus* are codon optimized. In another aspect, the one or more heterologous nucleic acids are placed under an inducible promoter or a constitutive promoter. In some aspects, the one or more heterologous nucleic acids are cloned into a multicopy plasmid. In another aspect, the one or more heterologous nucleic acids is integrated into a chromosome of the cells. In yet another aspect, the cells are gram-positive bacterial cells or gram-negative bacterial cells. In other aspects, the cells are selected from the group consisting of *E. coli*, *P. citrea*, *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, *B. thuringiensis*, *S. albus*, *S. lividans*, *S. coelicolor*, *S. griseus*, *Pseudomonas* sp., and *P. alcaligenes* cells. In another aspect, the cells are *E. coli*. In one aspect the polypeptides of the lower MVA pathway comprise enzymes selected from: (a) an enzyme that phosphorylates mevalonate to mevalonate 5-phosphate; (b) an enzyme that converts mevalonate 5-phosphate to mevalonate 5-pyrophosphate; and (c) an enzyme that converts mevalonate 5-pyrophosphate to isopentenyl pyrophosphate. In another aspect, the enzyme that phosphorylates mevalonate to mevalonate 5-phosphate is selected from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase. In another aspect, the polyprenyl pyrophosphate synthase polypeptide comprises farnesyl pyrophosphate (FPP) synthase. In another aspect, the isoprenoid is selected from group consisting of monoterpenes, diterpenes, triterpenes, tetraterpenes, sequiterpene, and polyterpene. In other aspects, the isoprenoid is a sesquiterpene. In some aspects, the isoprenoid is selected from the group consisting of abietadiene, amorphadiene, carene, α-farnesene, β-farnesene, farnesol, geraniol, geranylgeraniol, linalool, limonene, myrcene, nerolidol, ocimene, patchoulol, β-pinene, sabinene, γ-terpinene, terpindene and valencene.

In another aspect, the invention provides recombinant cells (such as bacterial cells) capable of increased production of isoprenoid precursors and/or isoprenoids, the cells comprising one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus*, wherein the mvaE gene and mvaS gene encode polypeptides having thiolase, HMG-CoA synthase, and HMG-CoA reductase catalytic activities, and wherein the cell further comprises (i) one or more heterologous nucleic acids encoding polypeptides of the lower MVA pathway; (ii) a heterologous nucleic acid encoding a polyprenyl pyrophosphate synthase polypeptide; and (iii) one or more heterologous nucleic acids encoding polypeptides of the DXP pathway, wherein the cells produce greater amounts of isoprene compared to isoprene-producing cells (such as bacterial cells) that do not comprise said mvaE gene and mvaS gene. In one aspect, the mvaE gene from *L. grayi* comprises a nucleic acid corresponding to SEQ ID NO:1. In another aspect, the mvaS gene from *L. grayi* comprises a nucleic acid corresponding to SEQ ID NO:2. In another aspect, the mvaE gene from *E. faecium* comprises a nucleic acid corresponding to SEQ ID NO:3. In another aspect, the mvaS gene from *E. faecium* comprises a nucleic acid corresponding to SEQ ID NO:4. In another aspect, the mvaE gene from *E. gallinarum* comprises a nucleic acid corresponding to SEQ ID NO:5. In another aspect, the mvaS gene from *E. gallinarum* comprises a nucleic acid corresponding to SEQ ID NO:6. In another aspect, the mvaE gene from *E. casseliflavus* comprises a nucleic acid corresponding to SEQ ID NO:7. In another aspect, the mvaS gene from *E. casseliflavus* comprises a nucleic acid corresponding to SEQ ID NO:8. In one aspect, the one or more heterologous nucleic acids comprising nucleotide sequences selected from the group consisting of (a) an mvaE gene and an mvaS gene from *L. grayi*; (b) an mvaE gene and an mvaS gene from *E. faecium*; (c) an mvaE gene and an mvaS gene from *E. gallinarum*; and (d) an mvaE gene and an mvaS gene from *E. casseliflavus* are codon optimized. In one aspect the polypeptides of the lower MVA pathway comprise enzymes selected from the group consisting of: (a) an enzyme that phosphorylates mevalonate to mevalonate 5-phosphate; (b) an enzyme that converts mevalonate 5-phosphate to mevalonate 5-pyrophosphate; and (c) an enzyme that converts mevalonate 5-pyrophosphate to isopentenyl pyrophosphate. In another aspect, the enzyme that phosphorylates mevalonate to mevalonate 5-phosphate is selected from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase. In another aspect, the polyprenyl pyrophosphate synthase polypeptide comprises farnesyl pyrophosphate (FPP) synthase. In one aspect the cells (such as bacterial cells) further comprise one or more nucleic acids encoding an isopentenyl-diphosphate delta-isomerase (IDI) polypeptide. In another aspect, the nucleic acid encoding an IDI polypeptide is a heterologous nucleic acid encoding an IDI polypeptide. In another aspect, the IDI polypeptide is a yeast IDI polypeptide. In one aspect, the nucleic acid encoding an IDI polypeptide is a copy of an endogenous nucleic acid encoding an IDI polypeptide. In one aspect the polypeptides of the DXP pathway comprise enzymes selected from the group consisting of: (a) an enzyme that converts pyruvate and D-glyceraldehyde 3-phosphate into 1-deoxy-d-xylulose 5-phosphate (DXP); (b) an enzyme that converts 1-deoxy-d-xylulose 5-phosphate (DXP) into 2-C-methyl-D-erythritol 4-phosphate (MEP); (c) an enzyme that converts 2-C-methyl-D-erythritol 4-phosphate (MEP) into 4-(cytidine 5'-diphospho)-2-methyl-D-erythritol (CDP-ME); (d) an enzyme that converts 4-(cytidine 5'-diphospho)-2-C-methyl-D-erythritol (CDP-ME) into 2-phospho-4-(cytidine 5'-diphospho)-2-C-methyl-D-erythritol (CDP-MEP); (e) an enzyme that converts 2-phospho-4-(cytidine 5'-diphospho)-2-C-methyl-D-erythritol (CDP-MEP) into 2-C-methyl-D-erythritol 2, 4-cyclodiphosphate (ME-CPP or cMEPP); (f) an enzyme that converts 2-C-methyl-D-erythritol 2, 4-cyclodiphosphate into (E)-4-hydroxy-3-methylbut-2-en-1-yl diphosphate (HMBPP or HDMAPP); and (g) an enzyme that converts (E)-4-hydroxy-3-methylbut-2-en-1-yl diphosphate into isopentenyl diphosphate (IPP) and dimethylallyl diphosphate (DMAPP). In another aspect, the one or more heterologous nucleic acids are placed under an inducible promoter or a constitutive promoter. In some aspects, the one or more heterologous nucleic acids are cloned into a multicopy plasmid. In another aspect, the one or more heterologous nucleic acids is integrated into a chromosome of the cells. In yet another aspect, the cells are gram-positive bacterial cells or gram-negative bacterial cells. In other aspects, the cells are selected from the group consisting of E. coli, P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas sp., and P. alcaligenes cells. In another aspect, the cells are E. coli.

In another aspect, the invention provides methods for increased production of isoprenoid and/or isoprenoid precursor molecules, the method comprising: (a) culturing cells comprising one or more heterologous nucleic acids comprising nucleotide sequences selected from the group consisting of (a) an mvaE gene and an mvaS gene from L. grayi; (b) an mvaE gene and an mvaS gene from E. faecium; (c) an mvaE gene and an mvaS gene from E. gallinarum; and (d) an mvaE gene and an mvaS gene from E. casseliflavus, wherein the mvaE gene and mvaS gene encode polypeptides having thiolase, HMG-CoA synthase, and HMG-CoA reductase catalytic activities, and wherein the cell further comprises (i) one or more heterologous nucleic acids encoding polypeptides of the lower MVA pathway; and (ii) a heterologous nucleic acid encoding an polyprenyl pyrophosphate synthase, wherein the cells produce greater amounts of isoprenoid and/or isoprenoid precursor molecules compared to isoprenoid and/or isoprenoid precursor molecules-producing cells (such as bacterial cells) that do not comprise said mvaE gene and mvaS gene. In some aspects, the cells further comprise one or more heterologous nucleic acids encoding polypeptides of the DXP pathway. In some aspects, the method further comprises the step of recovering the isoprenoid and/or isoprenoid precursor molecules. In some aspects, the cells are cultured at 34° C. In some aspects, the one or more heterologous nucleic acids are expressed on an extra chromosomal plasmid. In some aspects, the one or more heterologous nucleic acids are integrated into a cell chromosome (such as a bacterial cell chromosome).

In another aspect, the invention provides for recombinant host (e.g., bacterial) cells capable of increased production of mevalonate wherein the cells comprise a degradation resistant mvaE gene product from one of the following organisms: E. gallinarum, E. faecium, E. casseliflavus, or L. grayi.

In another aspect, the invention provides for recombinant host (e.g., bacterial) cells capable of increased production of isoprene wherein the cells comprise a degradation resistant mvaE gene product from one of the following organisms: E. gallinarum, E. faecium, E. casseliflavus, or L. grayi that produces isoprene.

In another aspect, the invention provides for recombinant host (e.g., bacterial) cells capable of increased production of an isoprenoid wherein the cells comprise a degradation resistant mvaE gene product from one of the following organisms: E. gallinarum, E. faecium, E. casseliflavus, or L. grayi that produces isoprenoids.

BRIEF DESCRIPTION OF THE DRAWINGS

FIG. 5 depicts volumetric productivity achieved in each 15-L fermentation over time. All runs using the E. gallinarum or E. casseliflavus (triangles and squares, respectively) achieved a higher overall volumetric productivity than the two runs using E. faecalis upper pathway enzymes (open and closed diamonds. Volumetric Productivity was calculated using the following formula: Volumetric productivity (g/L/hr)=[Σ(HGER(t)/1000*68.117)]/[t−$t_0$], where the summation is from $t_0$ to t. Tank turnaround time is not factored in.

DETAILED DESCRIPTION

Figure 1:
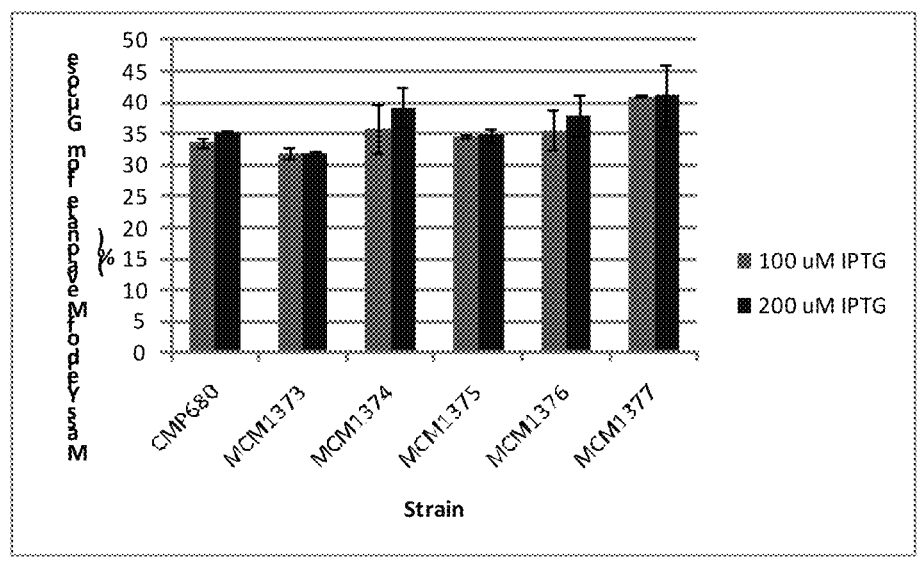
FIG. 1 depicts a graph showing mass yield of mevalonate from glucose. Error bars represent one standard deviation of two replicates.

Microbial cells, such as bacterial cells, are widely used hosts for the production of recombinant proteins. They can also be used to produce other products, such as mevalonate, isoprene, isoprenoid precursor molecules, and isoprenoids. The invention provides, inter alia, compositions and methods for the production of increased yields and titers of mevalonate, isoprene, isoprenoid precursor molecules, and isoprenoids using cells (such as bacterial cells) heterologously expressing polypeptides encoded by the mvaE and mvaS genes from the microorganisms Listeria grayi_DSM 20601, Enterococcus faecium, Enterococcus gallinarum EG2, and/or Enterococcus casseliflavus.

The mevalonate-dependent biosynthetic pathway is particularly important for the production of the isoprenoid precursor molecules mevalonate (MVA), dimethylallyl diphosphate (DMAPP) and isopentenyl pyrophosphate (IPP). The enzymes of the upper mevalonate pathway convert acetyl CoA, produced from glucose, into mevalonate via three enzymatic reactions. Together, the mvaE and mvaS genes from the above-mentioned bacterial species encode polypeptides that possess the enzymatic activities of the upper mevalonate pathway. Without being bound to theory, it is believed that increasing the efficiency and productivity of these three enzymatic activities in the upper mevalonate-dependent biosynthetic pathway will substantially increase intracellular concentrations of mevalonate and, consequently, of downstream isoprenoid precursor molecules such as DMAPP and IPP. The increased yield of mevalonate production by these strains is therefore advantageous for commercial applications.

The mvaE and mvaS genes of a different bacterial species, *E. faecalis*, have been incorporated into *E. coli* strains previously to produce mevalonate (see U.S. Patent Application Publication No. 2005/0287655 A1; Tabata, K. and Hashimoto, S.-I. *Biotechnology Letters* 26: 1487-1491, 2004). However, the inventors have observed that the mass yield of mevalonate produced in cells (such as bacterial cells) expressing the mvaE and mvaS genes from *L. grayi, E. faecium, E. gallinarum,* and *E. casseliflavus* is greater than the mass yield of mevalonate produced by *E. coli* strains containing the mvaE and mvaS genes from *E. faecalis*. The compositions and methods of the present application, therefore, represent an improvement over what has previously been practiced in the art, both in the number of strains of microorganisms available for increased production of mevalonate as well as in the amount of mevalonate produced by those cells (such as bacterial cells).

General Techniques

The practice of the present invention will employ, unless otherwise indicated, conventional techniques of molecular biology (including recombinant techniques), microbiology, cell biology, biochemistry, and immunology, which are within the skill of the art. Such techniques are explained fully in the literature, "*Molecular Cloning: A Laboratory Manual*", second edition (Sambrook et al., 1989); "*Oligonucleotide Synthesis*" (M. J. Gait, ed., 1984); "*Animal Cell Culture*" (R. I. Freshney, ed., 1987); "*Methods in Enzymology*" (Academic Press, Inc.); "*Current Protocols in Molecular Biology*" (F. M. Ausubel et al., eds., 1987, and periodic updates); "*PCR: The Polymerase Chain Reaction*", (Mullis et al., eds., 1994). Singleton et al., *Dictionary of Microbiology and Molecular Biology* 2nd ed., J. Wiley & Sons (New York, N.Y. 1994), and March, *Advanced Organic Chemistry Reactions, Mechanisms and Structure* 4th ed., John Wiley & Sons (New York, N.Y. 1992), provide one skilled in the art with a general guide to many of the terms used in the present application.

Definitions

The term "isoprene" refers to 2-methyl-1,3-butadiene (CAS#78-79-5). It can be the direct and final volatile C5 hydrocarbon product from the elimination of pyrophosphate from 3,3-dimethylallyl diphosphate (DMAPP). It may not involve the linking or polymerization of IPP molecules to DMAPP molecules. The term "isoprene" is not generally intended to be limited to its method of production unless indicated otherwise herein.

As used herein, the term "polypeptides" includes polypeptides, proteins, peptides, fragments of polypeptides, and fusion polypeptides.

As used herein, an "isolated polypeptide" is not part of a library of polypeptides, such as a library of 2, 5, 10, 20, 50 or more different polypeptides and is separated from at least one component with which it occurs in nature. An isolated polypeptide can be obtained, for example, by expression of a recombinant nucleic acid encoding the polypeptide.

By "heterologous polypeptide" is meant a polypeptide encoded by a nucleic acid sequence derived from a different organism, species, or strain than the host cell. In some embodiments, a heterologous polypeptide is not identical to a wild-type polypeptide that is found in the same host cell in nature.

As used herein, a "nucleic acid" refers to two or more deoxyribonucleotides and/or ribonucleotides covalently joined together in either single or double-stranded form.

By "recombinant nucleic acid" is meant a nucleic acid of interest that is free of one or more nucleic acids (e.g., genes) which, in the genome occurring in nature of the organism from which the nucleic acid of interest is derived, flank the nucleic acid of interest. The term therefore includes, for example, a recombinant DNA which is incorporated into a vector, into an autonomously replicating plasmid or virus, or into the genomic DNA of a prokaryote or eukaryote, or which exists as a separate molecule (e.g., a cDNA, a genomic DNA fragment, or a cDNA fragment produced by PCR or restriction endonuclease digestion) independent of other sequences.

By "heterologous nucleic acid" is meant a nucleic acid sequence derived from a different organism, species or strain than the host cell. In some embodiments, the heterologous nucleic acid is not identical to a wild-type nucleic acid that is found in the same host cell in nature. For example, a nucleic acid encoded by the mvaE and mvaS genes from *L. grayi, E. faecium, E. gallinarum,* and *E. casseliflavus* transformed in or integrated into the chromosome of *E. coli* is a heterologous nucleic acid.

As used herein, an "expression control sequence" means a nucleic acid sequence that directs transcription of a nucleic acid of interest. An expression control sequence can be a promoter, such as a constitutive or an inducible promoter, or an enhancer. An expression control sequence can be "native" or heterologous. A native expression control sequence is derived from the same organism, species, or strain as the gene being expressed. A heterologous expression control sequence is derived from a different organism, species, or strain as the gene being expressed. An "inducible promoter" is a promoter that is active under environmental or developmental regulation.

By "operably linked" is meant a functional linkage between a nucleic acid expression control sequence (such as a promoter) and a second nucleic acid sequence, wherein the expression control sequence directs transcription of the nucleic acid corresponding to the second sequence.

As used herein, the terms "minimal medium" or "minimal media" refer to growth medium containing the minimum nutrients possible for cell growth, generally without the presence of amino acids. Minimal medium typically contains: (1) a carbon source for cell (such as bacterial cell) growth; (2) various salts, which can vary among cellular species (such as bacterial cellular species) species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

As used herein, the term "isoprenoid" refers to a large and diverse class of naturally-occurring class of organic compounds composed of two or more units of hydrocarbons, with each unit consisting of five carbon atoms arranged in a specific pattern. As used herein, "isoprene" is expressly excluded from the definition of "isoprenoid."

As used herein, the term "terpenoid" refers to a large and diverse class of organic molecules derived from five-carbon isoprenoid units assembled and modified in a variety of ways and classified in groups based on the number of isoprenoid units used in group members. Hemiterpenoids have one isoprenoid unit. Monoterpenoids have two isoprenoid units. Sesquiterpenoids have three isoprenoid units. Diterpenoids have four isoprene units. Sesterterpenoids have five isoprenoid units. Triterpenoids have six isoprenoid units. Tetraterpenoids have eight isoprenoid units. Polyterpenoids have more than eight isoprenoid units.

As used herein, "isoprenoid precursor" refers to any molecule that is used by organisms in the biosynthesis of terpenoids or isoprenoids. Non-limiting examples of isoprenoid precursor molecules include, e.g., mevalonate (MVA), isopentenyl pyrophosphate (IPP) and dimethylallyl diphosphate (DMAPP).

As used herein, the term "mass yield" refers to the mass of the product produced by the cells (such as bacterial cells) divided by the mass of the glucose consumed by the cells (such as bacterial cells) multiplied by 100.

By "specific productivity," it is meant the mass of the product produced by the cells (such as bacterial cells) divided by the product of the time for production, the cell density, and the volume of the culture.

By "titer," it is meant the mass of the product produced by the cells (such as bacterial cells) divided by the volume of the culture.

As used herein, the term "cell productivity index (CPI)" refers to the mass of the product produced by the cells (such as bacterial cells) divided by the mass of the cells (such as bacterial cells) produced in the culture.

Unless defined otherwise herein, all technical and scientific terms used herein have the same meaning as commonly understood by one of ordinary skill in the art to which this invention pertains.

As used herein, the singular terms "a," "an," and "the" include the plural reference unless the context clearly indicates otherwise.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Recombinant Cells (Such as Bacterial Cells) Capable of Increased Production of Isoprenoid Precursors (e.g. Mevalonate)

The mevalonate-dependent biosynthetic pathway (MVA pathway) is a key metabolic pathway present in all higher eukaryotes and certain bacteria. In addition to being important for the production of molecules used in processes as diverse as protein prenylation, cell membrane maintenance, protein anchoring, and N-glycosylation, the mevalonate pathway provides a major source of the isoprenoid precursor molecules MVA, DMAPP and IPP, which serve as the basis for the biosynthesis of terpenes, terpenoids, isoprenoids, and isoprene.

In the upper portion of the MVA pathway, acetyl Co-A produced during cellular metabolism is converted to mevalonate via the actions of polypeptides having thiolase, HMG-CoA reductase, and HMG-CoA synthase enzymatic activity. First, acetyl Co-A is converted to acetoacetyl CoA via the action of a thiolase. Next, acetoacetyl CoA is converted to 3-hydroxy-3-methylglutaryl-CoA (HMG-CoA) by the enzymatic action of HMG-CoA synthase. This Co-A derivative is reduced to mevalonate by HMG-CoA reductase, which is the rate-limiting step of the mevalonate pathway of isoprenoid production. Mevalonate is then converted into mevalonate-5-phosphate via the action of mevalonate kinase which is subsequently transformed into mevalonate-5-pyrophosphate by the enzymatic activity of phosphomevalonate kinase. Finally, IPP is formed from mevalonate-5-pyrophosphate by the activity of the enzyme mevalonate-5-pyrophosphate decarboxylase.

Genes Encoding mvaE and mvaS Polypeptides

In *L. grayi, E. faecium, E. gallinarum*, and *E. casseliflavus*, the mvaE gene encodes a polypeptide that possesses both thiolase and HMG-CoA reductase activities. In fact, the mvaE gene product represented the first bifunctional enzyme of IPP biosynthesis found in eubacteria and the first example of HMG-CoA reductase fused to another protein in nature (Hedl, et al., *J Bacteriol.* 2002 April; 184(8): 2116-2122). The mvaS gene, on the other hand, encodes a polypeptide having an HMG-CoA synthase activity.

Accordingly, cells (such as bacterial (e.g., *E. coli*) cells), can be engineered to express one or more mvaE and mvaS genes from *L. grayi, E. faecium, E. gallinarum*, and/or *E. casseliflavus*, to increase production, peak titer, and cell productivity of an isoprenoid precursor (e.g., mevalonate). The one or more mvaE and mvaS genes can be expressed on a multicopy plasmid. The plasmid can be a high copy plasmid, a low copy plasmid, or a medium copy plasmid. Alternatively, the one or more mvaE and mvaS genes can be integrated into the host cell's chromosome. For both heterologous expression of the one or more mvaE and mvaS genes on a plasmid or as an integrated part of the host cell's chromosome, expression of the genes can be driven by either an inducible promoter or a constitutively expressing promoter. The promoter can be a strong driver of expression, it can be a weak driver of expression, or it can be a medium driver of expression of the one or more mvaE and mvaS genes.

Various options of mvaE and mvaS genes from *L. grayi, E. faecium, E. gallinarum*, and/or *E. casseliflavus* alone or in combination with one or more other mvaE and mvaS genes encoding proteins from the upper MVA pathway are contemplated within the scope of the invention. Thus, any of the combinations of genes contemplated in Table 1 can be expressed in cells (such as bacterial cells) in any of the ways described above.

TABLE 1

Options for expression of mvaE and mvaS genes in host cells contemplated for the present invention.

|  | L. grayi, mvaE | E. faecium, mvaE | E. gallinarum, mvaE | E. casseliflavus, mvaE |
|---|---|---|---|---|
| L. grayi, mvaS | L. grayi, mvaE<br>L. grayi, mvaS | E. faecium, mvaE<br>L. grayi, mvaS | E. gallinarum, mvaE<br>L. grayi, mvaS | E. casseliflavus, mvaE<br>L. grayi, mvaS |
| E. faecium, mvaS | L. grayi, mvaE<br>E. faecium, mvaS | E. faecium, mvaE<br>E. faecium, mvaS | E. gallinarum, mvaE<br>E. faecium, mvaS | E. casseliflavus, mvaE<br>E. faecium, mvaS |
| E. gallinarum, mvaS | L. grayi, mvaE<br>E. gallinarum, mvaS | E. faecium, mvaE<br>E. gallinarum, mvaS | E. gallinarum, mvaE<br>E. gallinarum, mvaS | E. casseliflavus, mvaE<br>E. gallinarum, mvaS |
| E. casseliflavus, mvaS | L. grayi, mvaE<br>E. casseliflavus, mvaS | E. faecium, mvaE<br>E. casseliflavus, mvaS | E. gallinarum, mvaE<br>E. casseliflavus, mvaS | E. casseliflavus, mvaE<br>E. casseliflavus, mvaS |

Exemplary mvaE Polypeptides and Nucleic Acids

The mvaE gene encodes a polypeptide that possesses both thiolase and HMG-CoA reductase activities. The thiolase activity of the polypeptide encoded by the mvaE gene converts acetyl Co-A to acetoacetyl CoA whereas the HMG-CoA reductase enzymatic activity of the polypeptide converts 3-hydroxy-3-methylglutaryl-CoA to mevalonate. Exemplary mvaE polypeptides and nucleic acids include naturally-occurring polypeptides and nucleic acids from any of the source organisms described herein as well as mutant polypeptides and nucleic acids derived from any of the source organisms described herein that have at least one activity of a mvaE polypeptide.

Mutant mvaE polypeptides include those in which one or more amino acid residues have undergone an amino acid substitution while retaining mvaE polypeptide activity (i.e., the ability to convert acetyl Co-A to acetoacetyl CoA as well as the ability to convert 3-hydroxy-3-methylglutaryl-CoA to mevalonate). The amino acid substitutions can be conservative or non-conservative and such substituted amino acid residues can or can not be one encoded by the genetic code. The standard twenty amino acid "alphabet" has been divided into chemical families based on similarity of their side chains. Those families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). A "conservative amino acid substitution" is one in which the amino acid residue is replaced with an amino acid residue having a chemically similar side chain (i.e., replacing an amino acid having a basic side chain with another amino acid having a basic side chain). A "non-conservative amino acid substitution" is one in which the amino acid residue is replaced with an amino acid residue having a chemically different side chain (i.e., replacing an amino acid having a basic side chain with another amino acid having an aromatic side chain).

Amino acid substitutions in the mvaE polypeptide can be introduced to improve the functionality of the molecule. For example, amino acid substitutions that increase the binding affinity of the mvaE polypeptide for its substrate, or that improve its ability to convert acetyl Co-A to acetoacetyl CoA and/or the ability to convert 3-hydroxy-3-methylglutaryl-CoA to mevalonate can be introduced into the mvaE polypeptide. In some aspects, the mutant mvaE polypeptides contain one or more conservative amino acid substitutions.

In one aspect, mvaE proteins that are not degraded or less prone to degradation can be used for the production of mevalonate, isoprene, isoprenoid precursors, and/or isoprenoids. Examples of gene products of mvaEs that are not degraded or less prone to degradation which can be used include, but are not limited to, those from the organisms E. faecium, E. gallinarum, E. casseliflavus, and L. grayi. One of skill in the art can express mvaE protein in E. coli BL21 (DE3) and look for absence of fragments by any standard molecular biology techniques. For example, absence of fragments can be identified on Safestain stained SDS-PAGE gels following His-tag mediated purification or when expressed in mevalonate, isoprene or isoprenoid producing E. coli BL21 using the methods of detection described herein.

Standard methods, such as those described in Hedl et al., (J Bacteriol. 2002, April; 184(8): 2116-2122) can be used to determine whether a polypeptide has mvaE activity, by measuring acetoacetyl-CoA thiolase as well as HMG-CoA reductase activity. In an exemplary assay, acetoacetyl-CoA thiolase activity is measured by spectrophotometer to monitor the change in absorbance at 302 nm that accompanies the formation or thiolysis of acetoacetyl-CoA. Standard assay conditions for each reaction to determine synthesis of acetoacetyl-CoA, are 1 mM acetyl-CoA, 10 mM $MgCl_2$, 50 mM Tris, pH 10.5 and the reaction is initiated by addition of enzyme. Assays can employ a final volume of 2004 For the assay, 1 enzyme unit (eu) represents the synthesis or thiolysis in 1 min of 1 μmol of acetoacetyl-CoA. In another exemplary assay, of HMG-CoA reductase activity can be monitored by spectrophotometer by the appearance or disappearance of NADP(H) at 340 nm. Standard assay conditions for each reaction measured to show reductive deacylation of HMG-CoA to mevalonate are 0.4 mM NADPH, 1.0 mM (R,S)-HMG-CoA, 100 mM KCl, and 100 mM $K_xPO_4$, pH 6.5. Assays employ a final volume of 2004 Reactions are initiated by adding the enzyme. For the assay, 1 eu represents the turnover, in 1 min, of 1 μmol of NADP(H). This corresponds to the turnover of 0.5 μmol of HMG-CoA or mevalonate.

Alternatively, production of mevalonate in cells (such as bacterial cells) can be measured by, without limitation, gas chromatography (see U.S. Patent Application Publication No.: US 2005/0287655 A1) or HPLC (See U.S. patent application Ser. No. 12/978,324). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 μM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevalonate containing solutions of known concentration.

Exemplary mvaE nucleic acids include nucleic acids that encode a polypeptide, fragment of a polypeptide, peptide, or fusion polypeptide that has at least one activity of a mvaE polypeptide. Exemplary mvaE polypeptides and nucleic acids include naturally-occurring polypeptides and nucleic acids from any of the source organisms described herein as well as mutant polypeptides and nucleic acids derived from any of the source organisms described herein. Exemplary mvaE nucleic acids include, for example, mvaE nucleic acids isolated from *Listeria grayi*_DSM 20601, *Enterococcus faecium*, *Enterococcus gallinarum* EG2, and/or *Enterococcus casseliflavus*. The mvaE nucleic acid encoded by the *Listeria grayi* DSM 20601 mvaE gene can have at least about 99%, 98%, 97%, 96%, 95%, 95%, 93%, 92%, 91%, 90%, 89%, 88%, 87%, 86%, 85% sequence identity to SEQ ID NO:1. In another aspect, the mvaE nucleic acid encoded by the *Listeria grayi* DSM 20601 mvaE gene can have at least about 84%, 83%, 82%, 81%, or 80% sequence identity to SEQ ID NO:1. The mvaE nucleic acid encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:3. In another aspect, the mvaE nucleic acid encoded by the *Enterococcus faecium* mvaE gene can have at least about 84%, 83%, 82%, 81%, or 80% sequence identity to SEQ ID NO:3. The mvaE nucleic acid encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:5. In another aspect, the mvaE nucleic acid encoded by the *Enterococcus gallinarum* EG2 mvaE gene can have at least about 84%, 83%, 82%, 81%, or 80% sequence identity to SEQ ID NO:5. The mvaE nucleic acid encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:7. In another aspect, the mvaE nucleic acid encoded by the *Enterococcus casseliflavus* mvaE gene can have at least about 84%, 83%, 82%, 81%, or 80% sequence identity to SEQ ID NO:7. In any of the aspects herein, the upper MVA pathway polypeptides may be encoded by a nucleic acid with at least about 99%, 98%, 97%, 96%, 95%, 95%, 93%, 92%, 91%, 90%, 89%, 88%, 87%, 86%, 85%, 84%, 83%, 82%, 81%, or 80% sequence identity to any one of SEQ ID NOs:1-8. In any of the aspects herein, the upper MVA pathway polypeptides may be encoded by a nucleic acid with of any one of SEQ ID NOs:1-8.

Exemplary mvaE polypeptides include fragments of a polypeptide, peptide, or fusion polypeptide that has at least one activity of an mvaE polypeptide. Exemplary mvaE polypeptides and include naturally-occurring polypeptides from any of the source organisms described herein as well as mutant polypeptides derived from any of the source organisms described herein. Exemplary mvaE polypeptides include, for example, mvaE polypeptides isolated from *Listeria grayi* DSM 20601, *Enterococcus faecium*, *Enterococcus gallinarum* EG2, and/or *Enterococcus casseliflavus*.

The mvaE polypeptide encoded by the *Listeria grayi*_DSM 20601 mvaE gene can have at least about 99%, 98%, 97%, 96%, 95%, 95%, 93%, 92%, 91%, 90%, 89%, 88%, 87%, 86%, 85% sequence identity to SEQ ID NO:11. In another aspect, the mvaE polypeptide encoded by the *Listeria grayi* DSM 20601 mvaE gene can have at least about 84%, 83%, 82%, 81%, or 80% sequence identity to SEQ ID NO:11. The mvaE polypeptide encoded by the *Enterococcus faecium* mvaE gene can have at least about 99%, 98%, 97%, 96%, 95%, 95%, 93%, 92%, 91%, 90%, 89%, 88%, 87%, 86%, or 85% sequence identity to SEQ ID NO:13. In another aspect, the mvaE polypeptide encoded by the *Enterococcus faecium* mvaE gene can have at least about 84%, 83%, 82%, 81%, or 80% sequence identity to SEQ ID NO:13. The mvaE polypeptide encoded by the *Enterococcus gallinarum* EG2 mvaE gene can have at least about 99%, 98%, 97%, 96%, 95%, 95%, 93%, 92%, 91%, 90%, 89%, 88%, 87%, 86%, or 85% sequence identity to SEQ ID NO:9. In another aspect, the mvaE polypeptide encoded by the *Enterococcus gallinarum* EG2 mvaE gene can have at least about 84%, 83%, 82%, 81%, or 80% sequence identity to SEQ ID NO:9. The mvaE polypeptide encoded by the *Enterococcus casseliflavus* mvaE gene can have at least about 99%, 98%, 97%, 96%, 95%, 95%, 93%, 92%, 91%, 90%, 89%, 88%, 87%, 86%, or 85% sequence identity to SEQ ID NO:15. In another aspect, the mvaE polypeptide encoded by the *Enterococcus casseliflavus* mvaE gene can have at least about 84%, 83%, 82%, 81%, or 80% sequence identity to SEQ ID NO:15. In any of the aspects herein, the upper MVA pathway polypeptides may be encoded by a polypeptide with at least about 99%, 98%, 97%, 96%, 95%, 95%, 93%, 92%, 91%, 90%, 89%, 88%, 87%, 86%, 85%, 84%, 83%, 82%, 81%, or 80% sequence identity to any one of SEQ ID NOs:9-16. In any of the aspects herein, the upper MVA pathway polypeptides may be encoded by a polypeptide with any one of SEQ ID NOs:9-16.

The mvaE nucleic acid can be expressed in a cell (such as a bacterial cell) on a multicopy plasmid. The plasmid can be a high copy plasmid, a low copy plasmid, or a medium copy plasmid. Alternatively, the mvaE nucleic acid can be integrated into the host cell's chromosome. For both heterologous expression of an mvaE nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaE nucleic acid.

Exemplary mvaS Polypeptides and Nucleic Acids

The mvaS gene encodes a polypeptide that possesses HMG-CoA synthase activity. This polypeptide can convert acetoacetyl CoA to 3-hydroxy-3-methylglutaryl-CoA (HMG-CoA). Exemplary mvaS polypeptides and nucleic acids include naturally-occurring polypeptides and nucleic acids from any of the source organisms described herein as well as mutant polypeptides and nucleic acids derived from any of the source organisms described herein that have at least one activity of a mvaS polypeptide.

Mutant mvaS polypeptides include those in which one or more amino acid residues have undergone an amino acid substitution while retaining mvaS polypeptide activity (i.e., the ability to convert acetoacetyl CoA to 3-hydroxy-3-methylglutaryl-CoA). Amino acid substitutions in the mvaS polypeptide can be introduced to improve the functionality of the molecule. For example, amino acid substitutions that increase the binding affinity of the mvaS polypeptide for its substrate, or that improve its ability to convert acetoacetyl CoA to 3-hydroxy-3-methylglutaryl-CoA can be introduced into the mvaS polypeptide. In some aspects, the mutant mvaS polypeptides contain one or more conservative amino acid substitutions.

Standard methods, such as those described in Quant et al. (*Biochem J.*, 1989, 262:159-164), can be used to determine whether a polypeptide has mvaS activity, by measuring HMG-CoA synthase activity. In an exemplary assay, HMG-CoA synthase activity can be assayed by spectrophotometrically measuring the disappearance of the enol form of acetoacetyl-CoA by monitoring the change of absorbance at 303 nm. A standard 1 ml assay system containing 50 mm-Tris/HCl, pH 8.0, 10 mM-MgCl2 and 0.2 mM-dithiothreitol at 30° C.; 5 mM-acetyl phosphate, 10,M-acetoacetyl-CoA and 5 ul samples of extracts can be added, followed by simultaneous addition of acetyl-CoA (100 uM) and 10 units of PTA. HMG-CoA synthase activity is then measured as the difference in the rate before and after acetyl-CoA addition. The absorption coefficient of acetoacetyl-CoA under the conditions used (pH 8.0, 10 mM-MgCl2), is $12.2 \times 10^3$ $M^{-1}$ $cm^{-1}$. By definition, 1 unit of enzyme activity causes 1 umol of acetoacetyl-CoA to be transformed per minute.

Alternatively, production of mevalonate in cells (such as bacterial cells) can be measured by, without limitation, gas chromatography (see U.S. Patent Application Publication No.: US 2005/0287655 A1, the contents of which is incorporated by reference herein in its entirety) or HPLC (see U.S. Patent Application Publication No.: 2011/0159557 A1, the contents of which is incorporated by reference herein in its entirety). As an exemplary assay, cultures can be inoculated in shake tubes containing LB broth supplemented with one or more antibiotics and incubated for 14 h at 34° C. at 250 rpm. Next, cultures can be diluted into well plates containing TM3 media supplemented with 1% Glucose, 0.1% yeast extract, and 200 μM IPTG to final OD of 0.2. The plate are then sealed with a Breath Easier membrane (Diversified Biotech) and incubated at 34° C. in a shaker/incubator at 600 rpm for 24 hours. 1 mL of each culture is then centrifuged at 3,000×g for 5 min. Supernatant is then added to 20% sulfuric acid and incubated on ice for 5 min. The mixture is then centrifuged for 5 min at 3000×g and the supernatant was collected for HPLC analysis. The concentration of mevalonate in samples is determined by comparison to a standard curve of mevalonate (Sigma). The glucose concentration can additionally be measured by performing a glucose oxidase assay according to any method known in the art. Using HPLC, levels of mevalonate can be quantified by comparing the refractive index response of each sample versus a calibration curve generated by running various mevonate containing solutions of known concentration.

Exemplary mvaS nucleic acids include nucleic acids that encode a polypeptide, fragment of a polypeptide, peptide, or fusion polypeptide that has at least one activity of a mvaS polypeptide. Exemplary mvaS polypeptides and nucleic acids include naturally-occurring polypeptides and nucleic acids from any of the source organisms described herein as well as mutant polypeptides and nucleic acids derived from any of the source organisms described herein. Exemplary mvaS nucleic acids include, for example, mvaS nucleic acids isolated from *Listeria grayi*_DSM 20601, *Enterococcus faecium*, *Enterococcus gallinarum* EG2, and/or *Enterococcus casseliflavus*. The mvaS nucleic acid encoded by the *Listeria grayi*_DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:2. The mvaS nucleic acid encoded by the *Listeria grayi*_DSM 20601 mvaS gene can also have at least about 84%, 83%, 82%, 81%, or 80% sequence identity to SEQ ID NO:2. The mvaS nucleic acid encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:4. The mvaS nucleic acid encoded by the *Enterococcus faecium* mvaS gene can have at least about 84%, 83%, 82%, 81%, or 80% sequence identity to SEQ ID NO:4. The mvaS nucleic acid encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:6. The mvaS nucleic acid encoded by the *Enterococcus gallinarum* EG2 mvaS gene can have at least about 84%, 83%, 82%, 81%, or 80% sequence identity to SEQ ID NO:6. The mvaS nucleic acid encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:8. The mvaS nucleic acid encoded by the *Enterococcus casseliflavus* mvaS gene can have at least about 84%, 83%, 82%, 81%, or 80% sequence identity to SEQ ID NO:8.

Exemplary mvaS polypeptides include fragments of a polypeptide, peptide, or fusion polypeptide that has at least one activity of an mvaS polypeptide. Exemplary mvaS polypeptides include naturally-occurring polypeptides and polypeptides from any of the source organisms described herein as well as mutant polypeptides derived from any of the source organisms described herein. Exemplary mvaS polypeptides include, for example, mvaS polypeptides isolated from *Listeria grayi*_DSM 20601, *Enterococcus faecium*, *Enterococcus gallinarum* EG2, and/or *Enterococcus casseliflavus*. The mvaS polypeptide encoded by the *Listeria grayi*_DSM 20601 mvaS gene can have at least about 99%, 98%, 97%, 96%, 95%, 95%, 93%, 92%, 91%, 90%, 89%, 88%, 87%, 86%, or 85% sequence identity to SEQ ID NO:12. The mvaS polypeptide encoded by the *Listeria grayi*_DSM 20601 mvaS gene can also have at least about 84%, 83%, 82%, 81%, or 80% sequence identity to SEQ ID NO:12. The mvaS polypeptide encoded by the *Enterococcus faecium* mvaS gene can have at least about 99%, 98%, 97%, 96%, 95%, 95%, 93%, 92%, 91%, 90%, 89%, 88%, 87%, 86%, or 85% sequence identity to SEQ ID NO:14. The mvaS polypeptide encoded by the *Enterococcus faecium* mvaS gene can have at least about 84%, 83%, 82%, 81%, or 80% sequence identity to SEQ ID NO:14. The mvaS polypeptide encoded by the *Enterococcus gallinarum* EG2 mvaS gene can have at least about 99%, 98%, 97%, 96%, 95%, 95%, 93%, 92%, 91%, 90%, 89%, 88%, 87%, 86%, or 85% sequence identity to SEQ ID NO:10. The mvaS polypeptide encoded by the *Enterococcus gallinarum* EG2 mvaS gene can have at least about 84%, 83%, 82%, 81%, or 80% sequence identity to SEQ ID NO:10. The mvaS polypeptide encoded by the *Enterococcus casseliflavus* mvaS gene can have at least about 99%, 98%, 97%, 96%, 95%, 95%, 93%, 92%, 91%, 90%, 89%, 88%, 87%, 86%, or 85% sequence identity to SEQ ID NO:16. The mvaS polypeptide encoded by the *Enterococcus casseliflavus* mvaS gene can have at least about 84%, 83%, 82%, 81%, or 80% sequence identity to SEQ ID NO:16.

The mvaS nucleic acid can be expressed in a cell (such as a bacterial cell) on a multicopy plasmid. The plasmid can be a high copy plasmid, a low copy plasmid, or a medium copy plasmid. Alternatively, the mvaS nucleic acid can be integrated into the host cell's chromosome. For both heterologous expression of an mvaS nucleic acid on a plasmid or as an integrated part of the host cell's chromosome, expression of the nucleic acid can be driven by either an inducible promoter or a constitutively expressing promoter. The promoter can be a strong driver of expression, it can be a weak driver of expression, or it can be a medium driver of expression of the mvaS nucleic acid.

Exemplary Host Cells

One of skill in the art will recognize that expression vectors are designed to contain certain components which optimize gene expression for certain host strains. Such optimization components include, but are not limited to origin of replication, promoters, and enhancers. The vectors and components referenced herein are described for exemplary purposes and are not meant to narrow the scope of the invention.

Any microorganism or progeny thereof that can be used to heterologously express genes can be used to express one or more mvaE and mvaS genes from *L. grayi, E. faecium, E. gallinarum*, and/or *E. casseliflavus*. Recombinant cells can be made to heterologously express genes can be used to express one or more mvaE and mvaS genes from *L. grayi, E. faecium, E. gallinarum*, and/or *E. casseliflavus*. Bacteria cells, including gram positive or gram negative bacteria can be used to express any of the mvaE and mvaS genes described above. In particular, the mvaE and mvaS genes can be expressed in any one of *P. citrea, B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus, B. thuringiensis, S. albus, S. lividans, S. coelicolor, S. griseus, Pseudomonas* sp., and *P. alcaligenes* cells. Additionally, the mvaE and mvaS genes can be expressed in any *Lactobacillus* spp., such as *Lactobacillus lactis* or *Lactobacillus plantarum*.

There are numerous types of anaerobic cells that can be used as host cells in the compositions and methods of the present invention. In one aspect of the invention, the cells described in any of the compositions or methods described herein are obligate anaerobic cells and progeny thereof. Obligate anaerobes typically do not grow well, if at all, in conditions where oxygen is present. It is to be understood that a small amount of oxygen may be present, that is, there is some tolerance level that obligate anaerobes have for a low level of oxygen. In one aspect, obligate anaerobes engineered to produce mevalonate, isoprene, isoprenoid precursors, and isoprenoids can serve as host cells for any of the methods and/or compositions described herein and are grown under substantially oxygen-free conditions, wherein the amount of oxygen present is not harmful to the growth, maintenance, and/or fermentation of the anaerobes.

In another aspect of the invention, the host cells described and/or used in any of the compositions or methods described herein are facultative anaerobic cells and progeny thereof. Facultative anaerobes can generate cellular ATP by aerobic respiration (e.g., utilization of the TCA cycle) if oxygen is present. However, facultative anaerobes can also grow in the absence of oxygen. This is in contrast to obligate anaerobes which die or grow poorly in the presence of greater amounts of oxygen. In one aspect, therefore, facultative anaerobes can serve as host cells for any of the compositions and/or methods provided herein and can be engineered to produce mevalonate, isoprene, isoprenoid precursors, and isoprenoids. Facultative anaerobic host cells can be grown under substantially oxygen-free conditions, wherein the amount of oxygen present is not harmful to the growth, maintenance, and/or fermentation of the anaerobes, or can be alternatively grown in the presence of greater amounts of oxygen.

The host cell can additionally be a filamentous fungal cell and progeny thereof. (See, e.g., Berka & Barnett, *Biotechnology Advances*, (1989), 7(2):127-154). In some aspects, the filamentous fungal cell can be any of *Trichoderma longibrachiatum, T. viride, T. koningii, T. harzianum, Penicillium* sp., *Humicola insolens, H. lanuginose, H. grisea, Chrysosporium* sp., *C. lucknowense, Gliocladium* sp., *Aspergillus* sp., such as *A. oryzae, A. niger, A sojae, A. japonicus, A. nidulans*, or *A. awamori, Fusarium* sp., such as *F. roseum, F. graminum F. cerealis, F. oxysporuim*, or *F. venenatum, Neurospora* sp., such as *N. crassa, Hypocrea* sp., *Mucor* sp., such as *M. miehei, Rhizopus* sp. or *Emericella* sp. In some aspects, the fungus is *A. nidulans, A. awamori, A. oryzae, A. aculeatus, A. niger, A. japonicus, T. reesei, T. viride, F. oxysporum*, or *F. solani*. In certain embodiments, plasmids or plasmid components for use herein include those described in U.S. Patent Application Publication No. US 2011/0045563, the contents of which are incorporated by reference herein in its entirety.

The host cell can also be a yeast, such as *Saccharomyces* sp., *Schizosaccharomyces* sp., *Pichia* sp., or *Candida* sp. In some aspects, the *Saccharomyces* sp. is *Saccharomyces cerevisiae* (See, e.g., Romanos et al., *Yeast*, (1992), 8(6): 423-488, the contents of which are incorporated by reference herein in its entirety). In certain embodiments, plasmids or plasmid components for use herein include those described in U.S. Pat. No. 7,659,097 and U.S. Patent Application Publication No. 2011/0045563, the contents of which are incorporated by reference herein in their entireties.

The host cell can additionally be a species of algae, such as a green algae, red algae, glaucophytes, chlorarachniophytes, euglenids, chromista, or dinoflagellates. (See, e.g., Saunders & Warmbrodt, "*Gene Expression in Algae and Fungi, Including Yeast*," (1993), National Agricultural Library, Beltsville, Md., the contents of which are incorporated by reference herein in their entireties). In certain embodiments, plasmids or plasmid components for use herein include those described in U.S. Patent Pub. No. US 2011/0045563, the contents of which are incorporated by reference herein in its entirety. In some aspects, the host cell is a cyanobacterium, such as cyanobacterium classified into any of the following groups based on morphology: Chlorococcales, Pleurocapsales, Oscillatoriales, Nostocales, or Stigonematales (See, e.g., Lindberg et al., Metab. Eng., (2010) 12(1):70-79). In certain embodiments, plasmids or plasmid components for use herein include those described in U.S. patent pub. No. US 2010/0297749; US 2009/0282545 and Intl. Pat. Appl. No. WO 2011/034863, the contents of which are incorporated by reference herein in their entireties.

*E. coli* host cells can be used to express one or more mvaE and mvaS polypeptides from *L. grayi, E. faecium, E. gallinarum*, and/or *E. casseliflavus* in the compositions and methods described herein. In one aspect, the host cell is a recombinant cell of an *Escherichia coli* (*E. coli*) strain, or progeny thereof, capable of producing mevalonate that expresses one or more nucleic acids encoding mvaE and mvaS polypeptides from *L. grayi, E. faecium, E. gallinarum*, and/or *E. casseliflavus*. The *E. coli* host cells can produce mevalonate in amounts, peak titers, and cell productivities greater than that of the same cells lacking one or more heterologously expressed nucleic acids encoding mvaE and mvaS polypeptides from *L. grayi, E. faecium, E. gallinarum*, and/or *E. casseliflavus*. In addition, the one or more heterologously expressed nucleic acids encoding mvaE and mvaS polypeptides from *L. grayi, E. faecium, E. gallinarum,* and/or *E. casseliflavus* in *E. coli* can be chromosomal copies (e.g., integrated into the *E. coli* chromosome). In other aspects, the *E. coli* cells are in culture.

Exemplary Cell Culture Media

As used herein, the terms "minimal medium" or "minimal media" refer to growth medium containing the minimum nutrients possible for cell growth, generally, but not always, without the presence of one or more amino acids (e.g., 1, 2, 3, 4, 5, 6, 7, 8, 9, 10, or more amino acids). Minimal medium typically contains: (1) a carbon source for cellular (e.g. bacterial) growth; (2) various salts, which can vary among cellular (e.g. bacterial) species and growing conditions; and (3) water. The carbon source can vary significantly, from simple sugars like glucose to more complex hydrolysates of other biomass, such as yeast extract, as discussed in more detail below. The salts generally provide essential elements such as magnesium, nitrogen, phosphorus, and sulfur to allow the cells to synthesize proteins and nucleic acids. Minimal medium can also be supplemented with selective agents, such as antibiotics, to select for the maintenance of certain plasmids and the like. For example, if a microorganism is resistant to a certain antibiotic, such as ampicillin or tetracycline, then that antibiotic can be added to the medium in order to prevent cells lacking the resistance from growing. Medium can be supplemented with other compounds as necessary to select for desired physiological or biochemical characteristics, such as particular amino acids and the like.

Any minimal medium formulation can be used to cultivate the host cells. Exemplary minimal medium formulations include, for example, M9 minimal medium and TM3 minimal medium. Each liter of M9 minimal medium contains (1) 200 ml sterile M9 salts (64 g $Na_2HPO_4 \cdot 7H_2O$, 15 g $KH_2PO_4$, 2.5 g NaCl, and 5.0 g $NH_4Cl$ per liter); (2) 2 ml of 1M $MgSO_4$ (sterile); (3) 20 ml of 20% (w/v) glucose (or other carbon source); and (4) 100 µl of 1M $CaCl_2$ (sterile). Each liter of TM3 minimal medium contains (1) 13.6 g $K_2HPO_4$; (2) 13.6 g $KH_2PO_4$; (3) 2 g $MgSO_4 \cdot 7H_2O$; (4) 2 g Citric Acid Monohydrate; (5) 0.3 g Ferric Ammonium Citrate; (6) 3.2 g $(NH_4)_2SO_4$; (7) 0.2 g yeast extract; and (8) 1 ml of 1000× Trace Elements solution; pH is adjusted to ~6.8 and the solution is filter sterilized. Each liter of 1000× Trace Elements contains: (1) 40 g Citric Acid Monohydrate; (2) 30 g $MnSO_4 \cdot H_2O$; (3) 10 g NaCl; (4) 1 g $FeSO_4 \cdot 7H_2O$; (4) 1 g $CoCl_2 \cdot 6H_2O$; (5) 1 g $ZnSO_4 \cdot 7H_2O$; (6) 100 mg $CuSO_4 \cdot 5H_2O$; (7) 100 mg $H_3BO_3$; and (8) 100 mg $NaMoO_4 \cdot 2H_2O$; pH is adjusted to ~3.0.

An additional exemplary minimal media includes (1) potassium phosphate $K_2HPO_4$, (2) Magnesium Sulfate $MgSO_4 \cdot 7H_2O$, (3) citric acid monohydrate $C_6H_8O_7 \cdot H_2O$, (4) ferric ammonium citrate $NH_4FeC_6H_5O_7$, (5) yeast extract (from biospringer), (6) 1000× Modified Trace Metal Solution, (7) sulfuric acid 50% w/v, (8) foamblast 882 (Emerald Performance Materials), and (9) Macro Salts Solution 3.36 ml All of the components are added together and dissolved in deionized $H_2O$ and then heat sterilized. Following cooling to room temperature, the pH is adjusted to 7.0 with ammonium hydroxide (28%) and q.s. to volume. Vitamin Solution and spectinomycin are added after sterilization and pH adjustment.

Any carbon source can be used to cultivate the host cells. The term "carbon source" refers to one or more carbon-containing compounds capable of being metabolized by a host cell or organism. For example, the cell medium used to cultivate the host cells can include any carbon source suitable for maintaining the viability or growing the host cells. In some aspects, the carbon source is a carbohydrate (such as monosaccharide, disaccharide, oligosaccharide, or polysaccharides), or invert sugar (e.g., enzymatically treated sucrose syrup).

In some aspects, the carbon source includes yeast extract or one or more components of yeast extract. In some aspects, the concentration of yeast extract is 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. In some aspects, the carbon source includes both yeast extract (or one or more components thereof) and another carbon source, such as glucose.

Exemplary monosaccharides include glucose and fructose; exemplary oligosaccharides include lactose and sucrose, and exemplary polysaccharides include starch and cellulose. Exemplary carbohydrates include C6 sugars (e.g., fructose, mannose, galactose, or glucose) and C5 sugars (e.g., xylose or arabinose).

Exemplary Cell Culture Conditions

Materials and methods suitable for the maintenance and growth of the recombinant cells of the invention are described infra, e.g., in the Examples section. Other materials and methods suitable for the maintenance and growth of cell (e.g. bacterial) cultures are well known in the art. Exemplary techniques can be found in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, *Manual of Methods for General Bacteriology* Gerhardt et al., eds), American Society for Microbiology, Washington, D.C. (1994) or Brock in *Biotechnology: A Textbook of Industrial Microbiology,* Second Edition (1989) Sinauer Associates, Inc., Sunderland, Mass. In some aspects, the cells are cultured in a culture medium under conditions permitting the expression of one or more mvaE, mvaS, isoprene synthase, DXP pathway (e.g., DXS), IDI, MVA pathway, or PGL polypeptides encoded by a nucleic acid inserted into the host cells.

Standard cell culture conditions can be used to culture the cells (see, for example, WO 2004/033646 and references cited therein). In some aspects, cells are grown and maintained at an appropriate temperature, gas mixture, and pH (such as at about 20° C. to about 37° C., at about 6% to about 84% $CO_2$, and at a pH between about 5 to about 9). In some aspects, cells are grown at 35° C. in an appropriate cell medium. In some aspects, the pH ranges for fermentation are between about pH 5.0 to about pH 9.0 (such as about pH 6.0 to about pH 8.0 or about 6.5 to about 7.0). Cells can be grown under aerobic, anoxic, or anaerobic conditions based on the requirements of the host cells. In addition, more specific cell culture conditions can be used to culture the cells. For example, in some embodiments, the cells (for example, bacterial cells (such as *E. coli* cells)) express one or more heterologous nucleic acids encoding mvaE and mvaS polypeptides from *L. grayi, E. faecium, E. gallinarum,* and/or *E. casseliflavus* under the control of a strong promoter in a low to medium copy plasmid and are cultured at 34° C.

Standard culture conditions and modes of fermentation, such as batch, fed-batch, or continuous fermentation that can be used are described in International Publication No. WO 2009/076676, U.S. patent application Ser. No. 12/335,071 (U.S. Publ. No. 2009/0203102), WO 2010/003007, US Publ. No. 2010/0048964, WO 2009/132220, US Publ. No. 2010/0003716, the contents of each of which are incorporated by reference herein in their entireties. Batch and Fed-Batch fermentations are common and well known in the art and examples can be found in Brock, Biotechnology: *A Textbook of Industrial Microbiology*, Second Edition (1989) Sinauer Associates, Inc.

In some aspects, the cells are cultured under limited glucose conditions. By "limited glucose conditions" is meant that the amount of glucose that is added is less than or about 105% (such as about 100%, 90%, 80%, 70%, 60%, 50%, 40%, 30%, 20%, or 10%) of the amount of glucose that is consumed by the cells. In particular aspects, the amount of glucose that is added to the culture medium is approximately the same as the amount of glucose that is consumed by the cells during a specific period of time. In some aspects, the rate of cell growth is controlled by limiting the amount of added glucose such that the cells grow at the rate that can be supported by the amount of glucose in the cell medium. In some aspects, glucose does not accumulate during the time the cells are cultured. In various aspects, the cells are cultured under limited glucose conditions for greater than or about 1, 2, 3, 5, 10, 15, 20, 25, 30, 35, 40, 50, 60, or 70 hours. In various aspects, the cells are cultured under limited glucose conditions for greater than or about 5, 10, 15, 20, 25, 30, 35, 40, 50, 60, 70, 80, 90, 95, or 100% of the total length of time the cells are cultured. While not intending to be bound by any particular theory, it is believed that limited glucose conditions can allow more favorable regulation of the cells.

In some aspects, the cells (such as bacterial cells) are grown in batch culture. The cells (such as bacterial cells) can also be grown in fed-batch culture or in continuous culture. Additionally, the cells (such as bacterial cells) can be cultured in minimal medium, including, but not limited to, any of the minimal media described above. The minimal medium can be further supplemented with 1.0% (w/v) glucose, or any other six carbon sugar, or less. Specifically, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose. Additionally, the minimal medium can be supplemented 0.1% (w/v) or less yeast extract. Specifically, the minimal medium can be supplemented with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract. Alternatively, the minimal medium can be supplemented with 1% (w/v), 0.9% (w/v), 0.8% (w/v), 0.7% (w/v), 0.6% (w/v), 0.5% (w/v), 0.4% (w/v), 0.3% (w/v), 0.2% (w/v), or 0.1% (w/v) glucose and with 0.1% (w/v), 0.09% (w/v), 0.08% (w/v), 0.07% (w/v), 0.06% (w/v), 0.05% (w/v), 0.04% (w/v), 0.03% (w/v), 0.02% (w/v), or 0.01% (w/v) yeast extract.

Recombinant Cells (Such as Bacterial Cells) Capable of Increased Production of Isoprenoid Precursors (e.g. Mevalonate)

The recombinant cells (such as bacterial cells) described herein have the ability to produce isoprenoid precursors (e.g. mevalonate) at a concentration greater than that of the same cells lacking one or more copies of a heterologous nucleic acid encoding mvaE and mvaS polypeptides from *L. grayi, E. faecium, E. gallinarum,* and/or *E. casseliflavus*. In one embodiment, the recombinant cells (such as bacterial cells) described herein have the ability to produce mevalonate at a concentration greater than that of the same cells lacking one or more copies of a heterologous nucleic acid encoding mvaE and mvaS polypeptides from *L. grayi, E. faecium, E. gallinarum,* and/or *E. casseliflavus*, optionally when cultured in minimal medium. In some cases, the one or more copies of a heterologous nucleic acid encoding mvaE and mvaS polypeptides from *L. grayi, E. faecium, E. gallinarum,* and/or *E. casseliflavus* is a heterologous nucleic acid that is integrated into the host cell's chromosome. The cells (such as bacterial cells) can produce greater than about 85 mg/L/hr/OD of mevalonate or another isoprenoid precursor. Alternatively, the cells (such as bacterial cells) can produce greater than about 30 mg/L/hr/OD, 40 mg/L/hr/OD, 50 mg/L/hr/OD, 60 mg/L/hr/OD, 70 mg/L/hr/OD, 80 mg/L/hr/OD, 90 mg/L/hr/OD, 100 mg/L/hr/OD, 110 mg/L/hr/OD, 120 mg/L/hr/OD, 130 mg/L/hr/OD, 140 mg/L/hr/OD, 150 mg/L/hr/OD, 160 mg/L/hr/OD, 170 mg/L/hr/OD, 180 mg/L/hr/OD, 190 mg/L/hr/OD, or 200 mg/L/hr/OD of mevalonate or another isoprenoid precursor, inclusive, as well as any numerical value in between these numbers.

The cells (such as bacterial cells) described herein produce isoprenoid precursors (e.g. mevalonate) at a higher peak titer than that of the same cells lacking one or more copies of a heterologous nucleic acid encoding mvaE and mvaS polypeptides from *L. grayi, E. faecium, E. gallinarum,* and/or *E. casseliflavus*. In one embodiment, the cells (such as bacterial cells) described herein produce mevalonate at a higher peak titer than that of the same cells lacking one or more copies of a heterologous nucleic acid encoding mvaE and mvaS polypeptides from *L. grayi, E. faecium, E. gallinarum,* and/or *E. casseliflavus*, optionally when cultured in minimal medium. The cells (such as bacterial cells) can produce greater than about 105 g/L peak titer of mevalonate (or another isoprenoid precursor) after 48 hours of fermentation. Alternatively, the cells (such as bacterial cells) can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, 200 g/L, 210 g/L, 220 g/L, 230 g/L, 240 g/L, 250 g/L, 260 g/L, 270 g/L, 280 g/L, 290 g/L, 300 g/L peak titer of mevalonate (or another isoprenoid precursor) after 48 hours of fermentation, inclusive, as well as any numerical value in between these numbers.

The cells (such as bacterial cells) described herein have a higher cell productivity index (CPI) than that of the same cells lacking one or more copies of a heterologous nucleic acid encoding mvaE and mvaS polypeptides from *L. grayi, E. faecium, E. gallinarum,* and/or *E. casseliflavus*. The cells (such as bacterial cells) described herein have a higher cell productivity index (CPI) than that of the same cells lacking one or more copies of a heterologous nucleic acid encoding mvaE and mvaS polypeptides from *L. grayi, E. faecium, E. gallinarum,* and/or *E. casseliflavus*, optionally when cultured in minimal medium. The cells (such as bacterial cells) can have a CPI for mevalonate (or another isoprenoid precursor) of at least about 4.5 (g/g). Alternatively, the cells (such as bacterial cells) can have a CPI for mevalonate (or another isoprenoid precursor) of at least about 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers.

The cells (such as bacterial cells) described herein have a higher mass yield of isoprenoid precursors (e.g. mevalonate) from glucose than that of the same cells lacking one or more copies of a heterologous nucleic acid encoding mvaE and mvaS polypeptides from *L. grayi, E. faecium, E. gallinarum,* and/or *E. casseliflavus*. In one embodiment, the cells (such as bacterial cells) described herein have a higher mass yield of mevalonate from glucose than that of the same cells lacking one or more copies of a heterologous nucleic acid encoding mvaE and mvaS polypeptides from *L. grayi, E. faecium, E. gallinarum,* and/or *E. casseliflavus* when cultured in minimal medium. The cells (such as bacterial cells)

can produce a mass yield of mevalonate (or another isoprenoid precursor) from glucose of at least about 38%. Alternatively, the cells (such as bacterial cells) can produce a mass yield of mevalonate (or another isoprenoid precursor) from glucose of at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, or 55%, inclusive, as well as any numerical value in between these numbers.

In some aspects, the cells described herein are mevalonate-producing cells. In one aspect, mevalonate producing cells are wild type cells capable of producing mevalonate. In another aspect, mevalonate producing cells are non-naturally occurring cells engineered to contain one or more non-native upper MVA pathway polypeptides.

Methods of Using Recombinant Cells (Such as Bacterial Cells) to Produce High Amounts of Isoprenoid Precursor (e.g. Mevalonate)

Also provided herein are methods for the production of isoprenoid precursors, such as mevalonate. In some aspects, the method for producing isoprenoid precursors comprises: (a) culturing a composition comprising recombinant cells (including any of the bacterial cells described herein), or progeny thereof, capable of producing isoprenoid precursors; and (b) producing isoprenoid precursor. In some aspects, the method of producing isoprenoid precursor comprises the steps of culturing any of the recombinant cells described herein under conditions suitable for the production of isoprenoid precursor and allowing the recombinant cells to produce isoprenoid precursor. In some aspects, the method of producing isoprenoid precursor further comprises a step of recovering the isoprenoid precursor.

In some aspects, the method for producing mevalonate comprises: (a) culturing a composition comprising recombinant bacterial cells (including any of the bacterial cells described above), or progeny thereof, capable of producing mevalonate; and (b) producing mevalonate. In some aspects, the method of producing mevalonate comprises the steps of culturing any of the recombinant cells described herein under conditions suitable for the production of mevalonate and allowing the recombinant cells to produce mevalonate. In some aspects, the method of producing mevalonate further comprises a step of recovering the mevalonate.

The method of producing mevalonate (or another isoprenoid precursor) can also comprise the steps of: (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus*, optionally in minimal medium, wherein the cells heterologously express one or more copies of a gene encoding a mvaE polypeptide and an mvaS polypeptide from *L. grayi, E. faecium, E. gallinarum,* or *E. casseliflavus*; and (b) producing mevalonate (or another isoprenoid precursor). The cells (such as bacterial cells) can produce mevalonate (or another isoprenoid precursor) in concentrations greater than that of the same cells lacking one or more heterologous copies of a gene encoding an mvaE polypeptide and an mvaS polypeptide from *L. grayi, E. faecium, E. gallinarum*, or *E. casseliflavus*, optionally, when the cells are cultured in minimal medium. In some cases, the one or more copies of a heterologous nucleic acid encoding an mvaE and an mvaS polypeptide from *L. grayi, E. faecium, E. gallinarum*, and/or *E. casseliflavus* is a heterologous nucleic acid that is integrated into the host cell's chromosome.

The instant methods for the production of isoprenoid precursors can produce greater than about 85 mg/L/hr/OD of isoprenoid precursors. Alternatively, isoprenoid precursors can be produced in amounts greater than about 30 mg/L/hr/OD, 40 mg/L/hr/OD, 50 mg/L/hr/OD, 60 mg/L/hr/OD, 70 mg/L/hr/OD, 80 mg/L/hr/OD, 90 mg/L/hr/OD, 100 mg/L/hr/OD, 110 mg/L/hr/OD, 120 mg/L/hr/OD, 130 mg/L/hr/OD, 140 mg/L/hr/OD, 150 mg/L/hr/OD, 160 mg/L/hr/OD, 170 mg/L/hr/OD, 180 mg/L/hr/OD, 190 mg/L/hr/OD, or 200 mg/L/hr/OD of isoprenoid precursors, inclusive, as well as any numerical value in between these numbers. In some aspects, the method of producing isoprenoid precursors further comprises a step of recovering the isoprenoid precursors.

The instant methods for the production of mevalonate can produce greater than about 85 mg/L/hr/OD of mevalonate. Alternatively, mevalonate can be produced in amounts greater than about 30 mg/L/hr/OD, 40 mg/L/hr/OD, 50 mg/L/hr/OD, 60 mg/L/hr/OD, 70 mg/L/hr/OD, 80 mg/L/hr/OD, 90 mg/L/hr/OD, 100 mg/L/hr/OD, 110 mg/L/hr/OD, 120 mg/L/hr/OD, 130 mg/L/hr/OD, 140 mg/L/hr/OD, 150 mg/L/hr/OD, 160 mg/L/hr/OD, 170 mg/L/hr/OD, 180 mg/L/hr/OD, 190 mg/L/hr/OD, or 200 mg/L/hr/OD of mevalonate, inclusive, as well as any numerical value in between these numbers. In some aspects, the method of producing mevalonate further comprises a step of recovering the mevalonate.

The method of producing isoprenoid precursors can comprise the steps of: (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus*, wherein the cells (such as bacterial cells) heterologously express one or more copies of a gene encoding a mvaE polypeptide and an mvaS polypeptide from *L. grayi, E. faecium, E. gallinarum*, or *E. casseliflavus*; and (b) producing isoprenoid precursors, wherein the cells (such as bacterial cells) produce isoprenoid precursors with a higher peak titer after 48 hours of fermentation than that of the same cells lacking one or more heterologous copies of a gene encoding an mvaE polypeptide and an mvaS polypeptide from *L. grayi, E. faecium, E. gallinarum*, or *E. casseliflavus*. Optionally, the cells described above are cultured in minimal medium.

The instant methods for the production of isoprenoid precursors can produce greater than about 105 g/L peak titer of isoprenoid precursors after 48 hours of fermentation. Alternatively, the cells (such as bacterial cells) can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, or 200 g/L peak titer of isoprenoid precursors after 48 hours of fermentation, inclusive, as well as any numerical value in between these numbers. In some aspects, the method of producing isoprenoid precursors further comprises a step of recovering the isoprenoid precursors.

The method of producing mevalonate can similarly comprise the steps of: (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus*, optionally in minimal medium, wherein the cells (such as bacterial cells) heterologously express one or more copies of a gene encoding a mvaE polypeptide and an mvaS polypeptide from *L. grayi, E. faecium, E. gallinarum*, or *E. casseliflavus*; and (b) producing mevalonate, wherein the cells (such as bacterial cells) produce mevalonate with a higher peak titer after 48 hours of fermentation than that of the same cells lacking one or more heterologous copies of a gene encoding an mvaE polypeptide and an mvaS polypeptide from *L. grayi, E. faecium, E. gallinarum*, or *E. casseliflavus*, when the cells are cultured in minimal medium.

The instant methods for the production of mevalonate can produce greater than about 105 g/L peak titer of mevalonate after 48 hours of fermentation. Alternatively, the cells (such as bacterial cells) can produce greater than about 50 g/L, 60 g/L, 70 g/L, 80 g/L, 90 g/L, 100 g/L, 110 g/L, 120 g/L, 130 g/L, 140 g/L, 150 g/L, 160 g/L, 170 g/L, 180 g/L, 190 g/L, or 200 g/L peak titer of mevalonate after 48 hours of fermentation, inclusive, as well as any numerical value in between these numbers. In some aspects, the method of producing mevalonate further comprises a step of recovering the mevalonate.

The method of producing isoprenoid precursors can comprise the steps of: (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus*, wherein the cells (such as bacterial cells) heterologously express one or more copies of a gene encoding a mvaE polypeptide and an mvaS polypeptide from *L. grayi, E. faecium, E. gallinarum*, or *E. casseliflavus*; and (b) producing isoprenoid precursors, wherein the cells (such as bacterial cells) have a CPI for isoprenoid precursors higher than that of the same cells lacking one or more heterologous copies of a gene encoding an mvaE polypeptide and an mvaS polypeptide from *L. grayi, E. faecium, E. gallinarum*, or *E. casseliflavus*. Optionally, the cells above are cultured in minimal medium.

The instant methods for the production of isoprenoid precursors can produce isoprenoid precursors using cells with a CPI for isoprenoid precursors of at least 4.5 (g/g). Alternatively, the cells (such as bacterial cells) can have a CPI of at least 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers. In some aspects, the method of producing isoprenoid precursors further comprises a step of recovering the isoprenoid precursors.

The method of producing mevalonate can similarly comprise the steps of: (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus*, optionally in minimal medium, wherein the cells (such as bacterial cells) heterologously express one or more copies of a gene encoding a mvaE polypeptide and an mvaS polypeptide from *L. grayi, E. faecium, E. gallinarum*, or *E. casseliflavus*; and (b) producing mevalonate, wherein the cells (such as bacterial cells) have a CPI for mevalonate higher than that of the same cells lacking one or more heterologous copies of a gene encoding an mvaE polypeptide and an mvaS polypeptide from *L. grayi, E. faecium, E. gallinarum*, or *E. casseliflavus*, when the cells are cultured in minimal medium.

The instant methods for the production of mevalonate can produce mevalonate using cells with a CPI for mevalonate of at least 4.5 (g/g). Alternatively, the cells (such as bacterial cells) can have a CPI of at least 1 (g/g), 2 (g/g), 3 (g/g), 4 (g/g), 5 (g/g), 6 (g/g), 7 (g/g), 8 (g/g), 9 (g/g), 10 (g/g), 11 (g/g), 12 (g/g), 13 (g/g), 14 (g/g), 15 (g/g), 20 (g/g), 25 (g/g), or 30 (g/g) inclusive, as well as any numerical value in between these numbers. In some aspects, the method of producing mevalonate further comprises a step of recovering the mevalonate.

Provided herein are methods of using any of the cells described above for enhanced mevalonate production and/or production of other isoprenoid precursors. The production of mevalonate (or other isoprenoid precursors) by the cells can be enhanced by the expression of one or more heterologous nucleic acids encoding mvaE and mvaS polypeptides from *L. grayi, E. faecium, E. gallinarum*, and/or *E. casseliflavus*. The production of mevalonate (or other isoprenoid precursors) can be enhanced by about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of mevalonate (or other isoprenoid precursors) by cells without the expression of one or more heterologous nucleic acids encoding mvaE and mvaS polypeptides from *L. grayi, E. faecium, E. gallinarum*, and/or *E. casseliflavus*.

The production of mevalonate (or other isoprenoid precursors) by the cells according to any of the methods described herein can be enhanced (e.g., enhanced by the expression of one or more heterologous nucleic acids encoding the mvaE and mvaS polypeptides from *L. grayi, E. faecium, E. gallinarum*, and/or *E. casseliflavus*). The production of mevalonate (or other isoprenoid precursors) can be enhanced by about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of mevalonate (or other isoprenoid precursors) by naturally-occurring cells (e.g., cells not expressing one or more heterologous nucleic acids encoding mvaE and mvaS polypeptides from *L. grayi, E. faecium, E. gallinarum*, and/or *E. casseliflavus*).

The production of mevalonate (or other isoprenoid precursors) can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of mevalonate (or other isoprenoid precursors) by naturally-occurring cells or by cells without the expression of one or more heterologous nucleic acids encoding mvaE and mvaS polypeptides from *L. grayi, E. faecium, E. gallinarum*, and/or *E. casseliflavus*.

In addition, more specific cell culture conditions can be used to culture the cells in the methods described herein. For example, in some aspects, the method for the production of mevalonate comprises the steps of (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus* in minimal medium at 34° C., wherein the cells (such as bacterial cells) heterologously express one or more copies of a gene encoding a mvaE polypeptide and an mvaS polypeptide from *L. grayi, E. faecium, E. gallinarum*, or *E. casseliflavus* on a low to medium copy plasmid and under the control of a strong promoter; and (b) producing mevalonate. In some aspects, the method of producing mevalonate further comprises a step of recovering the mevalonate. In other aspects, the method for the production of isoprenoid precursors comprises the steps of (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus* in minimal medium at 34° C., wherein the cells (such as bacterial cells) heterologously express one or more copies of a gene encoding a mvaE polypeptide and an mvaS polypeptide from *L. grayi, E. faecium, E. gallinarum*, or *E. casseliflavus* on a low to medium copy plasmid and under the control of a strong promoter; and (b) producing isoprenoid precursors. In some aspects, the method of producing isoprenoid precursors further comprises a step of recovering the isoprenoid precursors.

Recombinant Cells (Such as Bacterial Cells) Capable of Increased Production of Isoprene Isoprene (2-methyl-1,3-butadiene) is an important organic compound used in a wide array of applications. For instance, isoprene is employed as an intermediate or a starting material in the synthesis of numerous chemical compositions and polymers, including in the production of synthetic rubber. Isoprene is also an important biological material that is synthesized naturally by many plants and animals.

Isoprene is produced from DMAPP by the enzymatic action of isoprene synthase. Therefore, without being bound to theory, it is thought that increasing the cellular production of isoprenoid precursors in cells (such as bacterial cells) by any of the compositions and methods described above will similarly result in the production of higher amounts of isoprene. Increasing the molar yield of isoprenoid precursors production from glucose translates into higher molar yields of isoprene produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production. Without being bound to theory, it is thought that increasing the cellular production of mevalonate in cells (such as bacterial cells) by any of the compositions and methods described above will similarly result in the production of higher amounts of isoprene. Increasing the molar yield of mevalonate production from glucose translates into higher molar yields of isoprenoid precursors and isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production.

Any of the recombinant host cells expressing one or more copies of a heterologous nucleic acid encoding an mvaE and an mvaS polypeptide from *L. grayi, E. faecium, E. gallinarum*, or *E. casseliflavus* capable of increased production of mevalonate or other isoprenoid precursors described above can also be capable of increased production of isoprene. In some aspects, these cells further comprise one or more heterologous nucleic acids encoding polypeptides of the lower MVA pathway and a heterologous nucleic acid encoding an isoprene synthase polypeptide. In some aspects, these cells further comprise one or more nucleic acids encoding polypeptides of the lower MVA pathway and a heterologous nucleic acid encoding an isoprene synthase polypeptide.

In some aspects, the cells described herein are isoprene-producing cells. In one aspect, isoprene producing cells are wild type cells capable of producing isoprene. In another aspect, isoprene producing cells are non-naturally occurring cells engineered to contain one or more heterologous upper MVA pathway polypeptides, lower MVA pathway polypeptides, isoprene synthase polypeptides, DXP pathway polypeptides, and/or IDI polypeptides. In a further aspect, the isoprene producing cells may contain both endogenous and heterologous upper MVA pathway polypeptides, lower MVA pathway polypeptides, isoprene synthase polypeptides, DXP pathway polypeptides, and/or IDI polypeptides.

Nucleic Acids Encoding Polypeptides of the Lower MVA Pathway

In some aspects of the invention, the cells described in any of the compositions or methods described herein further comprise one or more nucleic acids encoding a lower mevalonate (MVA) pathway polypeptide(s). In some aspects, the lower MVA pathway polypeptide is an endogenous polypeptide. In some aspects, the endogenous nucleic acid encoding a lower MVA pathway polypeptide is operably linked to a constitutive promoter. In some aspects, the endogenous nucleic acid encoding a lower MVA pathway polypeptide is operably linked to an inducible promoter. In some aspects, the endogenous nucleic acid encoding a lower MVA pathway polypeptide is operably linked to a strong promoter. In a particular aspect, the cells are engineered to over-express the endogenous lower MVA pathway polypeptide relative to wild-type cells. In some aspects, the endogenous nucleic acid encoding a lower MVA pathway polypeptide is operably linked to a weak promoter.

The lower mevalonate biosynthetic pathway comprises mevalonate kinase (MVK), phosphomevalonate kinase (PMK), and diphosphomevalonte decarboxylase (MVD). In some aspects, the lower MVA pathway can further comprise isopentenyl diphosphate isomerase (IDI). Cells provided herein can comprise at least one nucleic acid encoding isoprene synthase, one or more upper MVA pathway polypeptides, and/or one or more lower MVA pathway polypeptides. Polypeptides of the lower MVA pathway can be any enzyme (a) that phosphorylates mevalonate to mevalonate 5-phosphate; (b) that converts mevalonate 5-phosphate to mevalonate 5-pyrophosphate; and (c) that converts mevalonate 5-pyrophosphate to isopentenyl pyrophosphate. More particularly, the enzyme that phosphorylates mevalonate to mevalonate 5-phosphate can be from the group consisting of *M. mazei* mevalonate kinase, *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Methanococcoides* mevalonate kinase polypeptide, *Streptococcus pneumoniae* mevalonate kinase polypeptide, *Streptomyces* mevalonate kinase polypeptide, and *Streptomyces* CL190 mevalonate kinase polypeptide. In another aspect, the enzyme that phosphorylates mevalonate to mevalonate 5-phosphate is *M. mazei* mevalonate kinase.

In some aspects, the lower MVA pathway polypeptide is a heterologous polypeptide. In some aspects, the cells comprise more than one copy of a heterologous nucleic acid encoding a lower MVA pathway polypeptide. In some aspects, the heterologous nucleic acid encoding a lower MVA pathway polypeptide is operably linked to a constitutive promoter. In some aspects, the heterologous nucleic acid encoding a lower MVA pathway polypeptide is operably linked to an inducible promoter. In some aspects, the heterologous nucleic acid encoding a lower MVA pathway polypeptide is operably linked to a strong promoter. In some aspects, the heterologous nucleic acid encoding a lower MVA pathway polypeptide is operably linked to a weak promoter. In some aspects, the heterologous lower MVA pathway polypeptide is a polypeptide from *Saccharomyces cerevisiae, Enterococcus faecalis, Methanococcoides burtonii*, or *Methanosarcina mazei*. In some aspects, the heterologous lower MVA pathway polypeptide is a mevalonate kinase from *M. burtonii*.

The nucleic acids encoding a lower MVA pathway polypeptide(s) can be integrated into a genome of the cells or can be stably expressed in the cells. The nucleic acids encoding a lower MVA pathway polypeptide(s) can additionally be on a vector.

Exemplary lower MVA pathway polypeptides are also provided below: (i) mevalonate kinase (MVK); (ii) phosphomevalonate kinase (PMK); (iii) diphosphomevalonate decarboxylase (MVD); and (iv) isopentenyl diphosphate isomerase (IDI). In particular, the lower MVK polypeptide can be from the genus *Methanosarcina* and, more specifically, the lower MVK polypeptide can be from *Methanosarcina mazei*. Additional examples of lower MVA pathway polypeptides can be found in U.S. Patent Application Publication 2010/0086978 the contents of which are expressly incorporated herein by reference in their entirety with respect to lower MVK pathway polypeptides and lower MVK pathway polypeptide variants.

Any one of the cells described herein can comprise IDI nucleic acid(s) (e.g., endogenous or heterologous nucleic acid(s) encoding IDI). Isopentenyl diphosphate isomerase polypeptides (isopentenyl-diphosphate delta-isomerase or IDI) catalyzes the interconversion of isopentenyl diphosphate (IPP) and dimethylallyl diphosphate (DMAPP) (e.g., converting IPP into DMAPP and/or converting DMAPP into IPP). Exemplary IDI polypeptides include polypeptides, fragments of polypeptides, peptides, and fusions polypeptides that have at least one activity of an IDI polypeptide. Standard methods (such as those described herein) can be used to determine whether a polypeptide has IDI polypeptide activity by measuring the ability of the polypeptide to interconvert IPP and DMAPP in vitro, in a cell extract, or in vivo. Exemplary IDI nucleic acids include nucleic acids that encode a polypeptide, fragment of a polypeptide, peptide, or fusion polypeptide that has at least one activity of an IDI polypeptide. Exemplary IDI polypeptides and nucleic acids include naturally-occurring polypeptides and nucleic acids from any of the source organisms described herein as well as mutant polypeptides and nucleic acids derived from any of the source organisms described herein.

Lower MVA pathway polypeptides include polypeptides, fragments of polypeptides, peptides, and fusions polypeptides that have at least one activity of a lower MVA pathway polypeptide. Exemplary lower MVA pathway nucleic acids include nucleic acids that encode a polypeptide, fragment of a polypeptide, peptide, or fusion polypeptide that has at least one activity of a lower MVA pathway polypeptide. Exemplary lower MVA pathway polypeptides and nucleic acids include naturally-occurring polypeptides and nucleic acids from any of the source organisms described herein. In addition, variants of lower MVA pathway polypeptides that confer the result of better isoprene production can also be used as well.

In some aspects, the lower MVA pathway polypeptide is a polypeptide from *Saccharomyces cerevisiae, Enterococcus faecalis*, or *Methanosarcina mazei*. In some aspects, the MVK polypeptide is selected from the group consisting of *Lactobacillus* mevalonate kinase polypeptide, *Lactobacillus sakei* mevalonate kinase polypeptide, yeast mevalonate kinase polypeptide, *Saccharomyces cerevisiae* mevalonate kinase polypeptide, *Streptococcus* mevalonate kinase polypeptide, *Streptococcus pneumoniae* mevalonate kinase polypeptide, *Streptomyces* mevalonate kinase polypeptide, *Streptomyces* CL190 mevalonate kinase polypeptide, and *Methanosarcina mazei* mevalonate kinase polypeptide. Any one of the promoters described herein (e.g., promoters described herein and identified in the Examples of the present disclosure including inducible promoters and constitutive promoters) can be used to drive expression of any of the MVA polypeptides described herein.

Nucleic Acids Encoding Isoprene Synthase Polypeptides

In some aspects of the invention, the cells described in any of the compositions or methods described herein further comprise one or more nucleic acids encoding an isoprene synthase polypeptide or a polypeptide having isoprene synthase activity. In some aspects, the isoprene synthase polypeptide is an endogenous polypeptide. In some aspects, the endogenous nucleic acid encoding an isoprene synthase polypeptide is operably linked to a constitutive promoter. In some aspects, the endogenous nucleic acid encoding an isoprene synthase polypeptide is operably linked to an inducible promoter. In some aspects, the endogenous nucleic acid encoding an isoprene synthase polypeptide is operably linked to a strong promoter. In a particular aspect, the cells are engineered to over-express the endogenous isoprene synthase pathway polypeptide relative to wild-type cells. In some aspects, the endogenous nucleic acid encoding an isoprene synthase polypeptide is operably linked to a weak promoter. In some aspects, the isoprene synthase polypeptide is a polypeptide from *Pueraria* or *Populus* or a hybrid such as *Populus alba×Populus tremula*.

In some aspects, the isoprene synthase polypeptide is a heterologous polypeptide. In some aspects, the cells comprise more than one copy of a heterologous nucleic acid encoding an isoprene synthase polypeptide. In some aspects, the heterologous nucleic acid encoding an isoprene synthase polypeptide is operably linked to a constitutive promoter. In some aspects, the heterologous nucleic acid encoding an isoprene synthase polypeptide is operably linked to an inducible promoter. In some aspects, the heterologous nucleic acid encoding an isoprene synthase polypeptide is operably linked to a strong promoter. In some aspects, the heterologous nucleic acid encoding an isoprene synthase polypeptide is operably linked to a weak promoter.

The nucleic acids encoding an isoprene synthase polypeptide(s) can be integrated into a genome of the host cells or can be stably expressed in the cells. The nucleic acids encoding an isoprene synthase polypeptide(s) can additionally be on a vector.

Exemplary isoprene synthase nucleic acids include nucleic acids that encode a polypeptide, fragment of a polypeptide, peptide, or fusion polypeptide that has at least one activity of an isoprene synthase polypeptide. Isoprene synthase polypeptides convert dimethylallyl diphosphate (DMAPP) into isoprene. Exemplary isoprene synthase polypeptides include polypeptides, fragments of polypeptides, peptides, and fusions polypeptides that have at least one activity of an isoprene synthase polypeptide. Exemplary isoprene synthase polypeptides and nucleic acids include naturally-occurring polypeptides and nucleic acids from any of the source organisms described herein. In addition, variants of isoprene synthase can possess improved activity such as improved enzymatic activity. In some aspects, an isoprene synthase variant has other improved properties, such as improved stability (e.g., thermo-stability), and/or improved solubility.

Standard methods can be used to determine whether a polypeptide has isoprene synthase polypeptide activity by measuring the ability of the polypeptide to convert DMAPP into isoprene in vitro, in a cell extract, or in vivo. Isoprene synthase polypeptide activity in the cell extract can be measured, for example, as described in Silver et al., J. Biol. Chem. 270:13010-13016, 1995. In one exemplary assay, DMAPP (Sigma) can be evaporated to dryness under a stream of nitrogen and rehydrated to a concentration of 100 mM in 100 mM potassium phosphate buffer pH 8.2 and stored at −20° C. To perform the assay, a solution of 5 µL of 1M MgCl2, 1 mM (250 µg/ml) DMAPP, 65 µL of Plant Extract Buffer (PEB) (50 mM Tris-HCl, pH 8.0, 20 mM MgCl2, 5% glycerol, and 2 mM DTT) can be added to 25 µL of cell extract in a 20 ml Headspace vial with a metal screw cap and teflon coated silicon septum (Agilent Technologies) and cultured at 370 C for 15 minutes with shaking. The reaction can be quenched by adding 200 µL of 250 mM EDTA and quantified by GC/MS.

In some aspects, the isoprene synthase polypeptide is a plant isoprene synthase polypeptide or a variant thereof. In some aspects, the isoprene synthase polypeptide is an isoprene synthase from *Pueraria* or a variant thereof. In some aspects, the isoprene synthase polypeptide is an isoprene synthase from *Populus* or a variant thereof. In some aspects, the isoprene synthase polypeptide is a poplar isoprene synthase polypeptide or a variant thereof. In some aspects, the isoprene synthase polypeptide is a kudzu isoprene synthase polypeptide or a variant thereof. In some aspects, the isoprene synthase polypeptide is a polypeptide from *Pueraria* or *Populus* or a hybrid, *Populus alba×Populus tremula*, or a variant thereof.

In some aspects, the isoprene synthase polypeptide or nucleic acid is from the family Fabaceae, such as the Faboideae subfamily. In some aspects, the isoprene synthase polypeptide or nucleic acid is a polypeptide or nucleic acid from *Pueraria montana* (kudzu) (Sharkey et al., *Plant Physiology* 137: 700-712, 2005), *Pueraria lobata*, poplar (such as *Populus alba, Populus nigra, Populus trichocarpa*, or *Populus alba×tremula* (CAC35696) (Miller et al., *Planta* 213: 483-487, 2001), aspen (such as *Populus tremuloides*) (Silver et al., JBC 270(22): 13010-1316, 1995), English Oak (*Quercus robur*) (Zimmer et al., WO 98/02550), or a variant thereof. In some aspects, the isoprene synthase polypeptide is an isoprene synthase from *Pueraria montana, Pueraria lobata, Populus tremuloides, Populus alba, Populus nigra*, or *Populus trichocarpa* or a variant thereof. In some aspects, the isoprene synthase polypeptide is an isoprene synthase from *Populus alba* or a variant thereof. In some aspects, the nucleic acid encoding the isoprene synthase (e.g., isoprene synthase from *Populus alba* or a variant thereof) is codon optimized.

In some aspects, the isoprene synthase nucleic acid or polypeptide is a naturally-occurring polypeptide or nucleic acid (e.g., naturally-occurring polypeptide or nucleic acid from *Populus*). In some aspects, the isoprene synthase nucleic acid or polypeptide is not a wild-type or naturally-occurring polypeptide or nucleic acid. In some aspects, the isoprene synthase nucleic acid or polypeptide is a variant of a wild-type or naturally-occurring polypeptide or nucleic acid (e.g., a variant of a wild-type or naturally-occurring polypeptide or nucleic acid from *Populus*).

In some aspects, the isoprene synthase polypeptide is a variant. In some aspects, the isoprene synthase polypeptide is a variant of a wild-type or naturally occurring isoprene synthase. In some aspects, the variant has improved activity such as improved catalytic activity compared to the wild-type or naturally occurring isoprene synthase. The increase in activity (e.g., catalytic activity) can be at least about any of 10%, 20%, 30%, 40%, 50%, 60%, 70%, 80%, 90%, or 95%. In some aspects, the increase in activity such as catalytic activity is at least about any of 1 fold, 2 folds, 5 folds, 10 folds, 20 folds, 30 folds, 40 folds, 50 folds, 75 folds, or 100 folds. In some aspects, the increase in activity such as catalytic activity is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the variant has improved solubility compared to the wild-type or naturally occurring isoprene synthase. The increase in solubility can be at least about any of 10%, 20%, 30%, 40%, 50%, 60%, 70%, 80%, 90%, or 95%. The increase in solubility can be at least about any of 1 fold, 2 folds, 5 folds, 10 folds, 20 folds, 30 folds, 40 folds, 50 folds, 75 folds, or 100 folds. In some aspects, the increase in solubility is about 10% to about 100 folds (e.g., about 20% to about 100 folds, about 50% to about 50 folds, about 1 fold to about 25 folds, about 2 folds to about 20 folds, or about 5 folds to about 20 folds). In some aspects, the isoprene synthase polypeptide is a variant of naturally occurring isoprene synthase and has improved stability (such as thermo-stability) compared to the naturally occurring isoprene synthase.

In some aspects, the variant has at least about 10%, at least about 20%, at least about 30%, at least about 40%, at least about 50%, at least about 60%, at least about 70%, at least about 80%, at least about 90%, at least about 100%, at least about 110%, at least about 120%, at least about 130%, at least about 140%, at least about 150%, at least about 160%, at least about 170%, at least about 180%, at least about 190%, at least about 200% of the activity of a wild-type or naturally occurring isoprene synthase. The variant can share sequence similarity with a wild-type or naturally occurring isoprene synthase. In some aspects, a variant of a wild-type or naturally occurring isoprene synthase can have at least about any of 40%, 50%, 60%, 70%, 75%, 80%, 90%, 91%, 92%, 93%, 94%, 95%, 96%, 97%, 98%, 99%, 99.5%, or 99.9% amino acid sequence identity as that of the wild-type or naturally occurring isoprene synthase. In some aspects, a variant of a wild-type or naturally occurring isoprene synthase has any of about 70% to about 99.9%, about 75% to about 99%, about 80% to about 98%, about 85% to about 97%, or about 90% to about 95% amino acid sequence identity as that of the wild-type or naturally occurring isoprene synthase.

In some aspects, the variant comprises a mutation in the wild-type or naturally occurring isoprene synthase. In some aspects, the variant has at least one amino acid substitution, at least one amino acid insertion, and/or at least one amino acid deletion. In some aspects, the variant has at least one amino acid substitution. In some aspects, the number of differing amino acid residues between the variant and wild-type or naturally occurring isoprene synthase can be one or more, e.g. 1, 2, 3, 4, 5, 10, 15, 20, 30, 40, 50, or more amino acid residues. Naturally occurring isoprene synthases can include any isoprene synthases from plants, for example, kudzu isoprene synthases, poplar isoprene synthases, English oak isoprene synthases, and willow isoprene synthases. In some aspects, the variant is a variant of isoprene synthase from *Populus alba*. In some aspects, the variant of isoprene synthase from *Populus alba* has at least one amino acid substitution, at least one amino acid insertion, and/or at least one amino acid deletion. In some aspects, the variant is a truncated *Populus alba* isoprene synthase. In some aspects, the nucleic acid encoding variant (e.g., variant of isoprene synthase from *Populus alba*) is codon optimized (for example, codon optimized based on host cells where the heterologous isoprene synthase is expressed).

In some aspects, the variant comprises one or more (i.e. 2, 3, 4, 5, 6, etc.) mutations from the following table (Table 2) corresponding to the amino acid sequence of *P. alba*:

TABLE 2

Isoprene Synthase Variants of *P. Alba* (MEA)

| | | | | |
|---|---|---|---|---|
| A118E | E472R | S510V | K161K | A118P |
| S22K | K463F | I342I | W392A | A118Q |
| S21R | K463T | K348F | W392C | A118A |
| S22K | R71K | K348Y | W392F | E41M |
| S22R | R71L | K348K | S288Y | G111S |
| E58L | R71M | C437L | M228Y | S74Q |
| T481V | R71V | T240C | A3T | S74S |
| T481Y | R71R | M460M | W392Y | K36D |
| T502F | K393L | R461A | W392W | S282H |
| T381L | F542L | H424P | F89D | S282I |
| T381M | P538K | H424H | F89E | S282W |
| T381Y | P538R | A448L | F89F | S282Y |
| T383H | P538P | A448Q | E41Y | S282S |
| T383L | A503A | A448V | E41E | K36S |
| E480I | L436I | G389D | R43E | K36T |
| E480R | L436Y | S444E | R43L | K36W |
| K393V | L436F | S444S | K36E | K36Y |
| K393I | E488L | H511Y | K36H | K36K |
| E415H | E488M | H511H | K36N | |
| E415V | E488T | R071I | K36P | |
| E415Y | E488W | R071K | K36Q | |
| R71H | E488E | R071L | A453I | |
| R71I | I342Y | K374Y | A453V | |
| E58Y | C437M | K374K | A453A | |
| E135G | C437W | L526E | V409I | |
| A363L | C437Y | L526Q | V409T | |
| K374Y | C437C | L526L | K161C | |
| T381I | M460A | R242G | K161E | |
| L436L | I447T | R242R | K161N | |
| H254R | I447V | A443G | K161Q | |
| H254C | I447Y | A443Q | G99E | |
| E488C | S444D | A443R | G99G | |
| E488F | G389E | A443S | S288A | |
| T383Y | L376I | S13S | S288C | |
| K414I | L376M | V268I | S288T | |
| K414R | L376L | V268V | W392I | |
| K414S | I504F | K161A | W392M | |
| K414W | I504I | V409V | W392S | |
| E472C | E467W | D323F | W392T | |
| E472L | S510C | G99D | W392V | |

The isoprene synthase polypeptide provided herein can be any of the isoprene synthases or isoprene synthase variants described in WO 2009/132220, WO 2010/124146, and U.S. Patent Application Publication No.: 2010/0086978, the contents of which are expressly incorporated herein by reference in their entirety with respect to the isoprene synthases and isoprene synthase variants.

Any one of the promoters described herein (e.g., promoters described herein and identified in the Examples of the present disclosure including inducible promoters and constitutive promoters) can be used to drive expression of any of the isoprene synthases described herein.

Suitable isoprene synthases include, but are not limited to, those identified by Genbank Accession Nos. AY341431, AY316691, AY279379, AJ457070, and AY182241. Types of isoprene synthases which can be used in any one of the compositions or methods including methods of making microorganisms encoding isoprene synthase described herein are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/124146, WO2010/078457, and WO2010/148256.

Nucleic Acids Encoding DXP Pathway Polypeptides

In some aspects of the invention, the cells described in any of the compositions or methods described herein further comprise one or more heterologous nucleic acids encoding a DXS polypeptide or other DXP pathway polypeptides. In some aspects, the cells further comprise a chromosomal copy of an endogenous nucleic acid encoding a DXS polypeptide or other DXP pathway polypeptides. In some aspects, the *E. coli* cells further comprise one or more nucleic acids encoding an IDI polypeptide and a DXS polypeptide or other DXP pathway polypeptides. In some aspects, one nucleic acid encodes the isoprene synthase polypeptide, IDI polypeptide, and DXS polypeptide or other DXP pathway polypeptides. In some aspects, one plasmid encodes the isoprene synthase polypeptide, IDI polypeptide, and DXS polypeptide or other DXP pathway polypeptides. In some aspects, multiple plasmids encode the isoprene synthase polypeptide, IDI polypeptide, and DXS polypeptide or other DXP pathway polypeptides.

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary DXP pathways polypeptides include, but are not limited to any of the following polypeptides: DXS polypeptides, DXR polypeptides, MCT polypeptides, CMK polypeptides, MCS polypeptides, HDS polypeptides, HDR polypeptides, and polypeptides (e.g., fusion polypeptides) having an activity of one, two, or more of the DXP pathway polypeptides. In particular, DXP pathway polypeptides include polypeptides, fragments of polypeptides, peptides, and fusions polypeptides that have at least one activity of a DXP pathway polypeptide. Exemplary DXP pathway nucleic acids include nucleic acids that encode a polypeptide, fragment of a polypeptide, peptide, or fusion polypeptide that has at least one activity of a DXP pathway polypeptide. Exemplary DXP pathway polypeptides and nucleic acids include naturally-occurring polypeptides and nucleic acids from any of the source organisms described herein as well as mutant polypeptides and nucleic acids derived from any of the source organisms described herein. Exemplary DXP pathway polypeptides and nucleic acids and methods of measuring DXP pathway polypeptide activity are described in more detail in International Publication No.: WO 2010/148150

Exemplary DXS polypeptides include polypeptides, fragments of polypeptides, peptides, and fusions polypeptides that have at least one activity of a DXS polypeptide. Standard methods (such as those described herein) can be used to determine whether a polypeptide has DXS polypeptide activity by measuring the ability of the polypeptide to convert pyruvate and D-glyceraldehyde-3-phosphate into 1-deoxy-D-xylulose-5-phosphate in vitro, in a cell extract, or in vivo. Exemplary DXS polypeptides and nucleic acids and methods of measuring DXS activity are described in more detail in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

In particular, DXS polypeptides convert pyruvate and D-glyceraldehyde 3-phosphate into 1-deoxy-d-xylulose 5-phosphate (DXP). Standard methods can be used to determine whether a polypeptide has DXS polypeptide activity by measuring the ability of the polypeptide to convert pyruvate and D-glyceraldehyde 3-phosphate in vitro, in a cell extract, or in vivo.

DXR polypeptides convert 1-deoxy-d-xylulose 5-phosphate (DXP) into 2-C-methyl-D-erythritol 4-phosphate (MEP). Standard methods can be used to determine whether a polypeptide has DXR polypeptides activity by measuring the ability of the polypeptide to convert DXP in vitro, in a cell extract, or in vivo.

MCT polypeptides convert 2-C-methyl-D-erythritol 4-phosphate (MEP) into 4-(cytidine 5'-diphospho)-2-methyl-D-erythritol (CDP-ME). Standard methods can be used to determine whether a polypeptide has MCT polypeptides activity by measuring the ability of the polypeptide to convert MEP in vitro, in a cell extract, or in vivo.

CMK polypeptides convert 4-(cytidine 5'-diphospho)-2-C-methyl-D-erythritol (CDP-ME) into 2-phospho-4-(cytidine 5'-diphospho)-2-C-methyl-D-erythritol (CDP-MEP). Standard methods can be used to determine whether a polypeptide has CMK polypeptides activity by measuring the ability of the polypeptide to convert CDP-ME in vitro, in a cell extract, or in vivo.

MCS polypeptides convert 2-phospho-4-(cytidine 5'-diphospho)-2-C-methyl-D-erythritol (CDP-MEP) into 2-C-methyl-D-erythritol 2, 4-cyclodiphosphate (ME-CPP or cMEPP). Standard methods can be used to determine whether a polypeptide has MCS polypeptides activity by measuring the ability of the polypeptide to convert CDP-MEP in vitro, in a cell extract, or in vivo.

HDS polypeptides convert 2-C-methyl-D-erythritol 2, 4-cyclodiphosphate into (E)-4-hydroxy-3-methylbut-2-en-1-yl diphosphate (HMBPP or HDMAPP). Standard methods can be used to determine whether a polypeptide has HDS polypeptides activity by measuring the ability of the polypeptide to convert ME-CPP in vitro, in a cell extract, or in vivo.

HDR polypeptides convert (E)-4-hydroxy-3-methylbut-2-en-1-yl diphosphate into isopentenyl diphosphate (IPP) and dimethylallyl diphosphate (DMAPP). Standard methods can be used to determine whether a polypeptide has HDR polypeptides activity by measuring the ability of the polypeptide to convert HMBPP in vitro, in a cell extract, or in vivo.

Source Organisms for Lower MVA Pathway, Isoprene Synthase, IDI, and DXP Pathway Polypeptides Isoprene synthase, IDI, DXP pathway, and/or lower MVA pathway nucleic acids (and their encoded polypeptides) can be obtained from any organism that naturally contains isoprene synthase, IDI, DXP pathway, and/or lower MVA pathway nucleic acids. Isoprene is formed naturally by a variety of organisms, such as bacteria, yeast, plants, and animals. Some organisms contain the MVA pathway for producing isoprene. Isoprene synthase nucleic acids can be obtained, e.g., from any organism that contains an isoprene synthase. MVA pathway nucleic acids can be obtained, e.g., from any organism that contains the MVA pathway. IDI and DXP pathway nucleic acids can be obtained, e.g., from any organism that contains the IDI and DXP pathway.

The nucleic acid sequence of the isoprene synthase, DXP pathway, IDI, and/or MVA pathway nucleic acids can be isolated from a bacterium, fungus, plant, algae, or cyanobacterium. Exemplary source organisms include, for example, yeasts, such as species of *Saccharomyces* (e.g., *S. cerevisiae*), bacteria, such as species of *Escherichia* (e.g., *E. coli*), or species of *Methanosarcina* (e.g., *Methanosarcina mazei*), plants, such as kudzu or poplar (e.g., *Populus alba* or *Populus alba×tremula* CAC35696) or aspen (e.g., *Populus tremuloides*). Exemplary sources for isoprene synthases, IDI, and/or MVA pathway polypeptides which can be used are also described in International Patent Application Publication Nos. WO2009/076676, WO2010/003007, WO2009/132220, WO2010/031062, WO2010/031068, WO2010/031076, WO2010/013077, WO2010/031079, WO2010/148150, WO2010/078457, and WO2010/148256.

In some aspects, the source organism is a yeast, such as *Saccharomyces* sp., *Schizosaccharomyces* sp., *Pichia* sp., or *Candida* sp.

In some aspects, the source organism is a bacterium, such as strains of *Bacillus* such as *B. lichenformis* or *B. subtilis*, strains of *Pantoea* such as *P. citrea*, strains of *Pseudomonas* such as *P. alcaligenes*, strains of *Streptomyces* such as *S. lividans* or *S. rubiginosus*, strains of *Escherichia* such as *E. coli*, strains of *Enterobacter*, strains of *Streptococcus*, or strains of Archaea such as *Methanosarcina mazei*.

As used herein, "the genus *Bacillus*" includes all species within the genus "*Bacillus*," as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus,* and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus,* and *Virgibacillus*.

In some aspects, the source organism is a gram-positive bacterium. Non-limiting examples include strains of *Streptomyces* (e.g., *S. lividans, S. coelicolor,* or *S. griseus*) and *Bacillus*. In some aspects, the source organism is a gram-negative bacterium, such as *E. coli* or *Pseudomonas* sp.

In some aspects, the source organism is a plant, such as a plant from the family Fabaceae, such as the Faboideae subfamily. In some aspects, the source organism is kudzu, poplar (such as *Populus alba×tremula* CAC35696), aspen (such as *Populus tremuloides*), or *Quercus robur*.

In some aspects, the source organism is an algae, such as a green algae, red algae, glaucophytes, chlorarachniophytes, euglenids, chromista, or dinoflagellates.

In some aspects, the source organism is a cyanobacteria, such as cyanobacteria classified into any of the following groups based on morphology: Chroococcales, Pleurocapsales, Oscillatoriales, Nostocales, or Stigonematales.

Nucleic Acids Encoding Phosphoketolase Polypeptides

In some aspects of the invention, the recombinant cells described in any of the compositions or methods described herein can further comprise one or more nucleic acids encoding a phosphoketolase polypeptide or a polypeptide having phosphoketolase activity. In some aspects, the phosphoketolase polypeptide is an endogenous polypeptide. In some aspects, the endogenous nucleic acid encoding a phosphoketolase polypeptide is operably linked to a constitutive promoter. In some aspects, the endogenous nucleic acid encoding a phosphoketolase polypeptide is operably linked to an inducible promoter. In some aspects, the endogenous nucleic acid encoding a phosphoketolase polypeptide is operably linked to a strong promoter. In some aspects, more than one endogenous nucleic acid encoding a phosphoketolase polypeptide is used (e.g, 2, 3, 4, or more copies of an endogenous nucleic acid encoding a phosphoketolase polypeptide). In a particular aspect, the cells are engineered to overexpress the endogenous phosphoketolase polypeptide relative to wild-type cells. In some aspects, the endogenous nucleic acid encoding a phosphoketolase polypeptide is operably linked to a weak promoter.

Phosphoketolase enzymes catalyze the conversion of xylulose 5-phosphate to glyceraldehyde 3-phosphate and acetyl phosphate and/or the conversion of fructose 6-phosphate to erythrose 4-phosphate and acetyl phosphate. In certain embodiments, the phosphoketolase enzyme is capable of catalyzing the conversion of xylulose 5-phosphate to glyceraldehyde 3-phosphate and acetyl phosphate. In other embodiments, the phosphoketolase enzyme is capable of catalyzing the conversion of fructose 6-phosphate to erythrose 4-phosphate and acetyl phosphate. Thus, without being bound by theory, the expression of phosphoketolase as set forth herein can result in an increase in the amount of acetyl phosphate produced from a carbohydrate source. This acetyl phosphate can be converted into acetyl-CoA which can then be utilized by the enzymatic activities of the MVA pathway to produces mevalonate, isoprenoid precursor molecules, isoprene and/or isoprenoids. Thus the amount of these compounds produced from a carbohydrate substrate may be increased. Alternatively, production of Acetyl-P and AcCoA can be increased without the increase being reflected in higher intracellular concentration. In certain embodiments, intracellular acetyl-P or acetyl-CoA concentrations will remain unchanged or even decrease, even though the phosphoketolase reaction is taking place.

Exemplary phosphoketolase nucleic acids include nucleic acids that encode a polypeptide, fragment of a polypeptide, peptide, or fusion polypeptide that has at least one activity of a phosphoketolase polypeptide. Exemplary phosphoketolase polypeptides and nucleic acids include naturally-occurring polypeptides and nucleic acids from any of the source organisms described herein as well as mutant polypeptides and nucleic acids derived from any of the source organisms described herein. In some aspects, the phosphoketolase nucleic acid is a heterologous nucleic acid encoding a phosphoketolase polypeptide.

Standard methods can be used to determine whether a polypeptide has phosphoketolase peptide activity by measuring the ability of the peptide to convert D-fructose 6-phosphate or D-xylulose 5-phosphate into acetyl-P. Acetyl-P can then be converted into ferryl acetyl hydroxamate, which can be detected spectrophotometrically (Meile et al., J. Bact. 183:2929-2936, 2001). Any polypeptide identified as having phosphoketolase peptide activity as described herein is suitable for use in the present invention.

In other aspects, exemplary phosphoketolase nucleic acids include, for example, a phosphoketolase isolated from *Lactobacillus reuteri*, *Bifidobacterium longum*, *Ferrimonas balearica*, *Pedobactor saltans*, *Streptomyces griseus*, and/or *Nocardiopsis dassonvillei*. Additional examples of phosphoketolase enzymes which can be used herein are described in U.S. Pat. No. 7,785,858, which is incorporated by reference herein.

Pathways Involving the Entner-Doudoroff Pathway

The Entner-Doudoroff (ED) pathway is an alternative to the Emden-Meyerhoff-Parnass (EMP—glycolysis) pathway. Some organisms, like *E. coli*, harbor both the ED and EMP pathways, while others have only one or the other. *Bacillus subtilis* has only the EMP pathway, while *Zymomonas mobilis* has only the ED pathway (Peekhaus and Conway. 1998. J. Bact. 180:3495-3502; Stulke and Hillen. 2000. Annu. Rev. Microbiol. 54, 849-880; Dawes et al. 1966. Biochem. J. 98:795-803).

Phosphogluconate dehydratase (edd) removes one molecule of $H_2O$ from 6-phospho-D-gluconate to form 2-dehydro-3-deoxy-D-gluconate 6-phosphate, while 2-keto-3-deoxygluconate 6-phosphate aldolase (eda) catalyzes an aldol cleavage (Egan et al. 1992. *J. Bact.* 174:4638-4646). The two genes are in an operon.

Metabolites that can be directed into the phosphoketolase pathway can also be diverted into the ED pathway. To avoid metabolite loss to the ED-pathway, phosphogluconate dehydratase gene (e.g., the endogenous phosphogluconate dehydratase gene) and/or a 2-keto-3-deoxygluconate 6-phosphate aldolase gene (e.g., the endogenous 2-keto-3-deoxygluconate 6-phosphate aldolase gene) activity is attenuated. One way of achieving attenuation is by deleting phosphogluconate dehydratase (edd) and/or 2-keto-3-deoxygluconate 6-phosphate aldolase (eda). This can be accomplished by replacing one or both genes with a chloramphenicol or kanamycin cassette followed by looping out of the cassette. Without these enzymatic activities, more carbon can flux through the phosphoketolase enzyme, thus increasing the yield of mevalonate, isoprene, isoprenoid precursor molecules, and/or isoprenoids.

The activity of phosphogluconate dehydratase (edd) and/or 2-keto-3-deoxygluconate 6-phosphate aldolase (eda) can also be decreased by other molecular manipulations of the enzymes. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

In some cases, attenuating the activity of the endogenous phosphogluconate dehydratase gene and/or the endogenous 2-keto-3-deoxygluconate 6-phosphate aldolase gene results in more carbon flux into the mevalonate dependent biosynthetic pathway in comparison to cells that do not have attenuated endogenous phosphogluconate dehydratase gene and/or endogenous acetate kinase2-keto-3-deoxygluconate 6-phosphate aldolase gene expression.

Pathways Involving the Oxidative Branch of the Pentose Phosphate Pathway

*E. coli* uses the pentose phosphate pathway to break down hexoses and pentoses and to provide cells with intermediates for various anabolic pathways. It is also a major producer of NADPH. The pentose phosphate pathway is composed from an oxidative branch (with enzymes like glucose 6-phosphate 1-dehydrogenase (zwf), 6-phosphogluconolactonase (pgl) or 6-phosphogluconate dehydrogenase (gnd)) and a non-oxidative branch (with enzymes such as transketolase (tktA), transaldolase (talA or talB), ribulose-5-phosphate-epimerase and (or) ribose-5-phosphate epimerase) (Sprenger. 1995. *Arch. Microbiol.* 164:324-330).

In order to direct carbon towards the phosphoketolase enzyme, the non-oxidative branch of the pentose phosphate pathway (transketolase, transaldolase, ribulose-5-phosphate-epimerase and (or) ribose-5-phosphate epimerase) expression can be modulated (e.g., increase enzyme activity) to allow more carbon to flux towards fructose 6-phosphate and xylulose 5-phosphate, thereby increasing the eventual production of mevalonate, isoprene, isoprenoid precursor molecules, and/or isoprenoids. Increase of transketolase, transaldolase, ribulose-5-phosphate-epimerase and (or) ribose-5-phosphate epimerase activity can be any amount of increase of specific activity or total activity as compared to when no manipulation has been effectuated. In some instances, the enzyme activity is increased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%, or 100%. In some aspects, the activity of transketolase, transaldolase, ribulose-5-phosphate-epimerase and (or) ribose-5-phosphate epimerase is modulated by increasing the activity of an endogenous transketolase, transaldolase, ribulose-5-phosphate-epimerase and (or) ribose-5-phosphate epimerase. This can be accomplished by replacing the endogenous transketolase, transaldolase, ribulose-5-phosphate-epimerase and (or) ribose-5-phosphate epimerase gene promoter with a synthetic constitutively high expressing promoter. The genes encoding transketolase, transaldolase, ribulose-5-phosphate-epimerase and (or) ribose-5-phosphate epimerase can also be cloned on a plasmid behind an appropriate promoter. The increase of the activity of transketolase, transaldolase, ribulose-5-phosphate-epimerase and (or) ribose-5-phosphate epimerase can result in more carbon flux into the mevalonate dependent biosynthetic pathway in comparison to cells that do not have increased expression of transketolase, transaldolase, ribulose-5-phosphate-epimerase and (or) ribose-5-phosphate epimerase.

Pathways Involving Phosphofructokinase

Phosphofructokinase is a crucial enzyme of glycolysis which catalyzes the phosphorylation of fructose 6-phosphate. *E. coli* has two isozymes encoded by pfkA and pfkB. Most of the phosphofructokinase activity in the cell is due to pfkA (Kotlarz et al. 1975, *Biochim. Biophys. Acta,* 381:257-268).

In order to direct carbon towards the phosphoketolase enzyme, phosphofructokinase expression can be modulated (e.g., decrease enzyme activity) to allow more carbon to flux towards fructose 6-phosphate and xylulose 5-phosphate, thereby increasing the eventual production of mevalonate, isoprene, isoprenoid precursor molecules, and/or isoprenoids. Decrease of phosphofructokinase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, 99%. Or 100%. In some aspects, the activity of phosphofructokinase is modulated by decreasing the activity of an endogenous phosphofructokinase. This can be accomplished by replacing the endogenous phosphofructokinase gene promoter with a synthetic constitutively low expressing promoter. The gene encoding phosphofructokinase can also be deleted. The decrease of the activity of phosphofructokinase can result in more carbon flux into the mevalonate dependent biosynthetic pathway in comparison to cells that do not have decreased expression of phosphofructokinase.

Host Cell Mutations

The invention also contemplates additional host cell mutations that increase carbon flux through the MVA pathway. By increasing the carbon flow, more isoprene, mevalonate, isoprenoid precursor molecules, and/or isoprenoids can be produced. The recombinant cells as described herein can also be engineered for increased carbon flux towards mevalonate, isoprene, isoprenoid, and/or isoprenoid precursor production wherein the activity of one or more enzymes from the group consisting of: (a) citrate synthase, (b) phosphotransacetylase; (c) acetate kinase; (d) lactate dehydrogenase; (e) NADP-dependent malic enzyme, and; (f) pyruvate dehydrogenase is modulated. In some aspects, modulation of the any of the enzymes referred to herein can affect the expression (e.g., transcription or translation), production, post-translational modification or any other function of the enzyme. In some embodiments, the function of the enzyme (e.g., catalytic ability) in recombinant cells is increased or decreased as compared to a cell that has not been engineered for such modulation. In one embodiment, the function of the enzyme (e.g. activity) is increased as compared to a cell that has not been engineered. In another embodiment, the function of the enzyme (e.g. activity) is decreased as compared to a cell that has not been engineered.

Citrate Synthase Pathway

Figure 5:
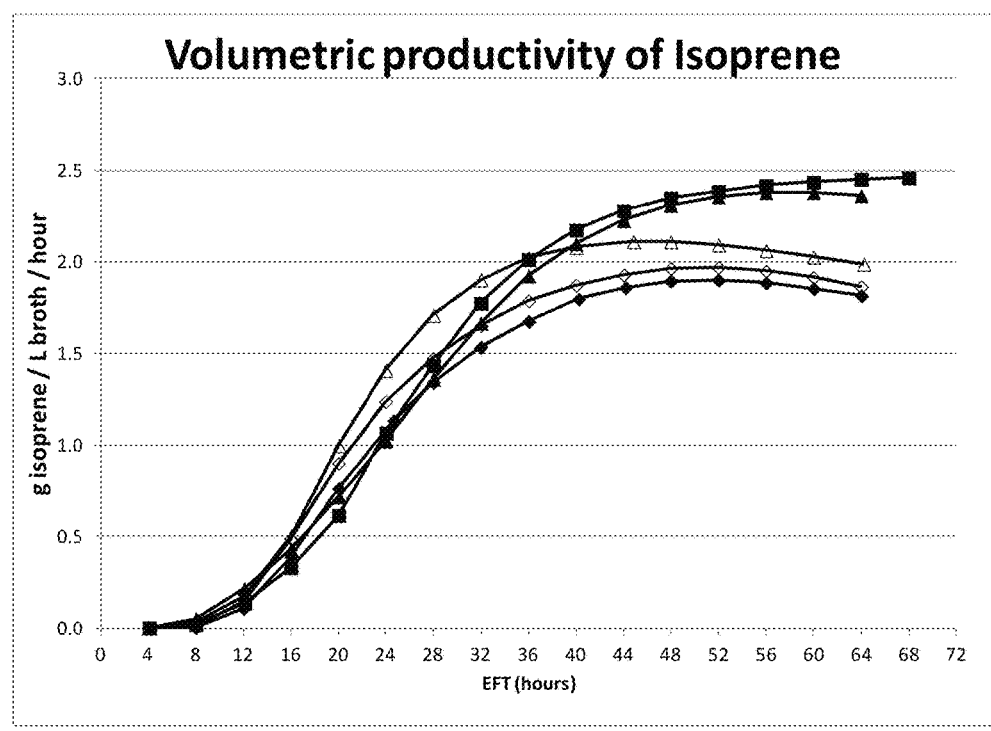

Citrate synthase catalyzes the condensation of oxaloacetate and acetyl-CoA to form citrate, a metabolite of the Tricarboxylic acid (TCA) cycle (Ner, S. et al., 1983, *Biochemistry,* 22: 5243-5249; Bhayana, V. & Duckworth, H. 1984, *Biochemistry* 23: 2900-2905; FIG. 5). In *E. coli*, this enzyme, encoded by gltA, behaves like a trimer of dimeric subunits. The hexameric form allows the enzyme to be allosterically regulated by NADH. This enzyme has been widely studied (Wiegand, G., and Remington, S. 1986. *Annual Rev. Biophysics Biophys. Chem.* 15: 97-117; Duckworth et al. 1987. *Biochem Soc Symp.* 54:83-92; Stockell, D. et al. 2003. *J. Biol. Chem.* 278: 35435-43; Maurus, R. et al. 2003. *Biochemistry.* 42:5555-5565). To avoid allosteric inhibition by NADH, replacement by or supplementation with the *Bacillus subtilis* NADH-insensitive citrate synthase has been considered (Underwood et al. 2002. *Appl. Environ. Microbiol.* 68:1071-1081; Sanchez et al. 2005. *Met. Eng.* 7:229-239).

The reaction catalyzed by citrate synthase is directly competing with the thiolase catalyzing the first step of the mevalonate pathway, as they both have acetyl-CoA as a substrate (Hedl et al. 2002. *J. Bact.* 184:2116-2122). Therefore, one of skill in the art can modulate citrate synthase expression (e.g., decrease enzyme activity) to allow more carbon to flux into the mevalonate pathway, thereby increasing the eventual production of mevalonate and isoprene. Decrease of citrate synthase activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%. In some aspects, the activity of citrate synthase is modulated by decreasing the activity of an endogenous citrate synthase gene. This can be accomplished by chromosomal replacement of an endogenous citrate synthase gene with a transgene encoding an NADH-insensitive citrate synthase or by using a transgene encoding an NADH-insensitive citrate synthase that is derived from *Bacillus subtilis*. The activity of citrate synthase can also be modulated (e.g., decreased) by replacing the endogenous citrate synthase gene promoter with a synthetic constitutively low expressing promoter. The decrease of the activity of citrate synthase can result in more carbon flux into the mevalonate dependent biosynthetic pathway in comparison to microorganisms that do not have decreased expression of citrate synthase.

Pathways Involving Phosphotransacetylase and/or Acetate Kinase

Phosphotransacetylase (pta) (Shimizu et al. 1969. *Biochim. Biophys. Acta* 191: 550-558) catalyzes the reversible conversion between acetyl-CoA and acetylphosphate (acetyl-P), while acetate kinase (ackA) (Kakuda, H. et al. 1994. *J. Biochem.* 11:916-922) uses acetyl-P to form acetate. These genes can be transcribed as an operon in *E. coli*. Together, they catalyze the dissimilation of acetate, with the release of ATP. Thus, one of skill in the art can increase the amount of available acetyl Co-A by attenuating the activity of phosphotransacetylase gene (e.g., the endogenous phosphotransacetylase gene) and/or an acetate kinase gene (e.g., the endogenous acetate kinase gene). One way of achieving attenuation is by deleting phosphotransacetylase (pta) and/or acetate kinase (ackA). This can be accomplished by replacing one or both genes with a chloramphenicol cassette followed by looping out of the cassette. Acetate is produced by *E. coli* for a variety of reasons (Wolfe, A. 2005. *Microb. Mol. Biol. Rev.* 69:12-50). Without being bound by theory, since ackA-pta use acetyl-CoA, deleting those genes might allow carbon not to be diverted into acetate and to increase the yield of mevalonate, isorpenoids, isoprenoid precursor molecules, and/or isoprene. In some aspects, the eutD gene, which exhibits phosphotransacetylase-like enzymatic activity (e.g., the eutD gene in organisms such as, but not limited to, *E. coli* and *Saccharomyces cerevisiae*) is attenuated or deleted.

In some aspects, the recombinant microorganism produces decreased amounts of acetate in comparison to microorganisms that do not have attenuated endogenous phosphotransacetylase gene and/or endogenous acetate kinase gene expression. Decrease in the amount of acetate produced can be measured by routine assays known to one of skill in the art. The amount of acetate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of phosphotransacetylase (pta) and/or acetate kinase (ackA) can also be decreased by other molecular manipulation of the enzymes. The decrease of enzyme activity can be any amount of reduction of specific activity or total activity as compared to the specific activity or total activity that occurs when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 91%, 92%, 93%, 94%, 95%, 96%, 97%, 98%, or 99%, inclusive, including any values in between these percentages.

In some cases, attenuating the activity of the endogenous phosphotransacetylase gene and/or the endogenous acetate kinase gene results in more carbon flux into the mevalonate dependent biosynthetic pathway in comparison to microorganisms that do not have attenuated endogenous phosphotransacetylase gene and/or endogenous acetate kinase gene expression.

Pathways Involving Lactate Dehydrogenase

In *E. coli*, D-Lactate is produced from pyruvate through the enzyme lactate dehydrogenase (ldhA—FIG. 5) (Bunch, P. et al. 1997. *Microbiol.* 143:187-195). Production of lactate is accompanied with oxidation of NADH, hence lactate is produced when oxygen is limited and cannot accommodate all the reducing equivalents. Thus, production of lactate could be a source for carbon consumption. As such, to improve carbon flow through to mevalonate production (and isoprene, isoprenoid precursor molecule, and/or isoprenoid production, if desired), one of skill in the art can modulate the activity of lactate dehydrogenase, such as by decreasing the activity of the enzyme.

Accordingly, in one aspect, the activity of lactate dehydrogenase can be modulated by attenuating the activity of an endogenous lactate dehydrogenase gene. Such attenuation can be achieved by deletion of the endogenous lactate dehydrogenase gene. Other ways of attenuating the activity of lactate dehydrogenase gene known to one of skill in the art may also be used. By manipulating the pathway that involves lactate dehydrogenase, the recombinant microorganism produces decreased amounts of lactate in comparison to microorganisms that do not have attenuated endogenous lactate dehydrogenase gene expression. Decrease in the amount of lactate produced can be measured by routine assays known to one of skill in the art. The amount of lactate reduction is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of lactate dehydrogenase can also be decreased by other molecular manipulations of the enzyme. The decrease of enzyme activity can be any amount of reduction of specific activity or total activity as compared to when no manipulation has been effectuated. In some instances, the decrease of enzyme activity is decreased by at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%, inclusive, including any percentage in between these values.

Accordingly, in some cases, attenuation of the activity of the endogenous lactate dehydrogenase gene results in more carbon flux into the mevalonate dependent biosynthetic pathway in comparison to microorganisms that do not have attenuated endogenous lactate dehydrogenase gene expression.

Pathways Involving Malic Enzyme

Malic enzyme (in *E. coli* sfcA and maeB) is an anaplerotic enzyme that catalyzes the conversion of malate into pyruvate (using NAD+ or NADP+) by the equation below:

(S)-malate+NAD(P)$^+$ 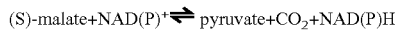 pyruvate+CO$_2$+NAD(P)H

Thus, the two substrates of this enzyme are (S)-malate and NAD(P)$^+$, whereas its 3 products are pyruvate, CO$_2$, and NADPH.

Expression of the NADP-dependent malic enzyme (maeB—FIG. 5) (Iwikura, M. et al. 1979, *J. Biochem.* 85: 1355-1365) can help increase mevalonate and/or isoprene yield by 1) bringing carbon from the TCA cycle back to pyruvate, direct precursor of acetyl-CoA, itself direct precursor of the mevalonate pathway and 2) producing extra NADPH which could be used in the HMG-CoA reductase reaction (Oh, M K et al. (2002) *J. Biol. Chem.* 277: 13175-13183; Bologna, F. et al. (2007) *J. Bact.* 189:5937-5946).

As such, more starting substrate (pyruvate or acetyl-CoA) for the downstream production of mevalonate, isoprenoid precursor molecules, isoprenoids, and/or isoprene can be achieved by modulating, such as increasing, the activity and/or expression of malic enzyme. The NADP-dependent malic enzyme gene can be an endogenous gene. One non-limiting way to accomplish this is by replacing the endogenous NADP-dependent malic enzyme gene promoter with a synthetic constitutively expressing promoter. Another non-limiting way to increase enzyme activity is by using one or more heterologous nucleic acids encoding an NADP-dependent malic enzyme polypeptide. One of skill in the art can monitor the expression of maeB RNA during fermentation or culturing using readily available molecular biology techniques.

Accordingly, in some embodiments, the recombinant microorganism produces increased amounts of pyruvate in comparison to microorganisms that do not have increased expression of an NADP-dependent malic enzyme gene. In some aspects, increasing the activity of an NADP-dependent malic enzyme gene results in more carbon flux into the mevalonate dependent biosynthetic pathway in comparison to microorganisms that do not have increased NADP-dependent malic enzyme gene expression.

Increase in the amount of pyruvate produced can be measured by routine assays known to one of skill in the art. The amount of pyruvate increase can be at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99% as compared when no molecular manipulations are done.

The activity of malic enzyme can also be increased by other molecular manipulations of the enzyme. The increase of enzyme activity can be any amount of increase of specific activity or total activity as compared to when no manipulation has been effectuated. In some instances, the increase of enzyme activity is at least about 1%, 2%, 3%, 4%, 5%, 6%, 7%, 8%, 9%, 10%, 15%, 20%, 25%, 30%, 35%, 35%, 40%, 45%, 50%, 55%, 60%, 65%, 70%, 75%, 80%, 85%, 90%, 95%, 96%, 97%, 98%, or 99%.

Pathways Involving Pyruvate Dehydrogenase Complex

The pyruvate dehydrogenase complex, which catalyzes the decarboxylation of pyruvate into acetyl-CoA, is composed of the proteins encoded by the genes aceE, aceF and lpdA. Transcription of those genes is regulated by several regulators. Thus, one of skill in the art can increase acetyl-CoA by modulating the activity of the pyruvate dehydrogenase complex. Modulation can be to increase the activity and/or expression (e.g., constant expression) of the pyruvate dehydrogenase complex. This can be accomplished by different ways, for example, by placing a strong constitutive promoter, like PL.6 (aattcatataaaaaacatacagataaccatctgcggt-gataaattatctctggcggtgttgacataaataccactggcggtgatactgagca-catca gcaggacgcactgaccaccatgaaggtg—lambda promoter, GenBank NC_001416(SEQ ID NO:65)), in front of the operon or using one or more synthetic constitutively expressing promoters.

Accordingly, in one aspect, the activity of pyruvate dehydrogenase is modulated by increasing the activity of one or more genes of the pyruvate dehydrogenase complex consisting of (a) pyruvate dehydrogenase (E1), (b) dihydrolipoyl transacetylase, and (c) dihydrolipoyl dehydrogenase. It is understood that any one, two or three of these genes can be manipulated for increasing activity of pyruvate dehydrogenase. In another aspect, the activity of the pyruvate dehydrogenase complex can be modulated by attenuating the activity of an endogenous pyruvate dehydrogenase complex repressor gene, further detailed below. The activity of an endogenous pyruvate dehydrogenase complex repressor can be attenuated by deletion of the endogenous pyruvate dehydrogenase complex repressor gene.

In some cases, one or more genes of the pyruvate dehydrogenase complex are endogenous genes. Another way to increase the activity of the pyruvate dehydrogenase complex is by introducing into the microorganism one or more heterologous nucleic acids encoding one or more polypeptides from the group consisting of (a) pyruvate dehydrogenase (E1), (b) dihydrolipoyl transacetylase, and (c) dihydrolipoyl dehydrogenase.

By using any of these methods, the recombinant microorganism can produce increased amounts of acetyl Co-A in comparison to microorganisms wherein the activity of pyruvate dehydrogenase is not modulated. Modulating the activity of pyruvate dehydrogenase can result in more carbon flux into the mevalonate dependent biosynthetic pathway in comparison to microorganisms that do not have modulated pyruvate dehydrogenase expression.

Combinations of Mutations

It is understood that for any of the enzymes and/or enzyme pathways described herein, molecular manipulations that modulate any combination (two, three, four, five or six) of the enzymes and/or enzyme pathways described herein is expressly contemplated. For ease of the recitation of the combinations, citrate synthase (OA) is designated as A, phosphotransacetylase (ptaB) is designated as B, acetate kinase (ackA) is designated as C, lactate dehydrogenase (ldhA) is designated as D, malic enzyme (sfcA or maeB) is designated as E, and pyruvate decarboxylase (aceE, aceF, and/or lpdA) is designated as F. As discussed above, aceE, aceF, and/or lpdA enzymes of the pyruvate decarboxylase complex can be used singly, or two of three enzymes, or three of three enzymes for increasing pyruvate decarboxylase activity.

Accordingly, for combinations of any two of the enzymes A-F, non-limiting combinations that can be used are: AB, AC, AD, AE, AF, BC, BD, BE, BF, CD, CE, CF, DE, DF and EF. For combinations of any three of the enzymes A-F, non-limiting combinations that can be used are: ABC, ABD, ABE, ABF, BCD, BCE, BCF, CDE, CDF, DEF, ACD, ACE, ACF, ADE, ADF, AEF, BDE, BDF, BEF, and CEF. For combinations of any four of the enzymes A-F, non-limiting combinations that can be used are: ABCD, ABCE, ABCF, ABDE, ABDF, ABEF, BCDE, BCDF, CDEF, ACDE, ACDF, ACEF, BCEF, BDEF, and ADEF. For combinations of any five of the enzymes A-F, non-limiting combinations that can be used are: ABCDE, ABCDF, ABDEF, BCDEF, ACDEF, and ABCEF. In another aspect, all six enzyme combinations are used: ABCDEF.

Accordingly, the recombinant microorganism as described herein can achieve increased mevalonate production that is increased compared to microorganisms that are not grown under conditions of tri-carboxylic acid (TCA) cycle activity, wherein metabolic carbon flux in the recombinant microorganism is directed towards mevalonate production by modulating the activity of one or more enzymes from the group consisting of (a) citrate synthase, (b) phosphotransacetylase and/or acetate kinase, (c) lactate dehydrogenase, (d) malic enzyme, and (e) pyruvate decarboxylase complex.

Other Regulators and Factors for Increased Isoprene Production

Other molecular manipulations can be used to increase the flow of carbon towards isoprene production. One method is to reduce, decrease or eliminate the effects of negative regulators for pathways that feed into the mevalonate pathway. For example, in some cases, the genes aceEF-lpdA are in an operon, with a fourth gene upstream pdhR. pdhR is a negative regulator of the transcription of its operon. In the absence of pyruvate, it binds its target promoter and represses transcription. It also regulates ndh and cyoABCD in the same way (Ogasawara, H. et al. 2007. *J. Bact.* 189:5534-5541). In one aspect, deletion of pdhR regulator can improve the supply of pyruvate, and hence the production mevalonate and/or isoprene.

In other aspects, the introduction of 6-phosphogluconolactonase (PGL) into microorganisms (such as various *E. coli* strains) which lack PGL can be used to improve production of mevalonate and/or isoprene. PGL may be introduced using chromosomal integration or extra-chromosomal vehicles, such as plasmids. In other aspects, PGL may be deleted from the genome of cells (for example, microorganisms, such as various *E. coli* strains) which express an endogenous PGL to improve production of mevalonate and/or isoprene. In some aspects, deletion of PGL results in any of about 10%, 20%, 30%, 40%, 50%, 60%, 70%, 80%, 90%, or 100%, inclusive, including any values in between these percentages, higher percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher instantaneous percent yield of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher cell productivity index for isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher volumetric productivity of isoprene in comparison to microorganisms that express PGL. In other aspects, deletion of PGL results in any of about 10%, 20%, 30%, 40%, 50%, 60%, 70%, 80%, 90%, or 100%, inclusive, including any values in between these percentages, higher peak specific productivity of isoprene in comparison to microorganisms that express PGL. In some aspects the deletion of PGL results in peak specific productivity being maintained for a longer period of time in comparison to microorganisms that express PGL.

Recombinant Cells (Such as Bacterial Cells) Capable of Increased Production of Isoprene The recombinant cells (such as bacterial cells) described herein have the ability to produce isoprene at a concentration greater than that of the same cells lacking one or more copies of a heterologous nucleic acid encoding mvaE and mvaS polypeptides from *L. grayi, E. faecium, E. gallinarum*, and/or *E. casseliflavus*, one or more copies of a heterologous nucleic acid encoding a lower MVA pathway polypeptide, and one or more heterologous nucleic acids encoding an isoprene synthase polypeptide, optionally when cultured in minimal media. In some cases, the one or more copies of a heterologous nucleic acid encoding mvaE and mvaS polypeptides from *L. grayi, E. faecium, E. gallinarum*, and/or *E. casseliflavus* one or more copies of a heterologous nucleic acid encoding a lower MVA pathway polypeptide, and one or more heterologous nucleic acids encoding an isoprene synthase polypeptide are heterologous nucleic acids that are integrated into the host cell's chromosome. The cells (such as bacterial cells) can produce at least 5% greater amounts of isoprene compared to isoprene-producing cells (such as bacterial cells) that do not comprise the mvaE and mvaS polypeptides from *L. grayi, E. faecium, E. gallinarum*, and/or *E. casseliflavus*. Alternatively, the cells (such as bacterial cells) can produce greater than about 1%, 2%, 3%, 4%, 5%, 6%, 7%, 8%, 9%, 10%, 11%, 12%, 13%, 14%, or 15% of isoprene, inclusive, as well as any numerical value in between these numbers.

In one aspect of the invention, there are provided cells (such as bacterial cells) comprising one or more heterologous nucleic acids encoding mvaE and mvaS polypeptides from *L. grayi, E. faecium, E. gallinarum*, and/or *E. casseliflavus*, one or more heterologous nucleic acids encoding a lower mevalonate (MVA) pathway polypeptide(s), one or more heterologous nucleic acids encoding a DXP pathway polypeptide(s), and one or more heterologous nucleic acids encoding an isoprene synthase polypeptide. The cells can further comprise one or more heterologous nucleic acids encoding an IDI polypeptide. The one or more heterologous nucleic acids can be operably linked to constitutive promoters, can be operably linked to inducible promoters, or can be operably linked to a combination of inducible and constitutive promoters. The one or more heterologous nucleic acids can additionally be operably linked strong promoters, weak promoters, and/or medium promoters. One or more of the heterologous nucleic acids encoding mvaE and mvaS polypeptides from *L. grayi, E. faecium, E. gallinarum*, and/or *E. casseliflavus*, a lower mevalonate (MVA) pathway polypeptide(s), a DXP pathway polypeptide(s), and an isoprene synthase polypeptide can be integrated into a genome of the host cells or can be stably expressed in the cells. The one or more heterologous nucleic acids can additionally be on a vector.

The production of isoprene by the cells according to any of the compositions or methods described herein can be enhanced (e.g., enhanced by the expression of one or more heterologous nucleic acids encoding an isoprene synthase polypeptide, a lower MVA pathway polypeptide(s), a DXP pathway polypeptide(s), and/or the mvaE and mvaS polypeptides from *L. grayi, E. faecium, E. gallinarum*, and/or *E. casseliflavus*). As used herein, "enhanced" isoprene production refers to an increased cell productivity index (CPI) for isoprene, an increased titer of isoprene, an increased mass yield of isoprene, and/or an increased specific productivity of isoprene by the cells described by any of the compositions and methods described herein compared to cells which do not have one or more heterologous nucleic acids encoding an isoprene synthase polypeptide, a lower MVA pathway polypeptide(s), a DXP pathway polypeptide(s), and/or the mvaE and mvaS polypeptides from *L. grayi, E. faecium, E. gallinarum*, and/or *E. casseliflavus*. The production of isoprene can be enhanced by about 5% to about 1,000,000 folds. The production of isoprene can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by cells that do not express one or more heterologous nucleic acids encoding mvaE and mvaS polypeptides from *L. grayi, E. faecium, E. gallinarum*, and/or *E. casseliflavus*.

The production of isoprene can also enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds.

Methods of Using the Recombinant Cells to Produce Isoprene

Also provided herein are methods of producing isoprene comprising culturing cells (such as bacterial cells) comprising one or more heterologous nucleic acids encoding an mvaE and an mvaS polypeptide from *L. grayi, E. faecium, E. gallinarum*, and/or *E. casseliflavus*, a lower MVA pathway polypeptide, and an isoprene synthase polypeptide. The isoprene can be produced from any of the cells described herein and according to any of the methods described herein. Any of the cells can be used for the purpose of producing isoprene from carbohydrates, including six carbon sugars such as glucose.

Thus, also provided herein are methods of producing isoprene comprising culturing cells (such as bacterial cells) comprising one or more heterologous nucleic acids encoding an mvaE and an mvaS polypeptide from *L. grayi, E. faecium, E. gallinarum*, and/or *E. casseliflavus*, in a suitable condition for producing isoprene and (b) producing isoprene. The cells can further comprise one or more nucleic acid molecules encoding the lower MVA pathway polypeptide(s) described above (e.g., MVK, PMK, MVD, and/or IDI) and any of the isoprene synthase polypeptide(s) described above (e.g. *Pueraria* isoprene synthase). In some aspects, the cells (such as bacterial cells) can be any of the cells described herein. Any of the isoprene synthases or variants thereof described herein, any of the microorganism (such as bacterial) strains or plant cells described herein, any of the promoters described herein, and/or any of the vectors described herein can also be used to produce isoprene using any of the energy sources (e.g. glucose or any other six carbon sugar) described herein. In some aspects, the method of producing isoprene further comprises a step of recovering the isoprene.

In some aspects, the amount of isoprene produced is measured at the peak absolute productivity time point. In some aspects, the peak absolute productivity for the cells is about any of the amounts of isoprene disclosed herein. In some aspects, the amount of isoprene produced is measured at the peak specific productivity time point. In some aspects, the peak specific productivity for the cells is about any of the amounts of isoprene per cell disclosed herein. In some aspects, the cumulative, total amount of isoprene produced is measured. In some aspects, the cumulative total productivity for the cells is about any of the amounts of isoprene disclosed herein. In some aspects, the amount of isoprene produced is measured at the peak volumetric productivity time point. In some aspects, the peak volumetric productivity for the cells is about any of the amounts of isoprene disclosed herein. In some aspects, the amount of isoprene produced is measured at the cumulative percent yield on glucose time point. In some aspects, the cumulative percent yield on glucose is about any of the amounts of isoprene disclosed herein.

In some aspects, any of the cells described herein (for examples the cells in culture) produce isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, or more nmole of isoprene/gram of cells for the wet weight of the cells/hour (nmole/$g_{wcm}$/hr). In some aspects, the amount of isoprene is between about 2 to about 5,000 nmole/$g_{wcm}$/hr, such as between about 2 to about 100 nmole/$g_{wcm}$/hr, about 100 to about 500 nmole/$g_{wcm}$/hr, about 150 to about 500 nmole/$g_{wcm}$/hr, about 500 to about 1,000 nmole/$g_{wcm}$/hr, about 1,000 to about 2,000 nmole/$g_{wcm}$/hr, or about 2,000 to about 5,000 nmole/$g_{wcm}$/hr. In some aspects, the amount of isoprene is between about 20 to about 5,000 nmole/$g_{wcm}$/hr, about 100 to about 5,000 nmole/$g_{wcm}$/hr, about 200 to about 2,000 nmole/$g_{wcm}$/hr, about 200 to about 1,000 nmole/$g_{wcm}$/hr, about 300 to about 1,000 nmole/$g_{wcm}$/hr, or about 400 to about 1,000 nmole/$g_{wcm}$/hr.

In some aspects, the cells in culture produce isoprene at greater than or about 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 100,000, or more ng of isoprene/gram of cells for the wet weight of the cells/hr (ng/$g_{wcm}$/h). In some aspects, the amount of isoprene is between about 2 to about 5,000 ng/$g_{wcm}$/h, such as between about 2 to about 100 ng/$g_{wcm}$/h, about 100 to about 500 ng/$g_{wcm}$/h, about 500 to about 1,000 ng/$g_{wcm}$/h, about 1,000 to about 2,000 ng/$g_{wcm}$/h, or about 2,000 to about 5,000 ng/$g_{wcm}$/h. In some aspects, the amount of isoprene is between about 20 to about 5,000 ng/$g_{wcm}$/h, about 100 to about 5,000 ng/$g_{wcm}$/h, about 200 to about 2,000 ng/$g_{wcm}$/h, about 200 to about 1,000 ng/$g_{wcm}$/h, about 300 to about 1,000 ng/$g_{wcm}$/h, or about 400 to about 1,000 ng/$g_{wcm}$/h.

In some aspects, the cells in culture produce a cumulative titer (total amount) of isoprene at greater than about any of or about any of 1, 10, 25, 50, 100, 150, 200, 250, 300, 400, 500, 600, 700, 800, 900, 1,000, 1,250, 1,500, 1,750, 2,000, 2,500, 3,000, 4,000, 5,000, 10,000, 50,000, 100,000, or more mg of isoprene/L of broth (mg/$L_{broth}$, wherein the volume of broth includes the volume of the cells and the cell medium). In some aspects, the amount of isoprene is between about 2 to about 5,000 mg/$L_{broth}$, such as between about 2 to about 100 mg/$L_{broth}$, about 100 to about 500 mg/$L_{broth}$, about 500 to about 1,000 mg/$L_{broth}$, about 1,000 to about 2,000 mg/$L_{broth}$, or about 2,000 to about 5,000 mg/$L_{broth}$. In some aspects, the amount of isoprene is between about 20 to about 5,000 mg/$L_{broth}$, about 100 to about 5,000 mg/$L_{broth}$, about 200 to about 2,000 mg/$L_{broth}$, about 200 to about 1,000 mg/$L_{broth}$, about 300 to about 1,000 mg/$L_{broth}$, or about 400 to about 1,000 mg/$L_{broth}$.

In some aspects, the isoprene produced by the cells in culture comprises at least about 1, 2, 5, 10, 15, 20, or 25% by volume of the fermentation offgas. In some aspects, the isoprene comprises between about 1 to about 25% by volume of the offgas, such as between about 5 to about 15%, about 15 to about 25%, about 10 to about 20%, or about 1 to about 10%.

Provided herein are cells having enhanced isoprene production. The production of isoprene by the cells can be enhanced by the expression of one or more heterologous nucleic acids encoding mvaE and mvaS polypeptides from *L. grayi, E. faecium, E. gallinarum*, and/or *E. casseliflavus*, one or more copies of a heterologous nucleic acid encoding a lower MVA pathway polypeptide, and one or more heterologous nucleic acids encoding an isoprene synthase polypeptide. As used herein, "enhanced" isoprene production refers to an increased cell productivity index (CPI) for isoprene, an increased titer of isoprene, an increased mass yield of isoprene, increased volumetric productivity, and/or an increased specific productivity of isoprene by the cells described by any of the compositions and methods described herein compared to cells which do not have one or more heterologous nucleic acids encoding an isoprene synthase polypeptide, a lower MVA pathway polypeptide(s), a DXP pathway polypeptide(s), and/or the mvaE and mvaS polypeptides from L. grayi, E. faecium, E. gallinarum, and/or E. casseliflavus. The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by the cells that do not endogenously have mvaE and mvaS polypeptides from L. grayi, E. faecium, E. gallinarum, and/or E. casseliflavus.

The production of isoprene by the cells according to any of the methods described herein can be enhanced (e.g., enhanced by the expression of one or more heterologous nucleic acids encoding the isoprene synthase polypeptide). The production of isoprene can be enhanced by about 5% to about 1,000,000 folds. The production of isoprene can be enhanced by about 10% to about 1,000,000 folds (e.g., about 50% to about 1,000,000 folds, about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprene by the naturally-occurring cells (e.g., the cells without the expression of one or more heterologous nucleic acids encoding an isoprene synthase polypeptide). The production of isoprene can also enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprene by naturally-occurring cells or by cells without the expression of one or more heterologous nucleic acids encoding mvaE and mvaS polypeptides from L. grayi, E. faecium, E. gallinarum, and/or E. casseliflavus.

Recombinant Cells (Such as Bacterial Cells) Capable of Increased Production of Isoprenoids Isoprenoids can be produced in many organisms from the synthesis of the isoprenoid precursor molecules which are produced by the MVA pathway. As stated above, isoprenoids represent an important class of compounds and include, for example, food and feed supplements, flavor and odor compounds, and anticancer, antimalarial, antifungal, and antibacterial compounds.

As a class of molecules, isoprenoids are classified based on the number of isoprene units comprised in the compound. Monoterpenes comprise ten carbons or two isoprene units, sesquiterpenes comprise 15 carbons or three isoprene units, diterpenes comprise 20 carbons or four isoprene units, sesterterpenes comprise 25 carbons or five isoprene units, and so forth. Steroids (generally comprising about 27 carbons) are the products of cleaved or rearranged isoprenoids.

Isoprenoids can be produced from the isoprenoid precursor molecules IPP and DMAPP. These diverse compounds are derived from these rather simple universal precursors and are synthesized by groups of conserved polyprenyl pyrophosphate synthases (Hsieh et al., *Plant Physiol.* 2011 March; 155(3):1079-90). The various chain lengths of these linear prenyl pyrophosphates, reflecting their distinctive physiological functions, in general are determined by the highly developed active sites of polyprenyl pyrophosphate synthases via condensation reactions of allylic substrates (dimethylallyl diphosphate ($C_5$-DMAPP), geranyl pyrophosphate ($C_{10}$-GPP), farnesyl pyrophosphate ($C_{15}$-FPP), geranylgeranyl pyrophosphate ($C_{20}$-GGPP)) with corresponding number of isopentenyl pyrophosphates ($C_5$-IPP) (Hsieh et al., *Plant Physiol.* 2011 March; 155(3):1079-90).

Any of the recombinant host cells expressing one or more copies of a heterologous nucleic acid encoding an mvaE and an mvaS polypeptide from L. grayi, E. faecium, E. gallinarum, or E. casseliflavus capable of increased production of mevalonate or isoprenoid precursors or isoprene described above can also be capable of increased production of isoprenoid precursors and/or isoprenoids. In some aspects, these cells further comprise one or more heterologous nucleic acids encoding polypeptides of the lower MVA pathway, IDI, and/or the DXP pathway, as described above, and a heterologous nucleic acid encoding a polyprenyl pyrophosphate synthase polypeptide. Without being bound to theory, increasing the cellular production of isoprenoid precursors in cells (such as bacterial cells) by any of the compositions and methods described above can result in the production of higher amounts of isoprenoids. Increasing the molar yield of isoprenoid precursor production from glucose translates into higher molar yields of isoprenoids produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprenoid production. Also without being bound to theory, it is thought that increasing the cellular production of mevalonate in cells (such as bacterial cells) by any of the compositions and methods described above will similarly result in the production of higher amounts of isoprenoid precursor molecules and/or isoprenoids. Increasing the molar yield of mevalonate production from glucose translates into higher molar yields of isoprenoid precursor molecules and/or isoprenoids, including isoprene, produced from glucose when combined with appropriate enzymatic activity levels of mevalonate kinase, phosphomevalonate kinase, diphosphomevalonate decarboxylase, isopentenyl diphosphate isomerase and other appropriate enzymes for isoprene and isoprenoid production.

In some aspects, the cells described herein are isoprenoid-producing cells. In one aspect, isoprenoid producing cells are wild type cells capable of producing isoprenoid. In another aspect, isoprenoid producing cells are non-naturally occurring cells engineered to contain one or more heterologous upper MVA pathway polypeptides, lower MVA pathway polypeptides, polyprenyl pyrophosphate synthase polypeptides, DXP pathway polypeptides, and/or IDI polypeptides. In a further aspect, the isoprene producing cells may contain both endogenous and heterologous upper MVA pathway polypeptides, lower MVA pathway polypeptides, polyprenyl pyrophosphate synthase polypeptides, DXP pathway polypeptides, and/or IDI polypeptides.

Types of Isoprenoids

The cells (such as bacterial cells) of the present invention are capable of increased production of isoprenoids. Examples of isoprenoids include, without limitation, hemiterpenoids, monoterpenoids, sesquiterpenoids, diterpenoids, sesterterpenoids, triterpenoids, tetraterpenoids, and higher polyterpenoids. In some aspects, the hemiterpenoid is prenol (i.e., 3-methyl-2-buten-1-ol), isoprenol (i.e., 3-methyl-3-buten-1-ol), 2-methyl-3-buten-2-ol, or isovaleric acid. In some aspects, the monoterpenoid can be, without limitation, geranyl pyrophosphate, eucalyptol, limonene, or pinene. In some aspects, the sesquiterpenoid is farnesyl pyrophosphate, artemisinin, or bisabolol. In some aspects, the diterpenoid can be, without limitation, geranylgeranyl pyrophosphate, retinol, retinal, phytol, taxol, forskolin, or aphidicolin. In some aspects, the triterpenoid can be, without limitation, squalene or lanosterol. The isoprenoid can also be selected from the group consisting of abietadiene, amorphadiene, carene, α-famesene, β-farnesene, farnesol, geraniol, geranylgeraniol, linalool, limonene, myrcene, nerolidol, ocimene, patchoulol, β-pinene, sabinene, γ-terpinene, terpindene and valencene.

In some aspects, the tetraterpenoid is lycopene or carotene (a carotenoid). As used herein, the term "carotenoid" refers to a group of naturally-occurring organic pigments produced in the chloroplasts and chromoplasts of plants, of some other photosynthetic organisms, such as algae, in some types of fungus, and in some bacteria. Carotenoids include the oxygen-containing xanthophylls and the non-oxygen-containing carotenes. In some aspects, the carotenoids are selected from the group consisting of xanthophylls and carotenes. In some aspects, the xanthophyll is lutein or zeaxanthin. In some aspects, the carotenoid is α-carotene, β-carotene, γ-carotene, β-cryptoxanthin or lycopene.

Heterologous Nucleic Acids Encoding Polyprenyl Pyrophosphate Synthases Polypeptides In some aspects of the invention, the cells described in any of the compositions or methods herein further comprise one or more nucleic acids encoding a lower mevalonate (MVA) pathway polypeptide(s), as described above, as well as one or more nucleic acids encoding a polyprenyl pyrophosphate synthase polypeptide(s). The polyprenyl pyrophosphate synthase polypeptide can be an endogenous polypeptide. The endogenous nucleic acid encoding a polyprenyl pyrophosphate synthase polypeptide can be operably linked to a constitutive promoter or can similarly be operably linked to an inducible promoter. The endogenous nucleic acid encoding a polyprenyl pyrophosphate synthase polypeptide can additionally be operably linked to a strong promoter. Alternatively, the endogenous nucleic acid encoding a polyprenyl pyrophosphate synthase polypeptide can be operably linked to a weak promoter. In particular, the cells can be engineered to over-express the endogenous polyprenyl pyrophosphate synthase polypeptide relative to wild-type cells.

In some aspects, the polyprenyl pyrophosphate synthase polypeptide is a heterologous polypeptide. The cells of the present invention can comprise more than one copy of a heterologous nucleic acid encoding a polyprenyl pyrophosphate synthase polypeptide. In some aspects, the heterologous nucleic acid encoding a polyprenyl pyrophosphate synthase polypeptide is operably linked to a constitutive promoter. In some aspects, the heterologous nucleic acid encoding a polyprenyl pyrophosphate synthase polypeptide is operably linked to an inducible promoter. In some aspects, the heterologous nucleic acid encoding a polyprenyl pyrophosphate synthase polypeptide is operably linked to a strong promoter. In some aspects, the heterologous nucleic acid encoding a polyprenyl pyrophosphate synthase polypeptide is operably linked to a weak promoter.

The nucleic acids encoding a polyprenyl pyrophosphate synthase polypeptide(s) can be integrated into a genome of the host cells or can be stably expressed in the cells. The nucleic acids encoding a polyprenyl pyrophosphate synthase polypeptide(s) can additionally be on a vector.

Exemplary polyprenyl pyrophosphate synthase nucleic acids include nucleic acids that encode a polypeptide, fragment of a polypeptide, peptide, or fusion polypeptide that has at least one activity of a polyprenyl pyrophosphate synthase. Polyprenyl pyrophosphate synthase polypeptides convert isoprenoid precursor molecules into more complex isoprenoid compounds. Exemplary polyprenyl pyrophosphate synthase polypeptides include polypeptides, fragments of polypeptides, peptides, and fusions polypeptides that have at least one activity of an isoprene synthase polypeptide. Exemplary polyprenyl pyrophosphate synthase polypeptides and nucleic acids include naturally-occurring polypeptides and nucleic acids from any of the source organisms described herein. In addition, variants of polyprenyl pyrophosphate synthase can possess improved activity such as improved enzymatic activity. In some aspects, a polyprenyl pyrophosphate synthase variant has other improved properties, such as improved stability (e.g., thermo-stability), and/or improved solubility. Exemplary polyprenyl pyrophosphate synthase nucleic acids can include nucleic acids which encode polyprenyl pyrophosphate synthase polypeptides such as, without limitation, geranyl diphosphosphate (GPP) synthase, farnesyl pyrophosphate (FPP) synthase, and geranylgeranyl pyrophosphate (GGPP) synthase, or any other known polyprenyl pyrophosphate synthase polypeptide.

In some aspects of the invention, the cells described in any of the compositions or methods herein further comprise one or more nucleic acids encoding a farnesyl pyrophosphate (FPP) synthase. The FPP synthase polypeptide can be an endogenous polypeptide encoded by an endogenous gene. In some aspects, the FPP synthase polypeptide is encoded by an endogenous ispA gene in E. coli. The endogenous nucleic acid encoding an FPP synthase polypeptide can be operably linked to a constitutive promoter or can similarly be operably linked to an inducible promoter. The endogenous nucleic acid encoding an FPP synthase polypeptide can additionally be operably linked to a strong promoter. In particular, the cells can be engineered to over-express the endogenous FPP synthase polypeptide relative to wild-type cells.

In some aspects, the FPP synthase polypeptide is a heterologous polypeptide. The cells of the present invention can comprise more than one copy of a heterologous nucleic acid encoding a FPP synthase polypeptide. In some aspects, the heterologous nucleic acid encoding a FPP synthase polypeptide is operably linked to a constitutive promoter. In some aspects, the heterologous nucleic acid encoding a FPP synthase polypeptide is operably linked to an inducible promoter. In some aspects, the heterologous nucleic acid encoding a polyprenyl pyrophosphate synthase polypeptide is operably linked to a strong promoter.

The nucleic acids encoding an FPP synthase polypeptide can be integrated into a genome of the host cells or can be stably expressed in the cells. The nucleic acids encoding an FPP synthase can additionally be on a vector.

Standard methods can be used to determine whether a polypeptide has polyprenyl pyrophosphate synthase polypeptide activity by measuring the ability of the polypeptide to convert IPP into higher order isoprenoids in vitro, in a cell extract, or in vivo. These methods are well known in the art and are described, for example, in U.S. Pat. No. 7,915,026; Hsieh et al., *Plant Physiol.* 2011 March; 155(3):1079-90; Danner et al., *Phytochemistry.* 2011 Apr. 12 [Epub ahead of print]; Jones et al., *J Biol Chem.* 2011 Mar. 24 [Epub ahead of print]; Keeling et al., *BMC Plant Biol.* 2011 Mar. 7; 11:43; Martin et al., *BMC Plant Biol.* 2010 Oct. 21; 10:226; Kumeta & Ito, *Plant Physiol.* 2010 December; 154(4):1998-2007; and Köllner & Boland, *J Org Chem.* 2010 Aug. 20; 75(16):5590-600.

Recombinant Cells (Such as Bacterial Cells) Capable of Increased Production of Isoprenoids The recombinant cells (such as bacterial cells) described herein have the ability to produce isoprenoids at a concentration greater than that of the same cells lacking one or more copies of a heterologous nucleic acid encoding mvaE and mvaS polypeptides from *L. grayi, E. faecium, E. gallinarum,* and/or *E. casseliflavus,* one or more copies of a heterologous nucleic acid encoding a lower MVA pathway polypeptide, and one or more heterologous nucleic acids encoding a polyprenyl pyrophosphate synthase polypeptide, optionally when cultured in minimal media. In some cases, the one or more copies of a heterologous nucleic acid encoding mvaE and mvaS polypeptides from *L. grayi, E. faecium, E. gallinarum,* and/or *E. casseliflavus,* one or more copies of a heterologous nucleic acid encoding a lower MVA pathway polypeptide, and one or more heterologous nucleic acid encoding a polyprenyl pyrophosphate synthase polypeptide are heterologous nucleic acids that are integrated into the host cell's chromosome. The cells (such as bacterial cells) can produce at least 5% greater amounts of isoprenoids when compared to isoprenoids-producing cells (such as bacterial cells) that do not comprise the mvaE and mvaS polypeptides from *L. grayi, E. faecium, E. gallinarum,* and/or *E. casseliflavus.* Alternatively, the cells (such as bacterial cells) can produce greater than about 1%, 2%, 3%, 4%, 5%, 6%, 7%, 8%, 9%, 10%, 11%, 12%, 13%, 14%, or 15% of isoprenoids, inclusive, as well as any numerical value in between these numbers.

In one aspect of the invention, there are provided cells (such as bacterial cells) comprising one or more heterologous nucleic acids encoding mvaE and mvaS polypeptides from *L. grayi, E. faecium, E. gallinarum,* and/or *E. casseliflavus,* one or more heterologous nucleic acids encoding a lower mevalonate (MVA) pathway polypeptide(s), one or more heterologous nucleic acids encoding a DXP pathway polypeptide(s), and one or more heterologous nucleic acids encoding polyprenyl pyrophosphate synthase. The cells can further comprise one or more heterologous nucleic acids encoding an IDI polypeptide. Additionally, the polyprenyl pyrophosphate synthase polypeptide can be an FPP synthase polypeptide. The one or more heterologous nucleic acids can be operably linked to constitutive promoters, can be operably linked to inducible promoters, or can be operably linked to a combination of inducible and constitutive promoters. The one or more heterologous nucleic acids can additionally be operably linked strong promoters, weak promoters, and/or medium promoters. One or more of the heterologous nucleic acids encoding mvaE and mvaS polypeptides from *L. grayi, E. faecium, E. gallinarum,* and/or *E. casseliflavus,* a lower mevalonate (MVA) pathway polypeptide(s), and a DXP pathway polypeptide(s), and a polyprenyl pyrophosphate synthase polypeptide can be integrated into a genome of the host cells or can be stably expressed in the cells. The one or more heterologous nucleic acids can additionally be on a vector.

Provided herein are methods of using any of the cells described above for enhanced isoprenoid production. The production of isoprenoids by the cells can be enhanced by the expression of one or more heterologous nucleic acids encoding mvaE and mvaS polypeptides from *L. grayi, E. faecium, E. gallinarum,* and/or *E. casseliflavus,* one or more heterologous nucleic acids encoding a lower MVA pathway polypeptide, and one or more heterologous nucleic acids encoding a polyprenyl pyrophosphate synthase polypeptide. As used herein, "enhanced" isoprenoid production refers to an increased cell productivity index (CPI) for isoprenoid production, an increased titer of isoprenoids, an increased mass yield of isoprenoids, and/or an increased specific productivity of isoprenoids by the cells described by any of the compositions and methods described herein compared to cells which do not have one or more heterologous nucleic acids encoding a polyprenyl pyrophosphate synthase polypeptide, a lower MVA pathway polypeptide(s), a DXP pathway polypeptide(s), and/or the mvaE and mvaS polypeptides from *L. grayi, E. faecium, E. gallinarum,* and/or *E. casseliflavus.* The production of isoprenoids can be enhanced by about 5% to about 1,000,000 folds. The production of isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoid by cells without the expression of one or more heterologous nucleic acids encoding mvaE and mvaS polypeptides from *L. grayi, E. faecium, E. gallinarum,* and/or *E. casseliflavus.*

The production of isoprenoids by the cells according to any of the methods described herein can be enhanced (e.g., enhanced by the expression of one or more heterologous nucleic acids encoding the mvaE and mvaS polypeptides from *L. grayi, E. faecium, E. gallinarum,* and/or *E. casseliflavus,* one or more heterologous nucleic acids encoding a lower MVA pathway polypeptide, and one or more heterologous nucleic acids encoding a polyprenyl pyrophosphate synthase polypeptide). The production of isoprenoids can be enhanced by about 5% to about 1,000,000 folds. The production of isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoids by naturally-occurring cells (e.g., cells without the expression of one or more heterologous nucleic acids encoding mvaE and mvaS polypeptides from *L. grayi, E. faecium, E. gallinarum,* and/or *E. casseliflavus*).

The production of isoprenoids can also enhanced by at least about any of 5%, 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoids by naturally-occurring cells or by cells without the expression of one or more heterologous nucleic acids encoding mvaE and mvaS polypeptides from *L. grayi, E. faecium, E. gallinarum*, and/or *E. casseliflavus*.

Methods of Using the Recombinant Cells to Produce Isoprenoid Molecules

Also provided herein are methods of producing isoprenoids comprising culturing cells (such as bacterial cells) comprising one or more heterologous nucleic acids encoding an mvaE and an mvaS polypeptide from *L. grayi, E. faecium, E. gallinarum*, and/or *E. casseliflavus*, a lower MVA pathway polypeptide, and an polyprenyl pyrophosphate synthase polypeptide. The isoprenoids can be produced from any of the cells described herein and according to any of the methods described herein. Any of the cells can be used for the purpose of producing isoprenoids from carbohydrates, including six carbon sugars such as glucose.

Thus, provided herein are methods of producing isoprenoids comprising culturing cells (such as bacterial cells) comprising one or more heterologous nucleic acids encoding an mvaE and an mvaS polypeptide from *L. grayi, E. faecium, E. gallinarum*, and/or *E. casseliflavus*, in a suitable condition for producing isoprene and (b) producing isoprenoid precursor molecules and/or isoprenoids. The cells can further comprise one or more nucleic acid molecules encoding the lower MVA pathway polypeptide(s) described above (e.g., MVK, PMK, MVD, and/or IDI) and any of the polyprenyl pyrophosphate synthase polypeptide(s) described above. In some aspects, the cells (such as bacterial cells) can be any of the cells described herein. Any of the polyprenyl pyrophosphate synthase or variants thereof described herein, any of the microorganism (such as bacterial) strains or plant cells described herein, any of the promoters described herein, and/or any of the vectors described herein can also be used to produce isoprenoids using any of the energy sources (e.g. glucose or any other six carbon sugar) described herein. In some aspects, the method of producing isoprenoids further comprises a step of recovering the isoprenoids.

The method of producing isoprenoids can similarly comprise the steps of: (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus*, wherein the cells (such as bacterial cells) heterologously express one or more copies of a gene encoding a mvaE polypeptide and an mvaS polypeptide from *L. grayi, E. faecium, E. gallinarum*, or *E. casseliflavus*; and (b) producing isoprenoids, wherein the cells (such as bacterial cells) produce greater amounts of isoprenoids when compared to isoprenoid-producing cells (such as bacterial cells) that do not comprise the mvaE and mvaS polypeptides from *L. grayi, E. faecium, E. gallinarum*, and/or *E. casseliflavus*.

The instant methods for the production of isoprenoids can produce at least 5% greater amounts of isoprenoids when compared to isoprenoids-producing cells (such as bacterial cells) that do not comprise the mvaE and mvaS polypeptides from *L. grayi, E. faecium, E. gallinarum*, and/or *E. casseliflavus*. Alternatively, the cells (such as bacterial cells) can produce greater than about 1%, 2%, 3%, 4%, 5%, 6%, 7%, 8%, 9%, 10%, 11%, 12%, 13%, 14%, or 15% of isoprenoids, inclusive. In some aspects, the method of producing isoprenoids further comprises a step of recovering the isoprenoids.

Provided herein are methods of using any of the cells described above for enhanced isoprenoid production. The production of isoprenoids by the cells can be enhanced by the expression of one or more heterologous nucleic acids encoding mvaE and mvaS polypeptides from *L. grayi, E. faecium, E. gallinarum*, and/or *E. casseliflavus*, one or more heterologous nucleic acids encoding a lower MVA pathway polypeptide, and one or more heterologous nucleic acids encoding a polyprenyl pyrophosphate synthase polypeptide. As used herein, "enhanced" isoprenoid production refers to an increased cell productivity index (CPI) for isoprenoid production, an increased titer of isoprenoids, an increased mass yield of isoprenoids, and/or an increased specific productivity of isoprenoids by the cells described by any of the compositions and methods described herein compared to cells which do not have one or more heterologous nucleic acids encoding a polyprenyl pyrophosphate synthase polypeptide, a lower MVA pathway polypeptide(s), a DXP pathway polypeptide(s), and/or the mvaE and mvaS polypeptides from *L. grayi, E. faecium, E. gallinarum*, and/or *E. casseliflavus*. The production of isoprenoids can be enhanced by about 5% to about 1,000,000 folds. The production of isoprenoids can be enhanced by about 10% to about 1,000,000 folds (e.g., about 1 to about 500,000 folds, about 1 to about 50,000 folds, about 1 to about 5,000 folds, about 1 to about 1,000 folds, about 1 to about 500 folds, about 1 to about 100 folds, about 1 to about 50 folds, about 5 to about 100,000 folds, about 5 to about 10,000 folds, about 5 to about 1,000 folds, about 5 to about 500 folds, about 5 to about 100 folds, about 10 to about 50,000 folds, about 50 to about 10,000 folds, about 100 to about 5,000 folds, about 200 to about 1,000 folds, about 50 to about 500 folds, or about 50 to about 200 folds) compared to the production of isoprenoids by cells without the expression of one or more heterologous nucleic acids encoding mvaE and mvaS polypeptides from *L. grayi, E. faecium, E. gallinarum*, and/or *E. casseliflavus*.

The production of isoprenoids can also enhanced by at least about any of 10%, 20%, 30%, 40%, 50%, 60%, 70%, 80%, 90%, 1 fold, 2 folds, 5 folds, 10 folds, 20 folds, 50 folds, 100 folds, 200 folds, 500 folds, 1000 folds, 2000 folds, 5000 folds, 10,000 folds, 20,000 folds, 50,000 folds, 100,000 folds, 200,000 folds, 500,000 folds, or 1,000,000 folds compared to the production of isoprenoids by cells without the expression of one or more heterologous nucleic acids encoding mvaE and mvaS polypeptides from *L. grayi, E. faecium, E. gallinarum*, and/or *E. casseliflavus*.

In addition, more specific cell culture conditions can be used to culture the cells in the methods described herein. For example, in some aspects, the method for the production of isoprenoids comprises the steps of (a) culturing cells (such as bacterial cells; including, but not limited to, *E. coli* cells) that do not endogenously have an mvaE gene and an mvaS gene from *L. grayi, E. faecium, E. gallinarum*, and/or *E. casseliflavus* at 34° C., wherein the cells (such as bacterial cells) heterologously express one or more copies of a gene encoding a mvaE polypeptide and an mvaS polypeptide from *L. grayi, E. faecium, E. gallinarum*, or *E. casseliflavus* on a low to medium copy plasmid and under the control of a strong promoter; and (b) producing isoprenoid, such as mevalonate. In some aspects, the method of producing mevalonate further comprises a step of recovering the isoprenoid precursor molecules and/or isoprenoids.

Vectors

Suitable vectors can be used for any of the compositions and methods described herein. For example, suitable vectors can be used to optimize the expression of one or more copies of a gene encoding an mvaE polypeptide and an mvaS polypeptide from L. grayi, E. faecium, E. gallinarum, or E. casseliflavus, an isoprene synthase, a polyprenyl pyrophosphate synthase, and/or one or more MVA pathway polypeptides in anaerobes. In some aspects, the vector contains a selective marker. Examples of selectable markers include, but are not limited to, antibiotic resistance nucleic acids (e.g., kanamycin, ampicillin, carbenicillin, gentamicin, hygromycin, phleomycin, bleomycin, neomycin, or chloramphenicol) and/or nucleic acids that confer a metabolic advantage, such as a nutritional advantage on the host cell. In some aspects, one or more copies of an mvaE and an mvaS nucleic acid from L. grayi, E. faecium, E. gallinarum, or E. casseliflavus, an isoprene synthase, a polyprenyl pyrophosphate synthase, and/or one or more MVA pathway polypeptides nucleic acid(s) integrate into the genome of host cells without a selective marker.

Any one of the vectors characterized or used in the Examples of the present disclosure can be used.

Transformation Methods

Nucleic acids encoding one or more copies of an mvaE and an mvaS nucleic acid from L. grayi, E. faecium, E. gallinarum, or E. casseliflavus, isoprene synthase, and/or lower MVA pathway polypeptides can be inserted into a microorganism using suitable techniques. Additionally, isoprene synthase, IDI, DXP pathway, and/or polyprenyl pyrophosphate synthase nucleic acids or vectors containing them can be inserted into a host cell (e.g., a plant cell, a fungal cell, a yeast cell, or a bacterial cell described herein) using standard techniques for introduction of a DNA construct or vector into a host cell, such as transformation, electroporation, nuclear microinjection, transduction, transfection (e.g., lipofection mediated or DEAE-Dextrin mediated transfection or transfection using a recombinant phage virus), incubation with calcium phosphate DNA precipitate, high velocity bombardment with DNA-coated microprojectiles, and protoplast fusion. General transformation techniques are known in the art (See, e.g., *Current Protocols in Molecular Biology* (F. M. Ausubel et al. (eds.) Chapter 9, 1987; Sambrook et al., *Molecular Cloning: A Laboratory Manual*, 2$^{nd}$ ed., Cold Spring Harbor, 1989; and Campbell et al., *Curr. Genet.* 16:53-56, 1989). The introduced nucleic acids can be integrated into chromosomal DNA or maintained as extrachromosomal replicating sequences. Transformants can be selected by any method known in the art. Suitable methods for selecting transformants are described in International Publication No. WO 2009/076676, U.S. patent application Ser. No. 12/335,071 (US Publ. No. 2009/0203102), WO 2010/003007, US Publ. No. 2010/0048964, WO 2009/132220, and US Publ. No. 2010/0003716.

Exemplary Purification Methods

In some aspects, any of the methods described herein further include a step of recovering the compounds produced. In some aspects, any of the methods described herein further include a step of recovering the isoprene. In some aspects, the isoprene is recovered by absorption stripping (See, e.g., US Publ. No. 2011/0178261, the contents of which is incorporated by reference, especially with respect to the absorption stripping and purification techniques disclosed therein). In some aspects, any of the methods described herein further include a step of recovering the heterologous polypeptide. In some aspects, any of the methods described herein further include a step of recovering the terpenoid or carotenoid.

Suitable purification methods are described in more detail in U.S. Patent Application Publication US2010/0196977A1.

The invention can be further understood by reference to the following examples, which are provided by way of illustration and are not meant to be limiting.

EXAMPLES

Example 1: Construction of *E. coli* Strain CMP451 (Containing BL21 Pgl+PL.2 mKKDyI GI1.2 gltA), CMP452 and CMP453

The promoter in front of the citrate synthase gene (gltA) in BL21 (Novagen) has been replaced by a constitutive low expression promoter, namely GI1.2 (U.S. Pat. No. 7,371,558). Two wild-type promoters have been described for gltA (Wilde, R, and J. Guest. 1986. *J. Gen. Microbiol.* 132:3239-3251) and the synthetic promoter was inserted just after the −35 region of the distal promoter. A PCR product was obtained using primers UpgltACm-F (5'-TATTTAATTTT-TAATCATCTAATTTGACAATCATTCAACAAAGTTGT-TACAATTAACCCT CACTAAAGGGCGG-3'(SEQ ID NO:24)) and DngltA1.xgiCm-R (5'-TCAACAGCTGTATC-CCCGTTGAGGGTGAGTTTTGCTTTTGTATCAGC-CATATATTCCACC AGCTATTTGTTAGT-GAATAAAAGTGGTTGAATTATTTGCTCAGGATGTG GCATHGTCAA GGGCTAATACGACTCAC-TATAGGGCTCG-3'(SEQ ID NO:25)), and plasmid FRT-gb2-Cm-FRT from Gene Bridges (Heidelberg, Germany) as a template. The PCR product was purified and used in a lambda red-mediated recombination as described by the manufacturer (Gene Bridges, Heidelberg, Germany). Several colonies were selected for further characterization. The promoter region was PCR-amplified using primers gltAPromSeqF: 5'-GGCAGTATAGGCTGTTCA-CAAAATC-3' (SEQ ID NO:26) and gltApromSeqR: 5'-CT-TGACCCAGCGTGCCTTTCAGC-3' (SEQ ID NO:27) and, as a template, DNA extracted by resuspending a colony in 30 uL H2O, heating at 95 C for 4 min, spinning down, and using 2 uL of that material as a template in a 50 uL reaction. After observing the sequencing results of the PCR products obtained, a colony harboring each of the three different promoters GI1.2, GI1.5 and GI1.6 (U.S. Pat. No. 7,371,558) was saved for further use (CMP141, CMP142 and CMP143; Table 3).

TABLE 3

*E. coli* strains

| Strain | Description | Parent |
|--------|-------------|--------|
| CMP141 | BL21 Cm-GI1.2 gltA | BL21 |
| CMP142 | BL21 Cm-GI1.5 gltA | BL21 |
| CMP143 | BL21 Cm-GI1.6 gltA | BL21 |
| CMP258 | BL21 pgl+ | BL21 |
| CMP374 | BL21 pgl+ PL.2-mKKDyI ldhA::Kan | MD09-314 |
| CMP440 | BL21 pgl+ PL.2 mKKDyI Cm-GI1.2 gltA | MD09-314 |
| CMP441 | BL21 pgl+ PL.2 mKKDyI Cm-GI1.5 gltA | MD09-314 |
| CMP442 | BL21 pgl+ PL.2 mKKDyI Cm-GI1.6 gltA | MD09-314 |
| CMP451 | BL21 pgl+ PL.2 mKKDyI GI1.2 gltA | CMP440 |
| CMP452 | BL21 pgl+ PL.2 mKKDyI GI1.5 gltA | CMP441 |
| CMP453 | BL21 pgl+ PL.2 mKKDyI GI1.6 gltA | CMP442 |
| CMP604 | BL21 pgl+ PL.2 mKKDyI GI 1.2 gltA ackA-pta::Cm | CMP451 |
| CMP620 | BL21 pgl+ PL.2 mKKDyI GI 1.2 gltA ML ackA-pta::Cm ldhA::Kan | CMP604 |
| CMP635 | BL21 pgl+ PL.2 mKKDyI GI 1.2 gltA ML ackA-pta ldhA | CMP620 |

TABLE 3-continued

E. coli strains

| Strain | Description | Parent |
|---|---|---|
| CMP646 | BL21 attB:Cm (to restore LowerP) col1 | BL21 (Novagen) |
| CMP676 | BL21 pgl+ PL.2 mKKDyI GI 1.2 gltA ML ackA-pta ldhA attB::Cm | CMP635 |
| CMP680 | BL21 pgl+ PL.2 mKKDyI GI 1.2 gltA ML ackA-pta ldhA attB::Cm, pCHL276 | CMP676 |
| MCM521 | BL21 neo-PL.2-mKKDyI | (U.S. patent application No. 12/978,324) |
| MD09-313 | BL21 pgl+ neo-PL.2-mKKDyI | CMP258 |
| MD09-314 | BL21 pgl+ PL.2-mKKDyI | MD09-313 |
| MD491 | BL21 pgl+ ackA-pta::Cm | CMP258 |

Strain MD09-313 was built by transducing CMP258 (see U.S. patent application Ser. No. 12/978,324) with a P1 lysate from strain MCM521 (see U.S. Patent Application Publication No. 2011/0159557) and selecting for colonies on Luria-Bertani plates containing 20 ug/ml kanamycin. P1 lysates are prepared according to the method described in Ausubel, et al., Current Protocols in Molecular Biology, John Wiley and Sons, Inc. The kanamycin marker was removed using the protocol recommended by the manufacturer (Gene Bridges, Heidelberg, Germany) to form strain MD09-314.

A P1 lysate was made from strains CMP141, CMP142 and CMP143 and was used to transduce strain MD09-314, to form CMP440, CMP441 and CMP442 respectively (Table 3). The chloramphenicol marker was removed using the protocol recommended by the manufacturer (Gene Bridges, Heidelberg, Germany) to form strains CMP451, CMP452 and CMP453 respectively (Table 3).

Example 2: Construction of E. coli Strain CMP604 (Containing BL21 Pgl+PL.2 mKKDyI GI 1.2 gltA ML ackA-pta::Cm)

A DNA fragment containing the ackA-pta genes interrupted by a chloramphenicol marker was amplified by PCR using strain Triple Triple in which the chloramphenicol marker is still in (U.S. Pat. No. 7,745,184 B2) as a template and primers ackACF (5'-GTGCAAATTCACAACTCA-GCGG) (SEQ ID NO:28)) and ptaCR (CACCAACG-TATCGGGCAT TGCC-3'(SEQ ID NO:29)). The PCR product obtained was used in a recombineering reaction as recommended by the manufacturer (Gene Bridges, Heidelberg, Germany) to integrate the PCR product at the ackA-pta locus in strain CMP258 (U.S. patent application Ser. No. 12/978,324). Colonies were selected on LB+5 ug/ml of chloramphenicol. One colony was picked and was named MD491. A P1 lysate of MD491 was made and was used to transduce strain CMP451. Colonies were selected on LB+5 ug/ml of chloramphenicol. One colony was picked and was named CMP604.

Example 3: Construction of E. coli Strain CMP620 (Containing BL21 Pgl+PL.2 mKKDyI GI 1.2 gltA ML ackA-pta::Cm ldhA::Kan) and CMP635 (containing BL21 pgl+PL.2 mKKDyI GI 1.2 gltA ML ackA-pta ldhA)

A DNA fragment containing the ldhA gene interrupted by a kanamycin marker was amplified by PCR using strain JW 1375 from the Keio collection (Baba et al. 2006. Mol. Syst. Biol. 2: 2006.0008) as a template, and primers ldhAseqR (5'-GGCTTACCGTTTACGCTTTCCAGC-3'(SEQ ID NO:30)) and ldhAseqF2 (5'-CTAATGCAATACGTGTC-CCGAGC-3'(SEQ ID NO:31)). The PCR product obtained was used in a recombineering reaction as recommended by the manufacturer (Gene Bridges, Heidelberg, Germany) to integrate the PCR product at the ldhA locus in strain MD09-313. Colonies were selected on LB+20 ug/ml of kanamycin. One colony was picked and was named CMP374. A P1 lysate of CMP374 was made and was used to transduce CMP604. Colonies were selected on LB+20 ug/ml of kanamycin. One colony was picked and was named CMP620. The chloramphenicol and kanamycin markers were looped out simultaneously by electroporating pCP20 (Datsenko and Wanner. 2000. PNAS 97:6640-5) in the strain, selecting two colonies on LB+50 ug/ml carbenicillin at 30° C., then restreaking those colonies on an LB plate at 42° C. A $Cm^S$ and $Kan^S$ colony was selected from those plates and named CMP635.

Example 4: Construction of E. coli Strain CMP676 (Containing BL21 pgl+PL.2 mKKDyI GI 1.2 gltA ML ackA-pta ldhA attB::Cm)

A DNA fragment containing a chloramphenicol marker flanked by DNA homologous to the upstream and downstream regions of the λ attachment site attB was amplified by PCR using plasmid pKD3 (Datsenko & Wanner, 2000, PNAS 97:6640-5) as a template, and primers CMP171 (5'-AAAATTTTCATTCTGTGACAGAGAAAAAGTAGC-CGAAGATGACGGTTTGTCACATGGA GTTGGCAG-GATGTTTGATTACATGGGAATTAGCCATGGTCC-3' (SEQ ID NO:32)) and CMP172 (5'-GACCAGCCGCGTAACCTGGCAAAATCGGTTACG GTTGAGTAATAAATGGATGCCCTGC GTAAGCGGGGCATTTTTCTTGGTGTAGGCTG-GAGCTGCTTCG-3'(SEQ ID NO:33)). The PCR product obtained was used in a recombineering reaction in BL21 (Novagen) as recommended by the manufacturer (Gene Bridges, Heidelberg, Germany) to integrate the PCR product at the λ attachment site attB. Strain CMP646 was thereby generated, selected on LB+5 ug/ml chlroamphenicol. A P1 lysate of CMP646 was made and was used in a transduction reaction on strain CMP635, thereby removing the lower mevalonate pathway (mevalonate kinase, phosphomevalonate kinase, diphosphomevalonate decarboxylase, and isopentenyl diphosphate isomerase) from the chromosome of that strain. The transduction reaction was plated on LB+chloramphenicol 5 ug/ml and one colony was picked and named CMP676.

Example 5: Construction of E. coli Strain CMP680 (BL21 pgl+PL.2 mKKDyI GI 1.2 gltA ML ackA-pta ldhA attB::Cm, pCHL276) and Detection of Mevalonate Plasmid pCHL276 (see example 6 (iii)) was introduced into CMP676 by electroporation. Colonies were selected on LB+50 ug/mL spectinomycin. One colony was picked and named CMP680.

(i) Mevalonate Yield Assay

Overnight cultures of the above-identified strains were inoculated in shake tubes containing 2 mL LB broth supplemented with 50 μg/mL spectinomycin (Novagen). Cultures were then incubated for 14 h at 34° C. at 250 rpm. Next, the cultures were diluted into an 5 mL 48-well plate (Axygen Scientific) containing 2 mL TM3 media supplemented with 1% Glucose, yeast extract to a final concentration of 0.1%, and 200 µM IPTG to final OD of 0.2. The plate was sealed with a Breath Easier membrane (Diversified Biotech) and incubated at 34° C. in a Shel Lab shaker/incubator at 600 rpm for 24 hours. 1 mL of each culture was centrifuged at 3,000×g for 5 min. 250 µl of supernatant was added to 19 µL of 20% sulfuric acid and incubated on ice for 5 min. The mixture was then centrifuged for 5 min at 3000×g and the supernatant was collected for HPLC analysis. 200 µl of supernatant was transferred to a HPLC compatible 96-well conical bottom polypropylene plate (Nunc). The concentration of mevalonate in samples was determined by comparison to a standard curve of mevalonate (Sigma). The glucose concentration was measured by performing a glucose oxidase assay according to the manufacturer's specifications (Pointe Scientific, Inc.)

(ii) HPLC Detection of Mevalonate

HPLC analysis was performed on an Agilent 1100 series HPLC system containing a refractive index detector using a 300 mm×7.8 mm BioRad—Aminex HPX-87H ion exclusion column (catalog #125-0140) incubated at 50° C. and equipped with a BioRad—Microguard Cation H refill 30 mm×4.6 mm (Catalog #125-0129). Samples were run at a flow rate of 0.6 ml/min in 0.01N sulfuric acid running buffer. Mevalonate was detected using a refractive index detector.

Example 6: Construction of *E. coli* Strains MCM1373-1377 Expressing mvaE and mvaS Genes from *Listeria grayi* DSM 20601, *Enterococcus faecium*, *Enterococcus gallinarum* EG2, and *Enterococcus casseliflavus*

(i) Gene Identification and Selection

A primary sequence homology search using the *E. faecalis* mvaE gene product as the query was performed using the BLASTp program located at the NCBI website (Stephen F. Altschul, Thomas L. Madden, Alejandro A. Schäffer, Jinghui Zhang, Zheng Zhang, Webb Miller, and David J. Lipman (1997), "Gapped BLAST and PSI-BLAST: a new generation of protein database search programs", *Nucleic Acids Res.* 25:3389-3402). Sequences of interest were selected from the search results.

In general, sequences of interest for the mvaE and mvaS genes displayed from 59-66% nucleotide sequence identity (codon optimized; see Table 4) and between 59-71% amino acid sequence identity (Table 5) compared to the wild type *E. faecalis* mvaE and mvaS nucleic acid and protein sequences, respectively.

TABLE 4

Percent identity of mvaE and mvaS nucleotides (codon-optimized) compared to *Enterococcus faecalis* WT

| Species | mvaE gene (% identity) | mvaS gene (% identity) |
| --- | --- | --- |
| Listeria grayi | 62 | 64 |
| Enterococcus faecium | 60 | 59 |
| Enterococcus gallinarum EG2 | 60 | 65 |
| Enterococcus casseliflavus | 60 | 66 |

TABLE 5

Percent identity of mvaE and mvaS amino acid sequences compared to *Enterococcus faecalis* WT

| Species | mvaE gene (% identity) | mvaS gene (% identity) |
| --- | --- | --- |
| Listeria grayi | 59 | 70 |
| Enterococcus faecium | 61 | 60 |
| Enterococcus gallinarum EG2 | 60 | 69 |
| Enterococcus casseliflavus | 59 | 71 |

(ii) Plasmids pDW83, pMCM1223-pMCM1225

The coding sequences of MvaE and MvaS from *Enterococcus casseliflavus* EC10 were optimized for expression in *Escherichia coli* (GeneOracle), and subcloned into the expression vector MCM82 (U.S. Patent Application Publication No. US2010/0196977, para. [1023]) to yield pDW83. Specifically, the cassette harboring the mvaES operon was cut from the cloning vector GcD126 (GeneOracle) using the restriction enzymes BglII and PmeI (Roche) using standard molecular biology techniques. This fragment was then ligated (Roche Rapid Ligation) into MCM82 which had previously been subjected to restriction digest using the enzymes BamHI and PmeI (Roche) followed by agarose gel separation (Invitrogen E-Gel) to remove the expression cassette encoding mvaES from *Enterococcus faecalis* using standard molecular biology techniques. The ligation mixture was transformed into chemically competent Top10 cells (Invitrogen) according to the manufacturer's recommended protocol. Spectinomycin resistant positive transformants were grown in liquid LB medium, and plasmids were purified (Qiagen Miniprep) and verified by sequencing (Quintara Biosciences) using the primers Ec Seq 1F through 4R (Table 6).

TABLE 6

| Sequencing Primers | |
| --- | --- |
| Ec Seq 1F | 5'-GGGTATGAAAGCGATTCTGA-3' |
| Ec Seq 2F | 5'-AGCCCAAGGCGCTATTACCG-3' |
| Ec Seq 3F | 5'-GGATTAGTTCAAAATTTGGC-3' |
| Ec Seq 4F | 5'-CGGTTAATGGCACGTTATGA-3' |
| Ec Seq 1R | 5'-TCGTTCGCCTGTAAACTGCT-3' |
| Ec Seq 2R | 5'-TGCTCTATTTCAGTACCTTT-3' |
| Ec Seq 3R | 5'-TGTAAGTTCAGGCCCACGCC-3' |
| Ec Seq 4R | 5'-CCTCAGCCTTGTTGTAATAA-3' |

Plasmids encoding MvaE and MvaS from *Enterococcus faecium*, *Listeria grayi*, and *Enterococcus gallinarum* were constructed by GeneOracle (Mountain View, Calif.) using the design in Table 7. A synthetic DNA encoding mvaE-RBS-mvaS was created and then cloned into pMCM82 between the NcoI and PstI sites, replacing the existing operon. The vector provided an RBS for mvaE.

TABLE 7

Design for plasmids pMCM1223-pMCM1225 encoding MvaE and MvaS from
*Enterococcus faecium*, *Listeria grayi*, and *Enterococcus gallinarum*

| Plasmid Identifier | Plasmid Name | Source Organism | MvaE | MvaS | Origin and Selection |
|---|---|---|---|---|---|
| pMCM1223 | pCL-Ptrc-Upper_GcMM_161 (*Listeria grayi* DSM 20601) | *L. grayi*, DSM 20601 | gi\|229554876\|ref\|ZP_04442665.1\| acetyl-CoA acetyltransferase/hydroxymethylglutaryl-CoA reductase, degradative [*Listeria grayi* DSM 20601] | gi\|229554877\|ref\|ZP_04442666.1\| hydroxymethylglutaryl-CoA synthase [*Listeria grayi* DSM 20601] | pSC101, Spectinomycin (50 ug/mL) |
| pMCM1224 | pCL-Ptrc-Upper_GcMM_162 (*Enterococcus faecium*) | *E. faecium* | gi\|9937391\|gb\|AAG02444.1\| AF290094_2 acetyl-CoA acetyltransferase/HMG-CoA reductase [*Enterococcus faecium*] | gi\|9937390\|gb\|AAG02443.1\| AF290094_1 HMG-CoA synthase [*Enterococcus faecium*] | pSC101, Spectinomycin (50 ug/mL) |
| pMCM1225 | pCL-Ptrc-Upper_GcMM_163 (*Enterococcus gallinarum* EG2) | *E. gallinarum* EG2 | gi\|257869528\|ref\|ZP_05649181.1\| acetyl-CoA acetyltransferase/hydroxymethylglutaryl-CoA reductase [*Enterococcus gallinarum* EG2] | gi\|257869527\|ref\|ZP_05649180.1\| hydroxymethylglutaryl-CoA synthase [*Enterococcus gallinarum* EG2] | pSC101, Spectinomycin (50 ug/mL) |

(iii) pCLp_Trc-Upper(*E. faecalis*)-Leaderless Construction (pCHL276)

Primers (CL483F: 5'-AGGAGGAATAAACCAT-GAAAACAGTAGTTATTATTGATGCATTAC-3'(SEQ ID NO:42); CL484R: 5'-ACTACTGTTTTCATGGTTTATTC-CTCCTTATTTAATCGATAC-3'(SEQ ID NO:43)) were designed to remove an extra RBS on pCL_pTrc-Upper(*E. faecalis*), the MCM82 plasmid. The PCR reaction consisted of template DNA, MCM82 (100 ng), 50 uM of each forward and reverse primer, 1 ul of 10 mM dNTPs (Roche), 5 ul of 10×PfuII reaction buffer (Agilent), 1 ul of Pfu II fusion enzyme (Agilent) and 40 ul of water. Eighteen cycles were performed with a temperature profile of 50 seconds at 95 C, and 50 seconds at 60° C., and 9 min at 68° C. and an additional 10 min extension at 68° C. in a Bio-Rad thermocycler. DpnI (1 ul) was added after completion of the PCR reaction and incubated at 37° C. for two hours to remove template DNA. An additional 1 ul of DpnI was added and incubated at 37° C. overnight. Two microliters of the reaction was transformed into TOP10 cells (Invitrogen) and plate of LB+50 μg/mL spectinomycin. The correct clone was confirmed by sequencing.

(iv) pCL_pTrc-Upper(*E. casseliflavus*)-Leaderless Construction (pCHL277)

Primers (CL485F: 5'-AGGAGGAATAAACCATG-GAAGAAGTTGTCATCATTGACGCAC-3'(SEQ ID NO:44); CL486R: 5'-ACTTCTTCCATGGTTTATTCCTC-CTTATTTAATCG-3'(SEQ ID NO:45)) were designed to remove the extra RBS on pCL_pTrc-Upper(*E. casseliflavus*), pDW83 plasmid. The PCR reaction consisted of template DNA, pDW83 (100 ng), 50 uM of each forward (CL483F) and reverse primer (CL484R), 1 ul of 10 mM dNTPs(Roche), 5 ul of 10×PfuII reaction buffer(Agilent), 1 ul of Pfu II fusion enzyme (Agilent) and 40 ul of water. Eighteen cycles were performed with a temperature profile of 50 seconds at 95 C, and 50 seconds at 60° C., and 9 min at 68° C. and an additional 10 min extension at 68° C. in a Bio-Rad thermocycler. DpnI (1 ul) was added after PCR reaction and incubate at 37° C. for two hours to remove template DNA. An additional 1 ul of DpnI was added and incubate at 37° C. overnight. Two microliters of the reaction was transformed into TOP10 cell (Invitrogen) and plate of LA/spec50. The correct clone was confirmed by sequencing.

(v) Construction of High Yield MVA Production Strains MCM1373-1377

Host CMP676 was grown to mid-log in LB at 37 C and prepared for electroporation by washing 3× in one half culture volume iced ddH2O and resuspended in one tenth culture volume of the same. 100 uL of cell suspension was combined with 1 uL plasmid DNA, moved to a 2 mm electroporation cuvette, electroporated at 25 uFD, 200 ohms, 2.5 kV, and immediately quenched with 500 uL LB. Cells were recovered shaking at 37 C for 1 hr and then transformants selected overnight on LB plates with 50 ug/mL spectinomycin at 37 C. Single colonies were grown in LB+50 ug/mL spectinomycin at 37 C to OD600 ~1. 500 uL of broth was mixed with 1 mL 50% glycerol and frozen on dry ice. Frozen stocks were stored at −80 C.

Example 7: Examination of Mevalonate Productivity Metrics in Engineered *E. coli* Strains Expressing Genes from the Mevalonate Pathway, Grown in Fed-Batch Culture at the 15-L Scale (i) Materials Medium Recipe (Per Liter Fermentation Medium):
Potassium phosphate $K_2HPO_4$ 7.5 g, Magnesium Sulfate $MgSO_4*7H_2O$ 2 g, citric acid monohydrate $C_6H_8O_7*H_2O$ 2 g, ferric ammonium citrate $NH_4FeC_6H_5O_7$ 0.34 g, yeast extract (from biospringer) 0.5 g, 1000× Modified Trace Metal Solution 1.5 ml, sulfuric acid 50% w/v 2.26 ml, foamblast 882 (Emerald Performance Materials) 0.83 ml, Macro Salts Solution 3.36 ml. All of the components were added together and dissolved in deionized $H_2O$. This solution was heat sterilized (123° C. for 20 minutes). After cooling to run temperature, the pH was adjusted to 7.0 with ammonium hydroxide (28%) and q.s. to volume. Feed solution #1 16.7 g, Vitamin Solution 11.9 mL, and spectinomycin solution 5 ml, were added after sterilization and pH adjustment.

1000× Modified Trace Metal Solution (Per Liter):

Citric Acids*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component was dissolved one at a time in deionized $H_2O$, pH was adjusted to 3.0 with HCl/NaOH, and then the solution was q.s. to volume and filter sterilized with a 0.22 micron filter.

Macro Salt Solution (Per Liter):

$MgSO_4$*$7H_2O$ 296 g, citric acid monohydrate 296 g, ferric ammonium citrate 49.6 g. All components were dissolved in water, q.s. to volume and filter sterilized with 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Spectinomycin Solution (Per Liter):

50 g spectinomycin was q.s. to volume with deionized water and filter sterilized with 0.22 micron filter.

Feed Solution #1 (Per Kilogram):

Glucose 0.590 kg, Di $H_2O$ 0.394 kg, $K_2HPO_4$ 7.4 g, and Foamblast882 8.94 g. All components were mixed together and autoclaved.

(ii) Experimental Methods

Fermentation was performed in a 15-L bioreactor with *E. coli* BL21 strains described in Table 8. Each strain was run twice, in identical conditions, so productivity results could be reported as an average of the two results.

TABLE 8

List of mevalonate producing strains examined in fed-batch culture at 15 L scale

| Strain | Description |
|---|---|
| CMP680 | HMB GI 1.2 gltA ML ackA-pta ldhA attB::Cm, pCLPtrcUpper(rbs) (pCHL276)) |
| MCM1373 | HMB GI 1.2 gltA ML ackA-pta ldhA attB::Cm + pCL-Ptrc-Upper_Ef |
| MCM1374 | HMB GI 1.2 gltA ML ackA-pta ldhA attB::Cm + pCL-Ptrc-Upper_Ec |
| MCM1375 | HMB GI 1.2 gltA ML ackA-pta ldhA attB::Cm + pCL-Ptrc-Upper_Listeria |
| MCM1376 | HMB GI 1.2 gltA ML ackA-pta ldhA attB::Cm + pCL-Ptrc-Upper_Efaecium |
| MCM1377 | HMB GI 1.2 gltA ML ackA-pta ldhA attB::Cm + pCL-Ptrc-Upper_Eg |

A frozen vial of the *E. coli* strain was thawed and inoculated into tryptone-yeast extract medium (LB Miller medium) in a 2.8 L Erlynmeyer flask to be used as the inoculums for the bioreactor. After the inoculum grew to optical density 1.0, measured at 550 nm (OD550), 500 mL was used to inoculate a 15-L bioreactor and bring the initial tank volume to 5 L.

This experiment was carried out to monitor mevalonate formation from glucose at the desired fermentation pH 7.0 and temperature 34° C. Aerobic conditions were maintained for the duration of the run by sparging air at a rate of 8 standard liters per minute, holding back pressure of 0.7 bar gauge, and a stirring rate of 850 rotations per minute, with impellers and baffling to transfer the power to the liquid medium.

The glucose feed solution was fed using a pulse feed program. As soon as the batch glucose was depleted, signaled by a pH rise (pH>=7.05), a pulse of 3 g/min for 20 min was added. Afterwards, a glucose feed pulse was induced by a pH trigger (pH>=7.05). The pulse lasted 30 min and the magnitude (g/min) was equal to the total carbon dioxide evolution rate (mmol/hr) divided by a predetermined factor sufficient to keep the residual glucose in the broth in excess. The total amount of glucose feed delivered to the bioreactor during the 52 hr fermentation varied by strain. Induction was achieved by adding isopropyl-beta-D-1-thiogalactopyranoside (IPTG). A shot of IPTG was added to the tank to bring the concentration to 400 uM when the cells were at an OD550 of 4. The oxygen, nitrogen and carbon dioxide levels in the off-gas from the bioreactors were determined using a Hiden mass spectrometer. A time course of broth samples was taken at 4 hour intervals from each bioreactor. Broth concentration of glucose, citrate, and mevalonate were determined by HPLC. Optical density was determined by measuring the absorbance of dilute broth suspensions at 550 nm and multiplying by the dilution factor, to report the result (OD550). The OD550 reading was converted to dry cell mass by using previously generated factors that compare OD550 to dry cell weight over the time course of a fermentation. Productivity metrics of mass yield, specific productivity, titer, and cell productivity index are reported as an average of two results at comparable time points from each run, using the definitions given above (See "Definitions").

(iii) Small Scale Mevalonate Yield Assay

Overnight cultures were inoculated in shake tubes containing 2 mL LB broth supplemented with 50 μg/mL spectinomycin (Novagen) and 50 μg/mL carbenicillin (Novagen) from frozen stocks. Cultures were then incubated for 14 h at 34° C. at 250 rpm. Next, the cultures were diluted into an 5 mL 48-well plate (Axygen Scientific) containing 2 mL TM3 media supplemented with 1% Glucose, yeast extract to a total concentration of 1%, and 200 μM IPTG to final OD of 0.2. The plate was sealed with a Breath Easier membrane (Diversified Biotech) and incubated at 34° C. in a Shel Lab shaker/incubator at 600 rpm for 24 hours. 1 mL of each culture was centrifuged at 3,000×g for 5 min. 250 μl of supernatant was added to 19 μL of 20% sulfuric acid and incubated on ice for 5 min. The mixture was then centrifuged for 5 min at 3000×g and the supernatant was collected for HPLC analysis. 200 μl of supernatant was transferred to a HPLC compatible 96-well conical bottom polypropylene plate (Nunc). The concentration of mevalonate in samples was determined by comparison to a standard curve of mevalonate (Sigma). The glucose concentration was measured by performing a glucose oxidase assay according to the manufacturer's specifications (Pointe Scientific, Inc.).

(iv) HPLC Detection of Mevalonate

HPLC analysis was performed on a Waters 2695 Alliance HPLC system containing a Knauer K2301 refractive index detector using a 300 mm×7.8 mm BioRad—Aminex HPX-87H ion exclusion column (catalog #125-0140) incubated at 50° C. and equipped with a BioRad-Microguard Cation H refill 30 mm×4.6 mm (Catalog #125-0129). Samples were run at a flow rate of 0.6 ml/min in 0.01N sulfuric acid running buffer. Broth levels of mevalonate were able to be quantified by comparing the refractive index response of each sample versus a calibration curve generated by running various mevonate containing solutions of known concentration.

Production of mevalonate in batch culture at mass yields from glucose ranged from 34.8% to 41.1% from *E. coli* containing the mvaE and mvaS genes from the organisms *Listeria grayi*_DSM 20601, *Enterococcus faecium*, *Enterococcus gallinarum* EG2, *Enterococcus casseliflavus* (FIG. 1, Table 9).

TABLE 9

Mass yield of mevalonate from glucose.

| Strain | IPTG (μM) | Mass Yield (%) | S.D. |
|---|---|---|---|
| CMP680 | 100 | 33.6 | 0.8 |
| MCM1373 | 100 | 31.8 | 0.8 |
| MCM1374 | 100 | 35.8 | 3.9 |
| MCM1375 | 100 | 34.6 | 0.2 |
| MCM1376 | 100 | 35.6 | 3.2 |
| MCM1377 | 100 | 41.0 | 0.1 |
| CMP680 | 200 | 35.3 | 0.1 |
| MCM1373 | 200 | 31.9 | 0.2 |
| MCM1374 | 200 | 39.2 | 3.0 |
| MCM1375 | 200 | 34.8 | 1.0 |
| MCM1376 | 200 | 37.9 | 3.3 |
| MCM1377 | 200 | 41.1 | 4.9 |

S.D. represents one standard deviation of two replicates.

The production of mevalonate in fed batch culture in a 15 L fermentor at mass yields from glucose cumulatively ranged from 39.1% to 43.4% in *E. coli* containing the mvaE and mvaS genes from the organisms *Listeria grayi*_DSM 20601, *Enterococcus faecium*, *Enterococcus gallinarum* EG2, *Enterococcus casseliflavus*. (Table 10).

TABLE 10

Cumulative mass yield results (average of the 3 final points of the 2 runs for each strain)

| Strain | Upper enzymes | Mass Yield (Mevalonate on glucose) (w/w %) | Standard deviation (w/w %) | C.V. % |
|---|---|---|---|---|
| CMP680 | *E. faecalis* | 37.3 | 0.5 | 1.34% |
| MCM1374 | *Enterococcus casseliflavus* | 41.3 | 1.7 | 4.12% |
| MCM1375 | *Listeria grayi* DSM 20601 | 39.1 | 2.0 | 5.12% |
| MCM1376 | *Enterococcus faecium* | 39.7 | 0.7 | 1.76% |
| MCM1377 | *Enterococcus gallinarum* EG2 | 43.4 | 1.1 | 2.53% |

Mevalonate peak specific productivities ranged from 87.5 to 100.1 g/L/h/OD in fed batch culture in a 15 L fermentor in *E. coli* containing the mvaE and mvaS genes from the organisms *Listeria grayi*_DSM 20601, *Enterococcus faecium, Enterococcus gallinarum* EG2, *Enterococcus casseliflavus* (Table 11).

TABLE 11

Peak specific productivity observed for each strain (average of the peak observed values observed in the 2 runs for each strain)

| Strain | Upper enzymes | Peak Specific productivity (mg/L/hr/OD) | Standard deviation (mg/L/hr/OD) | C.V. % |
|---|---|---|---|---|
| CMP680 | *E. faecalis* | 87.4 | 7.2 | 8.2% |
| MCM1374 | *Enterococcus casseliflavus* | 100.1 | 11.6 | 11.6% |
| MCM1375 | *Listeria grayi* DSM 20601 | 87.5 | 26.7 | 30.5% |
| MCM1376 | *Enterococcus faecium* | 93.9 | 14.2 | 15.1% |
| MCM1377 | *Enterococcus gallinarum* EG2 | 88.6 | 13.9 | 15.7% |

Finally, mevalonate titers ranged from 108.2 to 115.4 g/L (Table 12), and CPIs ranged from 4.86 to 5.80 g mevalonate/g glucose (Table 13) in *E. coli* containing the mvaE and mvaS genes from the organisms *Listeria grayi*_DSM 20601, *Enterococcus faecium, Enterococcus gallinarum* EG2, *Enterococcus casseliflavus*.

TABLE 12

Peak mevalonate titer observed for each strain (average of the broth titer observed at 48 hrs for each set of runs)

| Strain | Upper enzymes | Peak Mevalonate Titer @ 48 hrs EFT (g/L) | Standard deviation (g/L) | C.V. % |
|---|---|---|---|---|
| CMP680 | *E. faecalis* | 122.8 | 5.8 | 4.7% |
| MCM1374 | *Enterococcus casseliflavus* | 115.4 | 4.1 | 3.6% |
| MCM1375 | *Listeria grayi* DSM 20601 | 108.2 | 4.8 | 4.4% |
| MCM1376 | *Enterococcus faecium* | 110.1 | 12.0 | 10.9% |
| MCM1377 | *Enterococcus gallinarum* EG2 | 111.2 | 6.1 | 5.5% |

TABLE 13

CPI values for each strain (average of the CPI values observed at 44 and 48 hours for each set of runs)

| Strain | Upper enzymes | CPI (g/g) | Standard deviation (g/g) | C.V. % |
|---|---|---|---|---|
| CMP680 | *E. faecalis* | 4.25 | 0.25 | 5.9% |
| MCM1374 | *Enterococcus casseliflavus* | 5.70 | 0.37 | 6.5% |
| MCM1375 | *Listeria grayi* DSM 20601 | 4.86 | 0.73 | 15.0% |
| MCM1376 | *Enterococcus faecium* | 5.29 | 0.12 | 2.3% |
| MCM1377 | *Enterococcus gallinarum* EG2 | 5.80 | 0.52 | 8.9% |

Example 8: Construction of Isoprene-Producing Strains

A lower mevalonate pathway can be introduced by transduction into CMP676 using a lysate from MCM521 (see Table 3). The kanamycin marker is looped out according to the manufacturer (Gene Bridges, Heidelberg, Germany).

Figure 2:
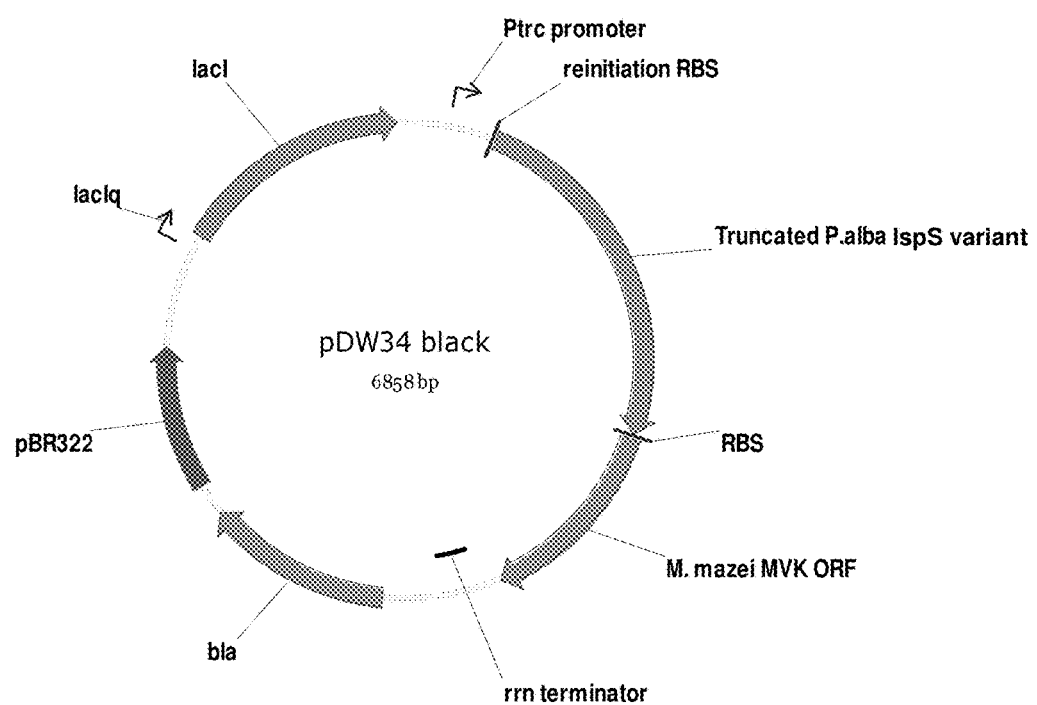
FIG. 2 depicts a plasmid map of pDW34.

The lower pathway from MCM521 can be modified by changing the promoter upstream of the operon by modifying the rbs in front of each gene via the use of alternative genes. Plasmids pMCM1223 (L. grayi), pMCM1224 (E. faecium), pMCM1225 (E. gallinarum), pCHL276 (E. faecalis) or pCHL277 (E. casseliflavus) are co-electroporated with a variation of plasmid pDW34 (See U.S. Patent Application Publication No: 2010/0196977; FIG. 2). The plasmids, which are variants of pDW34, contain an isoprene synthase variant, which is improved for activity. Colonies can be selected on LB+spectinomycin 50 ug/mL+carbenicillin 50 ug/mL.

Example 9: Increased MVP Levels Utilizing the Upper MVA Pathway from E. casseliflavus or E. gallinarum These experiments highlight increase in mevalonate-5-phosphate (MVP) levels when utilizing either the upper MVA pathway from E. casseliflavus or E. gallinarum compared to an upper MVA pathway from E. faecalis. Mevalonate 5-phosphate is a substrate for phosphomevalonate kinase (PMK). Accordingly, without being bound to theory, increased MVP concentrations in cells indicate increased carbon flux through the upper MVA pathway.

(i) Materials and Methods

Metabolite Extraction from E. coli:

The metabolism of bacterial cells grown in fermentors was rapidly inactivated by withdrawing approximately 3 mL of culture into a tube filled with 9 mL of dry ice-cold methanol. The resulting samples were weighed to calculate the amount of sampled broth and then stored at −80° C. until further analysis. For metabolite extraction and concentration, 0.25 mL aliquots of cell suspension (0.4 mL aliquot was used if cell density of the culture measured as OD600 was below 50) were diluted with 1.5 mL of methanol/ammonium acetate buffer (5 mM, pH=8.0) mixture (6:1, v/v) and cell debris was pelleted by a 4 minute centrifugation. The supernatant was collected and loaded onto Strata-X-AW columns from Phenomenex (33 μm 30 mg/3 mL Polymeric Weak Anion Exchange). The cell pellet was extracted two more times, first with 1.5 mL of the methanol/ammonium acetate buffer (5 mM, pH=8.0) mixture (6:1 v/v), and then with 1.5 mL of methanol/ammonium acetate buffer (5 mM, pH=8.0) mixture (1:1 v/v). Both times the cells were pelleted by centrifugation, and the resulting supernatants were consecutively loaded onto the same Strata-X-AW columns. During the extraction-centrifugation, samples with cells were kept below 4° C. After washing the columns with 1 mL of water and 1 mL of methanol, metabolites of interest were eluted from the columns first with 0.3 mL of concentrated NH$_4$OH/methanol (1:14, v/v) mixture and then with 0.3 mL of concentrated NH$_4$OH/methanol/water (1:12:2, v/v/v) mixture. The resulting eluant was neutralized by adding 20 μL of glacial acetic acid, and then cleared by centrifugation.

Metabolite Quantification.

Analysis of metabolites was carried out by mass spectrometry using a TSQ Quantum Access TSQ system (Thermo Scientific). All system control, data acquisition, and mass spectral data evaluation were performed using XCalibur and LCQuan software (Thermo Scientific). For the LC-ESI-MS/MS method, a chiral Nucleodex β-OH 5 μM HPLC column (100×2 mm, Macherey-Nagel, Germany) was used with a CC 8/4 Nucleodex beta-OH guard cartridge. A mobile phase gradient was applied as described in Table 14 in which mobile phase A was 100 mM ammonium acetate (SigmaUltra grade, Sigma) buffer (pH=8) in MilliQ-grade water, mobile phase B was MilliQ-grade water, and mobile phase C was LC-MS grade acetonitrile (Chromasolv, Riedel-de Haën). The column and sample tray temperatures were reduced to 5° C. and 4° C., respectively. The injection volume was 10 μL.

TABLE 14

HPLC gradient used to elute metabolites in the MVA pathway.

| Time | Solvent A | Solvent B | Solvent C | Flow rate |
| --- | --- | --- | --- | --- |
| 0.0 min | 20% | 0% | 80% | 0.4 mL/min |
| 0.5 min | 20% | 0% | 80% | 0.4 mL/min |
| 4.0 min | 60% | 0% | 40% | 0.4 mL/min |
| 6.5 min | 60% | 0% | 40% | 0.4 mL/min |
| 7.0 min | 0.5% | 59.5% | 40% | 0.5 mL/min |
| 13.0 min | 0.1% | 34.9% | 65% | 0.5 mL/min |
| 13.5 min | 20% | 0% | 80% | 0.5 mL/min |
| 14.0 min | 20% | 0% | 80% | 0.5 mL/min |

Mass detection was carried out using electrospray ionization in the negative mode (ESI spray voltage of 3.0 kV and ion transfer tube temperature of 390° C.). The following m/z values for precursor ions were selected to detect the metabolites of interest in SRM mode: 245.0 for IPP and DMAPP, 313.1 for GPP, 381.1 for FPP, 227.0 for MVP, and 307.1 for MVPP. To account for small variations in sensitivity while running the mass spectrometer, uniformly labeled $^{13}C_{10}$-ADP was also added in equal amounts (final concentration of 19.6 uM) to both samples and calibrants as an internal standard ($^{13}C_{10}$-ADP was prepared enzymatically from $^{13}C_{10}$-ATP obtained from Isotec, Sigma-Aldrich; m/z=436.1). Concentrations of metabolites were determined based on the sample/internal standard response ratio of integrated intensities of peaks generated by PO$_3^-$ product ion (m/z=79.0). Calibration curves obtained by injection of standards were used to calculate concentrations of metabolites in cell extracts. IPP, DMAPP, GPP, and FPP standards were purchased from Echelon Biosciences Inc and MVP and MVPP (R-forms) were purchased from Sigma-Aldrich.

Results

Figure 3:
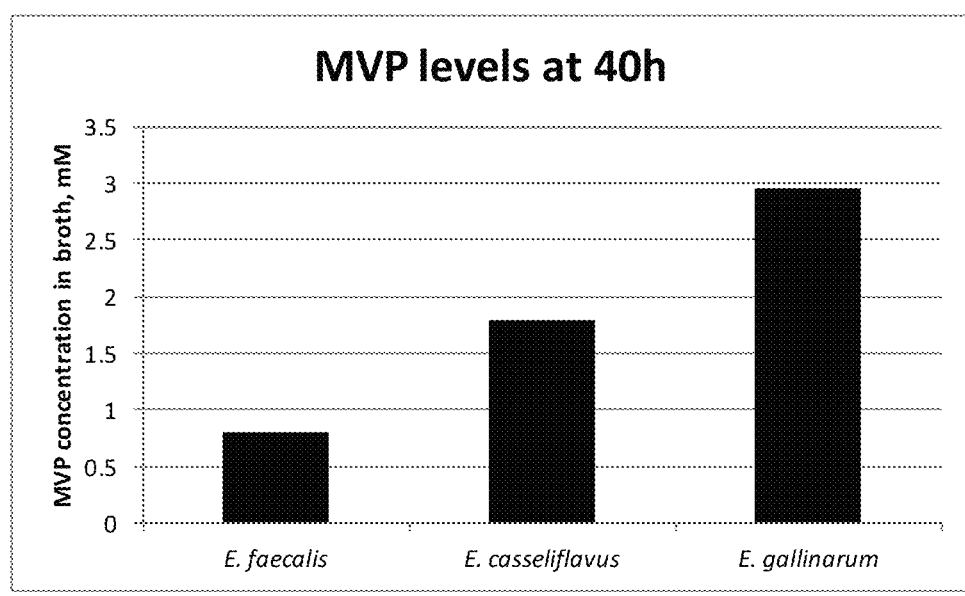
FIG. 3 depicts MVP concentration in E. faecalis, E. gallinarum, and E. casseliflavus at 40 hours.

MVP concentration using the upper MVA pathway from both E. gallinarum and E. casselflavis were higher than E. faecalis at 40 hours (FIG. 3).

Example 10: Increased Production of Isoprene in Strains Containing the Plasmids with Alternative Upper Mevalonate Pathways Compared to a Pathway with E. faecalis Upper Pathway (i) Materials TM3 Media Recipe (Per Liter Fermentation Media):

K$_2$HPO$_4$ 13.6 g, KH$_2$PO$_4$ 13.6 g, MgSO$_4$*7H$_2$O 2 g, citric acid monohydrate 2 g, ferric ammonium citrate 0.3 g, (NH$_4$)$_2$SO$_4$ 3.2 g, yeast extract 0.2 g, 1000× Trace Metals Solution 1 ml. All of the components are added together and dissolved in diH$_2$O. The pH is adjusted to 6.8 with ammonium hydroxide (30%) and brought to volume. Media is filter-sterilized with a 0.22 micron filter. Glucose 10.0 g and antibiotics are added after sterilization and pH adjustment.

1000× Trace Metal Solution (Per Liter Fermentation Media)

Citric Acid*$H_2O$ 40 g, $MnSO_4$*$H_2O$ 30 g, NaCl 10 g, $FeSO_4$*$7H_2O$ 1 g, $CoCl_2$*$6H_2O$ 1 g, $ZnSO_4$*$7H_2O$ 1 g, $CuSO_4$*$5H_2O$ 100 mg, $H_3BO_3$ 100 mg, $NaMoO_4$*$2H_2O$ 100 mg. Each component is dissolved one at a time in di$H_2O$. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+antibiotics. The day after, they are diluted to an OD600 of 0.05 in 20 mL TM3 medium containing 50 ug/ml of spectinomycin and 50 ug/mL carbenicillin (in a 250-mL baffled Erlenmeyer flask), and incubated at 34° C. and 200 rpm. After 2 h of growth, OD600 is measured and 200 uM IPTG is added. Samples are taken regularly during the course of the fermentation. At each timepoint, OD600 is measured. Also, off-gas analysis of isoprene is performed using a gas chromatograph-mass spectrometer (GC-MS) (Agilent) headspace assay. One hundred microliters of whole broth are placed in a sealed GC vial and incubated at 34° C. and 200 rpm for a fixed time of 30 minutes. Following a heat kill step, consisting of incubation at 70° C. for 5 minutes, the sample is loaded on the GC. The reported specific productivity is the amount of isoprene in ug/L read by the GC divided by the incubation time (30 min) and the measured OD600.

(iii) Results

When the strains containing pMCM1223 (*L. grayi*), pMCM1224 (*E. faecium*), pMCM1225 (*E. gallinarum*), or pCHL277 (*E. casseliflavus*) are compared to the same background containing pCHL276 (*E. faecalis*), increased specific productivity, yield, CPI and/or titer of isoprene are observed.

Example 11: Isoprene Production from *E. coli* Expressing Upper MVA Pathway Genes This example evaluated isoprene production in *E. coli* (BL21) expressing introduced genes from the mevalonate pathway and grown in fed-batch culture at the 15-L scale. The genes for the upper MVA pathway enzymes came from either *E. faecalis* (strain DW709 and DW717), *E. casseliflavus* (DW718) or *E. gallinarum* (DW719, MCM2158).

(i) Materials and Methods

Strain Construction:

Strains DW709, DW717, DW718, and DW719 were generated by co-transformation of a plasmid harboring an isoprene synthase (IspS) variant and one of four plasmids harboring different upper MVA pathways into a production host strain of *Escherichia coli*. Following standard molecular biology techniques, the host strain CMP1133 (BL21 Δpgl PL.2mKKDyI GI1.2gltA yhfSFRTPyddVIspAyhfS thiFRTtruncIspA) was electroporated with pDW240 (pTrc *P. alba* IspS MEA-mMVK (Carb50)), carrying an IspS variant, and either pMCM82 (U.S. Patent Application Publication No.: 2009/0203102), pCHL276 (pCLpTrc-Upper(*E. faecalis*)-leaderless), pCHL277 (pCLpTrc-Upper(*E. casseliflavus*)-leaderless), or pMCM1225 (see Table 7). Cells were recovered and plated on selective medium, and individual transformants, resistant to spectinomycin and carbenicillin, resulted in strains DW709, DW717, DW718, and DW719. These isoprene production strains expressed an IspS variant and either the upper MVA pathway from *Enterococcus faecalis*, the leaderless upper MVA pathway from *Enterococcus faecalis*, the upper MVA pathway from *Enterococcus casseliflavus*, or the upper MVA pathway from *Enterococcus gallinarum*, respectively (see Table 15).

TABLE 15 isoprene-producing strains

| Strain name | genotype | Host parent | plasmids |
|---|---|---|---|
| DW709 | BL21 GI1.2gltA PL.2 MKKDyI t pgl pgl-, yhfSFRTPyddVIspAyhfS thiFRTtruncIspA, pTrc(IspS variant)_mMVK, pCLPtrcUpper_E.faecalis | CMP1133 | pDW240, pMCM82 |
| DW717 | BL21 GI1.2gltA PL.2 MKKDyI t pgl pgl-, yhfSFRTPyddVIspAyhfS thiFRTtruncIspA, pTrc(IspS variant)_mMVK, pCLPtrcUpper_E.faecalis_leaderless | CMP1133 | pDW240, pCHL276 |
| DW718 | BL21 GI1.2gltA PL.2 MKKDyI t pgl pgl-, yhfSFRTPyddVIspAyhfS thiFRTtruncIspA, pTrc(IspS variant)_mMVK, pCLPtrcUpper_E.casseliflavus | CMP1133 | pDW240, pCHL277 |
| DW719 | BL21 GI1.2gltA PL.2 MKKDyI t pgl pgl-, yhfSFRTPyddVIspAyhfS thiFRTtruncIspA, pTrc(IspS variant)_mMVK, pCLPtrcUpper_E.gallinarum | CMP1133 | pDW240, pMCM1225 |
| MCM2158 | pgl- FRT-PL.2-2cis-RBS10000-MVK(burtonii) + pTrcAlba-MVKdel2 + pCL-Ptrc-Upper_Egallinarum | CMP1133 | pDW240 |

Medium Recipe (Per Liter Fermentation Medium):

K2HPO4 7.5 g, MgSO4*7H2O 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di H2O. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids*H2O 40 g, MnSO4*H2O 30 g, NaCl 10 g, FeSO4*7H2O 1 g, CoCl2*6H2O 1 g, ZnSO*7H2O 1 g, CuSO4*5H2O 100 mg, H3BO3 100 mg, NaMoO4*2H2O 100 mg. Each component was dissolved one at a time in Di H2O, pH was adjusted to 3.0 with HCl/NaOH, and then the solution was q.s. to volume and filter sterilized with a 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Feed Solution (Per Kilogram):

Glucose 0.590 kg, Di H2O 0.393 kg, K2HPO4 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

This experiment was carried out to monitor isoprene formation from glucose at the desired fermentation pH (7.0) and temperature (34° C.). A frozen vial of the E. coli strain was thawed and inoculated into a flask with tryptone-yeast extract medium and the appropriate antibiotics. After the inoculum grew to optical density 1.0, measured at 550 nm ($OD_{550}$), 500 mL was used to inoculate a 15-L bioreactor and bring the initial tank volume to 5 L. The isoprene producing strains were run in a fed-batch fermentation process.

The batched media had glucose batched in at 9.7 g/L. Induction was achieved by adding isopropyl-beta-D-1-thiogalactopyranoside (IPTG). A shot of IPTG was added to the tank to bring the concentration to 200 uM when the cells were at an OD550 of 6. Once the glucose was consumed by the culture, as signaled by a rise in pH, the glucose feed solution was fed to meet metabolic demands at rates less than or equal to 10 g/min. The fermentation was run long enough to determine the maximum isoprene mass yield on glucose, a total of 64 to 68 hrs elapsed fermentation time.

Analysis:

Isoprene is volatile and can be efficiently swept from the tank by the inlet gas. The isoprene level in the bioreactor off-gas was determined using two mass spectrometers, an iSCAN (Hamilton Sundstrand), and a Hiden HPR20 (Hiden Analytical) mass spectrometer. Oxygen, Nitrogen, and CO2 levels in the offgas were determined by the same mass spec units. Dissolved Oxygen in the fermentation broth is measured by sanitary, sterilizable probe with an optical sensor provided Hamilton Company.

The citrate, glucose, acetate, and mevalonate concentrations in the fermentor broth was determined in broth samples taken at 4 hour intervals by an HPLC analysis. Concentration in broth samples were determined by comparison of the refractive index response versus a previously generated calibration curve using standard of a known concentration.

(ii) Results

TABLE 16

Isoprene productivity metrics

| Strain description/Run Number | Overall Isoprene Volumetric Productivity (g/L/hr) (at peak yield) | Peak Overall % Yield of Isoprene on glucose (g/g) | Peak Specific Productivity (mg isoprene/L/hr/OD) |
|---|---|---|---|
| DW709/ 20120108 | 1.89 | 16.35 | 26.0 |
| DW717/ 20120131 | 1.97 | 16.46 | 27.7 |
| DW718/ 20120132 | 2.44 | 17.54 | 37.6 |
| DW719/ 20120133 | 2.38 | 18.16 | 34.3 |
| MCM2158/ 20120409 | 2.11 | 17.35 | 38.6 |

Figure 4:
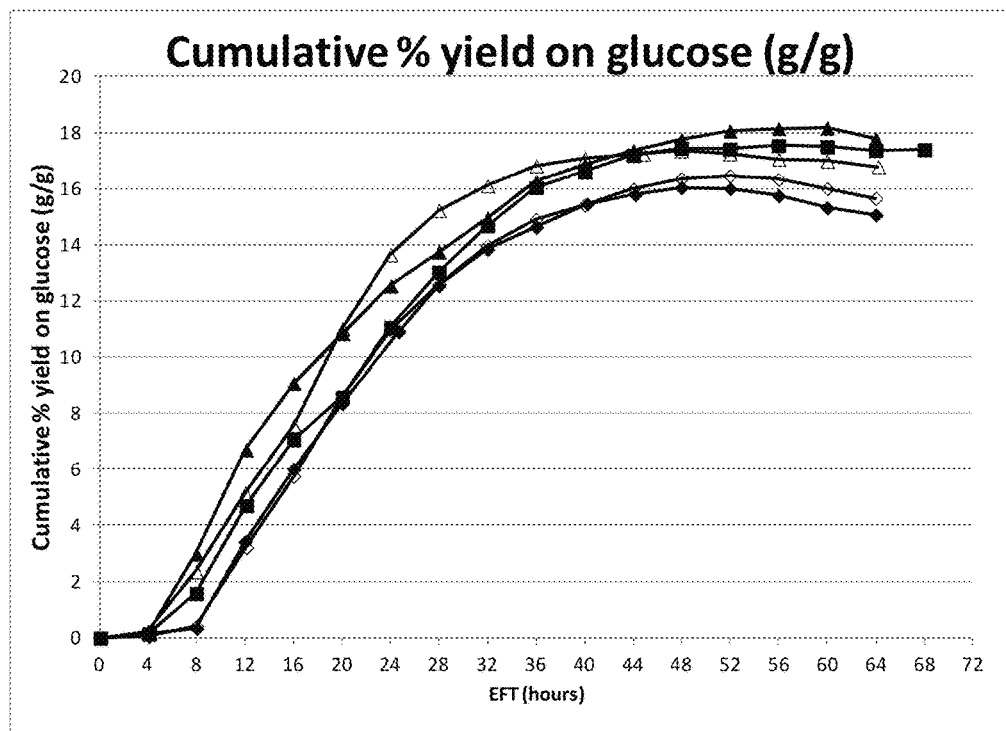
FIG. 4 depicts yield of isoprene on glucose achieved in each 15-L fermentation over time. All runs using the E. gallinarum or E. casseliflavus (triangles and squares, respectively) achieved a higher % yield of isoprene on glucose than the two runs using E. faecalis upper pathway enzymes (open and closed diamonds). % wt Yield on glucose calculated as isoprene total (t)/[(Feed Wt(0)−Feed Wt(t)+83.5)*0.59)], where 0.59 is the wt % of glucose in the glucose feed solution and 83.5 is the grams of this feed batched into the fermentor at t=0. Each feed had its weight % measured independently.
Figure 6:
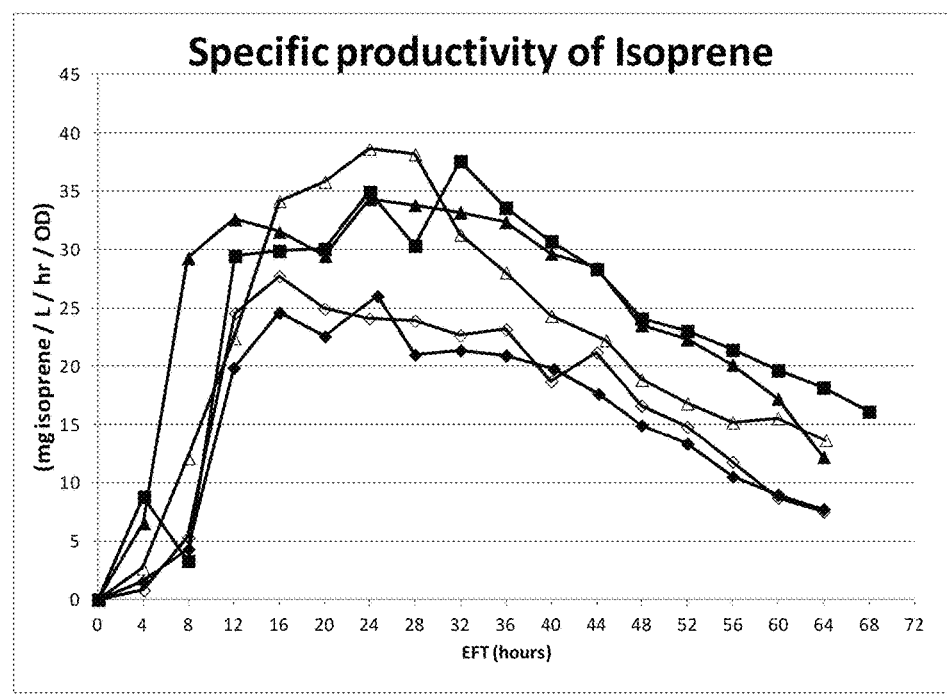
FIG. 6 depicts specific productivity achieved in each 15-L fermentation over time. All runs using the E. gallinarum or E. casseliflavus (triangles and squares, respectively) achieved a higher peak specific productivity than the two runs using E. faecalis upper pathway enzymes (open and closed diamonds). Specific Productivity was calculated using the following formula: Specific productivity (mg/L/hr/OD)=HgER*68.117 g/mol/OD. HgER is the Isoprene Evolution Rate in (mmol/L/hr). OD=optical density=Absorbance at 550 nm*dilution factor in water.

As summarized in Table 16, compared to fermentations using the upper MVA pathway of E. faecalis, fermentations using either E. gallinarum or E. casseliflavus upper MVA pathway enzymes exhibited overall higher mass yield (FIG. 4), higher peak volumetric productivity (FIG. 5), higher peak specific productivity (FIG. 6). Additionally, acetyl Co-A levels in the cells were lower when the strain harbored an E. casseliflavus or an E. gallinarum pathway (Table 17). This reduction is acetyl-CoA levels is indicative of increased carbon flux into the MVA pathway in cells.

TABLE 17

Acetyl-CoA levels (mM) at around 24 h of Elapsed Fermentation Time (EFT) in strains of identical background but with different Upper mevalonate pathway having upper MVA pathways from E. gallinarum or E. casseliflavus.

| Upper | E. faecalis (DW717) - 20 h | E. casseliflavus (DW718) - 24 h | E. gallinarum (DW719) - 24 h |
|---|---|---|---|
| Acetyl-CoA (mM) | 6.34 | 3.57 | 3.56 |

Example 12: Growth and Isoprene Productivity of E. coli Strains Expressing M. burtonii or M. mazei Mevalonate Kinase on the E. coli Chromosome This example details an examination of the growth and isoprene productivity in engineered E. coli strains expressing M. burtonii mevalonate kinase or M. mazei mevalonate kinase on the E. coli chromosome at small scale.

Materials and Methods

Growth Assays:

Overnight cultures were inoculated in shake tubes containing 2 mL of LB broth supplemented with 50 µg/mL carbenicillin (Novagen) and 50 µg/mL spectinomycin (Novagen) from frozen stocks. Cultures were then incubated for 14 h at 34° C. at 240 rpm. Next, the cultures were diluted into a 5 mL 48-well plate (Axygen Scientific) containing 2 mL TM3 media supplemented with 1% glucose, 0.02% yeast extract, 50 µg/mL carbenicillin and 50 µg/mL spectinomycin to a final OD of 0.2. The plate was sealed with Breath Easier membrane (Diversified Biotech) and incubated at 34° C. in a Shel Lab shaker/incubator at 600 rpm. The cultures were induced with 200 µM IPTG at OD of 0.4. One hour after induction mevalonate was added to the cultures to a final concentration of 0, 2, 4, 8, 16, 32 mM. OD measurements were taken at 0, 1, 2, 3, 4, and 5 hrs after induction with IPTG.

TABLE 18

List of the engineered *E. coli* strains examined at small scale

| Strain Name | Abbreviated Genotype |
|---|---|
| CMP1136 | pgl– + pTrcAlba-mMVK + pCL-Ptrc-Upper_Ef |
| DW708 | pgl– + pTrcAlba-mMVK + pCL-Ptrc-Upper_gallinarum |
| MCM2131 | pgl– FRT-PL.2-2cis-RBS10000-MVK(burtonii) + pTrcAlba-bMVK + pCL-Ptrc-Upper_gallinarum |
| MCM2125 | pgl– FRT-PL.2-2cis-RBS10000-MVK(burtonii) + pTrcAlba-mMVK(del) + pCL-Ptrc-Upper_gallinarum |
| MCM2126 | pgl– FRT-PL.2-2cis-RBS1000-mMVK + pTrcAlba-mMVK(del) + pCL-Ptrc-Upper_gallinarum |
| MCM2127 | pgl– FRT-PL.2-2cis-RBS100000-mMVK + pTrcAlba-mMVK(del) + pCL-Ptrc-Upper_gallinarum |
| MCM2129 | pgl– FRT-PL.2-2cis-RBS1000000-mMVK + pTrcAlba-mMVK(del) + pCL-Ptrc-Upper_gallinarum |
| MCM2130 | pgl– FRT-PL.2-2cis-RBS10000-mMVK + pTrcAlba-mMVK(del) + pCL-Ptrc-Upper_gallinarum |

Isoprene Productivity:

Samples for analysis of isoprene productivity by GC/MS from the engineered *E. coli* strains were taken at 1, 2, 3, 4, and 5 hrs after induction. 100 µL of culture broth was pippeted into deep-98-well glass block and sealed with aluminum sealer (Beckman Coulter). The glass block was incubated for 30 min at 34° C. water bath, after which it was transferred to 80° C. water bath for a 2 min heat-kill incubation. The glass block was cooled and transferred to the GC/MS for isoprene measurements.

Isoprene Detection by GC/MS:

GC/MS was performed using an Agilent 6890 GC/MS system interfaced with a CTC Analytics (Switzerland) CombiPAL autosampler operating in headspace mode. An Agilent HP-5MS GC/MS column (30 m×0.25 mm; 0.25 µm film thickness) was used for separation of analytes. The GC/MS method utilized helium as the carrier gas at a flow of 1 ml/min. The injection port was held at 250° C. with a split ratio of 50:1. The oven temperature was held at 37° C. for the 2 minute duration of the analysis. The Agilent 5793N mass selective detector was run in single ion monitoring (SIM) mode on m/z 67. The detector was switched off from 1.4 to 1.7 minutes to allow the elution of permanent gases. Under these conditions isoprene (2-methyl-1,3-butadiene) was observed to elute at 1.78 minutes. A calibration table was used to quantify the absolute amount of isoprene and was found to be linear from 1 µg/L to 2000 µg/L. The limit of detection was estimated to be 50 to 100 ng/L using this method.

(ii) Results

Growth of MCM2131 is not inhibited by mevalonate concentrations ranging between 0 and 16 mM. MCM2131 has the highest specific productivity ranging between 30-42 mg/L/h/OD with 32 mM mevalonate added, therefore it is able to support high carbon flux from the upper pathways.

Figure 7:
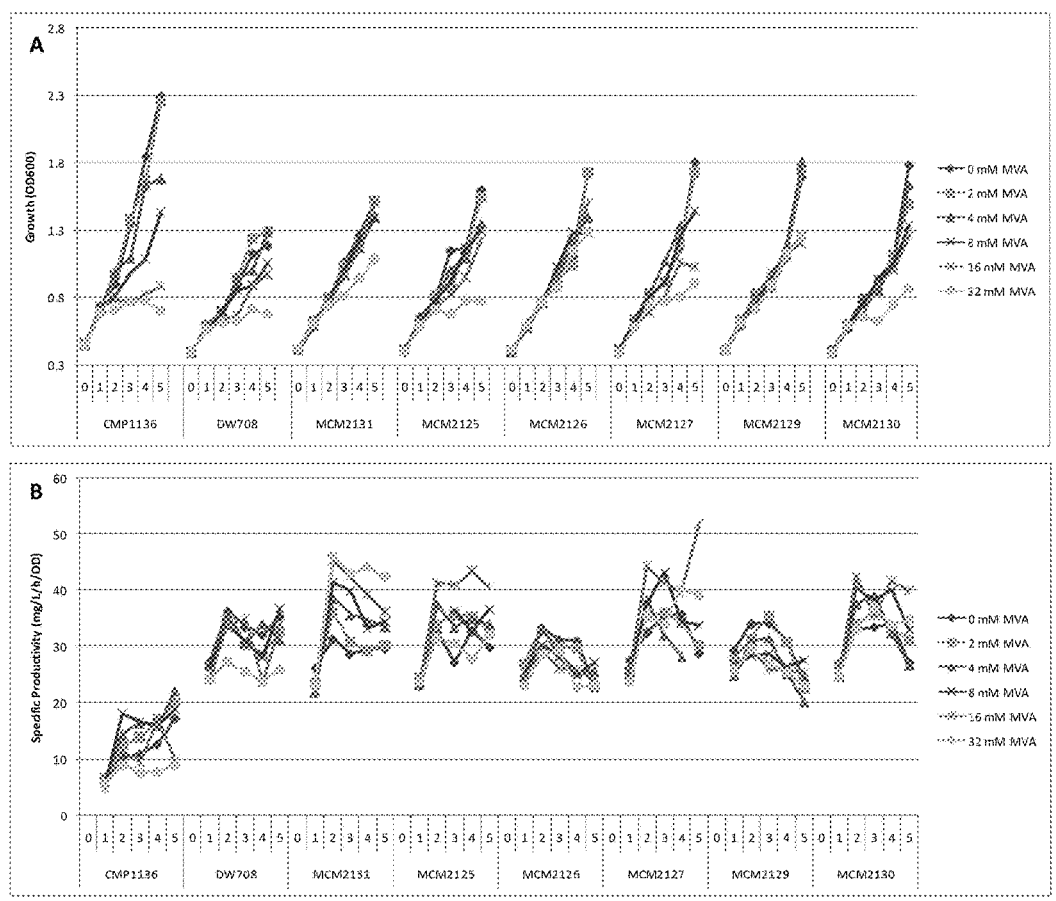
FIG. 7 depicts growth and isoprene productivity in engineered E. coli strains expressing M. burtonii mevalonate kinase or M. mazei mevalonate kinase on the E. coli chromosome at small scale.

Engineered strains MCM2125, MCM2127 and MCM2130 with one copy of chromosomal mevalonate kinase are able to achieve specific productivities of 40 mg/L/h/OD with 16 mM mevalonate feed. Their growth is also not inhibited by mevalonate concentrations between 0-16 mM (FIG. 7).

Example 13: Plasmid and Chormosomal Expression of *M. mazei* and *M. burtonii* Mevalonate Kinases in *E. coli*

Strains MCM2126 and MCM2127 were run to determine the effect of expressing the *Mazei* MVK off of the chromosome only.

Materials and Methods (i) Solutions

Medium Recipe (Per Liter Fermentation Medium):

$K_2HPO_4$ 7.5 g, $MgSO_4 \cdot 7H_2O$ 2 g, citric acid monohydrate 2 g, ferric ammonium citrate 0.3 g, yeast extract 0.5 g, 50% sulphuric acid 1.6 mL, 1000× Modified Trace Metal Solution 1 ml. All of the components were added together and dissolved in Di $H_2O$. This solution was heat sterilized (123° C. for 20 minutes). The pH was adjusted to 7.0 with ammonium hydroxide (28%) and q.s. to volume. Glucose 10 g, Vitamin Solution 8 mL, and antibiotics were added after sterilization and pH adjustment.

1000× Modified Trace Metal Solution (Per Liter):

Citric Acids·$H_2O$ 40 g, $MnSO_4 \cdot H_2O$ 30 g, NaCl 10 g, $FeSO_4 \cdot 7H_2O$ 1 g, $CoCl_2 \cdot 6H_2O$ 1 g, $ZnSO \cdot 7H_2O$ 1 g, $CuSO_4 \cdot 5H_2O$ 100 mg, $H_3BO_3$ 100 mg, $NaMoO^4 \cdot 2H_2O$ 100 mg. Each component was dissolved one at a time in Di H2O, pH was adjusted to 3.0 with HCl/NaOH, and then the solution was q.s. to volume and filter sterilized with a 0.22 micron filter.

Macro Salt Solution (Per Liter):

MgSO4*7H2O 296 g, citric acid monohydrate 296 g, ferric ammonium citrate 49.6 g. All components were dissolved in water, q.s. to volume and filter sterilized with 0.22 micron filter.

Vitamin Solution (Per Liter):

Thiamine hydrochloride 1.0 g, D-(+)-biotin 1.0 g, nicotinic acid 1.0 g, pyridoxine hydrochloride 4.0 g. Each component was dissolved one at a time in Di $H_2O$, pH was adjusted to 3.0 with HCl/NaOH, and then the solution was q.s. to volume and filter sterilized with 0.22 micron filter.

Feed Solution #1 (Per Kilogram):

Glucose 0.590 kg, Di $H_2O$ 0.393 kg, $K_2HPO_4$ 7.4 g, and 100% Foamblast882 8.9 g. All components were mixed together and autoclaved. After autoclaving the feed solution, nutrient supplements are added to the feed bottle in a sterile hood. Post sterilization additions to the feed are (per kilogram of feed solution), Macro Salt Solution 5.54 ml, Vitamin Solution 6.55 ml, 1000× Modified Trace Metal Solution 0.82 ml.

(ii) Methods

Samples were thawed and normalized to OD=20 in 100 mM Tris, 100 mM NaCl, pH 7.6, 0.1 mg/ml DNaseI, 1 mg/ml lysozyme, and 0.5 mM AEBSF (4-(2-Aminoethyl) benzenesulfonyl fluoride hydrochloride). OD normalized cell suspensions were lysed by repeated pass through the French pressure cell at 700 psi. Lysates were clarified by centrifugation at 14,000 rpm for 10 minutes. Clarified lysates were evaluated for total protein content using Bradford assay (BioRad, 500-0006). Samples were then protein normalized and ran on 4-12% SDS-PAGE gels (Life Technologies). Proteins were transferred onto Nitrocellulose membrane using iBlot transfer apparatus (Life Technologies). Nitrocellulose was developed using BenchPro™ 4100 Western Card Processing Station (Life Technologies), probing for either *M. mazei* and *M. burtonii* MVKs with primary polyclonal antibodies produced in rabbits by ProSci incorporated against purified enzymes and a secondary fluorescent antibody Alexa Fluor 488 goat anti-rabbit IgG (Life Technologies, A-11008). Specific protein quantitation was achieved using Storm imager and ImageQuant TL software from GE Healthcare.

(iii) Results

Figure 8:
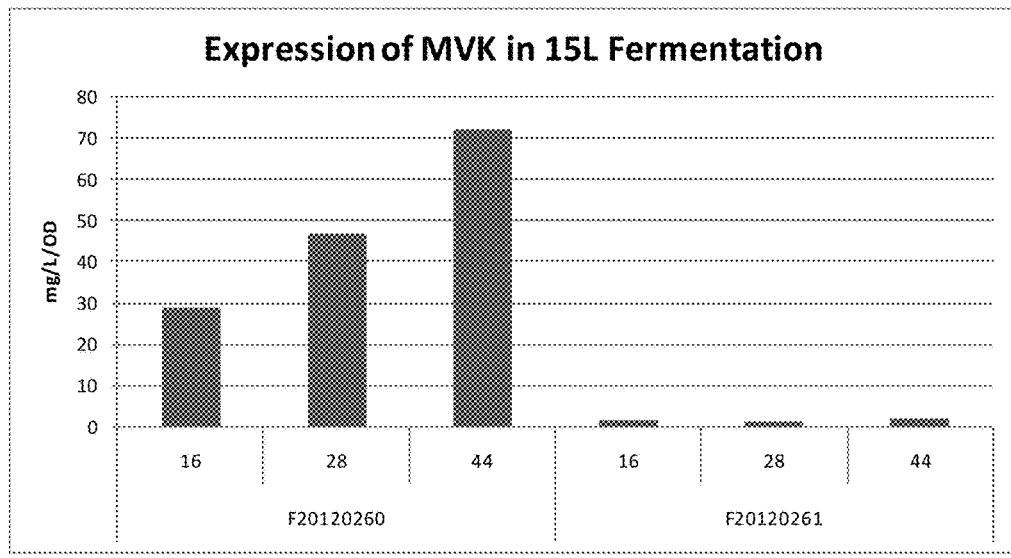
FIG. 8 depicts expression of M. mazei and M. burtonii mevalonate kinases in E. coli 15-L fermentations.

Expression of *M. burtonii* mevalonate kinase in MCM2125 is at least 15 fold lower than expression of *M. mazei* mevalonate kinase in DW708 strain, based on protein quantitation by western blot analysis (FIG. 8).

Example 14: Expression Constructs and *Lactobacillus* Strains Producing Mevalonate I. Construction of Plasmids Encoding the Upper MVA Pathway The vector pDM20 is an *E. coli-Lactobacillus* shuttle vector (U.S. Patent Appl. Publication No. 2010/0081182) which is herein incorporated by reference. The vector contains a minimal pLF1 replicon (~0.7 Kbp) and pemK-pemI toxin-antitoxin(TA) from *Lactobacillus plantarum* ATCC14917 plasmid pLF1, a P15A replicon from pACYC184, a chloramphenicol resistance marker for selection in both *E. coli* and *L. plantarum*, and a P30 synthetic promoter (Rud et al., *Microbiology* (2006) 152:1011-1019).

The pDM20 plasmid is modified by adding the rrnBT1T2 terminator from pTrc99a into the multiple cloning site downstream of the P30 promoter. The terminator region is amplified from pTrc99a with Phusion High Fidelity DNA Polymerase (New England Biolabs, Beverly, Mass.) using primers T1T2_F_Hind3_Sal (SEQ) and T1T2 R_Pst (SEQ)

Amplification is according to the manufacturer's protocol with HF Buffer in a 50 µl reaction. The cycle parameters are 98° C. for 30 seconds, then 30 cycles of 98° C. for 10 seconds, 55° C. for 30 seconds, 72° C. for 10 seconds, and a final extension at 72° C. for 10 minutes. The PCR product of the terminator is purified with DNA Clean and Concentrator-5 Kit (Zymo Research Corp., Irvine, Calif.) following the manufacturer's protocol.

The PCR product and pDM20 are each sequentially digested with HindIII and then PstI (NEB). The digested insert and vector are purified with a DNA Clean and Concentrator-5 Kit (Zymo Research Corp)

The insert and vector are ligated in a 20 µl volume using a Quick Ligation kit (NEB) according to manufacturer's instructions. The ligation is transformed into TOP10 chemically competent cells (Invitrogen Corp, Carlsbad, Calif.) according to manufacturer's protocols. The cells and ligation are mixed and incubated on ice for 30 minutes, then the cells are heat-shocked 42° C. for 45 seconds, followed by a 2 minute incubation on ice. SOC medium is added to the cells and the cells are then placed at 37° C. with shaking (220 rpm) for 1 hour. Cells are plated onto LB plates containing 25 µg/mL chloramphenicol (Sigma-Aldrich, St. Louis, Mo.). Transformant colonies are sequenced. After confirmation of the sequence, the plasmid pDM20_T is prepared using a Qiaprep Mini Kit (Qiagen Inc, Valencia, Calif.).

The upper mevalonate pathway comprising two genes, mvaE and mvaS from *Enterococcus faecalis* is PCR amplified using primers UP_EF_BamHI (SEQ) and UP_EF R Xho (SEQ) from template pCL-PtrcUpper (pCHL276). The resulting PCR product is digested with BamHI and XhoI and gel purified using the Zymoclean Gel DNA Recovery Kit (Zymo Research Corp).

The genes encoding mvaE and mvaS from *Enterococcus gallinarum* from template pCL-Ptrc-upper Gc-MM163 are PCR amplified using primers UP_EF_BamHI (SEQ) and UP_EG R Xho (SEQ). The resulting PCR product is digested with BamHI and XhoI and gel purified using the Zymoclean Gel DNA Recovery Kit (Zymo Research Corp).

Vector pDM20_T is double-digested with BamHI and SalI and purified with DNA Clean and Concentrator-5 Kit (Zymo Research Corp).

The digested vector pDM20_T and the UP_EF fragment are ligated using the Quick Ligation Kit (NEB) according to kit instructions. The ligation is transformed into TOP10 chemically competent cells (Invitrogen) and plated onto LB plates containing 25 µg/mL chloramphenicol. Transformants are sequenced. The resulting plasmid is designated pDM20_T_EF The digested vector pDM20_T and the UP_EG fragment are ligated using the Quick Ligation Kit (NEB) according to kit instructions. The ligation is transformed into TOP10 chemically competent cells (Invitrogen) and plated onto LB plates containing 25 µg/mL chloramphenicol. Transformants are sequenced. The resulting plasmid is designated pDM20_T_EG.

II. Creation of *Lactobacillus* Strains Expressing the Upper Mevalonate Pathway

Plasmids pDM20_T, pDM20_T_UP_EF and pDM20_T_UP_EG are transformed into *Lactobacillus plantarum* PN0512 (ATCC strain # PTA-7727; (U.S. Patent Application Publication No.: 2008/0124774 A1) by the following procedure as described in U.S. Patent Application Publication No.: 2011/0244536 A1. 5 ml of Lactobacilli MRS medium (Becton Dickenson, Sparks, Md.) containing 1% glycine (Sigma-Aldrich, St. Louis, Mo.) is inoculated with PN0512 cells and grown overnight at 30° C. 100 ml MRS medium with 1% glycine is inoculated with overnight culture to an OD600 of 0.1 and grown to an OD600 of 0.7 at 30° C. Cells are harvested at 3700×g for 8 min at 4° C., washed with 100 ml cold 1 mM $MgCl_2$ (Sigma-Aldrich, St. Louis, Mo.), centrifuged at 3700×g for 8 min at 4° C., washed with 100 ml cold 30% PEG-1000 (Sigma-Aldrich, St. Louis, Mo.), then centrifuged at 3700×g for 20 min at 4° C., then resuspended in 1 ml cold 30% PEG-1000. 60 µl cells are mixed with ~100 ng plasmid DNA in a cold 1 mm gap electroporation cuvette and electroporated in a BioRad Gene Pulser (Hercules, Calif.) at 1.7 kV, 25 µF, and 400Ω. Cells are resuspended in 1 ml MRS medium containing 500 mM sucrose (Sigma-Aldrich, St. Louis, Mo.) and 100 mM $MgCl_2$, incubated at 30° C. for 2 hrs, plated on MRS medium plates containing 10 µg/ml of chloramphenicol (Sigma-Aldrich, St. Louis, Mo.), then incubated at 30° C.

III. Testing for Mevalonate

The purpose of this example is to demonstrate the increased production of mevalonate in *Lactobacillus* strains with the *E. gallinarum* upper mevalonate pathway compared to strains carrying the upper mevalonate pathway from *Enterococcus faecalis*.

(i) Materials and Methods

Cell culture: *L. plantarum* PN0512 carrying, pDM20_T_UP_EF and pDM20_T_UP_EG as well as an empty control plasmid, pDM20_T are grown overnight in 20 mls of Lactobacilli MRS medium supplemented with 10 µg/ml chloramphenicol. Cultures are incubated for 14 hours overnight at 30° C. The overnight cultures are diluted into a 5 mL 48-well plate (Axygen Scientific) containing 2 mL MRS supplemented with 10 µg/ml chloramphenico to final OD of 0.2. The plate is sealed with a Breath Easier membrane (Diversified Biotech) and incubated at 30° C. in a Shel Lab shaker/incubator at 600 rpm for 24 hours. One mL of each culture is centrifuged at 3,000×g for 5 min. 250 µl of supernatant is added to 19 µL of 20% sulfuric acid and incubates on ice for 5 min. The mixture is then centrifuged for 5 min at 3000×g and the supernatant collected for HPLC analysis. 200 µl of supernatant is transferred to a HPLC compatible 96-well conical bottom polypropylene plate (Nunc). The concentration of mevalonate in samples is determined by comparison to a standard curve of mevalonate (Sigma). The glucose concentration is measured by performing a glucose oxidase assay according to the manufacturer's specifications (Pointe Scientific, Inc.).

HPLC Detection of Mevalonate:

HPLC analysis is performed on a Waters 2695 Alliance HPLC system containing a Knauer K2301 refractive index detector using a 300 mm×7.8 mm BioRad—Aminex HPX-87H ion exclusion column (catalog #125-0140) incubated at 50° C. and equipped with a BioRad—Microguard Cation H refill 30 mm×4.6 mm (Catalog #125-0129). Samples are run at a flow rate of 0.6 ml/min in 0.01N sulfuric acid running buffer. Broth levels of mevalonate are quantified by comparing the refractive index response of each sample versus a calibration curve generated by running various mevalonate containing solutions of known concentration.

(ii) Results

The specific productivity of mevalonate from *Lactobacillus* strains expressing the upper mevalonic pathway encoded by genes from *E. gallinarum* is compared to a strain that expresses the upper mevalonate pathway encoded by genes from *Enterococcus faecalis*. The bacteria were grown under identical conditions. HPLC analysis will show that the strain with the *E. gallinarum* upper pathway has higher specific productivity of isoprene compared to the strain with the upper pathway from *Enterococcus faecalis*. Both strains expressing the upper pathway from *E gallinarum* or *Enterococcus faecalis* will produce more mevalonate than the strain with an empty control plasmid.

Example 15: Construction of Strains for Producing Isoprene in *Lactobacillus*

Production of isoprene in *Lactobacillus* requires integrating the lower mevalonate pathway consisting of MVK, yPMK, MVD genes into the chromosome of *Lactobacillus*. The genes encoding isoprene synthase and IDI are cloned as an operon under the control of the PldhL promoter onto a plasmid. The Upper pathway genes (mvaE and mvaS) are cloned as an operon onto the same plasmid under the control of the P30 promoter. The plasmid carrying the IspS-IDI operon and Upper pathway operon is transformed into *Lactobacillus* with an integrated lower mevalonate pathway.

I. Cloning IspS IDI Operon into *E. coli-Lactobacillus* Shuttle Vector

The PldhL promoter is amplified from template pDM5-PldhL1-ilvC (United States Patent Application Publication No.: 2011/0136192) with primers PldhL F (SEQ) and PldhL R (SEQ) using Phusion High Fidelity DNA Polymerase in a 50 µl reaction with HF buffer according to kit instructions. The annealing temperature is 55° C. and extension at 72° C. is for 10 seconds. The PCR reaction is cleaned with the DNA Clean and Concentrator-5 Kit (Zymo Research Corp) following kit protocol. The purified PCR product and the vector pDM20_T1 are digested with PstI at 37° C. for 2 hours. The vector and insert are incubated at 80° C. for 20 minutes to inactivate PstI. The PstI digested vector is treated with Shrimp Alkaline Phosphatase (Affymetrix Inc, Santa Clara, Calif.) at 37° C. for 30 minutes. The phosphatase reaction is stopped by heating at 65° C. for 15 minutes. Both the treated vector and digested PCR product are cleaned with DNA Clean and Concentrator-5 Kit (Zymo Research Corp) following kit protocol.

The digested PCR product and vector are ligated using the Quick Ligation kit (NEB). The ligation mixture is transformed into chemically competent *E. coli* Top10 cells (Invitrogen Corp, Carlsbad, Calif.). Transformants are selected on LB plates containing 25 µg/mL chloramphenicol at 37° C. Transformants are screened by DNA sequencing. The resulting plasmid is called pDM20_T_PldhL.

The *Populus alba* ispS gene and yIDI gene are synthesized codon optimized for *Lactobacillus* by Gene Oracle Inc. (Mountain View, Calif.). The genes are synthesized as an operon with *Lactobacillus* ribosome binding sites preceding each of the ATG starts of the genes. The IspS-yIDI operon is cloned into pCR Blunt II TOPO (Invitrogen) creating pCR Blunt II TOPO-II.

The ispS-yIDI operon is amplified from pCR Blunt II TOPO-II with primers II F Avr2 (SEQ) and II R Nde (SEQ) with Phusion High Fidelity DNA Polymerase using an annealing of 55 C and an extension of 1 minute.

Vector pDM20_T_PldhL and ispS-yIDI PCR product are digested with AvrII and NdeI. The vector and insert is ligated and transformed into TOP10 cells. Transformants are selected on LB plates containing 25 µg/mL chloramphenicol at 37° C. Transformants are verified by DNA sequencing. The resulting plasmid is called pDM20_T_Pldh-II.

II. Addition of Upper Pathway to Plasmid with IspS-yIDI

Vector pDM20_T_Pldh-II is digested with BamHI and SalI. The digested vector is ligated with the BamHI and XhoI digested EF_UP PCR product (see Example 14). The digested vector is also ligated with the BamHI and XhoI digested EG_UP PCR product (see Example 14). The ligations are transformed into Top10 cells and plated on LB plates containing 25 µg/mL chloramphenicol for selection at 37° C. The resulting plasmids are named pDM20T-EF-Pldh-II and pDM20T-EG-Pldh-II.

III. Construction of the Lower Pathway Integration Vector and PN0512ΔldhL1:: MVK-yPMK-MVD Integration Strain This describes integration of the lower MVA pathway genes into the chromosome of *L. plantarum* strain PN0512 for expression of MVK, yPMK, MVD. Genes may be integrated into different locations in the chromosome, including neutral locations that have no effect on cellular metabolism or integrations may be designed to change the physiology of the cell.

Two DNA segments (homologous arms) are designed to provide regions of homology for the two genetic cross-overs such that integration would place the MVK, yPMK, MVD, coding region downstream of the ldhL1 promoter in strain PN0512. The left and right homologous arms cloned into the plasmid are each approximately 1200 base pairs. The left and right homologous arms are amplified from *L. plantarum* PN0512 genomic DNA. The construction of integration vector pFP996-ldhL1-arms is described in U.S. Patent Application Publication No.: 2011/0244536 A1, which is herein incorporated by reference.

The lower pathway genes are PCR amplified using genomic DNA from *E. coli* MVKCMP451, (which contains the coding sequence for MVK, yPMK, MVD, and yIDI) as template to amplify MPM operon. The genomic DNA is purified from a 1 ml cell pellet of culture grown in LB to stationary phase at 37° C. using Gentra Pure Gene Kit (Qiagen Inc., Valencia, Ca). The MPM operon is created by primers MPMI Xho Spe For (Table 23) containing a Xho I site, a Spe I site, and ribosome binding sequence and MPM Pme Xho Revl (Table 23) containing a Pme I and Xho I site, using Phusion High Fidelity PCR Kit (New England Biolabs). A typical PCR reaction (50 µl) contains 1×HF Buffer, 1 µl 10 mM dNTPs, 2.5 µl 10 µM each primer, 0.5 µl Phusion polymerase, and 250 ng genomic DNA. The cycling conditions are: 98° C. for 30 seconds for one cycle, followed by 30 cycles of 98° C. for 10 seconds, 56° C. for 30 seconds, 72° C. for 2 minutes 20 seconds. Following cycling, the reaction mixtures are held at 72° C. for 10 minutes. Reaction is cleaned using Zymo Clean and Concentrate-5 kit (Zymo Research). The resulting PCR fragment is restriction endonuclease digested with XhoI (New England Biolabs) at 37° C. The reaction is cleaned using Zymo Clean and Concentrate-5 kit (Zymo Research).

TABLE 18

Primers

| Name | Sequence |
| --- | --- |
| T1T2_F_Hind3_Sal | CATAAGCTTGTCGACCCATGCGAGAGTAGGG AACTGCC |
| T1T2 R_Pst | CATCTGCAGTCTCATGAGCGGATACATATTT GAA |
| UP_EF_BamHI | CATGGATCCCGATTAAATAAGGAGGAATAAA CC |
| UP_EF R Xho | GTCACTCGAGGGTACCAGCTGCAGATCTCTT AG |
| UP_EG R Xho | GTCACTCGAGCATATGGTACCAGCTGCAGTC A |
| PldhL F | CATCTGCAGTAAGTCGTATTGGCACCACTAC TCAC |
| PldhL R | CATCTGCAGCATATGATCCTAGGGCTTGACA AAATAAGTCATCCTCTC |
| II F Avr2 | CATCCTAGGAGGAGGAGAAAAAAAACCATG |
| II R Nde | CATCATATGTTACAACATTCTGTGAATTTGT CG |
| MPMI Xho Spe For | CAATCTCGAGACTAGTCAAAGGAGGTAAAAA AACATGGTATC |
| MPM Pme Xho Revl | GTTACTCGAGGTTTAAACTTATTCCTTTGGT AGACCAGTCTTTG |
| MPMIseqF5 | GTGGCCTGGGAAATGGGAAAAGCTG |
| ldhseqR3 | CCCCCAATCATAAGTCCACGTTTA |
| MPMIseqF3 | CAGATATTGGAAGTGCTACTTACGGC |
| MPMIseqR4 | TGCGGTAACGGATGCTGTGTAAACGG |

TABLE 18-continued

Primers

| Name | Sequence |
| --- | --- |
| ldhL left arm check UP | CAACCGAGGTCACGACCACTGCCG |
| MPMIseqR8 | GAACACGGGTACGCAGTTCCACCG |
| MPMIseqF6 | GATGTTGCCAGAGTGATTTTAACTC |
| ldhL right arm check DN | GAAACTGGTTGGGAATAACTTGAGCC |

The pFP996-ldhL1arms vector is restriction digested with XhoI (New England Biolabs). After digest, XhoI is heat inactivated at 65° C. for 20 min. Vector ends are then dephosphorylated using Shrimp Alkaline Phosphatase (Affymetrix). The reaction is incubated at 37° C. for 45 minutes, then the phosphatase is heat inactivated at 65° C. for 15 min. Vector is purified from an agarose gel using Zymoclean Gel DNA Recovery Kit (Zymo Research Corp.)

The resulting XhoI digested, dephosphorylated vector pFP996ldhL1arms and the XhoI-digested MPM fragment are ligated using Quick Ligation Kit (NEB) at 25° C. for 5 min. Chemically competent *E. coli* Stb13 (Invitrogen) cells are transformed with ligation mix. A typical transformation includes incubation of cells and ligation mix for 30 minutes on ice, a heat shock at 42° C. for 45 seconds, 2 minute incubation on ice, and recovery in SOC media for 1 hour at 30 C. The transformation is spread onto LB agar containing ampicillin (100 µg/ml) for selection. Incubate plates overnight at 30° C.

Transformants are PCR colony screened with primers MPMIseqF5 (Table 18) and ldhseqR3 (Table 18) using JumpStart™ REDTaq® ReadyMix™ Reaction Mix (Sigma-Aldrich, Inc., St. Louis Mo.). Several positive transformants are verified by DNA sequencing. The resulting integration plasmid is designated pFP996-ldhL1arms::MPM.

Plasmid DNA is isolated from cell pellets of overnight growth in LB containing ampicillin (100 µg/ml) from the *E. coli* Stb13/pFP996-ldhL1arms::MPM strains using Qiaprep Mini Kit (Qiagen Inc, Valencia, Calif.).

The MPM operon is integrated into the chromosome of the *Lactobacillus plantarum* PN0512 strain such that it would be expressed from the ldhL1 promoter and ldhL1 would be deleted. The chromosomal integration of a single copy of MVK, yPMK, MVD, coding region expressed from the ldhL1 promoter is constructed by the same two-step homologous recombination procedure used for unmarked deletions, as described (Ferain et al., 1994, *J. Bact.* 176: 596), except that the second crossover event yields either the wild type sequence or the intended integration rather than a deletion.

Integration of the MVK, yPMK, MVD coding region is obtained by transforming *L. plantarum* PN0512 with pFP996-ldhL1arms:: MPM. A culture with 5 ml of Lactobacilli MRS medium containing 0.5% glycine is inoculated with PN0512 and grown overnight at 30° C. 100 ml MRS medium with 0.5% glycine is inoculated with overnight culture to an $OD_{600}$ of 0.1 and grown to an OD600 of 0.7 at 30° C. Cells are harvested at 3700×g for 8 min at 4° C., washed with 100 ml cold 1 mM $MgCl_2$, centrifuged at 3700×g for 8 min at 4° C., washed with 100 ml cold 30% PEG-1000, recentrifuged at 3700×g for 20 min at 4° C., and then resuspended in 1 ml cold 30% PEG-1000. 60 µl of cells are mixed with ~100 ng of plasmid DNA in a cold 1 mm gap electroporation cuvette and electroporated in a BioRad Gene Pulser at 1.7 kV, 25 pF, and 400Ω. Cells are resuspended in 1 ml MRS medium containing 500 mM sucrose and 100 mM $MgCl_2$, incubated at 30° C. for 2 hrs, and then spread on MRS medium plates containing 2 µg/ml of erythromycin (Sigma-Aldrich, St. Louis, Mo.).

Transformants are screened by PCR using operon specific primers MPMIseqF3 (Table 18) and MPMIseqR4 (Table 18). Transformants are grown at 30° C. in Lactobacilli MRS medium containing erythromycin (1 µg/ml) for approximately 10 generations and then at 37° C. for approximately 40 generations by serial inoculations in Lactobacilli MRS medium. The culture is spread on Lactobacilli MRS medium with erythromycin (0.5 µg/ml). The isolates are screened by colony PCR for a single crossover with chromosomal specific primer ldhL left arm check DN (Table 18) and plasmid specific primer MPMIseqR8 (Table 18).

Single crossover integrants are then grown at 37° C. for approximately 40 generations by serial inoculations in Lactobacilli MRS medium. The cultures are spread on MRS medium. Colonies are patched to MRS plates and grown at 37° C. The isolates are then patched onto MRS medium with erythromycin (0.5 µg/ml). Erythromycin sensitive isolates are screened by colony PCR for the presence of a wild-type or integration second crossover using chromosomal specific primers and gene specific primer pairs, ldhL left arm check UP and MPMIseqR8 will yield an approximately 1400-bp product; MPMIseqF6 and ldhL right arm check DN. will yield an approximately 1600-bp product; The integration is confirmed by sequencing the PCR product and an identified integration strain is designated PN0512ΔldhL1:: MPM.

IV. Creation of LAB Strains Producing Isoprene

*Lactobacillus plantarum* PN0512ΔldhL1:: MPM is made electrocompetent as described above and transformed with either pDM20T-EF-Pldh-II and pDM20T EG-Pldh-II. Cells are plated onto MRS with 10 µg/ml chloramphenicol.

Example 16: Testing for Isoprene Production in *Lactobacillus*

The purpose of this example is to demonstrate the increased production of isoprene in *Lactobacillus* strains with the *E. gallinarum* upper mevalonate pathway compared to strains carrying the upper mevalonate pathway from *Enterococcus faecalis*.

(i) Materials and Methods

*L. plantarum* PN0512ΔldhL1:: MPM containing pDM20T-EF-Pldh-II or pDM20T EG-Pldh-II is inoculated in MRS medium supplemented with 10 µg/mL chloramphenicol and grown at 30° C. for 14 h. Isoprene production is analyzed by growing the strains in a Cellerator™ from MicroReactor Technologies, Inc. The working volume in each of the 24 wells is 4.5 ml. The overnight cultures are diluted into 4.5 ml of MRS with 10 µg/mL chloramphenicol to reach an optical density of 0.05 measured at 550 nm. The temperature is maintained at 30° C., the pH setpoint was 7.0, oxygen flow setpoint is 20 sccm and the agitation rate is 800 rpm.

Off-gas analysis of isoprene is performed using a gas chromatograph-mass spectrometer (GC-MS) (Agilent) headspace assay. Sample preparation is as follows: 100 µL of whole broth is placed in a sealed GC vial and incubated at 30° C. for a fixed time of 30 minutes. Following a heat kill step, consisting of incubation at 70° C. for 5 minutes, the sample is loaded on the GC.

Optical density (OD) at a wavelength of 550 nm is obtained using a microplate reader (Spectramax) during the course of the run. Specific productivity is obtained by dividing the isoprene concentration (m/L) by the OD reading. Samples are taken at three time points for each of the 24-wells over the course of the mini-fermentations.

(ii) Results

The specific productivity of isoprene from strains expressing the full mevalonic acid pathway with the upper pathway encoded by genes from *E. gallinarum* is compared to a strain that is expressing the full mevalonic acid pathway that carries the upper mevalonate pathway from *Enterococcus faecalis*. The bacteria were grown under identical conditions in mini-fermentations. Headspace measurements over time (see U.S. Patent Application Publication No.: 2010/0086978) show that the strain with the *E. gallinarum* upper pathway has higher specific productivity of isoprene compared to the strain with the upper pathway from *Enterococcus faecalis*.

Example 17: Construction of Amorphadiene- or Farnesene-Producing Strains

A lower mevalonate pathway is introduced by transduction into CMP676 using a lysate from MCM521 (see Table 3). The kanamycin marker is looped out according to the manufacturer (Gene Bridges, Heidelberg, Germany). The lower pathway from MCM521 can be modified by changing the promoter upstream of the operon by modifying the rbs in front of each gene via the use of alternative genes. Farnesyl diphosphate synthase (ispA) is overexpressed, either by altering the promoter and/or rbs on the chromosome, or by expressing it from a plasmid. Plasmids pMCM1223 (*L. grayi*), pMCM1224 (*E. faecium*), pMCM1225 (*E. gallinarum*), pCHL276 (*E. faecalis*) or pCHL277 (*E. casseliflavus*) are co-electroporated with a variation of plasmid pDW34 (See U.S. Patent Application Publication No: 2010/0196977; FIG. 2). The plasmids which are variants of pDW34 contain the farnesene synthase codon optimized for *E. coli* or amorphadiene synthase codon optimized for *E. coli*, instead of isoprene synthase. Colonies are selected on LB+spectinomycin 50 ug/mL+carbenicillin 50 ug/mL.

Example 18: Increased Production of Amorphadiene or Farnesene in Strains Containing the Plasmids with Alternative Upper Mevalonate Pathways Compared to a Pathway with *E. faecalis* Upper Pathway (i) Materials TM3 Media Recipe (Per Liter Fermentation Media):
$K_2HPO_4$ 13.6 g, $KH_2PO_4$ 13.6 g, $MgSO_4*7H_2O$ 2 g, citric acid monohydrate 2 g, ferric ammonium citrate 0.3 g, $(NH_4)_2SO_4$ 3.2 g, yeast extract 0.2 g, 1000× Trace Metals Solution 1 ml. All of the components are added together and dissolved in $diH_2O$. The pH is adjusted to 6.8 with ammonium hydroxide (30%) and brought to volume. Media is then filter-sterilized with a 0.22 micron filter. Glucose 10.0 g and antibiotics are added after sterilization and pH adjustment.

1000× Trace Metal Solution (Per Liter Fermentation Media):

Citric Acid*$H_2O$ 40 g, $MnSO_4*H_2O$ 30 g, NaCl 10 g, $FeSO_4*7H_2O$ 1 g, $CoCl_2*6H_2O$ 1 g, $ZnSO_4*7H_2O$ 1 g, $CuSO_4*5H_2O$ 100 mg, $H_3BO_3$ 100 mg, $NaMoO_4*2H_2O$ 100 mg. Each component is dissolved one at a time in diH₂O. The pH is adjusted to 3.0 with HCl/NaOH, and then the solution is brought to volume and filter-sterilized with a 0.22 micron filter.

(ii) Experimental Procedure

Cells are grown overnight in Luria-Bertani broth+antibiotics. The day after, they are diluted to an OD600 of 0.05 in 20 mL TM3 medium containing 50 ug/ml of spectinomycin and 50 ug/mL carbenicillin (in a 250-mL baffled Erlenmeyer flask), and incubated at 34° C. and 200 rpm. Prior to inoculation, an overlay of 20% (v/v) dodecane (Sigma-Aldrich) is added to each culture flask to trap the volatile sesquiterpene product as described previously (Newman et. al., 2006).

After 2 h of growth, OD600 is measured and 0.05-0.40 mM isopropyl β-d-1-thiogalactopyranoside (IPTG) is added. Samples are taken regularly during the course of the fermentation. At each timepoint, OD600 is measured. Also, amorphadiene or farnesene concentration in the organic layer is assayed by diluting the dodecane overlay into ethyl acetate. Dodecane/ethyl acetate extracts are analyzed by GC-MS methods as previously described (Martin et. al., *Nat. Biotechnol.* 2003, 21:96-802) by monitoring the molecular ion (204 m/z) and the 189 m/z fragment ion for amorphadiene or the molecular ion (204 m/z) for farnesene. Amorphadiene or farnesene samples of known concentration are injected to produce standard curves for amorphadiene or farnesene, respectively. The amount of amorphadiene or farnesene in samples is calculated using the amorphadiene or farnesene standard curves, respectively.

(iii) Results

When the strains containing pMCM1223 (*L. grayi*), pMCM1224 (*E. faecium*), pMCM1225 (*E. gallinarum*), or pCHL277 (*E. casseliflavus*) are compared to the same background containing pCHL276 (*E. faecalis*), increased specific productivity, yield, CPI and/or titer of amorphadiene or farnesene are observed.

(iv) References

Newman, J. D., Marshal, J. L., Chang, M. C. Y., Nowroozi, F., Paradise, E. M., Pitera, D. J., Newman, K. L., Keasling, J. D., 2006. High-level production of *amorpha*-4, 11-diene in a two-phase partitioning bioreactor of metabolically engineered *E. coli*. *Biotechnol. Bioeng.* 95:684-691.

Martin, V. J., Pitera, D. J., Withers, S. T., Newman, J. D., Keasling, J. D., 2003. Engineering a mevalonate pathway in *E. coli* for production of terpenoids. *Nat. Biotechnol.* 21:796-802.

Example 19: Identification of MvaE Proteins that are not Degraded when Expressed in *E. coli* BL21 or *E. coli* BL21(DE3)

Figure 9:
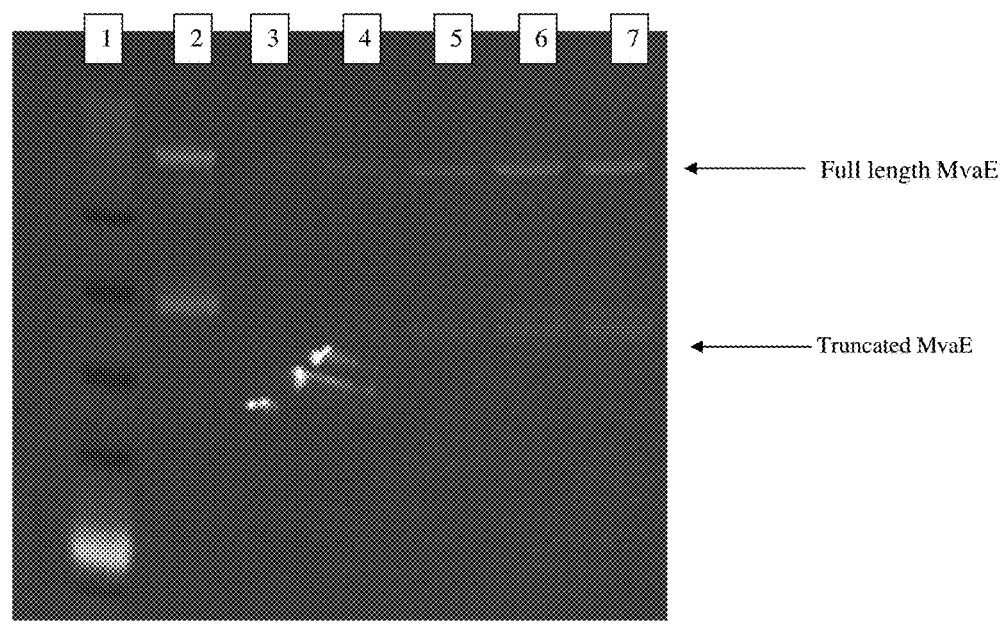
FIG. 9 depicts a Western blot where MvaE from strain DW326 is visualized. Lane 1—Benchmark marker, 2-0.4 ug of purified MvaE, 3-7, Lysate samples from strain DW326 induced with 0, 25, 50, 100, 200 µM IPTG.
Figure 10:
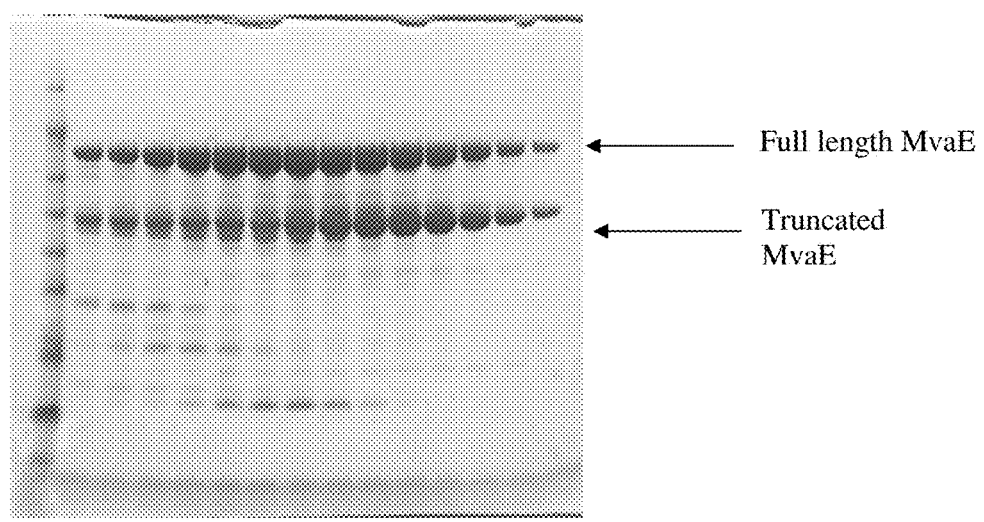
FIG. 10 depicts a SDS-PAGE gel stained with Safestain containing: Lane 1-Benchmark marker, 2-15-His-tag mediated purification of MvaE protein fractions eluted from a nickel column.

Degradation of heterologously expressed protein in a cell can result in loss of ATP due to the futile cycle of protein synthesis and protein degradation, decrease in catalytic activity of the protein being degraded, decrease in the steady state intracellular concentration of the protein of interest, induction of stress responses that can alter the physiology of the cell, and other effects that are potentially deleterious to the commercial production of biologically-derived products (S.-O. Enfors, 2004). Therefore, the expression of full length proteins that are less prone to degrade is beneficial for metabolic engineering. The mvaE gene product from *Enterococcus faecalis* is partially degraded when expressed in *E. coli* BL21 as indicated by fragments that can be identified by western blot (FIG. 9). Cleaved fragments of *E. faecalis* MvaE are also identified by Safestain staining of His-tagged purified material run on an SDS-PAGE gel (FIG. 10). Identification and use of degradation resistant mvaE gene products are beneficial for the increased production of mevalonate, isoprene and isoprenoids.

We demonstrate that the gene products of mvaEs from the organisms *E. faecium*, *E. gallinarum*, *E. casseliflavus*, and *L. grayi* are not degraded when expressed in *E. coli* BL21 (DE3) as indicated by absence of fragments that can be identified on Safestain stained SDS-PAGE gels following His-tag mediated purification or when expressed in mevalonate, isoprene or isoprenoid producing *E. coli* BL21 using the methods of detection described.

(i) Methods

Plasmids are constructed that contain DNA encoding His-tagged MvaE from *E. gallinarum*, *E. faecium*, *E. casseliflavus*, and *L. grayi*. MvaE is expressed in *E. coli* BL21 (DE3) and is purified by Ni-resin chromatography. Purified samples are analyzed by SDS-PAGE. Samples are further purified by anion exchange chromatography and in some cases gel filtration. Samples purified to >95% homogeneity are sent for production of polyclonal antibodies. Production strains are analysed by western blot and probed using the polyclonal antibodies developed against the MvaE of interest.

(ii) References

Enfors, S. O., Scheper, T. Physiological Stress Responses in Bioprocesses. Springer-Verlag Berlin Heidelberg 2004.

SEQUENCES

*L. grayi* mvaE:

SEQ ID NO: 1 atggttaaagacattgtaataattgatgccctccgtactcccatcggtaagtaccgcggtcagctctcaaagatgacggcggtggaattggg aaccgcagttacaaaggctctgttcgagaagaacgaccaggtcaaagaccatgtagaacaagtcattttttggcaacgttttacaggcaggga acggccagaatcccgcccgtcagatcgcccttaattctggcctgtccgcagagataccggcttcgactattaaccaggtgtgtggttctggc ctgaaagcaataagcatggcgcgccaacagatcctactcggagaagcggaagtaatagtagcaggaggtatcgaatccatgacgaatgcgcc gagtattacatattataataaagaagaagacaccctctcaaagcctgttcctacgatgaccttcgatggtctgaccgacgcgtttagcggaa -continued

SEQUENCES agattatgggtttaacagccgaaaatgttgccgaacagtacggcgtatcacgtgaggcccaggacgcctttgcgtatggatcgcagatgaaa
gcagcaaaggcccaagaacagggcattttcgcagctgaaatactgcctcttgaaatagggggacgaagttattactcaggacgagggggttcg
tcaagagaccaccctcgaaaaattaagtctgcttcggaccattttaaagaagatggtactgttacagcgggcaacgcctcaacgatcaatg
atggcgcctcagccgtgatcattgcatcaaaggagtttgctgagacaaaccagattccctaccttgcgatcgtacatgatattacagagata
ggcattgatccatcaataatgggcattgctcccgtgagtgcgatcaataaactgatcgatcgtaaccaaattagcatggaagaaatcgatct
ctttgaaattaatgaggcatttgcagcatcctcggtggtagttcaaaaagagttaagcattcccgatgaaaagatcaatattggcggttccg
gtattgcactaggccatcctcttggcgccacaggagcgcgcattgtaaccaccctagcgcaccagttgaaacgtacacacggacgctatggt
attgcctccctgtgcattggcggtggccttggcctagcaatattaatagaagtgcctcaggaagatcagccggttaaaaaattttatcaatt
ggcccgtgaggaccgtctggctagacttcaggagcaagccgtgatcagcccagctacaaaacatgtactggcagaaatgacacttcctgaag
atattgccgacaatctgatcgaaaatcaaatatctgaaatggaaatccctcttggtgtggctttgaatctgagggtcaatgataagagttat
accatcccactagcaactgaggaaccgagtgtaatcgctgcctgtaataatggtgcaaaaatggcaaaccacctgggcggttttcagtcaga
attaaaagatggtttcctgcgtgggcaaattgtacttatgaacgtcaaagaacccgcaactatcgagcatacgatcacggcagagaaagcgg
caatttttcgtgccgcagcgcagtcacatccatcgattgtgaaacgaggtgggggtctaaaagagatagtagtgcgtacgttcgatgatgat
ccgacgttcctgtctattgatctgatagttgatactaaagacgcaatgggcgctaacatcattaacaccattctcgagggtgtagccggctt
tctgagggaaatccttaccgaagaaattctgttctctattttatctaattacgcaaccgaatcaattgtgaccgccagctgtcgcatacctt
acgaagcactgagtaaaaaaggtgatggtaaacgaatcgctgaaaaagtggctgctgcatctaaatttgcccagttagatccttatcgagct
gcaacccacaacaaaggtattatgaatggtattgaggccgtcgttttggcctcaggaaatgacacacgggcggtcgcggcagccgcacatgc
gtatgcttcacgcgatcagcactatcggggcttaagccagtggcaggttgcagaaggcgcgttacacggggagatcagtctaccacttgcac
tcggcagcgttggcggtgcaattgaggtcttgcctaaagcgaaggcggcattcgaaatcatggggatcacagaggcgaaggagctggcagaa
gtcacagctgcggtagggctggcgcaaaacctggcggcgttaagagcgcttgttagtgaaggaatacagcaaggtcacatgtcgctccaggc
tcgctctcttgcattatcggtaggtgctacaggcaaggaagttgaaatcctggccgaaaaattacagggctctcgtatgaatcaggcgaacg
ctcagaccatactcgcagagatcagatcgcaaaaagttgaattgtga

*L. grayi* mvaS:

SEQ ID NO: 2 atgaccatgaacgttggaatcgataaaatgtcattcttttgttccaccttactttgtggacatgactgatctggcagtagcacgggatgtcga
tcccaataagtttctgattggtattggccaggaccagatggcagttaatccgaaaacgcaggatattgtgacatttgccacaaatgctgcca
aaacatactgtcagctgaggaccttgataaaattgatatggtcatagtcggcaccgagagtggaatcgatgaatccaaagcgagtgccgta
gtgcttcacaggttgctcggtatccgaagtttgctcgctcctttgaaatcaaagaagcctgttatgggggtaccgcggctttacagttcgc
tgtaaaccacattaggaatcatcctgaatcaaaggttcttgtagttgcatcagatatcgcgaaatacggcctggcttctggaggtgaaccaa
cgcaaggtgcaggcgctgtggctatgctcgtctcaactgaccctaagatcattgctttcaacgacgatagcctcgcgcttacacaagatatc
tatgacttctggcgaccagttggacatgactatcctatggtcgacgggcctcttagtacagagacctacatccagtcatttcagaccgtatg
gcaggaatacacaaaacggtcgcagcatgcactggcagactttgctgcccttagctttcatatcccgtatactaaaatgggcaaaaaggcgc
tgcttgcaatccttgaaggcgaatcagaggaggctcagaaccgtatactagcaaaatatgaaaagagtatagcctactccagaaaggcgggt
aacctgtataccggtagcctgtatctaggacttatttcacttctggaaaatgcagaagaccttaaagctggtgatttaataggcctcttttc
ttacggttccggtgctgttgcggagttttttctcaggaaggctggtgaggactatcaggaacagctacttaaaacaaaacatgccgaacagc
tggcccatagaaagcaactgacaatcgaggagtacgaaacgatgttctccgatcgcttggacgtggacaaagacgccgaatacgaagacaca
ttagcttatagcatttcgtcagtccgaaacaccgtacgtgagtacaggagttga

SEQUENCES

*E. faecium* mvaE:

SEQ ID NO: 3 atgaaagaagtggttatgattgatgcggctcgcacacccattgggaaatacagaggtagtcttagtcctttttacagcggtggagctggggac actggtcacgaaagggctgctggataaaacaaagcttaagaaagacaagatagaccaagtgatattcggcaatgtgcttcaggcaggaaacg gacaaaacgttgcaagacaaatagccctgaacagtggcttaccagttgacgtgccggcgatgactattaacgaagtttgcgggtccggaatg aaagcggtgattttagcccgccagttaatacagttagggggaggcagagttggtcattgcaggggtacggagtcaatgtcacaagcacccat gctgaaaccttaccagtcagagaccaacgaatacggagagccgatatcatcaatggttaatgacgggctgacggatgcgttttccaatgctc acatgggtcttactgccgaaaaggtggcgacccagttttcagtgtcgcgcgaggaacaagaccggtacgcattgtccagccaattgaaagca gcgcacgcggttgaagccggggtgttctcagaagagattattccggttaagattagcgacgaggatgtcttgagtgaagacgaggcagtaag aggcaacagcactttggaaaaactgggcaccttgcggacggtgttttctgaagagggcacggttaccgctggcaatgcttcaccgctgaatg acggcgctagtgtcgtgattcttgcatcaaaagaatacgcggaaaacaataatctgccttacctggcgacgataaaggaggttgcggaagtt ggtatcgatccttctatcatgggtattgccccaataaaggccattcaaaagttaacagatcggtcggcatgaacctgtccacgattgatct gttcgaaattaatgaagcattcgcggcatctagcattgttgtttctcaagagctgcaattggacgaagaaaaagtgaatatctatggcgggg cgatagctttaggccatccaatcggcgcaagcggagcccggatactgacaaccttagcatacggcctcctgcgtgagcaaaagcgttatggt attgcgtcattatgtatcggcggtggtcttggtctggccgtgctgttagaagctaatatggagcagacccacaaagacgttcagaagaaaaa gttttaccagcttaccccctccgagcggagatcgcagcttatcgagaagaacgttctgactcaagaaacggcacttatttttccaggagcaga cgttgtccgaagaactgtccgatcacatgattgagaatcaggtctccgaagtggaaattccaatgggaattgcacaaaattttcagattaat ggcaagaaaaaatggattcctatggcgactgaagaaccttcagtaatagcggcagcatcgaacggcgccaaaatctgcgggaacatttgcgc ggaaacgcctcagcggcttatgcgcgggcagattgtcctgtctggcaaatcagaatatcaagccgtgataaatgccgtgaatcatcgcaaag aagaactgattcttgcgcaaacgagtcgtacccgagtattgttaaacgcggggggaggtgttcaggatatttctacgcgggagtttatgggt tcttttcacgcgtatttatcaatcgactttctggtggacgtcaaggacgcaatggggcaaacatgatcaactctattctcgaaagcgttgc aaataaaactgcgtgaatggttcccggaagaggaaatactgttctccatcctgtcaaacttcgctacggagtccctggcatctgcatgttgcg agattccttttgaaagacttggtcgtaacaaagaaattggtgaacagatcgccaagaaaattcaacaggcaggggaatatgctaagcttgac ccttaccgcgcggcaacccataacaagggattatgaacggtatcgaagccgtcgttgccgcaacgggaaacgacacacgggctgttttccgc ttctattcacgcatacgccgcccgtaatggcttgtaccaaggtttaacggattggcagatcaagggcgataaactggttggtaaattaacag tcccactggctgtggcgactgtcggtggcgcgtcgaacatattaccaaaagccaaagcttccctcgccatgctggatattgattccgcaaaa gaactggcccaagtgatcgccgcggtaggtttagcacagaatctggcggcgttacgtgcattagtgacagaaggcattcagaaaggacacat gggcttgcaagcacgttctttagcgatttcgataggtgccatcggtgaggagatagagcaagtcgcgaaaaaactgcgtgaagctgaaaaaa tgaatcagcaaacggcaatacagatttttagaaaaaaattcgcgagaaatga

*E. faecium* mvaS:

SEQ ID NO: 4 atgaaaatcggtattgaccgtctgtccttcttcatcccgaatttgtatttggacatgactgagctggcagaatcacgcggggatgatccagc taaatatcatattggaatcggacaagatcagatggcagtgaatcgcgcaaacgaggacatcataacactgggtgcaaacgctgcgagtaaga tcgtgacagagaagaccgcgagttgattgatatggtaatcgttggcacggaatcaggaattgaccactccaaagcaagcgccgtgattatt caccatctccttaaaattcagtcgttcgcccgttctttcgaggtaaaagaagcttgctatggcggaactgctgccctgcacatggcgaagga gtatgtcaaaaatcatccggagcgtaaggtcttggtaattgcgtcagacatcgcgcgttatggtttggccagcggaggagaagttactcaag gcgtggggccgtagccatgatgattacacaaaaacccccggattctttcgattgaagacgatagtgtttttctcacagaggatatctatgat ttctggcggcctgattactccgagttccctgtagtggacgggcccctttcaaactcaacgtatatagagagttttcagaaagtttggaaccg gcacaaggaattgtccggaagagggctggaagattatcaagctattgcttttcacatacccttacgaagatgggtaagaaagcgctccaga gtgttttagaccaaaccgatgaagataaccaggagcgcttaatggctagatatgaggagtctctattcgctatagccggagaattggtaacctg

| SEQUENCES |
|---|
| tacacaggcagcttgtaccttggtcttacaagcttgttggaaaactctaaaagtttacaaccgggagatcggatcggcctcttttcctatgg |
| cagtggtgcggtgtccgagttctttaccgggtatttagaagaaaattaccaagagtacctgttcgctcaaagccatcaagaaatgctggata |
| gccggactcggattacggtcgatgaatacgagaccatcttttcagagactctgccagaacatggtgaatgcgccgaatatacgagcgacgtc |
| ccctttctataaccaagattgagaacgacattcgttattataaaatctga |

*E. gallinarum* mvaE:

SEQ ID NO: 5

| atggaagaagtggtaattatagatgcacgtcggactccgattggtaaatatcacgggtcgttgaagaagttttcagcggtggcgctggggac |
|---|
| ggccgtggctaaagacatgttcgaacgcaaccagaaaatcaaagaggagatcgcgcaggtcataattggtaatgtcttgcaggcaggaaatg |
| gccagaaccccgcgcggcaagttgctcttcaatcagggttgtccgttgacattcccgcttctacaattaacgaggtttgtgggtctggtttg |
| aaagctatcttgatgggcatgaacaaatccaactcggcaaagcgcaagtagtgctggcaggcggcattgaatcaatgacaaatgcgccaag |
| cctgtcccactataacaaggcggaggatacgtatagtgtcccagtgtcgagcatgacactggatggtctgacagacgcattttctagtaaac |
| ctatgggattaacagcggaaaacgtcgcacagcgctacggtatctcccgtgaggcgcaagatcaattcgcatatcaatctcagatgaaagca |
| gcaaaagcgcaggcagaaaacaaattcgctaaggaaattgtgccactggcggtgaaactaaaaccatcacagctgacgaagggatcagatc |
| ccaaacaacgatggagaaactggcaagtctcaaacctgttttaaaaccgatggcactgtaaccgcagggaatgctagcaccattaatgacg |
| gggccgcccttgtgctgcttgctagcaaaacttactgcgaaactaatgacataccgtaccttgcgacaatcaaagaaattgttgaagttgga |
| atcgatccggagattatgggcatctctccgataaaagcgatacaaacattgttacaaaatcaaaaagttagcctcgaagatattggagttttt |
| tgaaataaatgaagcctttgccgcaagtagcatagtggttgaatctgagttgggattagatccggctaaagttaaccgttatgggggtggta |
| tatccttaggtcatgcaattggggcaaccggcgctcgcctggccacttcactggtgtatcaaatgcaggagatacaagcacgttatggtatt |
| gcgagcctgtgcgttggtggtggacttggactggcaatgctttagaacgtccaactattgagaaggctaaaccgacagacaaaagttcta |
| tgaattgtcaccagctgaacggttgcaagagctggaaaatcaacagaaaatcagttctgaaactaaacagcagttatctcagatgatgcttg |
| ccgaggacactgcaaaccatttgatagaaaatcaaatatcagagattgaactcccaatgggcgtcgggatgaacctgaaggttgatgggaaa |
| gcctatgttgtgccaatggcgacggaagagccgtccgtcatcgcggccatgtctaatggtgccaaaatggccggcgaaattcacactcagtc |
| gaaagaacggctgctcagaggtcagattgttttcagcgcgaagaatccgaatgaaatcgaacagagaatagctgagaaccaagctttgattt |
| tcgaacgtgccgaacagtcctatccttccattgtgaaaagagagggaggtctccgccgcattgcacttcgtcattttcctgccgattctcag |
| caggagtctgcggaccagtccacatttttatcagtggacctttttgtagatgtgaaagacgcgatggggcaaatatcataaatgcaatact |
| tgagggcgtcgcagccctgtttcgcgaatggttccccaatgaggaaattctttttttctattctctcgaacttggctacggagagcttagtca |
| cggctgtttgtgaagtcccatttagtgcacttagcaagagaggtggtgcaacggtggcccagaaaattgtgcaggcgtcgctcttcgcaaag |
| acagacccataccgcgcagtgacccacaacaaagggattatgaacggtgtagaggctgttatgcttgccacaggcaacgacacgcgcgcagt |
| ctcagccgcttgtcatggatacgcagcgcgcaccggtagctatcagggtctgactaactggacgattgagtcggatcgcctggtaggcgaga |
| taacactgccgctggccatcgctacagttggaggcgctaccaaagtgttgcccaaagctcaagcggcactggagattagtgatgttcactct |
| tctcaagagcttgcagccttagcggcgtcagtaggtttagtacaaaatctcgcggccctgcgcgcactggtttccgaaggtatacaaaaagg |
| gcacatgtccatgcaagcccggtctctcgcaatcgcggtcggtgctgaaaaagccgagatcgagcaggtcgccgaaaagttgcggcagaacc |
| cgccaatgaatcagcagcaggcgctccgttttcttggcgagatccgcgaacaatga |

*E. gallinarum* mvaS:

SEQ ID NO: 6

| atgaacgtcggcattgacaaaattaattttttcgttccaccgtattatctggatatggtcgacctggcccacgcacgcgaagtggacccgaa |
|---|
| caaatttacaattggaattggacaggatcagatggctgtgagcaaaaagacgcacgatatcgtaacattcgcggctagtgccgcgaaggaaa |
| ttttagaacctgaggacttgcaagctatagacatggttatagttggtaccgaatcgggcattgacgagagcaaagcatccgcggtcgtttta |
| catcgtttgttgggcgtacaaccctttcgctcgcagttttgaaattaaagaagcctgttacggggcaaccgcaggcattcagtttgccaagac |
| tcatatacaagcgaacccgagagcaaggtcctggtaattgcaagcgatatagctcggtatggtcttcggtcaggtggagagcccacacaag |
| gcgcaggggcagttgctatgcttctcacggcaaatcccagaatcctgacctttcgaaaacgacaatctgatgttaacgcaggatatttatgac |

| SEQUENCES |
|---|
| ttctggagaccacttggtcacgcttaccctatggtagatggccacctttccaatcaagtctatattgacagttttaagaaggtctggcaagc |
| acattgcgaacgcaatcaagcttctatatccgactatgccgcgattagttttcatattccgtatacaaaaatgggtaagaaagccctgctcg |
| ctgttttgcagatgaagtggaaactgaacaggaacgcgttatggcacggtatgaagagtctatcgtatattcacgccggatcggcaacttg |
| tatacgggatcattgtacctggggctgatatccttattggaaaacagttctcacctgtcggcgggcgaccggataggattgtttagttatgg |
| gagtggcgctgtcagcgaattttctccggtcgtttagtggcaggctatgaaaatcaattgaacaaagaggcgcatacccagctcctggatc |
| agcgtcagaagctttccatcgaagagtatgaggcgattttttacagattccttagaaattgatcaggatgcagcgttctcggatgacctgcca |
| tattccatccgcgagataaaaaacacgattcggtactataaggagagctga |

E. casseliflavus mvaE:

SEQ ID NO: 7

| atggaagaagttgtcatcattgacgcactgcgtactccaataggaaagtaccacggttcgctgaaagattacacagctgttgaactggggac |
|---|
| agtagcagcaaaggcgttgctggcacgaaatcagcaagcaaaagaacacatagcgcaagttattattggcaacgtcctgcaagccggaagtg |
| ggcagaatccaggccgacaagtcagtttacagtcaggattgtcttctgatatccccgctagcacgatcaatgaagtgtgtggctcgggtatg |
| aaagcgattctgatgggtatggagcaaattcagctgaacaaagcctctgtggtcttaacaggcggaattgaaagcatgaccaacgcgccgct |
| gtttagttattacaacaaggctgaggatcaatattcggcgccggttagcacaatgatgcacgatggtctaacagatgcttcagttccaaac |
| caatgggcttaaccgcagagaccgtcgctgagagatatgaattacgcgtaaggaacaagatgaatttgcttatcactctcaaatgaaggcg |
| gccaaagcccaggcggcgaaaaagtttgatcaggaaattgtaccctgacggaaaaatccggaacggttctccaggacgaaggcatcagagc |
| cgcgacaacagtcgagaagctagctgagcttaaaacggtgttcaaaaaagacggaacagttacagcgggtaacgcctctacgataaatgatg |
| gcgctgctatggtattaatagcatcaaaatcttattgcgaagaacaccagattcctatctggccgttataaaggagatcgttgaggtgggt |
| tttgcccccgaaataatgggtatttcccccattaaggctatagacaccctgctgaaaaatcaagcactgaccatagaggatataggaatatt |
| tgagattaatgaagcctttgctgcgagttcgattgtggtagaacgcgagttgggcctggaccccaaaaaagttaatcgctatggcggtggta |
| tatcactcggccacgcaattggggcgacgggagctcgcattgcgacgaccgttgcttatcagctgaaagatacccaggagcgctacggtata |
| gcttccttatgcgttggtggggtcttggattggcgatgcttctggaaaacccatcggccactgcctcacaaactaattttgatgaggaatc |
| tgcttccgaaaaaactgagaagaagaagtttatgcgctagctcctaacgaacgcttagcgttttggaagcccaaggcgctattaccgctg |
| ctgaaaccctggtcttccaggagatgaccttaaacaaagagacagccaatcacttaatcgaaaaccaaatcagcgaagttgaaattcccttta |
| ggcgtgggcctgaacttacaggtgaatgggaaagcgtataatgttcctctggccacggaggaaccgtccgttatcgctgcgatgtcgaatgg |
| cgccaaaatggctggtcctattacaacaacaagtcaggagaggctgttacggggtcagattgtcttcatggacgtacaggacccagaagcaa |
| tattagcgaaagttgaatccgagcaagctaccattttcgcggtggcaaatgaaacatacccgtctatcgtgaaaagaggaggaggtctgcgt |
| agagtcattggcaggaatttcagtccggccgaaagtgacttagccacggcgtatgtatcaattgacctgatggtagatgttaaggatgcaat |
| gggtgctaatatcatcaatagtatcctagaaggtgttgcggaattgtttagaaaatggttcccagaagaagaaatcctgttctcaattctct |
| ccaatctcgcgacagaaagtctggtaacggcgacgtgctcagttccgtttgataaattgtccaaaactgggaatggtcgacaagtagctggt |
| aaaatagtgcacgcggcggactttgctaagatagatccatacagagctgccacacacaataaaggtattatgaatggcgttgaagcgttaat |
| cttagccaccggtaatgacacccgtgcggtgtcggctgcatgccacggttacgcggcacgcaatgggcgaatgcaagggcttacctcttgga |
| cgattatcgaagatcggctgataggctctatcacattacctttggctattgcgacagtgggggtgccacaaaaatcttgccaaaagcacag |
| gccgccctggcgctaactggcgttgagacggcgtcggaactggccagcctggcggcgagtgtgggattagttcaaaatttggccgctttacg |
| agcactagtgagcgagggcattcagcaagggcacatgagtatgcaagctagatccctggccattagcgtaggtgcgaaaggtactgaaatag |
| agcaactagctgcgaagctgagggcagcgacgcaaatgaatcaggagcaggctcgtaaatttctgaccgaaataagaaattaa |

E. casseliflavus mvaS:

SEQ ID NO: 8

| atgaacgttggaattgataaaatcaatttttttcgttccgccctatttcattgatatggtggatctcgctcatgcaagagaagttgaccccaa |
|---|
| caagttcactataggaataggccaagatcagatggcagtaaacaagaaaacgcaagatatcgtaacgttcgcgatgcacgccgcgaaggata |

| SEQUENCES | |
|---|---|
| ttctgactaaggaagatttacaggccatagatatggtaatagtggggactgagtctgggatcgacgagagcaaggcaagtgctgtcgtattg<br>catcggcttttaggtattcagccttttgcgcgctcctttgaaattaaggaggcatgctatggggccactgccggccttcagtttgcaaaagc<br>tcatgtgcaggctaatccccagagcaaggtcctggtggtagcttccgatatagcacgctacggactggcatccgaggagaaccgactcaag<br>gtgtaggtgctgtggcaatgttgatttccgctgatccagctatcttgcagttagaaaatgataatctcatgttgacccaagatatatacgat<br>ttttggcgcccggtcgggcatcaatatcctatggtagacggccatctgtctaatgccgtctatatagacagctttaaacaagtctggcaagc<br>acattgcgagaaaaccaacggactgctaaagattatgctgcattgtcgttccatattccgtacacgaaaatgggtaagaaagctctgttag<br>cggttttttgcggaggaagatgagacagaacaaaagcggttaatggcacgttatgaagaatcaattgtatacagtcgtcggactggaaatctg<br>tatactggctcactctatctgggcctgatttccttactggagaatagtagcagtttacaggcgaacgatcgcataggtctgtttagctatgg<br>ttcaggggccgttgcggaattttcagtggcctcttggtaccgggttacgagaaacaattagcgcaagctgcccatcaagctcttctggacg<br>accggcaaaaactgactatcgcagagtacgaagccatgtttaatgaaaccattgatattgatcaggaccagtcatttgaggatgacttactg<br>tactccatcagagagatcaaaaacactattcgctactataacgaggagaatgaataa | |
| *E. gallinarum* EG2 (mvaE): | SEQ ID NO: 9 |
| MEEVVIIDARRTPIGKYHGSLKKFSAVALGTAVAKDMFERNQKIKEEIAQVIIGNVLQAGNGQNPARQVA<br>LQSGLSVDIPASTINEVCGSGLKAILMGMEQIQLGKAQVVLAGGIESMTNAPSLSHYNKAEDTYSVPVSS<br>MTLDGLTDAFSSKPMGLTAENVAQRYGISREAQDQFAYQSMKAAKAQAENKFAKEIVPLAGETKTITAD<br>EGIRSQTTMEKLASLKPVFKTDGTVTAGNASTINDGAALVLLASKTYCETNDIPYLATIKEIVEVGIDPE<br>IMGISPIKAIQTLLQNQKVSLEDIGVFEINEAFAASSIVVESELGLDPAKVNRYGGGISLGHAIGATGAR<br>LATSLVYQMQEIQARYGIASLCVGGGLGLAMLLERPTIEKAKPTDKKFYELSPAERLQELENQQKISSET<br>KQQLSQMMLAEDTANHLIENQISEIELPMGVGMNLKVDGKAYVVPMATEEPSVIAAMSNGAKMAGEIHTQ<br>SKERLLRGQIVFSAKNPNEIEQRIAENQALIFERAEQSYPSIVKREGGLRRIALRHFPADSQQESADQST<br>FLSVDLFVDVKDAMGANIINAILEGVAALFREWFPNEEILFSILSNLATESLVTAVCEVPFSALSKRGGA<br>TVAQKIVQASLFAKTDPYRAVTHNKGIMNGVEAVMLATGNDTRAVSAACHGYAARTGSYQGLTNWTIESD<br>RLVGEITLPLAIATVGGATKVLPKAQAALEISDVHSSQELAALAASVGLVQNLAALRALVSEGIQKGHMS<br>MQARSLAIAVGAEKAEIEQVAEKLRQNPPMNQQQALRFLGEIREQ | |
| E. gallinarum EG2 (mvaS) | SEQ ID NO: 10 |
| MNVGIDKINFFVPPYYLDMVDLAHAREVDPNKFTIGIGQDQMAVSKKTHDIVTFAASAAKEILEPEDLQA<br>IDMVIVGTESGIDESKASAVVLHRLLGVQPFARSFEIKEACYGATAGIQFAKTHIQANPESKVLVIASDI<br>ARYGLRSGGEPTQGAGAVAMLLTANPRILTFENDNLMLTQDIYDFWRPLGHAYPMVDGHLSNQVYIDSFK<br>KVVWQAHCERNQASISDYAAISFHIPYTKMGKKALLAVFADEVETEQERVMARYEESIVYSRRIGNLYTGS<br>LYLGLISLLENSSHLSAGDRIGLFSYGSGAVSEFFSGRLVAGYENQLNKEAHTQLLDRQKLSIEEYEAI<br>FTDSLEIDQDAAFSDDLPYSIREIKNTIRYYKES | |
| *L. grayi* (mvaE): | SEQ ID NO: 11 |
| MVKDIVIIDALRTPIGKYRGQLSKMTAVELGTAVTKALFEKNDQVKDHVEQVIFGNVLQAGNGQNPARQI<br>ALNSGLSAEIPASTINQVCGSGLKAISMARQQILLGEAEVIVAGGIESMTNAPSITYYNKEEDTLSKPVP<br>TMTFDGLTDAFSGKIMGLTAENVAEQYGVSREAQDAFAYGSQMKAAKAQEQGIFAAEILPLEIGDEVITQ<br>DEGVRQETTLEKLSLLRTIFKEDGTVTAGNASTINDGASAVIIASKEFAETNQIPYLAIVHDITEIGIDP<br>SIMGIAPVSAINKLIDRNQISMEEIDLFEINEAFAASSVVVQKELSIPDEKINIGGSGIALGHPLGATGA<br>RIVTTLAHQLKRTHGRYGIASLCIGGGLGLAILIEVPQEDQPVKKFYQLAREDRLARLQEQAVISPATKH<br>VLAEMTLPEDIADNLIENQISEMEIPLGVALNLRVNDKSYTIPLATEEPSVIAACNNGAKMANHLGGFQS | |

| SEQUENCES | |
|---|---|
| ELKDGFLRGQIVLMNVKEPATIEHTITAEKAAIFRAAAQSHPSIVKRGGGLKEIVVRTFDDDPTFLSIDL<br>IVDTKDAMGANIINTILEGVAGFLREILTEEILFSILSNYATESIVTASCRIPYEALSKKGDGKRIAEKV<br>AAASKFAQLDPYRAATHNKGIMNGIEAVVLASGNDTRAVAAAAHAYASRDQHYRGLSQWQVAEGALHGEI<br>SLPLALGSVGGAIEVLPKAKAAFEIMGITEAKELAEVTAAVGLAQNLAALRALVSEGIQQGHMSLQARSL<br>ALSVGATGKEVEILAEKLQGSRMNQANAQTILAEIRSQKVEL | |
| *L. grayi* (mvaS):<br>MTMNVGIDKMSFFVPPYFVDMTDLAVARDVDPNKFLIGIGQDQMAVNPKTQDIVTFATNAAKNILSAEDL<br>DKIDMVIVGTESGIDESKASAVVLHRLLGIQKFARSFEIKEACYGGTAALQFAVNHIRNHPESKVLVVAS<br>DIAKYGLASGGEPTQGAGAVAMLVSTDPKIIAFNDDSLALTQDIYDFWRPVGHDYPMVDGPLSTETYIQS<br>FQTVWQEYTKRSQHALADFAALSFHIPYTKMGKKALLAILEGESEEAQNRILAKYEKSIAYSRKAGNLYT<br>GSLYLGLISLLENAEDLKAGDLIGLFSYGSGAVAEFFSGRLVEDYQEQLLKTKHAEQLAHRKQLTIEEYE<br>TMFSDRLDVDKDAEYEDTLAYSISSVRNTVREYRS | SEQ ID NO: 12 |
| *E. faecium* (mvaE):<br>MKEVVMIDAARTPIGKYRGSLSPFTAVELGTLVTKGLLDKTKLKKDKIDQVIFGNVLQAGNGQNVARQIA<br>LNSGLPVDVPAMTINEVCGSGMKAVILARQLIQLGEAELVIAGGTESMSQAPMLKPYQSETNEYGEPISS<br>MVNDGLTDAFSNAHMGLTAEKVATQFSVSREEQDRYALSSQLKAAHAVEAGVFSEEIIPVKISDEDVLSE<br>DEAVRGNSTLEKLGTLRTVFSEEGTVTAGNASPLNDGASVVILASKEYAENNNLPYLATIKEVAEVGIDP<br>SIMGIAPIKAIQKLTDRSGMNLSTIDLFEINEAFAASSIVVSQELQLDEEKVNIYGGAIALGHPIGASGA<br>RILTTLAYGLLREQKRYGIASLCIGGGLGLAVLLEANMEQTHKDVQKKKFYQLTPSERRSQLIEKNVLTQ<br>ETALIFQEQTLSEELSDHMIENQVSEVEIPMGIAQNFQINGKKKWIPMATEEPSVIAAASNGAKICGNIC<br>AETPQRLMRGQIVLSGKSEYQAVINAVNHRKEELILCANESYPSIVKRGGGVQDISTREFMGSFHAYLSI<br>DFLVDVKDAMGANMINSILESVANKLREWFPEEEILFSILSNFATESLASACCEIPFERLGRNKEIGEQI<br>AKKIQQAGEYAKLDPYRAATHNKGIMNGIEAVVAATGNDTRAVSASIHAYAARNGLYQGLTDWQIKGDKL<br>VGKLTVPLAVATVGGASNILPKAKASLAMLDIDSAKELAQVIAAVGLAQNLAALRALVTEGIQKGHMGLQ<br>ARSLAISIGAIGEEIEQVAKKLREAEKMNQQTAIQILEKIREK | SEQ ID NO: 13 |
| *E. faecium* (mvaS)<br>MKIGIDRLSFFIPNLYLDMTELAESRGDDPAKYHIGIGQDQMAVNRANEDIITLGANAASKIVTEKDREL<br>IDMVIVGTESGIDHSKASAVIIHHLLKIQSFARSFEVKEACYGGTAALHMAKEYVKNHPERKVLVIASDI<br>ARYGLASGGEVTQGVGAVAMMITQNPRILSIEDDSVFLTEDIYDFWRPDYSEFPVVDGPLSNSTYIESFQ<br>KVWNRHKELSGRGLEDYQAIAFHIPYTKMGKKALQSVLDQTDEDNQERLMARYEESIRYSRRIGNLYTGS<br>LYLGLTSLLENSKSLQPGDRIGLFSYGSGAVSEFFTGYLEENYQEYLFAQSHQEMLDSRTRITVDEYETI<br>FSETLPEHGECAEYTSDVPFSITKIENDIRYYKI | SEQ ID NO: 14 |
| *E. casseliflavus* (mvaE):<br>MEEVVIIDALRTPIGKYHGSLKDYTAVELGTVAAKALLARNQQAKEHIAQVIIGNVLQAGSGQNPGRQVS<br>LQSGLSSDIPASTINEVCGSGMKAILMGMEQIQLNKASVVLTGGIESMTNAPLFSYYNKAEDQYSAPVST<br>MMHDGLTDAFSSKPMGLTAETVAERYGITRKEQDEFAYHSQMKAAKAQAAKKFDQEIVPLTEKSGTVLQD<br>EGIRAATTVEKLAELKTVFKKDGTVTAGNASTINDGAAMVLIASKSYCEEHQIPYLAVIKEIVEVGFAPE<br>IMGISPIKAIDTLLKNQALTIEDIGIFEINEAFAASSIVVERELGLDPKKVNRYGGGISLGHAIGATGAR | SEQ ID NO: 15 |

| SEQUENCES | |
|---|---|
| IATTVAYQLKDTQERYGIASLCVGGGLGLAMLLENPSATASQTNFDEESASEKTEKKKFYALAPNERLAF<br>LEAQGAITAAETLVFQEMTLNKETANHLIENQISEVEIPLGVGLNLQVNGKAYNVPLATEEPSVIAAMSN<br>GAKMAGPITTTSQERLLRGQIVFMDVQDPEAILAKVESEQATIFAVANETYPSIVKRGGGLRRVIGRNFS<br>PAESDLATAYVSIDLMVDVKDAMGANIINSILEGVAELFRKWFPEEEILFSILSNLATESLVTATCSVPF<br>DKLSKTGNGRQVAGKIVHAADFAKIDPYRAATHNKGIMNGVEALILATGNDTRAVSAACHGYAARNGRMQ<br>GLTSWTIIEDRLIGSITLPLAIATVGGATKILPKAQAALALTGVETASELASLAASVGLVQNLAALRALV<br>SEGIQQGHMSMQARSLAISVGAKGTEIEQLAAKLRAATQMNQEQARKFLTEIRN | |
| *E. casseliflavus* (mvaS)<br>MNVGIDKINFFVPPYFIDMVDLAHAREVDPNKFTIGIGQDQMAVNKKTQDIVTFAMHAAKDILTKEDLQA<br>IDMVIVGTESGIDESKASAVVLHRLLGIQPFARSFEIKEACYGATAGLQFAKAHVQANPQSKVLVVASDI<br>ARYGLASGGEPTQGVGAVAMLISADPAILQLENDNLMLTQDIYDFWRPVGHQYPMVDGHLSNAVYIDSFK<br>QVWQAHCEKNQRTAKDYAALSFHIPYTKMGKKALLAVFAEEDETEQKRLMARYEESIVYSRRTGNLYTGS<br>LYLGLISLLENSSSLQANDRIGLFSYGSGAVAEFFSGLLVPGYEKQLAQAAHQALLDDRQKLTIAEYEAM<br>FNETIDIDQDQSFEDDLLYSIREIKNTIRYYNEENE | SEQ ID NO: 16 |

Isoprene synthase:
Atggaagctcgtcgactgcgaactacgaacctaacagctgggactatgattacctgctgtcctccgacacggacgagtccatcgaagtatac aaagacaaagcgaaaaagctggaagccgaagttcgtcgcgagattaataacgaaaaagcagaatactgaccctgctggaactgattgacaac gtccagcgcctgggcctgggttaccgatcgagtctgatatccgtggtgcgctggatcgcttcgtacctccggcggcttcgatgcggtaacca agacttccctgcacggtacggcactgtattccgtctgctgcgtcaacacggattgaggtactcaggaagcgttcagcggcttcaaagaccaa aacggcaacttcctggagaacctgaaggaagatatcaaagctatcctgagcctgtacgaggccagatcctggctctggaaggcgaaaacatc ctggacgaggcgaaggattcgcaatctctcatctgaaagaactgtctgaagaaagatcggtaaagagctggcagaacaggtgaaccatgca ctggaactgccactgcatcgccgtactcagcgtctggaagcagtatggtctatcgaggcctaccgtaaaaggaggacgcgaatcaggttct gctggagctggcaattctggattacaacatgatccagtctgtataccagcgtgatctgcgtgaaacgtcccgttggtggcgtcgtgtgggtc tggcgaccaaactgcactttgctcgtgaccgcctgattgagagcttctactgggccgtgggtgtagcattcgaaccgcaatactccgactgc cgtaactccgtcgcaaaaatgtttctttcgtaaccattatcgacgatatctacgatgtatacggcaccctggacgaactggagctgtttac tgatgcagttgagcgttgggacgtaaacgccatcaacgacctgccggattacatgaaactgtgctttctggctctgtataacactattaacg aaatcgcctacgacaacctgaaagataaaggtgagaacatcctgccgtatctgaccaaagcctgggctgacctgtgcaacgctttcctgcaa gaagccaagtggctgtacaacaaatctactccgaccttgacgactacttcggcaacgcatggaaatcctcttctggcccgctgcaactggt gttcgcttacttcgctgtcgtgcagaacattaaaaaggaagagatcgaaaacctgcaaaaataccatgacaccatctctcgtccttcccata tcttccgtctgtgcaatgacctggctagcgcgtctgcggaaattgcgcgtggtgaaaccgcaaatagcgtttcttgttacatgcgcactaaa ggtatctccgaagaactggctaccgaaagcgtgatgaatctgatcgatgaaacctggaaaaagatgaacaaggaaaaactgggtggtagcct gttcgcgaaaccgttcgtggaaaccgcgatcaacctggcacgtcaatctcactgcacttatcataacggcgacgcgcatacctctccggatg agctgacccgcaaacgcgttctgtctgtaatcactgaaccgattctgccgtttgaacgctaa ispA:
tggactttccgcagcaactcgaagcctgcgttaagcaggccaaccaggcgctgagccgttttatcgccccactgcccttcagaacactccc gtggtcgaaaccatgcagtatggcgcattattaggtggtaagcgcctgcgaccttttcctggtttatgccaccggtcatatgtttggcgttag cacaaacacgctggacgcaccgctgctgccgtagagtgtatccacgcttactcattaattcatgatgatttaccggcgatggatgatgacg atctgcgccgcggtttgccgacctgccatgtgaagtttggcgaagcaaacgcgattctcgctggcgacgctttacaaacgctggcgttctcg attctaagcgatgccgatatgccggaagtgtcggatcgcgacagaatttcgatgatttctgaactggcgagcgccagcggtattgccggaat gtgcggtggtcaggcactagatttagacgcggaaggcaaacacgtacctctggacgcgcttgagcgtattcatcgtcataaaaccggcgcat tgattcgcgccgccgttcgccttggtgcattaagcgccggagataaagggcgtcgtgctctgccagtactcgacaagtacgcagagagcatc
ggccttgccttccaggttcaagatgacatcctggatgtggtaggagatactgcaacgttgggaaaacgccagggtgccgaccagcaacttgg
taaaagtacctaccctgcacttctgggtcttgagcaagcccggaagaaagcccgggatctgatcgacgatgcccgtcagtcgctgaaacaac
tggctgaacagtcactcgatacctcggcactggaagcgctagcggactacatcatccagcgtaataaataa Amorphadiene synthase codon-optimized for E. coli:
ATGAGCCTGACCGAAGAAAAACCGATTCGTCCGATTGCAAATTTTCCGCCTAGCATTTGGGGTGATCAGTT
TCTGATTTATGAGAAACAGGTTGAACAGGGCGTTGAGCAGATTGTTAATGATCTGAAAAAAGAAGTTCGC
CAGCTGCTGAAAGAAGCACTGGATATTCCGATGAAACATGCCAATCTGCTGAAACTGATTGATGAAATTC
AGCGTCTGGGTATCCCGTATCATTTTGAACGTGAAATTGATCATGCCCTGCAGTGCATTTATGAAACCTAT
GGTGATAATTGGAATGGTGATCGTAGCAGCCTGTGGTTTCGTCTGATGCGTAAACAGGGTTATTATGTTAC
CTGCGACGTGTTTAACAACTATAAAGATAAAAACGGTGCCTTTAAACAGAGCCTGGCAAATGATGTTGAA
GGTCTGCTGGAACTGTATGAAGCAACCAGCATGCGTGTTCCGGGTGAAATTATTCTGGAAGATGCACTGG
GTTTTACCCGTAGCCGTCTGAGCATGATGACCAAAGATGCATTTAGCACCAATCCGGCACTGTTTACCGAA
ATCCAGCGTGCACTGAAACAGCCGCTGTGGAAACGTCTGCCTCGTATTGAAGCAGCACAGTATATTCCGT
TTTATCAGCAGCAGGATAGCCATAACAAAACCCTGCTGAAACTGGCAAAACTGGAATTTAATCTGCTGCA
GAGCCTGCATAAAGAAGAACTGAGCCACGTTTGTAAATGGTGGAAAGCCTTCGACATCAAAAAAACGC
ACCGTGTCTGCGTGATCGTATTGTTAATGTTATTTTTGGGGTCTGGGTAGCGGTTTTGAACCGCAGTATA
GCCGTGCACGTGTGTTTTTTACCAAAGCAGTTGCAGTTATTACCCTGATCGATGATACCTATGACGCATAT
GGCACCTATGAGGAACTGAAAATCTTTACCGAAGCCGTTGAACGTTGGAGCATTACCTGTCTGGATACCC
TGCCGGAATATATGAAACCGATCTATAAACTGTTCATGGACACCTATACCGAGATGGAAGAATTTCTGGC
AAAAGAAGGTCGTACCGACCTGTTTAATTGCGGTAAAGAATTTGTGAAAGAATTCGTGCGTAACCTGATG
GTTGAAGCAAAATGGGCCAATGAAGGTCATATTCCGACCACCGAAGAACATGATCCGGTTGTGATTATTA
CCGGTGGTGCAAACCTGCTGACCACCACCTGTTATCTGGGTATGAGCGATATTTTCACCAAAGAAAGCGTT
GAATGGGCAGTTAGCGCACCGCCTCTGTTTCGTTATAGCGGTATTCTGGGTCGTCGTCTGAACGATCTGAT
GACCCATAAAGCAGAACAAGAACGTAAACATAGCAGCAGCAGCCTGGAAAGCTATATGAAAGAATATAA
CGTGAACGAAGAGTATGCACAGACCCTGATTTACAAAGAAGTTGAGGACGTTTGGAAAGATATCAACCGT
GAATATCTGACCACGAAAAACATTCCGCGTCCGCTGCTGATGGCAGTTATTTATCTGTGTCAGTTCCTGGA
AGTTCAGTATGCAGGTAAAGATAACTTTACGCGTATGGGCGACGAATATAAACATCTGATTAAAAGCCTG
CTGGTGTATCCGATGAGCATTTAA
Farnesene synthase codon-optimized for E. coli:
ATGAGCACCCTGCCGATTAGCAGCGTTAGCTTTAGCAGCAGCACCAGTCCGCTGGTTGTTGATGATAAAG
TTAGCACCAAACCGGATGTTATTCGTCACACCATGAACTTTAATGCAAGCATTTGGGGTGATCAGTTTCTG
ACCTATGATGAACCGGAAGATCTGGTGATGAAAAAACAGCTGGTTGAAGAACTGAAAGAAGAAGTTAAA
AAAGAGCTGATCACCATCAAAGGTAGCAATGAACCGATGCAGCATGTTAAACTGATTGAACTGATCGATG
CCGTTCAGCGTCTGGGTATTGCATATCATTTTGAAGAAGAAATCGAAGAAGCCCTGCAGCATATTCATGTT
ACCTATGGTGAACAGTGGGTGGATAAAGAAAATCTGCAGAGCATTAGCCTGTGGTTTCGTCTGCTGCGTC
AGCAGGGTTTTAATGTTAGCAGCGGTGTGTTTAAAGATTTTATGGACGAGAAAGGCAAATTCAAAGAAAG
CCTGTGTAATGATGCACAGGGTATTCTGGCACTGTATGAAGCAGCATTTATGCGTGTTGAAGATGAAACC
ATTCTGGATAATGCACTGGAATTTACCAAAGTGCACCTGGATATCATTGCAAAAGATCCGAGCTGTGATA

SEQUENCES

GCAGCCTGCGTACCCAGATTCATCAGGCACTGAAACAGCCGCTGCGTCGTCGTCTGGCACGCATTGAAGC

ACTGCATTATATGCCGATTTATCAGCAAGAAACCAGCCATAATGAAGATCTGCTGAAACTGGCAAAACTG

GATTTTAGCGTTCTGCAGTCCATGCACAAAAAAGAACTGAGCCATATTTGTAAATGGTGGAAAGATCTGG

ATCTGCAGAATAAACTGCCGTATGTTCGTGATCGTGTTGTGGAAGGTTATTTTTGGATTCTGAGCATCTAT

TATGAACCGCAGCATGCACGTACCCGTATGTTTCTGATGAAAACCTGTATGTGGCTGGTTGTGCTGGATGA

TACGTTTGATAATTATGGCACCTACGAGGAACTGGAAATCTTTACCCAGGCAGTTGAACGTTGGAGCATT

AGTTGTCTGGATATGCTGCCGGAATACATGAAACTGATTTATCAAGAACTGGTGAACCTGCACGTTGAAA

TGGAAGAAAGTCTGGGCAAAGGTGGTAAAAACATTAGCAATAGTCTGTGTCAGGGTCGTTGGCAGAAAG

AACTGGGTAGTCAGATTACCCTGGTTGAAACCAAAATGGCAAAACGTGGTGTTCATGCCCAGCCGCTGGA

AGAGTATATGAGCGTTAGCATGGTTACCGGCACCTATGGTCTGATGATTGCACGTAGCTATGTTGGTCGTG

GTGATATTGTTACCGAAGATACCTTTAAATGGGTGAGCAGCTATCCGCCTATTATCAAAGCAAGCTGTGTT

ATTGTTCGCCTGATGGATGATATTGTGAGCCACAAAGAAGAACAAGAACGCGGTCATGTTGCCAGCAGCA

TTGAATGTTATAGCAAAGAAAGTGGTGCAAGCGAAGAAGAAGCCTGCGAATATATCAGCCGTAAAGTGG

AAGATGCCTGGAAAGTTATTAATCGTGAAAGCCTGCGTCCGACCGCAGTTCCGTTTCCGCTGCTGATGCCT

GCAATTAACCTGGCACGTATGTGTGAAGTTCTGTATAGCGTTAATGATGGTTTTACCCATGCCGAAGGTGA

TATGAAATCCTATATGAAAAGCTTCTTCGTGCATCCGATGGTTGTTTAA pMCM1223- pCL-Ptrc-Upper_GcMM_161 (*Listeria grayi* DSM 20601):
cccgtcttactgtcgggaattcgcgttggccgattcattaatgcagattctgaaatgagctgttgacaattaatcatccggctcgtataatg tgtggaattgtgagcggataacaatttcacacaggaaacagcgccgctgagaaaaagcgaagcggcactgctctttacaatttatcagacaa tctgtgtgggcactcgaccggaattatcgattaactttattattaaaaattaaagaggtatatattaatgtatcgattaaataaggaggaat aaaccatggttaaagacattgtaataattgatgccctccgtactcccatcggtaagtaccgcggtcagctctcaaagatgacggcggtggaa ttgggaaccgcagttacaaaggctctgttcgagaagaacgaccaggtcaaagaccatgtagaacaagtcattttttggcaacgttttacaggc agggaacggccagaatcccgcccgtcagatcgcccttaattctggcctgtccgcagagataccggcttcgactattaaccaggtgtgtggtt ctggcctgaaagcaataagcatggcgcgccaacagatcctactcggagaagcggaagtaatagtagcaggaggtatcgaatccatgacgaat gcgccgagtattacatattataataaagaagaagacaccctctcaaagcctgttcctacgatgaccttcgatggtctgaccgacgcgtttag cggaaagattatggggtttaacagccgaaaatgttgccgaacagtacggcgtatcacgtgaggcccaggacgcctttgcgtatggatcgcaga tgaaagcagcaaaggcccaagaacagggcattttcgcagctgaaatactgcctcttgaaatagggggacgaagttattactcaggacgaggg gttcgtcaagagaccaccctcgaaaaattaagtctgcttcggaccattttttaaagaagatggtactgttacagcgggcaacgcctcaacgat caatgatggcgcctcagccgtgatcattgcatcaaaggagtttgctgagacaaaccagattccctaccttgcgatcgtacatgatattacag agataggcattgatccatcaataatgggcattgctcccgtgagtgcgatcaataaactgatcgatcgtaaccaaattagcatggaagaaatc gatctctttgaaattaatgaggcatttgcagcatcctcggtggtagttcaaaaagagttaagcattcccgatgaaaagatcaatattggcgg ttccggtattgcactaggccatcctcttggcgccacaggagcgcgcattgtaaccaccctagcgcaccagttgaaacgtacacacggacgct atggtattgcctccctgtgcattggcggtggccttggcctagcaatattaatagaagtgcctcaggaagatcagccggttaaaaaatttat caattggcccgtgaggaccgtctggctagacttcaggagcaagccgtgatcagcccagctacaaaacatgtactggcagaaatgacacttcc tgaagatattgccgacaatctgatcgaaaatcaaatatctgaaatggaaatccctcttggtgtggctttgaatctgagggtcaatgataaga gttataccatcccactagcaactgaggaaccgagtgtaatcgctgcctgtaataatggtgcaaaaatggcaaaccacctgggcggttttcag tcagaattaaaagatggtttcctgcgtgggcaaattgtacttatgaacgtcaaagaacccgcaactatcgagcatacgatcacggcagagaa agcggcaattttttcgtgccgcagcgcagtcacatccatcgattgtgaaacgaggtgggggtctaaaagagatagtagtgcgtacgttcgatg atgatccgacgttcctgtctattgatctgatagttgatactaaagacgcaatgggcgctaacatcattaacaccattctcgagggtgtagcc

| SEQUENCES |
|---|
| ggctttctgagggaaatccttaccgaagaaattctgttctctattttatctaattacgcaaccgaatcaattgtgaccgccagctgtcgcat |
| accttacgaagcactgagtaaaaaaggtgatggtaaacgaatcgctgaaaaagtggctgctgcatctaaatttgcccagttagatccttatc |
| gagctgcaacccacaacaaaggtattatgaatggtattgaggccgtcgttttggcctcaggaaatgacacacgggcggtcgcggcagccgca |
| catgcgtatgcttcacgcgatcagcactatcggggcttaagccagtggcaggttgcagaaggcgcgttacacggggagatcagtctaccact |
| tgcactcggcagcgttggcggtgcaattgaggtcttgcctaaagcgaaggcggcattcgaaatcatgggatcacagaggcgaaggagctgg |
| cagaagtcacagctgcggtagggctggcgcaaaacctggcggcgttaagagcgcttgttagtgaaggaatacagcaaggtcacatgtcgctc |
| caggctcgctctcttgcattatcggtaggtgctacaggcaaggaagttgaaatcctggccgaaaaattacagggctctcgtatgaatcaggc |
| gaacgctcagaccatactcgcagagatcagatcgcaaaaagttgaattgtgatctagacgcactaggaggatataccaatgaccatgaacgt |
| tggaatcgataaaatgtcattctttgttccaccttactttgtggacatgactgatctggcagtagcacgggatgtcgatcccaataagtttc |
| tgattggtattggccaggaccagatggcagttaatccgaaaacgcaggatattgtgacatttgccacaaatgctgccaaaaacatactgtca |
| gctgaggaccttgataaaattgatatggtcatagtcggcaccgagagtggaatcgatgaatccaaagcgagtgccgtagtgcttcacaggtt |
| gctcggtatccagaagtttgctcgctcctttgaaatcaaagaagcctgttatgggggtaccgcggctttacagttcgctgtaaaccacatta |
| ggaatcatcctgaatcaaaggttcttgtagttgcatcagatatcgcgaaatacggcctggcttctggaggtgaaccaacgcaaggtgcaggc |
| gctgtggctatgctcgtctcaactgaccctaagatcattgctttcaacgacgatagcctcgcgcttacacaagatatctatgacttctggcg |
| accagttggacatgactatcctatggtcgacgggcctcttagtacagagacctacatccagtcatttcagaccgtatggcaggaatacacaa |
| aacggtcgcagcatgcactggcagactttgctgcccttagctttcatatcccgtatactaaaatgggcaaaaaggcgctgcttgcaatcctt |
| gaaggcgaatcagaggaggctcagaaccgtatactagcaaaatatgaaagagtatagcctactccagaaaggcgggtaacctgtataccgg |
| tagcctgtatctaggacttatttcacttctggaaaatgcagaagaccttaaagctggtgatttaataggcctcttttcttacggttccggtg |
| ctgttgcggagttttctcaggaaggctggttgaggactatcaggaacagctacttaaaacaaaacatgccgaacagctggcccatagaaag |
| caactgacaatcgaggagtacgaaacgatgttctccgatcgcttggacgtggacaaagacgccgaatacgaagcacattagcttatagcat |
| ttcgtcagtccgaaacaccgtacgtgagtacaggagttgactgcagctggtaccatatgggaattcgaagcttgggcccgaacaaaaactca |
| tctcagaagaggatctgaatagcgccgtcgaccatcatcatcatcatcattgagtttaaacggtctccagcttggctgttttggcggatgag |
| agaagattttcagcctgatacagattaaatcagaacgcagaagcggtctgataaaacagaatttgcctggcggcagtagcgcggtggtccca |
| cctgaccccatgccgaactcagaagtgaaacgccgtagcgccgatggtagtgtggggtctccccatgcgagagtagggaactgccaggcatc |
| aaataaaacgaaaggctcagtcgaaagactgggcctttcgttttatctgttgtttgtcggtgaacgctctcctgagtaggacaaatccgccg |
| ggagcggatttgaacgttgcgaagcaacgccccggagggtggcgggcaggacgcccgccataaactgccaggcatcaaattaagcagaaggc |
| catcctgacggatggcctttttgcgtttctacaaactctttttgtttattttttctaaatacattcaaatatgtatccgctcatgagacaata |
| accctgataaatgcttcaataatctggcgtaatagcgaagaggcccgcaccgatcgcccttcccaacagttgcgcagcctgaatggcgaatg |
| gcgcctgatgcggtattttctccttacgcatctgtgcggtatttcacaccgcatatggtgcactctcagtacaatctgctctgatgccgcat |
| agttaagccagccccgacacccgccaacacccgctgacgagcttagtaaagccctcgctagattttaatgcggatgttgcgattacttcgcc |
| aactattgcgataacaagaaaaagccagcctttcatgatatatctcccaatttgtgtagggcttattatgcacgcttaaaaataataaaagc |
| agacttgacctgatagtttggctgtgagcaattatgtgcttagtgcatcaacgcttgagttaagcgcgccgcgaagcggcgtcggcttga |
| acgaattgttagacattatttgccgactaccttggtgatctcgcctttcacgtagtggacaaattcttccaactgatctgcgcgcgaggcca |
| agcgatcttcttcttgtccaagataagcctgtctagcttcaagtatgacgggctgatactgggccggcaggcgctccattgcccagtcggca |
| gcgacatccttcggcgcgattttgccggttactgcgctgtaccaaatgcgggacaacgtaagcactacatttcgctcatcgccagcccagtc |
| gggcggcgagttccatagcgttaaggtttcatttagcgcctcaaatagatcctgttcaggaaccggatcaaagagttcctccgccgctggac |
| ctaccaaggcaacgctatgttctcttgcttttgtcagcaagatagccagatcaatgtcgatcgtggctggctcgaagatacctgcaagaatg |
| tcattgcgctgccattctccaaattgcagttcgcgcttagctggataacgccacggaatgatgtcgtcgtgcacaacaatggtgacttctac |
| agcgcggagaatctcgctctctccaggggaagccgaagtttccaaaaggtcgttgatcaaagctcgccgcgttgtttcatcaagccttacgg |

| SEQUENCES |
|---|
| tcaccgtaaccagcaaatcaatatcactgtgtggcttcaggccgccatccactgcggagccgtacaaatgtacggccagcaacgtcggttcg |
| agatggcgctcgatgacgccaactacctctgatagttgagtcgatacttcggcgatcaccgcttccctcatgatgtttaactttgttttagg |
| gcgactgccctgctgcgtaacatcgttgctgctccataacatcaaacatcgacccacggcgtaacgcgcttgctgcttggatgcccgaggca |
| tagactgtaccccaaaaaaacagtcataacaagccatgaaaaccgccactgcgccgttaccaccgctgcgttcggtcaaggttctggaccag |
| ttgcgtgagcgcatacgctacttgcattacagcttacgaaccgaacaggcttatgtccactgggttcgtgccttcatccgtttccacggtgt |
| gcgtcacccggcaaccttgggcagcagcgaagtcgaggcatttctgtcctggctggcgaacgagcgcaaggtttcggtctccacgcatcgtc |
| aggcattggcggccttgctgttcttctacggcaaggtgctgtgcacggatctgccctggcttcaggagatcggaagacctcggccgtcgcgg |
| cgcttgccggtggtgctgaccccggatgaagtggttcgcatcctcggttttctggaaggcgagcatcgtttgttcgcccagcttctgtatgg |
| aacgggcatgcggatcagtgagggtttgcaactgcgggtcaaggatctggatttcgatcacggcacgatcatcgtgcgggagggcaagggct |
| ccaaggatcgggccttgatgttacccgagagcttggcacccagcctgcgcgagcaggggaattaattcccacgggttttgctgcccgcaaac |
| gggctgttctggtgttgctagtttgttatcagaatcgcagatccggcttcagccggtttgccggctgaaagcgctatttcttccagaattgc |
| catgattttttccccacggaggcgtcactggctcccgtgttgtcggcagctttgattcgataagcagcatcgcctgtttcaggctgtctat |
| gtgtgactgttgagctgtaacaagttgtctcaggtgttcaatttcatgttctagttgctttgttttactggtttcacctgttctattaggtg |
| ttacatgctgttcatctgttacattgtcgatctgttcatggtgaacagctttgaatgcaccaaaaactcgtaaaagctctgatgtatctatc |
| ttttttacaccgttttcatctgtgcatatggacagttttcccttttgatatgtaacggtgaacagttgttctacttttgtttgttagtcttga |
| tgcttcactgatagatacaagagccataagaacctcagatccttccgtatttagccagtatgttctctagtgtggttcgttgtttttgcgtg |
| agccatgagaacgaaccattgagatcatacttactttgcatgtcactcaaaaattttgcctcaaaactggtgagctgaatttttgcagttaa |
| agcatcgtgtagtgtttttcttagtccgttatgtaggtaggaatctgatgtaatggttgttggtattttgtcaccattcatttttatctggt |
| tgttctcaagttcggttacgagatccatttgtctatctagttcaacttggaaaatcaacgtatcagtcgggcggcctcgcttatcaaccacc |
| aatttcatattgctgtaagtgtttaaatctttacttattggtttcaaaacccattggttaagccttttaaactcatggtagttattttcaag |
| cattaacatgaacttaaattcatcaaggctaatctctatatttgccttgtgagttttcttttgtgttagttcttttaataaccactcataaa |
| tcctcatagagtatttgttttcaaaagacttaacatgttccagattatattttatgaatttttttaactggaaaagataaggcaatatctct |
| tcactaaaaactaattctaattttcgcttgagaacttggcatagtttgtccactggaaaatctcaaagcctttaaccaaaggattcctgat |
| ttccacagttctcgtcatcagctctctggttgctttagctaatacaccataagcattttccctactgatgttcatcatctgagcgtattggt |
| tataagtgaacgataccgtccgttctttccttgtagggttttcaatcgtggggttgagtagtgccacacagcataaaattagcttggtttca |
| tgctccgttaagtcatagcgactaatcgctagttcatttgctttgaaaacaactaattcagacatacatctcaattggtctaggtgatttta |
| atcactataccaattgagatgggctagtcaatgataattactagtccttttcctttgagttgtgggtatctgtaaattctgctagacctttg |
| ctggaaaacttgtaaattctgctagaccctctgtaaattccgctagaccttttgtgtgttttttttgtttatattcaagtggttataatttat |
| agaataaagaagaataaaaaaagataaaaagaatagatcccagccctgtgtataactcactactttagtcagttccgcagtattacaaaag |
| gatgtcgcaaacgctgtttgctcctctacaaaacagaccttaaaaccctaaaggcttaagtagcaccctcgcaagctcgggcaaatcgctga |
| atattccttttgtctccgaccatcaggcacctgagtcgctgtcttttcgtgacattcagttcgctgcgctcacggctctggcagtgaatgg |
| gggtaaatggcactacaggcgccttttatggattcatgcaaggaaactacccataatacaagaaaagcccgtcacgggcttctcagggcgtt |
| ttatggcgggtctgctatgtggtgctatctgacttttttgctgttcagcagttcctgccctctgattttccagtctgaccacttcggattatc |
| ccgtgacaggtcattcagactggctaatgcacccagtaaggcagcggtatcatcaacaggctta | pMCM1224- pCL-Ptrc-Upper_GcMM_162 (*Enterococcus faecium*)

| |
|---|
| cccgtcttactgtcgggaattcgcgttggccgattcattaatgcagattctgaaatgagctgttgacaattaatcatccggctcgtataatg |
| tgtggaattgtgagcggataacaatttcacacaggaaacagcgccgctgagaaaaagcgaagcggcactgctctttacaatttatcagacaa |
| tctgtgtgggcactcgaccggaattatcgattaactttattattaaaaattaaagaggtatatattaatgtatcgattaaataaggaggaat |
| aaaccatgaaagaagtggttatgattgatgcggctcgcacacccattgggaaatacagaggtagtcttagtcctttacagcggtggagctg |

-continued

SEQUENCES gggacactggtcacgaaagggctgctggataaaacaaagcttaagaaagacaagatagaccaagtgatattcggcaatgtgcttcaggcagg aaacggacaaaacgttgcaagacaaatagccctgaacagtggcttaccagttgacgtgccggcgatgactattaacgaagtttgcgggtccg gaatgaaagcggtgattttagcccgccagttaatacagttaggggaggcagagttggtcattgcaggggggtacggagtcaatgtcacaagca cccatgctgaaaccttaccagtcagagaccaacgaatacggagagccgatatcatcaatggttaatgacgggctgacggatgcgttttccaa tgctcacatgggtcttactgccgaaaaggtggcgacccagttttcagtgtcgcgcgaggaacaagaccggtacgcattgtccagccaattga aagcagcgcacgcggttgaagccggggtgttctcagaagagattattccggttaagattagcgacgaggatgtcttgagtgaagacgaggca gtaagaggcaacagcactttggaaaaactgggcaccttgcggacggtgttttctgaagagggcacggttaccgctggcaatgcttcaccgct gaatgacggcgctagtgtcgtgattcttgcatcaaaagaatacgcggaaaacaataatctgccttacctggcgacgataaaggaggttgcgg aagttggtatcgatccttctatcatgggtattgccccaataaaggccattcaaaagttaacagatcggtcgggcatgaacctgtccacgatt gatctgttcgaaattaatgaagcattcgcggcatctagcattgttgtttctcaagagctgcaattggacgaagaaaagtgaatatctatgg cggggcgatagcttaggccatccaatcggcgcaagcggagcccggatactgacaaccttagcatacggcctcctgcgtgagcaaaagcgtt atggtattgcgtcattatgtatcggcggtggtcttggtctggccgtgctgttagaagctaatatggagcagacccacaaagacgttcagaag aaaaagttttaccagcttaccccctccgagcggagatcgcagcttatcgagaagaacgttctgactcaagaaacggcacttattttccagga gcagacgttgtccgaagaactgtccgatcacatgattgagaatcaggtctccgaagtggaaattccaatgggaattgcacaaaattttcaga ttaatggcaagaaaaaatggattcctatggcgactgaagaaccttcagtaatagcggcagcatcgaacggcgccaaaatctgcgggaacatt tgcgcggaaacgcctcagcggcttatgcgcgggcagattgtcctgtctggcaaatcagaatatcaagccgtgataaatgccgtgaatcatcg caaagaagaactgattcttgcgcaaacgagtcgtacccgagtattgttaaacgcggggaggtgttcaggatatttctacgcgggagttta tgggttcttttcacgcgtatttatcaatcgactttctggtggacgtcaaggacgcaatgggggcaaacatgatcaactctattctcgaaagc gttgcaaataaactgcgtgaatggttcccggaagaggaaatactgttctccatcctgtcaaacttcgctacggagtccctggcatctgcatg ttgcgagattccttttgaaagacttggtcgtaacaaagaaattggtgaacagatcgccaagaaaattcaacaggcaggggaatatgctaagc ttgacccttaccgcgcggcaacccataacaagggggattatgaacggtatcgaagccgtcgttgccgcaacgggaaacgacacacgggctgtt tccgcttctattcacgcatacgccgcccgtaatggcttgtaccaaggtttaacggattggcagatcaagggcgataaactggttggtaaatt aacagtcccactggctgtggcgactgtcggtggcgcgtcgaacatattaccaaaagccaaagcttccctcgccatgctggatattgattccg caaaagaactggcccaagtgatcgccgcggtaggtttagcacagaatctggcggcgttacgtgcattagtgacagaaggcattcagaaagga cacatgggcttgcaagcacgttctttagcgatttcgataggtgccatcggtgaggagatagagcaagtcgcgaaaaaactgcgtgaagctga aaaaatgaatcagcaaacggcaatacagatttagaaaaaattcgcgagaaatgatctagacgcactaggaggatataccaatgaaaatcgg tattgaccgtctgtccttcttcatcccgaatttgtatttggacatgactgagctggcagaatcacgcggggatgatccagctaaatatcata ttggaatcggacaagatcagatggcagtgaatcgcgcaaacgaggacatcataacactgggtgcaaacgctgcgagtaagatcgtgacagag aaagaccgcgagttgattgatatggtaatcgttggcacggaatcaggaattgaccactccaaagcaagcgccgtgattattcaccatctcct taaaattcagtcgttcgcccgttctttcgaggtaaaagaagcttgctatggcggaactgctgccctgcacatggcgaaggagtatgtcaaaa atcatccggagcgtaaggtcttggtaattgcgtcagacatcgcgcgttatggtttggccagcggaggagaagttactcaaggcgtgggggcc gtagccatgatgattacacaaaaccccggattctttcgattgaagacgatagtgttttctcacgaggatatctatgatttctggcggcc tgattactccgagttccctgtagtggacgggccccttcaaactcaacgtatatagagagttttcagaaagtttggaaccggcacaaggaat tgtccggaagagggctggaagattatcaagctattgcttttcacatacctatacgaagatgggtaagaaagcgctccagagtgttttagac caaaccgatgaagataaccaggagcgcttaatggctagatatgaggagtctattcgctatagccggagaattggtaacctgtacacaggcag cttgtaccttggtcttacaagcttgttggaaaactctaaaagtttacaaccgggagatcggatcggcctcttttcctatggcagtggtgcgg tgtccgagttctttaccgggtatttagaagaaaattaccaagagtacctgttcgctcaaagccatcaagaaatgctggatagccggactcgg attacggtcgatgaatacgagaccatcttttcagagactctgccagaacatggtgaatgcgccgaatatacgagcgacgtcccctttttctat -continued

| SEQUENCES |
|---|
| aaccaagattgagaacgacattcgttattataaaatctgactgcagctggtaccatatgggaattcgaagcttgggcccgaacaaaaactca |
| tctcagaagaggatctgaatagcgccgtcgaccatcatcatcatcattgagtttaaacggtctccagcttggctgttttggcggatgag |
| agaagattttcagcctgatacagattaaatcagaacgcagaagcggtctgataaaacagaatttgcctggcggcagtagcgcggtggtccca |
| cctgacccatgccgaactcagaagtgaaacgccgtagcgccgatggtagtgtggggtctccccatgcgagagtagggaactgccaggcatc |
| aaataaaacgaaaggctcagtcgaaagactgggcctttcgttttatctgttgtttgtcggtgaacgctctcctgagtaggacaaatccgccg |
| ggagcggatttgaacgttgcgaagcaacggcccgagggtggcgggcaggacgcccgccataaactgccaggcatcaaattaagcagaaggc |
| catcctgacggatggcctttttgcgtttctacaaactctttttgtttatttttctaaatacattcaaatatgtatccgctcatgagacaata |
| accctgataaatgcttcaataatctggcgtaatagcgaagaggcccgcaccgatcgcccttcccaacagttgcgcagcctgaatggcgaatg |
| gcgcctgatgcggtattttctccttacgcatctgtgcggtatttcacaccgcatatggtgcactctcagtacaatctgctctgatgccgcat |
| agttaagccagccccgacacccgccaacacccgctgacgagcttagtaaagccctcgctagattttaatgcggatgttgcgattacttcgcc |
| aactattgcgataacaagaaaaagccagcctttcatgatatatctcccaatttgtgtagggcttattatgcacgcttaaaaataataaaagc |
| agacttgacctgatagtttggctgtgagcaattatgtgcttagtgcatctaacgcttgagttaagccgcgccgcgaagcggcgtcggcttga |
| acgaattgttagacattatttgccgactaccttggtgatctcgcctttcacgtagtggacaaattcttccaactgatctgcgcgcgaggcca |
| agcgatcttcttcttgtccaagataagcctgtctagcttcaagtatgacgggctgatactgggccggcaggcgctccattgcccagtcggca |
| gcgacatccttcggcgcgattttgccggttactgcgctgtaccaaatgcgggacaacgtaagcactacatttcgctcatcgccagcccagtc |
| gggcggcgagttccatagcgttaaggtttcatttagcgcctcaaatagatcctgttcaggaaccggatcaaagagttcctccgccgctggac |
| ctaccaaggcaacgctatgttctcttgcttttgtcagcaagatagccagatcaatgtcgatcgtggctggctcgaagatacctgcaagaatg |
| tcattgcgctgccattctccaaattgcagttcgcgcttagctggataacgccacggaatgatgtcgtcgtgcacaacaatggtgacttctac |
| agcgcggagaatctcgctctctccaggggaagccgaagtttccaaaaggtcgttgatcaaagctcgccgcgttgtttcatcaagccttacgg |
| tcaccgtaaccagcaaatcaatatcactgtgtggcttcaggccgccatccactgcggagccgtacaaatgtacggccagcaacgtcggttcg |
| agatggcgctcgatgacgccaactacctctgatagttgagtcgatacttcggcgatcaccgcttccctcatgatgtttaactttgttttagg |
| gcgactgccctgctgcgtaacatcgttgctgctccataacatcaaacatcgacccacggcgtaacgcgcttgctgcttggatgcccgaggca |
| tagactgtaccccaaaaaaacagtcataacaagccatgaaaaccgccactgcgccgttaccaccgctgcgttcggtcaaggttctggaccag |
| ttgcgtgagcgcatacgctacttgcattacagcttacgaaccgaacaggcttatgtccactgggttcgtgccttcatccgtttccacggtgt |
| gcgtcacccggcaaccttgggcagcagcgaagtcgaggcatttctgtcctggctggcgaacgagcgcaaggtttcggtctccacgcatcgtc |
| aggcattggcggccttgctgttcttctacggcaaggtgctgtgcacggatctgccctggcttcaggagatcggaagacctcggccgtcgcgg |
| cgcttgccggtggtgctgacccggatgaagtggttcgcatcctcggttttctggaaggcgagcatcgtttgttcgcccagcttctgtatgg |
| aacgggcatgcggatcagtgagggtttgcaactgcggtcaaggatctggatttcgatcacggcacgatcatcgtgcgggagggcaagggct |
| ccaaggatcgggccttgatgttacccgagagcttggcacccagcctgcgcgagcaggggaattaattcccacgggttttgctgcccgcaaac |
| gggctgttctggtgttgctagtttgttatcagaatcgcagatccggcttcagccggtttgccggctgaaagcgctatttcttccagaattgc |
| catgattttttccccacgggaggcgtcactggctcccgtgttgtcggcagctttgattcgataagcagcatcgcctgtttcaggctgtctat |
| gtgtgactgttgagctgtaacaagttgtctcaggtgttcaatttcatgttctagttgctttgttttactggtttcacctgttctattaggtg |
| ttacatgctgttcatctgttacattgtcgatctgttcatggtgaacagctttgaatgcaccaaaaactcgtaaagctctgatgtatctatc |
| ttttttacaccgttttcatctgtgcatatggacagttttcccttttgatatgtaacggtgaacagttgttctacttttgtttgttagtcttga |
| tgcttcactgatagatacaagagccataagaacctcgatccttccgtatttagccagtatgttctctagtgtggttcgttgttttttgcgtg |
| agccatgagaacgaaccattgagatcatacttactttgcatgtcactcaaaaattttgcctcaaaactggtgagctgaattttttgcagttaa |
| agcatcgtgtagtgtttttcttagtccgttatgtaggtaggaatctgatgtaatggttgttggtattttgtcaccattcattttatctggt |
| tgttctcaagttcggttacgagatccatttgtctatctagttcaacttggaaaatcaacgtatcagtcgggcggcctcgcttatcaaccacc |
| aatttcatattgctgtaagtgtttaaatctttacttattggtttcaaaacccattggttaagccttttaaactcatggtagttattttcaag |

| SEQUENCES |
|---|
| cattaacatgaacttaaattcatcaaggctaatctctatatttgccttgtgagttttcttttgtgttagttcttttaataaccactcataaa |
| tcctcatagagtatttgttttcaaaagacttaacatgttccagattatattttatgaatttttttaactggaaaagataaggcaatatctct |
| tcactaaaaactaattctaattttttcgcttgagaacttggcatagtttgtccactggaaaatctcaaagcctttaaccaaaggattcctgat |
| ttccacagttctcgtcatcagctctctggttgctttagctaatacaccataagcattttccctactgatgttcatcatctgagcgtattggt |
| tataagtgaacgataccgtccgttctttccttgtagggttttcaatcgtggggttgagtagtgccacacagcataaaattagcttggtttca |
| tgctccgttaagtcatagcgactaatcgctagttcatttgctttgaaaacaactaattcagacatacatctcaattggtctaggtgattta |
| atcactataccaattgagatgggctagtcaatgataattactagtccttttcctttgagttgtgggtatctgtaaattctgctagacctttg |
| ctggaaaacttgtaaattctgctagaccctctgtaaattccgctagaccttgtgtgttttttgtttatattcaagtggttataattat |
| agaataaagaagaataaaaaaagataaaagaatagatcccagccctgtgtataactcactactttagtcagttccgcagtattacaaaag |
| gatgtcgcaaacgctgtttgctcctctacaaaacagaccttaaaaccctaaaggcttaagtagcaccctcgcaagctcgggcaaatcgctga |
| atattccttttgtctccgaccatcaggcacctgagtcgctgtcttttcgtgacattcagttcgctgcgctcacggctctggcagtgaatgg |
| gggtaaatggcactacaggcgccttttatggattcatgcaaggaaactacccataatacaagaaaagcccgtcacgggcttctcagggcgtt |
| ttatggcgggtctgctatgtggtgctatctgacttttttgctgttcagcagttcctgccctctgattttccagtctgaccacttcggattatc |
| ccgtgacaggtcattcagactggctaatgcacccagtaaggcagcggtatcatcaacaggctta | pMCM1225- pCL-Ptrc-Upper_GcMM_163 (*Enterococcus gallinarum* EG2):
cccgtcttactgtcgggaattcgcgttggccgattcattaatgcagattctgaaatgagctgttgacaattaatcatccggctcgtataatg
tgtggaattgtgagcggataacaatttcacacaggaaacagcgccgctgagaaaaagcgaagcggcactgctcttaacaatttatcagaca
atctgtgtgggcactcgaccggaattatcgattaactttattattaaaaattaaagaggtatatattaatgtatcgattaaataaggaggaa
taaaccatggaagaagtggtaattatagatgcacgtcggactccgattggtaaatatcacgggtcgttgaagaagttttcagcggtggcgct
ggggacggccgtggctaaagacatgttcgaacgcaaccagaaaatcaaagaggagatcgcgcaggtcataattggtaatgtcttgcaggcag
gaaatggccagaaccccgcgcggcaagttgctcttcaatcagggttgtccgttgacattcccgcttctacaattaacgagtttgtgggtct
ggtttgaaagctatcttgatgggcatggaacaaatccaactcggcaaagcgcaagtagtgctggcaggcggcattgaatcaatgacaaatgc
gccaagcctgtcccactataacaaggcggaggatacgtatagtgtcccagtgtcgagcatgacactggatggtctgacagacgcattttcta
gtaaacctatgggattaacagcggaaaacgtcgcacagcgctacggtatctcccgtgaggcgcaagatcaattcgcatatcaatctcagatg
aaagcagcaaaagcgcaggcagaaaacaaattcgctaaggaaattgtgccactggcgggtgaaactaaaaccatcacagctgacgaagggat
cagatcccaaacaacgatggagaaactggcaagtctcaaacctgtttttaaaaccgatggcactgtaaccgcagggaatgctagcaccatta
atgacggggccgcccttgtgctgcttgctagcaaaacttactgcgaaactaatgacataccgtaccttgcgacaatcaaagaaattgttgaa
gttggaatcgatccggagattatgggcatctctccgataaaagcgatacaaacattgttacaaaatcaaaaagttagcctcgaagatattgg
agtttttgaaataaatgaagcctttgccgcaagtagcatagtggttgaatctgagttgggattagatccggctaaagttaaccgttatgggg
gtggtatatccttaggtcatgcaattgggcaaccggcgctcgcctggccacttcactggtgtatcaaatgcaggagatacaagcacgttat
ggtattgcgagcctgtgcgttggtggtggacttggactggcaatgcttttagaacgtccaactattgagaaggctaaaccgacagacaaaaa
gttctatgaattgtcaccagctgaacggttgcaagagctggaaaatcaacagaaaatcagttctgaaactaaacagcagttatctcagatga
tgcttgccgaggacactgcaaaccatttgatagaaaatcaaatatcagagattgaactcccaatgggcgtcgggatgaacctgaaggttgat
gggaaagcctatgttgtgccaatggcgacggaagagccgtccgtcatcgcggccatgtctaatggtgccaaaatggccggcgaaattcacac
tcagtcgaaagaacggctgctcagaggtcagattgttttcagcgcgaagaatccgaatgaaatcgaacagagaatagctgagaaccaagctt
tgattttcgaacgtgccgaacagtcctatccttccattgtgaaaagagagggaggtctccgccgcattgcacttcgtcatttttcctgccgat
tctcagcaggagtctgcggaccagtccacatttttatcagtggaccttttgtagatgtgaaagacgcgatgggggcaaatatcataaatgc
aatacttgagggcgtcgcagccctgtttcgcgaatggttccccaatgaggaaattcttttttctattctctcgaacttggctacggagagct
tagtcacggctgtttgtgaagtcccatttagtgcacttagcaagagaggtggtgcaacggtggcccagaaaattgtgcaggcgtcgctcttc -continued

| SEQUENCES |
|---|
| gcaaagacagacccataccgcgcagtgacccacaacaaagggattatgaacggtgtagaggctgttatgcttgccacaggcaacgacacgcg |
| cgcagtctcagccgcttgtcatggatacgcagcgcgcaccggtagctatcagggtctgactaactggacgattgagtcggatcgcctggtag |
| gcgagataacactgccgctggccatcgctacagttggaggcgctaccaaagtgttgcccaaagctcaagcggcactggagattagtgatgtt |
| cactcttctcaagagcttgcagccttagcggcgtcagtaggtttagtacaaaatctcgcggccctgcgcgcactggtttccgaaggtataca |
| aaagggcacatgtccatgcaagcccggtctctcgcaatcgcggtcggtgctgaaaaagccgagatcgagcaggtcgccgaaaagttgcggc |
| agaacccgccaatgaatcagcagcaggcgctccgttttcttggcgagatccgcgaacaatgatctagacgcactaggaggatataccaatga |
| acgtcggcattgacaaaattaattttttcgttccaccgtattatctggatatggtcgacctggcccacgcacgcgaagtggacccgaacaaa |
| tttacaattggaattggacaggatcagatggctgtgagcaaaaagacgcacgatatcgtaacattcgcggctagtgccgcgaaggaaatttt |
| agaacctgaggacttgcaagctatagacatggttatagttggtaccgaatcgggcattgacgagagcaaagcatccgcggtcgttttacatc |
| gtttgttgggcgtacaacctttcgctcgcagttttgaaattaaagaagcctgttacggggcaaccgcaggcattcagtttgccaagactcat |
| atacaagcgaacccggagagcaaggtcctggtaattgcaagcgatatagctcggtatggtcttcggtcaggtggagagcccacacaaggcgc |
| aggggcagttgctatgcttctcacggcaaatcccagaatcctgaccttcgaaaacgacaatctgatgttaacgcaggatatttatgacttct |
| ggagaccacttggtcacgcttaccctatggtagatggccaccttccaatcaagtctatattgacagttttaagaaggtctggcaagcacat |
| tgcgaacgcaatcaagcttctatatccgactatgccgcgattagttttcatattccgtatacaaaaatgggtaagaaagccctgctcgctgt |
| ttttgcagatgaagtggaaactgaacaggaacgcgttatggcacggtatgaagagtctatcgtatattcacgccggatcggcaacttgtata |
| cgggatcattgtacctggggctgatatccttattggaaaacagttctcacctgtcggcgggcgaccggataggattgtttagttatgggagt |
| ggcgctgtcagcgaattttctccggtcgtttagtggcaggctatgaaaatcaattgaacaaagaggcgcatacccagctcctggatcagcg |
| tcagaagctttccatcgaagagtatgaggcgattttttacagattccttagaaattgatcaggatgcagcgttctcggatgacctgccatatt |
| ccatccgcgagataaaaaacacgattcggtactataaggagagctgactgcagctggtaccatatgggaattcgaagcttgggcccgaacaa |
| aaactcatctcagaagaggatctgaatagcgccgtcgaccatcatcatcatcatcattgagtttaaacggtctccagcttggctgttttggc |
| ggatgagagaagattttcagcctgatacagattaaatcagaacgcagaagcggtctgataaaacagaatttgcctggcggcagtagcgcggt |
| ggtcccacctgaccccatgccgaactcagaagtgaaacgccgtagcgccgatggtagtgtggggtctccccatgcgagagtagggaactgcc |
| aggcatcaaataaaacgaaaggctcagtcgaaagactgggcctttcgttttatctgttgtttgtcggtgaacgctctcctgagtaggacaaa |
| tccgccgggagcggatttgaacgttgcgaagcaacggcccggagggtggcgggcaggacgccgccataaactgccaggcatcaaattaagc |
| agaaggccatcctgacggatggcctttttgcgtttctacaaactcttttttgttttatttttctaaatacattcaaatatgtatccgctcatga |
| gacaataaccctgataaatgcttcaataatctggcgtaatagcgaagaggcccgcaccgatcgcccttcccaacagttgcgcagcctgaatg |
| gcgaatggcgcctgatgcggtattttctccttacgcatctgtgcggtatttcacaccgcatatggtgcactctcagtacaatctgctctgat |
| gccgcatagttaagccagccccgacacccgccaacacccgctgacgagcttagtaaagccctcgctagttttaatgcggatgttgcgatta |
| cttcgccaactattgcgataacaagaaaaagccagccttttcatgatatatctcccaatttgtgtagggcttattatgcacgcttaaaaataa |
| taaaagcagacttgacctgatagtttggctgtgagcaattatgtgcttagtgcatctaacgcttgagttaagccgcgccgcgaagcggcgtc |
| ggcttgaacgaattgttagacattatttgccgactaccttggtgatctcgcctttcacgtagtggacaaattcttccaactgatctgcgcgc |
| gaggccaagcgatcttcttcttgtccaagataagcctgtctagcttcaagtatgacgggctgatactgggccggcaggcgctccattgccca |
| gtcggcagcgacatccttcggcgcgattttgccggttactgcgctgtaccaaatgcgggacaacgtaagcactacatttcgctcatcgccag |
| cccagtcgggcggcgagttccatagcgttaaggtttcatttagcgcctcaaatagatcctgttcaggaaccggatcaaagagttcctccgcc |
| gctggacctaccaaggcaacgctatgttctcttgcttttgtcagcaagatagccagatcaatgtcgatcgtggctggctcgaagatacctgc |
| aagaatgtcattgcgctgccattctccaaattgcagttcgcgcttagctggataacgccacggaatgatgtcgtcgtgcacaacaatggtga |
| cttctacagcgcggagaatctcgctctctccaggggaagccgaagtttccaaaaggtcgttgatcaaagctcgccgcgttgtttcatcaagc |
| cttacggtcaccgtaaccagcaaatcaatatcactgtgtggcttcaggccgccatccactgcggagccgtacaaatgtacggccagcaacgt |

-continued

| SEQUENCES |
|---|
| cggttcgagatggcgctcgatgacgccaactacctctgatagttgagtcgatacttcggcgatcaccgcttccctcatgatgtttaactttg |
| ttttagggcgactgccctgctgcgtaacatcgttgctgctccataacatcaaacatcgacccacggcgtaacgcgcttgctgcttggatgcc |
| cgaggcatagactgtaccccaaaaaaacagtcataacaagccatgaaaaccgccactgcgccgttaccaccgctgcgttcggtcaaggttct |
| ggaccagttgcgtgagcgcatacgctacttgcattacagcttacgaaccgaacaggcttatgtccactgggttcgtgccttcatccgtttcc |
| acggtgtgcgtcacccggcaaccttgggcagcagcgaagtcgaggcatttctgtcctggctggcgaacgagcgcaaggtttcggtctccacg |
| catcgtcaggcattggcggccttgctgttcttctacggcaaggtgctgtgcacggatctgccctggcttcaggagatcggaagacctcggcc |
| gtcgcggcgcttgccggtggtgctgacccggatgaagtggttcgcatcctcggttttctggaaggcgagcatcgtttgttcgcccagcttc |
| tgtatggaacgggcatgcggatcagtgaggggtttgcaactgcgggtcaaggatctggatttcgatcacggcacgatcatcgtgcgggagggc |
| aagggctccaaggatcgggccttgatgttacccgagagcttggcacccagcctgcgcgagcaggggaattaattcccacgggttttgctgcc |
| cgcaaacgggctgttctggtgttgctagtttgttatcagaatcgcagatccggcttcagccggtttgccggctgaaagcgctatttcttcca |
| gaattgccatgattttttccccacgggaggcgtcactggctcccgtgttgtcggcagctttgattcgataagcagcatcgcctgtttcaggc |
| tgtctatgtgtgactgttgagctgtaacaagttgtctcaggtgttcaatttcatgttctagttgctttgttttactggtttcacctgttcta |
| ttaggtgttacatgctgttcatctgttacattgtcgatctgttcatggtgaacagctttgaatgcaccaaaaactcgtaaaagctctgatgt |
| atctatctttttacaccgttttcatctgtgcatatggacagttttcccttgatatgtaacggtgaacagttgttctacttttgtttgtta |
| gtcttgatgcttcactgatagatacaagagccataagaacctcagatccttccgtatttagccagtatgttctctagtgtggttcgttgttt |
| ttgcgtgagccatgagaacgaaccattgagatcatacttactttgcatgtcactcaaaaattttgcctcaaaactggtgagctgaattttg |
| cagttaaagcatcgtgtagtgttttcttagtccgttatgtaggtaggaatctgatgtaatggttgttggtattttgtcaccattcattttt |
| atctggttgttctcaagttcggttacgagatccatttgtctatctagttcaacttggaaaatcaacgtatcagtcgggcggcctcgcttatc |
| aaccaccaatttcatattgctgtaagtgtttaaatctttacttattggtttcaaaacccattggttaagccttttaaactcatggtagttat |
| tttcaagcattaacatgaacttaaattcatcaaggctaatctctatatttgccttgtgagttttcttttgtgttagttcttttaataaccac |
| tcataaatcctcatagagtatttgttttcaaaagacttaacatgttccagattatattttatgaattttttaactggaaaagataaggcaa |
| tatctcttcactaaaaactaattctaattttttcgcttgagaacttggcatagtttgtccactggaaaatctcaaagcctttaaccaaggat |
| tcctgatttccacagttctcgtcatcagctctctggttgctttagctaatacaccataagcattttccctactgatgttcatcatctgagcg |
| tattggttataagtgaacgataccgtccgttcttccttgtaggttttcaatcgtggggttgagtagtgccacacagcataaaattagctt |
| ggtttcatgctccgttaagtcatagcgactaatcgctagttcatttgctttgaaaacaactaattcagacatacatctcaattggtctaggt |
| gattttaatcactataccaattgagatgggctagtcaatgataattactagtccttttccttgagttgtgggtatctgtaaattctgctag |
| acctttgctggaaaacttgtaaattctgctagaccctctgtaaattccgctagacctttgtgtgttttttttgtttatattcaagtggttat |
| aatttatagaataaagaaagaataaaaaaagataaaagaatagatcccagccctgtgtataactcactactttagtcagttccgcagtatt |
| acaaaaggatgtcgcaaacgctgtttgctcctctacaaaacagaccttaaaaccctaaaggcttaagtagcaccctcgcaagctcgggcaaa |
| tcgctgaatattccttttgtctccgaccatcaggcacctgagtcgctgtcttttcgtgacattcagttcgctgcgctcacggctctggcag |
| tgaatgggggtaaatggcactacaggcgccttttatggattcatgcaaggaaactacccataatacaagaaaagcccgtcacgggcttctca |
| gggcgttttatggcgggtctgctatgtggtgctatctgacttttgctgttcagcagttcctgccctctgattttccagtctgaccacttcg |
| gattatcccgtgacaggtcattcagactggctaatgcacccagtaaggcagcggtatcatcaacaggctta |

What is claimed is:

1. Recombinant cells with increased production of mevalonate, the cells comprising one or more heterologous nucleic acids comprising a mevalonate E (mvaE) gene and a mevalonate S (mvaS) gene selected from the organisms *Listeria grayi* (*L. grayi*), *Enterococcus faecium* (*E. faecium*), *Enterococcus gallinarum* (*E. gallinarum*), and *Enterococcus casseliflavus* (*E. casseliflavus*), wherein the mvaE gene and mvaS gene encode polypeptides having thiolase, HMG-CoA synthase, and HMG-CoA reductase catalytic activities, and wherein the cells produce increased amounts of mevalonate compared to mevalonate-producing cells that (A) contain an mvaE gene and mvaS gene from *Enterococcus faecalis* (*E. faecalis*) and (B) do not contain said mvaE gene and mvaS gene from *E. gallinarum*, *E. casseliflavus*, *E. faecium*, or *L. grayi*.

2. The cells of claim 1, wherein the one or more nucleic acids is placed under an inducible promoter or a constitutive promoter.

3. The cells of claim 1, wherein the one or more nucleic acids is cloned into a multicopy plasmid.

4. The cells of claim 1 wherein the one or more nucleic acids is integrated into a chromosome of the cells.

5. The cells of claim 1, wherein the cells are gram-positive bacterial cells, gram-negative bacterial cells, *Escherichia* cells, *Pantoea* cells, fungal cells, filamentous fungal cells, *Trichoderma* cells, *Aspergillus* cells, or yeast cells.

6. The cells of claim 5, wherein the cells are selected from the group consisting of *E. coli*, *P. citrea*, *B. subtilis*, *B. licheniformis*, *B. lentus*, *B. brevis*, *B. stearothermophilus*, *B. alkalophilus*, *B. amyloliquefaciens*, *B. clausii*, *B. halodurans*, *B. megaterium*, *B. coagulans*, *B. circulans*, *B. lautus*, *B. thuringiensis*, *S. albus*, *S. lividans*, *S. coelicolor*, *S. griseus*, *Pseudomonas* sp., and *P. alcaligenes* cells.

7. The cells of claim 6, wherein the cells are *E. coli*.

8. The cells of claim 1, wherein the mvaE gene and mvaS gene are from different organisms.

9. The cells of claim 1, wherein a) the mvaE gene is from *L. grayi* and the mvaS gene is from *E. faecium*;

b) the mvaE gene is from *L. grayi* and the mvaS gene is from *E. gallinarum*;

c) the mvaE gene is from *L. grayi* and the mvaS gene is from *E. casseliflavus*;

d) the mvaE gene is from *E. faecium* and the mvaS gene is from *L. grayi*;

e) the mvaE gene is from *E. faecium* and the mvaS gene is from *E. gallinarum*;

f) the mvaE gene is from *E. faecium* and the mvaS gene is from *E. casseliflavus*;

g) the mvaE gene is from *E. gallinarum* and the mvaS gene is from *L. grayi*;

h) the mvaE gene is from *E. gallinarum* and the mvaS gene is from *E. faecium*;

i) the mvaE gene is from *E. gallinarum* and the mvaS gene is from *E. casseliflavus*;

j) the mvaE gene is from *E. casseliflavus* and the mvaS gene is from *L. grayi*;

k) the mvaE gene is from *E. casseliflavus* and the mvaS gene is from *E. faecium*; or l) the mvaE gene is from *E. casseliflavus* and the mvaS gene is from *E. gallinarum*.

10. The cells of claim 5, wherein the cells are yeast cells.

11. The cells of claim 10, wherein the yeast cells are selected from the group consisting of *Saccharomyces* sp., *Schizosaccharomyces* sp., *Pichia* sp., and *Candida* sp. cells.

12. The cells of claim 11, wherein the yeast cells are *Saccharomyces cerevisiae* cells.

13. A method of producing mevalonate, comprising: (a) culturing the host cells of claim 1 under suitable culture conditions for production of mevalonate; and (b) producing the mevalonate.

14. The method of claim 13, further comprising (c) recovering the mevalonate.

* * * * *